United States Patent
Deckert et al.

(10) Patent No.: US 9,175,086 B2
(45) Date of Patent: Nov. 3, 2015

(54) CD20 ANTIBODIES AND USES THEREOF

(75) Inventors: Jutta Deckert, Lexington, MA (US); Daniel J. Tavares, Natick, MA (US); Peter U. Park, Somerville, MA (US)

(73) Assignee: ImmunoGen, Inc., Waltham, MA (US)

( * ) Notice: Subject to any disclaimer, the term of this patent is extended or adjusted under 35 U.S.C. 154(b) by 540 days.

(21) Appl. No.: 13/024,671

(22) Filed: Feb. 10, 2011

(65) Prior Publication Data

US 2011/0195022 A1  Aug. 11, 2011

Related U.S. Application Data

(60) Provisional application No. 61/303,210, filed on Feb. 10, 2010.

(51) Int. Cl.

| | | |
|---|---|---|
| A61K 39/395 | (2006.01) | |
| C07K 16/28 | (2006.01) | |
| C07K 16/30 | (2006.01) | |
| A61K 47/48 | (2006.01) | |
| A61K 51/10 | (2006.01) | |
| G01N 33/574 | (2006.01) | |
| A61K 39/00 | (2006.01) | |

(52) U.S. Cl.
CPC ....... *C07K 16/2887* (2013.01); *A61K 39/39541* (2013.01); *A61K 47/48438* (2013.01); *A61K 47/48446* (2013.01); *A61K 47/48561* (2013.01); *A61K 51/1027* (2013.01); *G01N 33/57426* (2013.01); *A61K 2039/505* (2013.01); *C07K 2317/24* (2013.01); *C07K 2317/30* (2013.01); *C07K 2317/565* (2013.01); *C07K 2317/73* (2013.01); *C07K 2317/732* (2013.01); *C07K 2317/734* (2013.01); *C07K 2317/92* (2013.01); *C07K 2319/55* (2013.01)

(58) Field of Classification Search
CPC .................... C07K 16/2887; A61K 39/39541; A61K 39/39558
See application file for complete search history.

(56) References Cited

U.S. PATENT DOCUMENTS

| | | |
|---|---|---|
| 5,595,721 A | 1/1997 | Kaminski et al. |
| 5,736,137 A | 4/1998 | Anderson et al. |
| 6,399,061 B1 | 6/2002 | Anderson et al. |
| 2004/0093621 A1 | 5/2004 | Shitara et al. |
| 2004/0167319 A1 | 8/2004 | Teeling et al. |
| 2006/0018911 A1 | 1/2006 | Ault-Riche et al. |
| 2009/0087427 A1 | 4/2009 | Frendeus et al. |
| 2011/0195021 A1 | 8/2011 | Deckert et al. |
| 2012/0034185 A1 | 2/2012 | Hansen et al. |

FOREIGN PATENT DOCUMENTS

| | | |
|---|---|---|
| WO | 2004032828 | 4/2004 |
| WO | 2004035607 | 4/2004 |
| WO | WO 2008/156713 A2 | 12/2008 |

OTHER PUBLICATIONS

Rudikoff et al., "Single amino acid substitutions altering antigen-binding specificity", PNAS, 79:1979-83, 1982.*
MacCallum et al., "Antibody-antigen Interaction: Contact Analysis and Binding Site topography", J. Mol. biol. 262:732-745, 1996.*
De Pascalis et al., "Grafting of "abbreviated" complementarity-determining regions containing specificity-determining residues essential for ligand contact to engineer a less immunogenic humanized monoclonal antibody.", J. Immunol., 169:3076-3084, 2002.*
Adamson et al., "Antibody against CD20 in patients with B cell malignancy", Leukemia Research 25 (2001) 1047-1050.*
Nadler et al., "A Unique Cell Surface Antigen Identifying Lymphoid Malignancies of B Cell Origin", J. Clin. Invest., 67(1):134-140 (1981).
Stasheko et al., "Characterization of a human B lymphocyte-specific Antigen", J. of Immunology, 125(4):1678-1685 (1980).
Reff et al., "Depletion of B Cells In Vivo by a Chimeric Mouse Human Monoclonal Antibody to CD20", Blood, 83(2):435-445 (1994).
Lui et al., "Production of a Mouse-Human Chimeric Monoclonal Antibody to CD20 with Potent Fc-dependent Biologic Activity", 139(10):3521-3526 (1987).
Press et al., Monoclonal Antibody 1F5 (Anti-CD20) Serotherapy of Human B Cell Lymphomas, Blood, 69(2):584-291 (1987).
Tedder et al., "Isolation and Structure of a cDNA encoding the B1 (CD20) cell-surface antigen of human B lymphocytes", Proc. Natl. Acad. Sci., USA, 85(1):208-212 (1988).
Nadler et al., "Anti-B1 Monoclonal Antibody and Complement Treatment in Autologous Bone-Marrow Transplantation for Relapsed B-Cell Non-Hodgkin's Lymphoma", The Lancet, 2(4800):427-431 (1984).
Oettgen et al., "Further Biochemical Studies of the Human b-Cell Differentiation Antigens B1 and B2", Hybridoma, 2(1):17-28 (1983).
Deans, et al., Rapid Redistribution of CD20 to a Low Density Detergent-Insoluble Membrane Compartment. Journal of Biological Chemistry 1998, 273(1):344-348; p. 344, col. 2, para 1; p. 345, col. 1, para 5.
Rossi, E. A., et al., "Novel Designs of Multivalent Anti-CD20 Humanized Antibodies as Improved Lymphoma Therapeutics," *Cancer Res* 68:8384-8392, American Association for Cancer Research, United States (2008).

* cited by examiner

*Primary Examiner* — Ron Schwadron
(74) *Attorney, Agent, or Firm* — Sterne, Kessler, Goldstein & Fox P.L.L.C.

(57) ABSTRACT

CD20 is a transmembrane protein of the tetra-spanin family expressed on the surface of B-cells from peripheral blood as well as lymphoid tissues. CD20 expression persists from the early pre-B cell stage until the plasma cell differentiation stage. In addition to expression in normal B-cells, CD20 is expressed in B-cell derived malignancies such as non-Hodgkin's lymphoma (NHL) and B-cell chronic lymphocytic leukemia (CLL). The present invention includes anti-CD20 antibodies and antigen-binding fragments thereof comprising a light chain variable region and a heavy chain variable region, wherein the CDR-L1, CDR-L2, and CDR-L3 of said light chain variable region comprise the amino acid sequences of SEQ ID NOs: 23-25, respectively, and wherein the CDR-H1, CDR-H2, and CDR-H3 of said heavy chain variable region comprise the amino acid sequences of SEQ ID NOs: 26-28, respectively.

37 Claims, 33 Drawing Sheets

Fig. 2
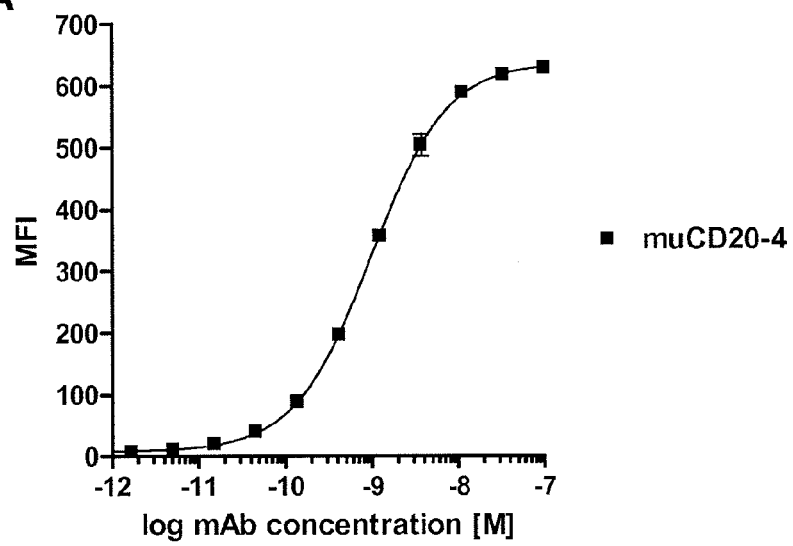
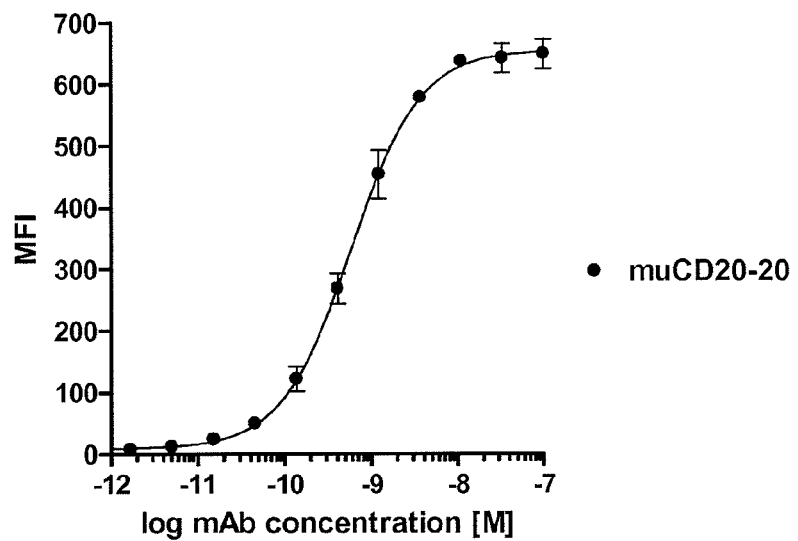

| CD20-4 LC Surface Residues ||||
|---|---|---|---|
| Kabat Position | muCD20-4 | L12a | huCD20-4 |
| 1 | D | D | D |
| 3 | V | Q | Q |
| 7 | S | S | S |
| 8 | Q | P | P |
| 9 | K | S | S |
| 10 | F | T | T |
| 15 | V | V | V |
| 18 | R | R | R |
| 40 | P | P | P |
| 41 | R | G | G |
| 42 | Q | K | K |
| 45 | K | K | K |
| 57 | G | G | G |
| 60 | D | S | S |
| 67 | S | S | S |
| 80 | S | P | P |
| 81 | D | D | D |
| 107 | K | K | K |
| 108 | R | R | R |

B

| CD20-4 HC Surface Residues ||||
|---|---|---|---|
| Kabat Position | muCD20-4 | Cos23 | huCD20-4 |
| 1 | E | E | E |
| 3 | K | Q | Q |
| 11 | L | L | L |
| 13 | K | Q | Q |
| 14 | T | P | P |
| 19 | K | R | R |
| 41 | P | P | P |
| 42 | E | G | G |
| 43 | K | K | K |
| 61 | E | D | D |
| 64 | K | K | K |
| 65 | G | G | G |
| 74 | S | S | S |
| 75 | K | K | K |
| 82B | N | N | N |
| 83 | R | R | R |
| 84 | A | A | A |
| 85 | E | E | E |
| 105 | Q | Q | Q |
| 112 | S | S | S |

Fig. 5

A
Light Chain Variable Region

```
              1                                                           60
muCD20-4LC    DIVMTQSQKFMSTSVGDRVSVNCKASQNVGTNVAWYQQKPRQSPKGLIYSASFRYSGVPD
huCD20-4LC    --Q----PST----------------------------GK------------------S
              61                                          108
muCD20-4LC    RFTGSGSGTDFTLTIFNVQSDDLAEYFCQQYNNYPLTFGGGTKLEIKR
huCD20-4LC    -------------------P----------------------------
```

B
Heavy Chain Variable Region

```
              1                                                           60
muCD20-4HC    EVKVEESGGGLVKTGGSMKLSCVASGFSFNNYWMNWVRQSPEKGLEWVAEIRLKSNNYAT
huCD20-4HC    --Q---------QP----R-----------------G-----------------------
              61                                                         119
muCD20-4HC    HYVESVKGRFTISRDDSKSSVYLQMNNLRAEDTGIYYCTGWDDYAMDHWGQGISVTVSS
huCD20-4HC    ---D-------------------------------------------------------
```

Fig. 11
A
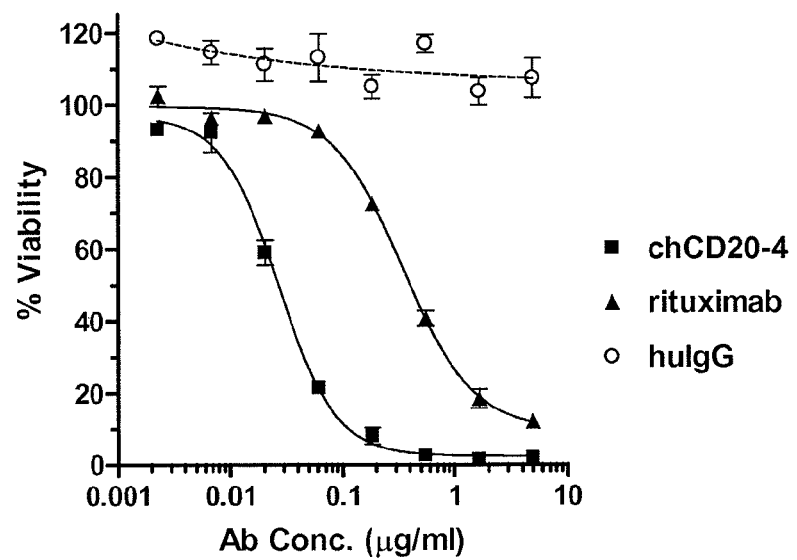
B
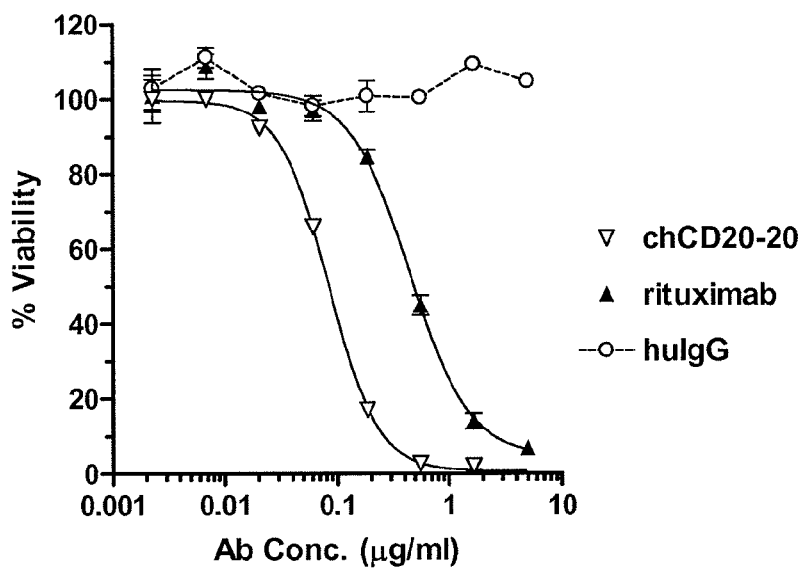

Fig. 12
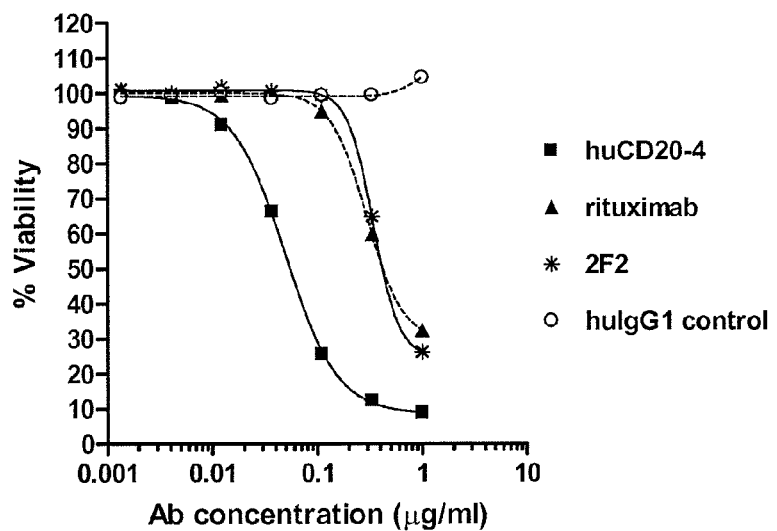
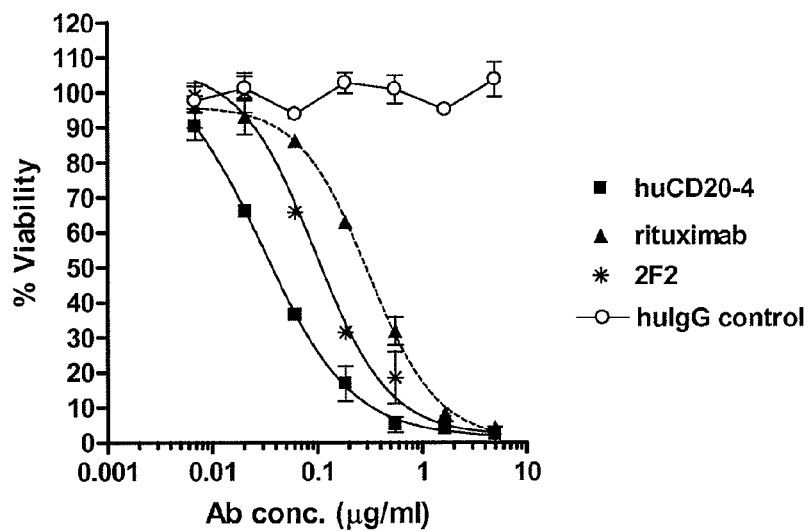

Fig. 13
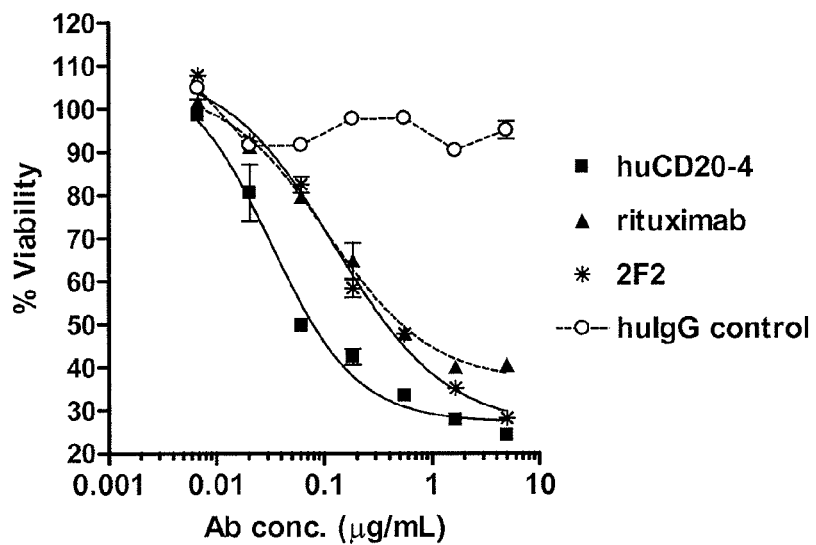
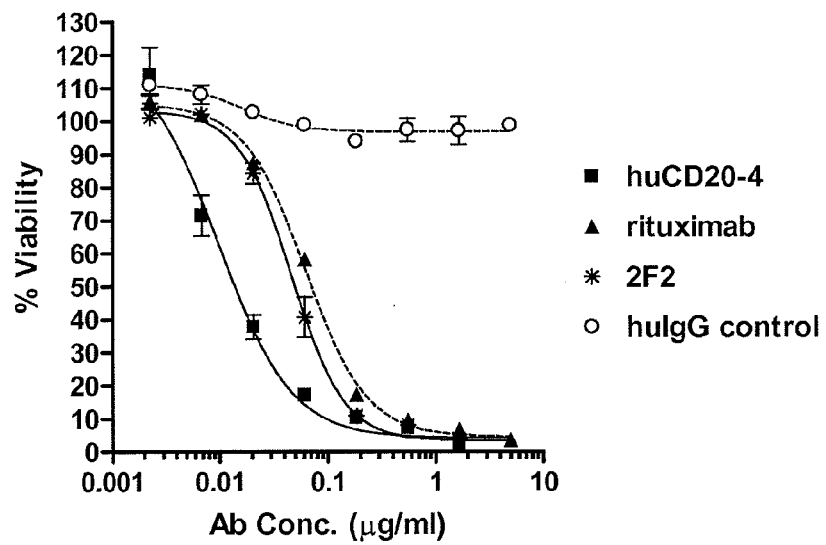

Fig. 14
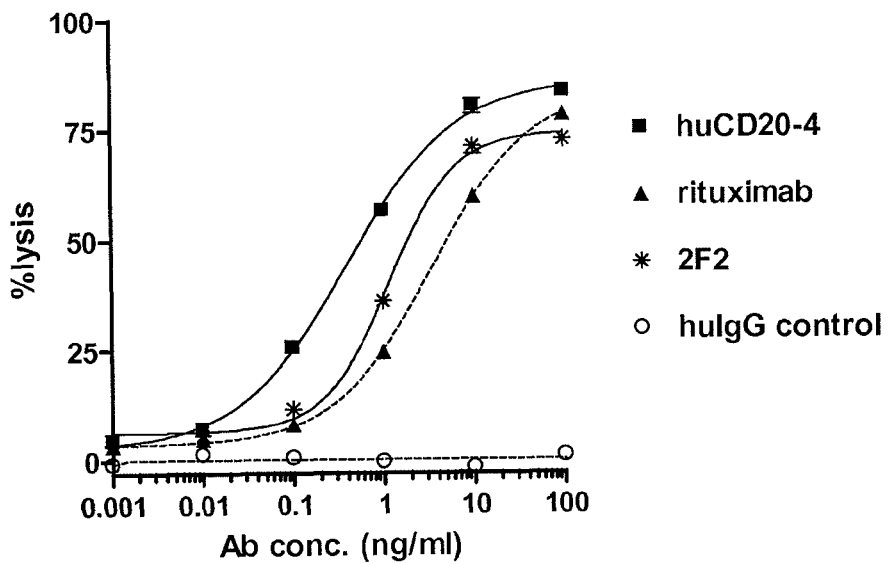
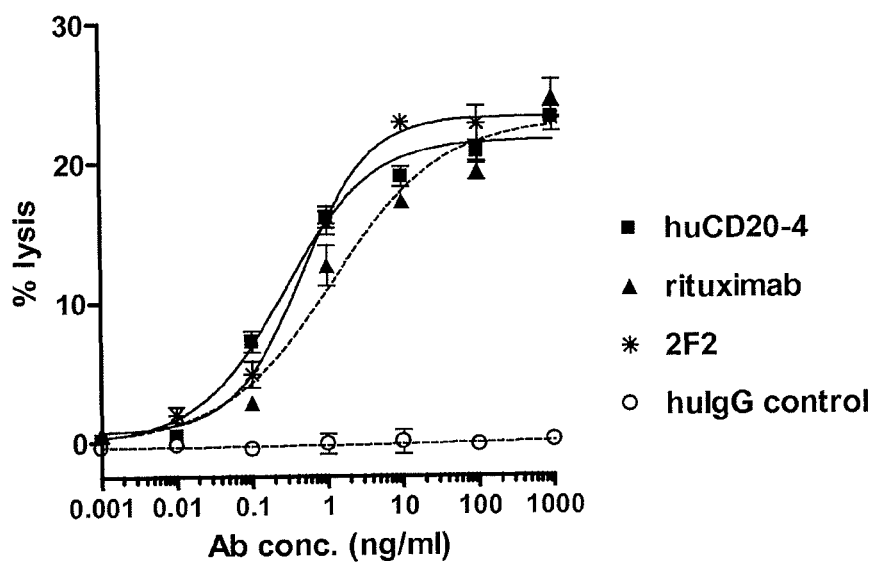

Fig. 15
A
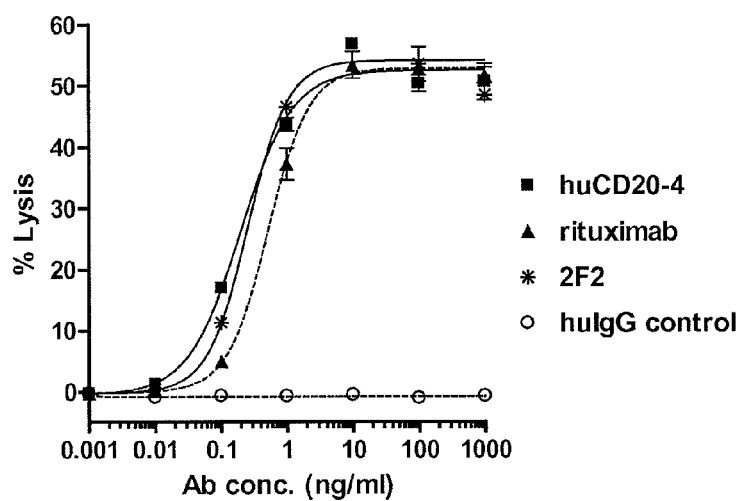
B
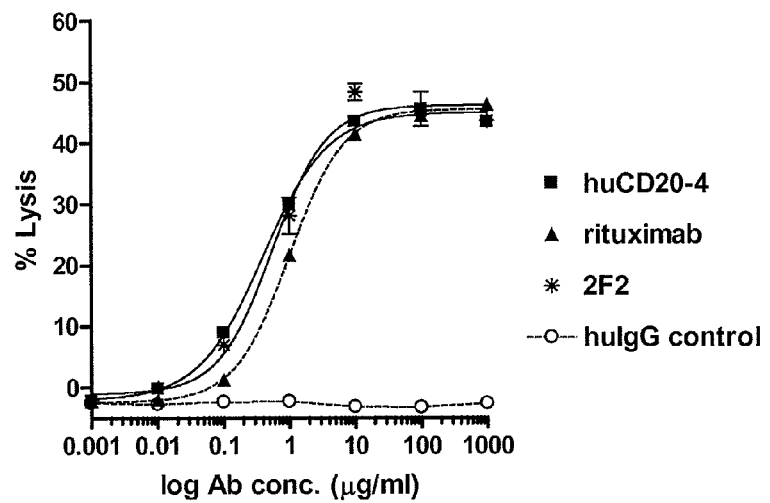

Fig. 16
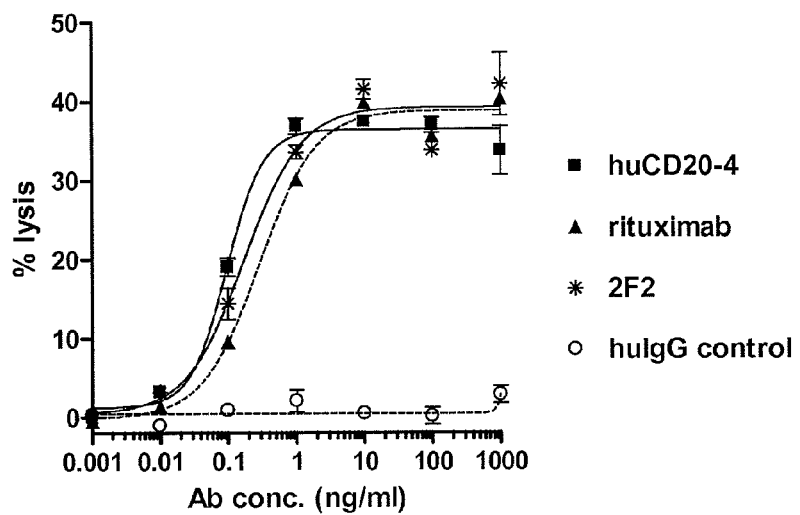
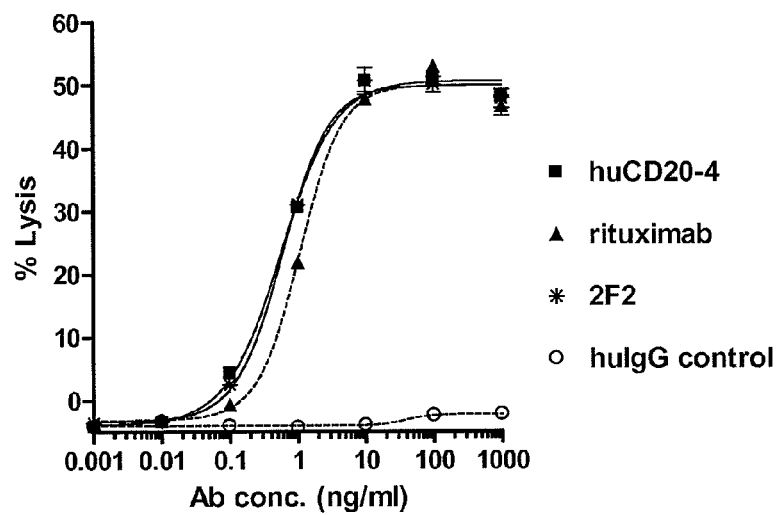

Fig. 19
A
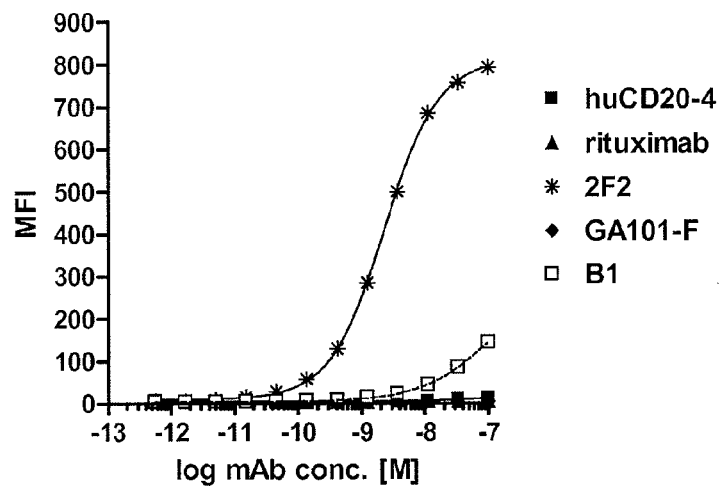
B
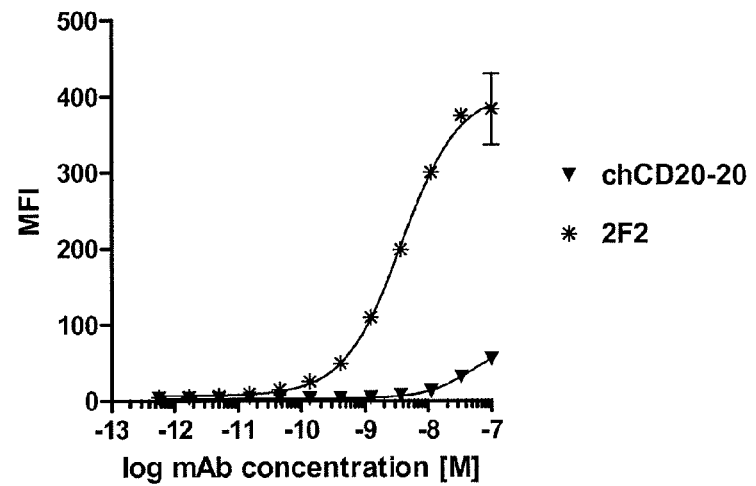

Fig. 21
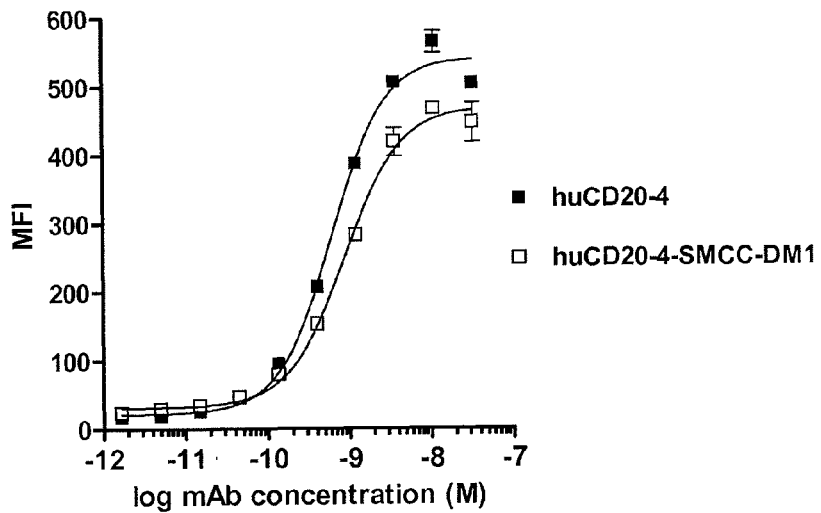
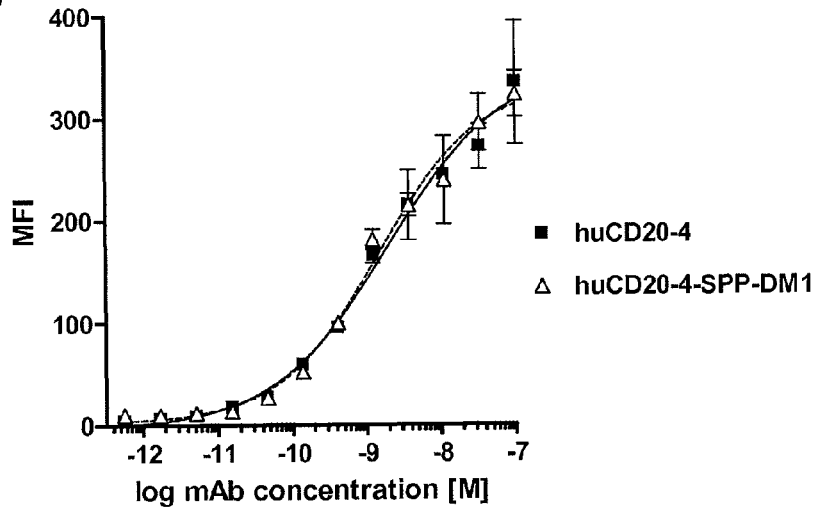

Fig. 22
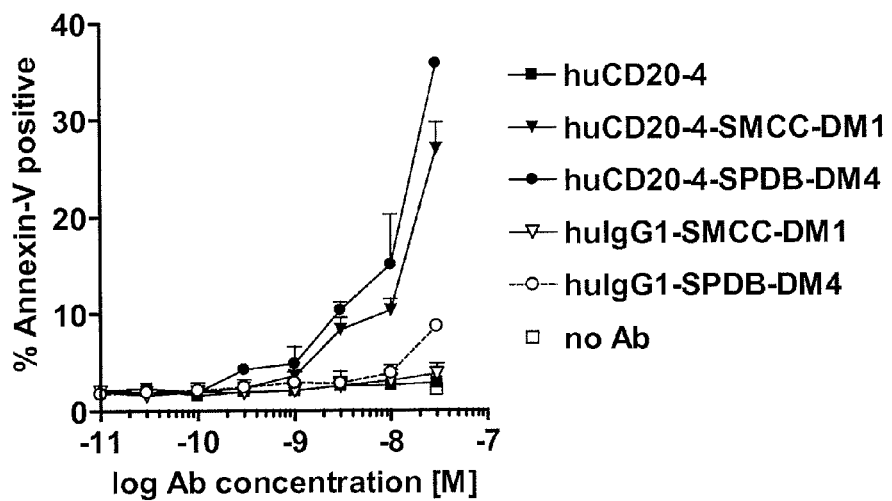
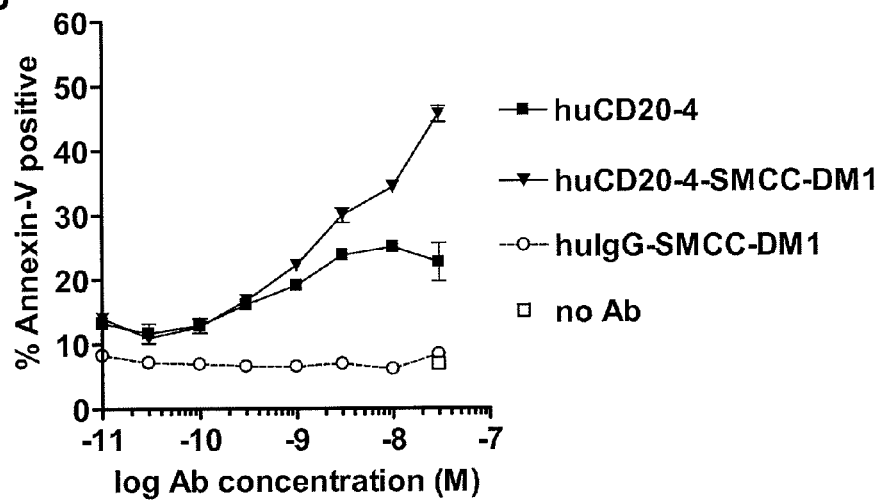

Fig. 23
A
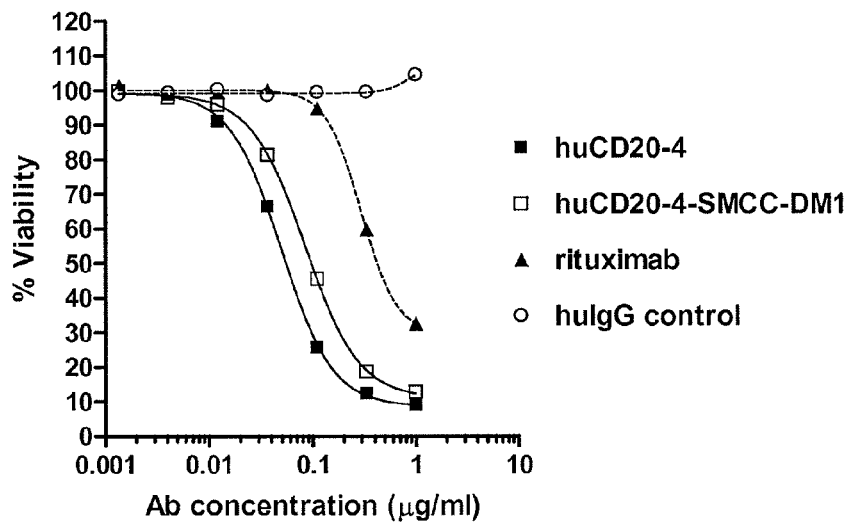
B
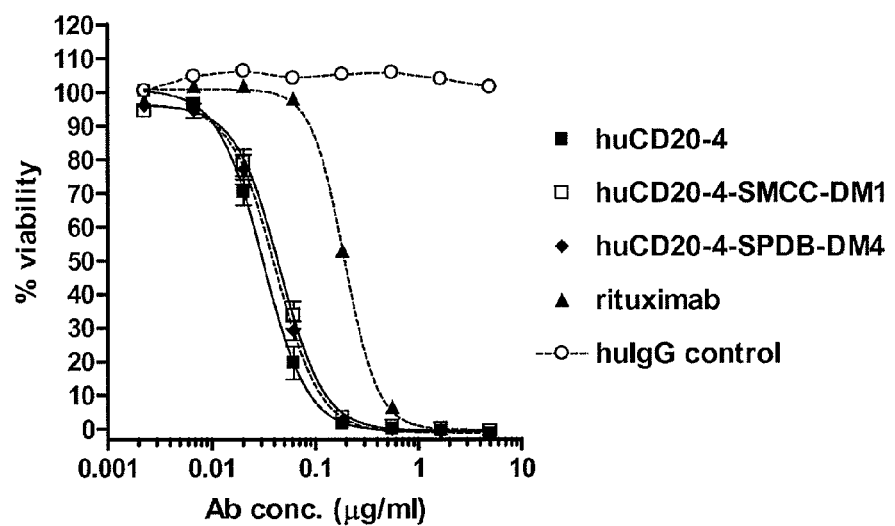

Fig. 24
A
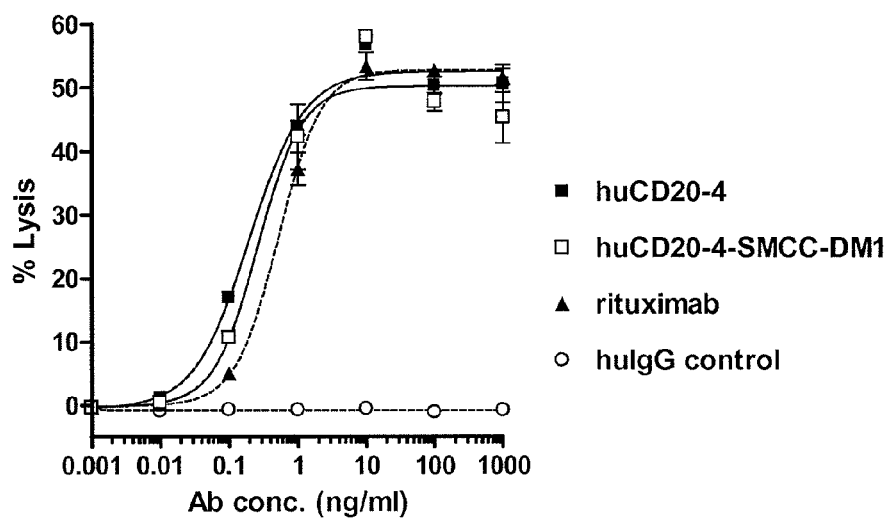
B
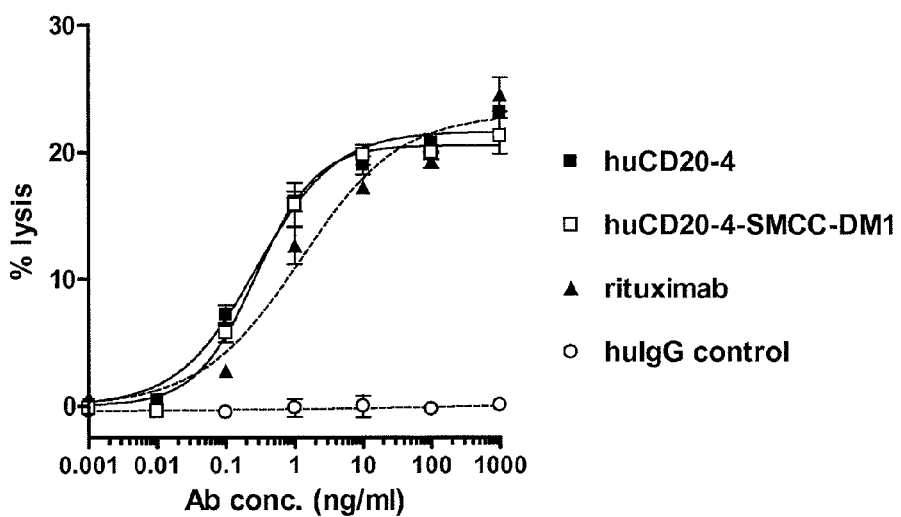

Fig. 25
A
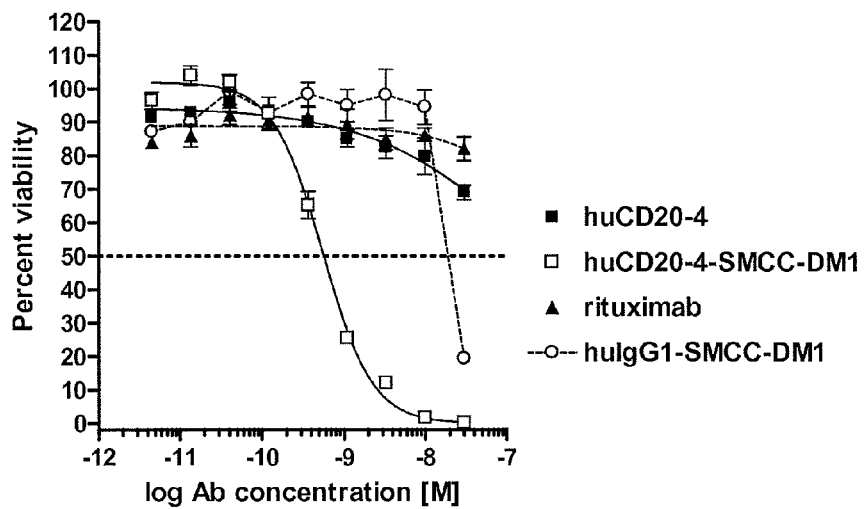
B
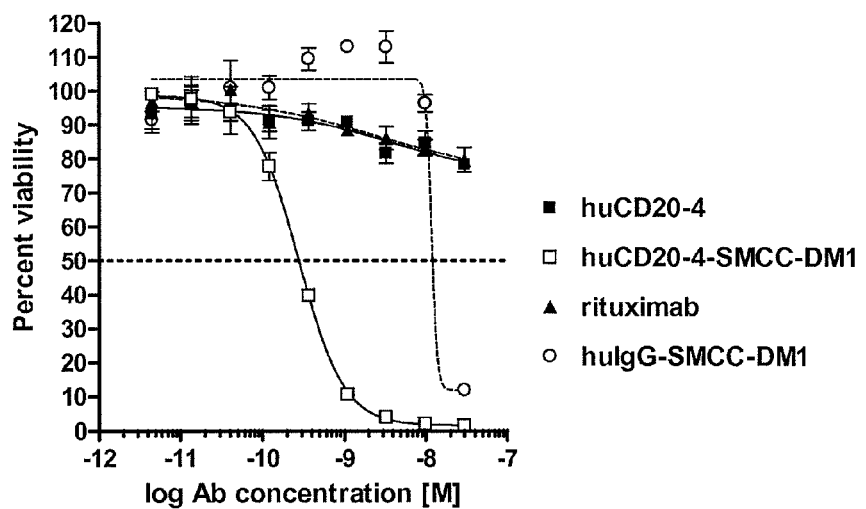

Fig. 26
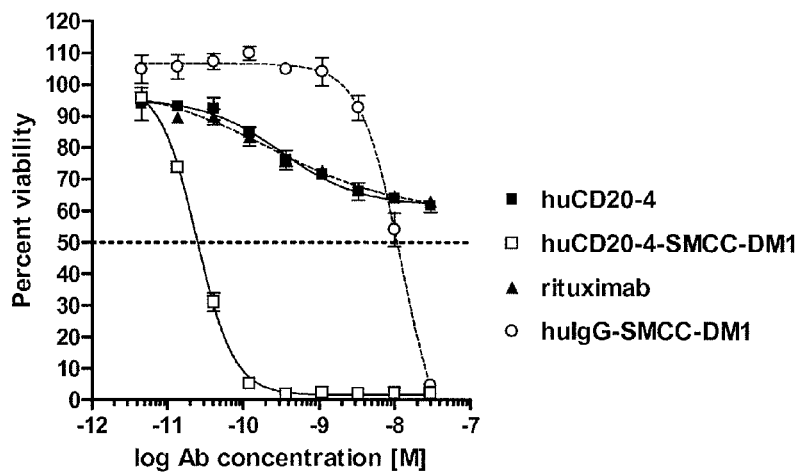
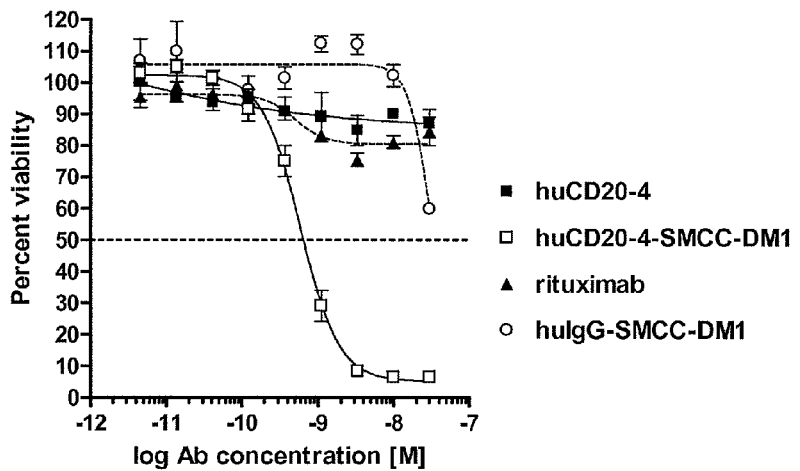

Fig. 27
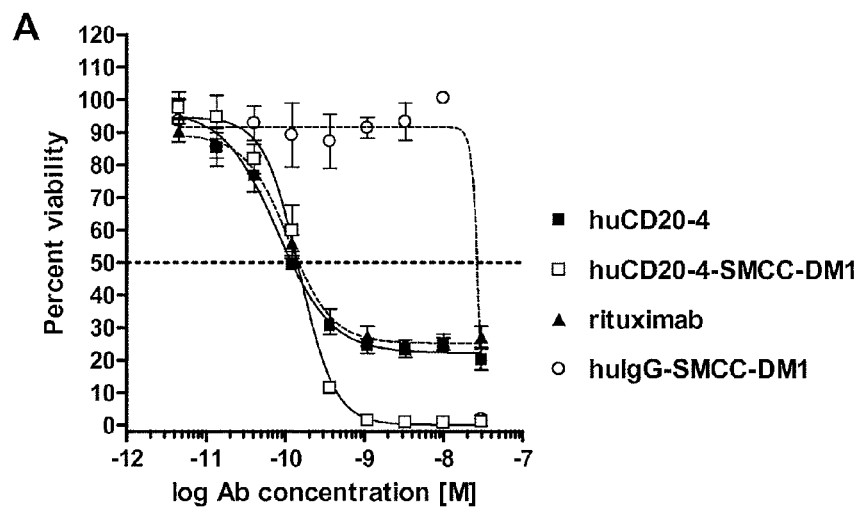
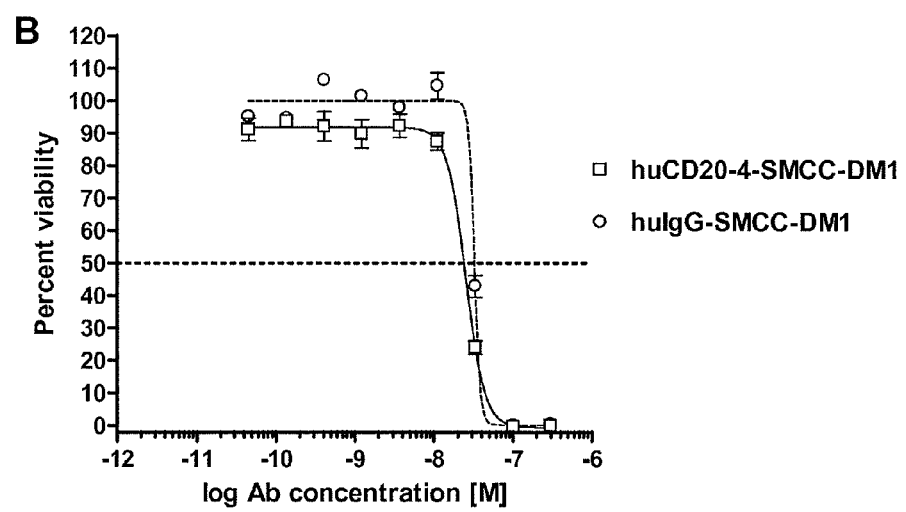

Fig. 28
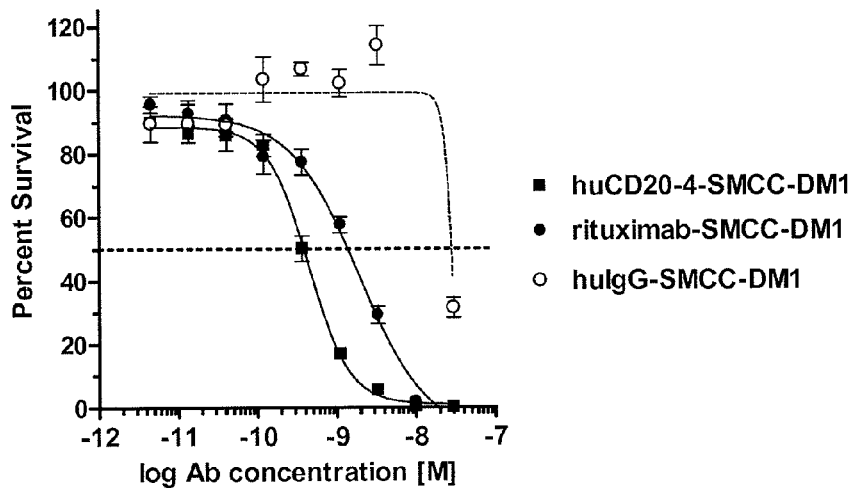
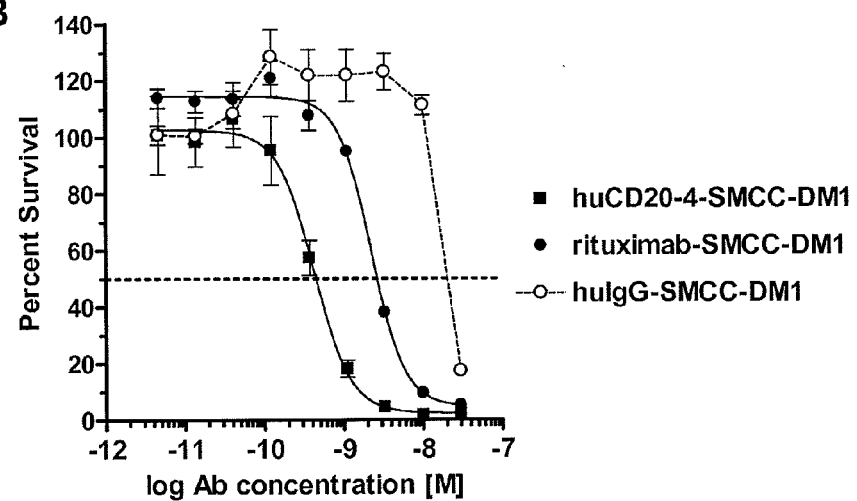

Fig. 29
A
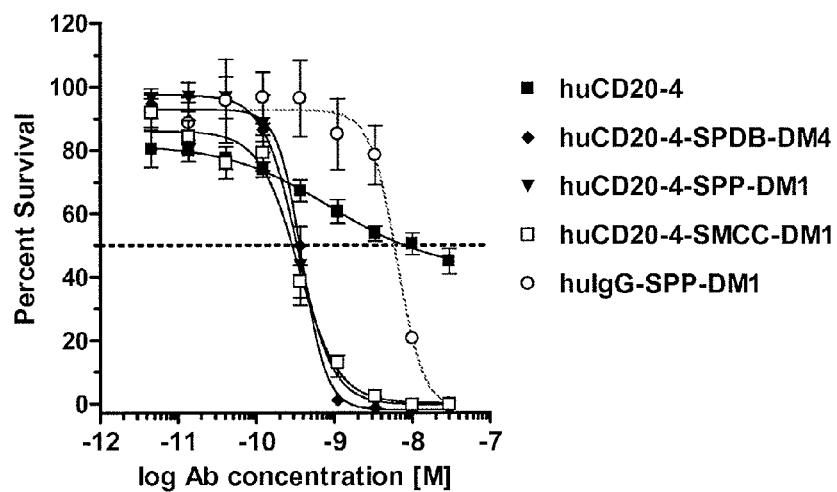
- huCD20-4
- huCD20-4-SPDB-DM4
- huCD20-4-SPP-DM1
- huCD20-4-SMCC-DM1
- huIgG-SPP-DM1
B
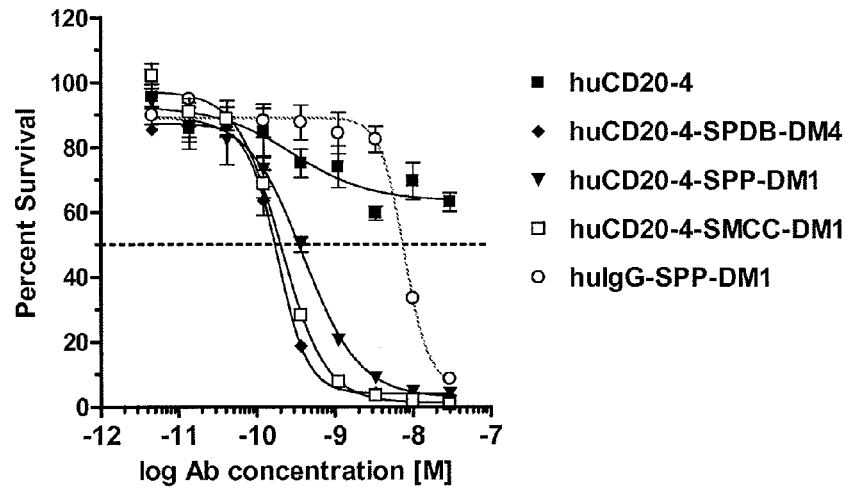
- huCD20-4
- huCD20-4-SPDB-DM4
- huCD20-4-SPP-DM1
- huCD20-4-SMCC-DM1
- huIgG-SPP-DM1

CD20 ANTIBODIES AND USES THEREOF

REFERENCE TO SEQUENCE LISTING SUBMITTED ELECTRONICALLY VIA EFS-WEB

The content of the electronically submitted Substitute Sequence Listing (Name: SubstituteSequenceListing.ascii.txt; Size: 38,446 bytes; and Date of Creation: Dec. 7, 2012) is herein incorporated by reference in its entirety.

BACKGROUND OF THE INVENTION

CD20 and CD20 isoforms ("CD20") are generally appreciated to be transmembrane proteins of the tetra-spanin family that are expressed on the surface of B-cells (Valentine et al., J. Biol. Chem., 264(19):11282-11287 (1989); Einfeld et al., EMBO J., 7(3):711-717 (1988)). CD20 is expressed by the vast majority of peripheral blood B-cells as well as B cells from various lymphoid tissues. CD20 expression generally persists from the early pre-B cell stage of development until the plasma cell differentiation stage of development (Tedder et al., J. Immunol., 135(2):973-979 (1985)). CD20 is not generally expressed by hematopoietic stem cells, pro-B cells, differentiated plasma cells or non-lymphoid tissues, or the like. In addition to expression in normal B-cells, CD20 is expressed in B-cell derived malignancies such as non-Hodgkin's lymphoma (NHL) and B-cell chronic lymphocytic leukemia (CLL) (Anderson et al., Blood, 63(6): 1424-1433 (1984)) and B cells involved in immune disorders, autoimmune disease and inflammatory diseases.

Although the exact function of CD20 is unclear, CD20 is implicated in calcium mobilization and may function as a calcium channel (Tedder et al., J. Cell Biochem., 14D:195 (1990)). CD20 might be involved in the activation and differentiation of B-cells (Tedder et al., Eur. J. Immunol., 16(8): 881-887 (1986)).

The expression profile of CD20 and knowledge of existing CD20 antibodies has made CD20 a target of interest for antibody therapies. It is known in the art that, generally, antibodies for CD20 are classified based on their functional properties. For example, Type I antibodies are characterized by their ability to distribute CD20 into lipid raft compartments and, when chimerized, can mediate complement-dependent cytotoxicity ("CDC") (Deans J P, J Biol Chem 1998; 273: 344-8; Cragg M S, Blood 2003; 101:1045-52; and Cragg M S Blood. 2004; 103:2738-2743). Type I antibodies typically do not have effective pro-apoptotic activity on their own, unless the antibodies are cross-linked. Examples of Type I antibodies requiring cross-linking are rituximab and 2F2 (Cragg et al., Blood, 101(3):1045-1052 (2003); and Teeling et al., Blood, 104(6):1793-1800 (2004)). In contrast, Type II antibodies are unable to distribute CD20 into lipid rafts. If chimerized, Type II antibodies have limited CDC activity. Type II antibodies are characterized by their strong pro-apoptotic activity. B1 and GA101 are examples of Type II antibodies (Cragg M S, Blood 2003; 101:1045-52; Cragg M S Blood. 2004; 103:2738-2743); and Umana et al., Blood, 108: 72a, Abstract 229 (2006)). Type I and Type II antibodies can potentially mediate antibody-dependent cell-mediated cytotoxicity (ADCC).

Given the expression of CD20 by unwanted cells, such as in B-cell lymphomas, this antigen is useful for targeting harmful CD20 positive cells (e.g., lymphoma cells). In essence, such targeting is generalized as follows: antibodies specific to CD20 surface antigen of B cells are administered to a patient. These anti-CD20 antibodies specifically bind to the CD20 antigen of both normal and unwanted (e.g., malignant and immunoreactive) B cells; the antibody bound to the CD20 surface antigen may lead to the destruction and depletion of the B cells.

Additionally, chemical agents or radioactive labels having the potential to destroy CD20 expressing tumor cells can be conjugated to the anti-CD20 antibody such that the agent is specifically "delivered" to the neoplastic B cells. Irrespective of the approach, a primary goal is to destroy the unwanted cells; the specific approach can be determined by the particular anti-CD20 antibody that is utilized, and thus, the available approaches to targeting the CD20 antigen can vary considerably. The rituximab (RITUXAN®) antibody is a genetically engineered chimeric murine/human monoclonal antibody directed against CD20. Rituximab is the antibody called "C2B8" in U.S. Pat. No. 5,736,137 (Anderson et al.). Rituximab is currently approved for the treatment of relapsed or refractory follicular lymphoma (Leget et al., Curr. Opin. Oncol., 10:548-551 (1998)). Reports indicate that with weekly infusions, rituximab resulted in overall response rates of 48%. However, many patients do not respond to rituximab treatment and responding patients taking rituximab eventually relapse and often develop resistance to rituximab treatment. Relapse and resistance, for example, to currently available therapies necessitate discovery of new CD20 directed agents and therapies.

Because of the limitations of available antibodies, there are next generation antibody therapeutics for CD20 in development which aim to improve specific functional aspects of rituximab. For example, afutuzumab or GA 101 has been reported to have marginal improvement of pro-apoptotic activity over rituximab in vitro, but GA101 fails to demonstrate CDC activity (Umana P, Blood 2006; 108:72a, Abstract 229 and WO 2005/044859). In addition, GA101 is a glycoengineered humanized antibody with improved ADCC activity (Umana et al., Blood 2006; 108:72a, Abstract 229; and WO 2005/044859). In the case of ofatumumab, a human monoclonal 2F2 antibody, improved in vitro CDC activity has been reported, especially in cells having lower CD20 antigen density (Teeling et al., J. Immunol., 177(1):362-371 (2006)). It has been proposed that this improved CDC activity results from the ability of 2F2 and related antibodies to recognize a novel epitope on CD20. Although ofatumumab with improved CDC activity is effective and was approved for treating patients with refractory chronic lymphocytic leukemia, ofatumumab was not active on rituximab-refractory NHL patients. American Society of Hematology Meeting 2009, Abstract #935.

Other compounds, in varying stages of development, have been reported to marginally improve certain intrinsic properties of rituximab or other known anti-CD20 antibodies. However, until now, no novel molecule having unique physical and functional features addressing the problems known in the art was available.

Rituximab has also been approved in the United States in combination with MTX to reduce signs and symptoms in adult patients with moderately- to severely-active RA who have had an inadequate response to at least one TNF antagonist. Many studies address the use of rituximab in a variety of non-malignant autoimmune or inflammatory disorders, including RA, in which B cells and autoantibodies appear to play a role in disease pathophysiology. Edwards et al., Biochem Soc. Trans. 30:824-828 (2002). Targeting of CD20 using anti-CD20 antibody has been reported to potentially relieve signs and symptoms of, for example, RA (Leandro et al., Ann. Rheum. Dis. 61:883-888 (2002); Edwards et al., Arthritis Rheum., 46 (Suppl. 9): S46 (2002); Stahl et al., Ann. Rheum. Dis., 62 (Suppl. 1): OP004 (2003); Emery et al., Arthritis Rheum. 48(9): 5439 (2003)), lupus (Eisenberg, Arthritis. Res. Ther. 5:157-159 (2003); Leandro et al. Arthritis Rheum. 46: 2673-2677 (2002); Gorman et al., Lupus, 13: 312-316 (2004)), immune thrombocytopenic purpura (D'Arena et al., Leuk. Lymphoma 44:561-562 (2003); Stasi et al., Blood, 98: 952-957 (2001); Saleh et al., Semin. Oncol., 27 (Supp 12):99-103 (2000); Zaja et al., Haematologica, 87:189-195 (2002); Ratanatharathorn et al., Ann. Int. Med., 133:275-279 (2000)), pure red cell aplasia (Auner et al., Br. J. Haematol., 116:725-728 (2002)); autoimmune anemia (Zaja et al., supra (erratum appears in Haematologica 87:336 (2002)), cold agglutinin disease (Layios et al., Leukemia, 15:187-8 (2001); Berentsen et al., Blood, 103: 2925-2928 (2004); Berentsen et al., Br. J. Haematol., 115:79-83 (2001); Bauduer, Br. J. Haematol., 112:1083-1090 (2001); Zaja et al., Br. J. Haematol., 115:232-233 (2001)), type B syndrome of severe insulin resistance (Coll et al., N. Engl. J. Med., 350: 310-311 (2004), mixed cryoglobulinermia (DeVita et al., Arthritis Rheum. 46 Suppl. 9:S206/S469 (2002)), myasthenia gravis (Zaja et al., Neurology, 55:1062-1063 (2000); Wylam et al., J. Pediatr., 143:674-677 (2003)), Wegener's granulomatosis (Specks et al., Arthritis & Rheumatism 44:2836-2840 (2001)), refractory pemphigus vulgaris (Dupuy et al., Arch Dermatol., 140:91-96 (2004)), dermatomyositis (Levine, Arthritis Rheum., 46 (Suppl. 9):S1299 (2002)), Sjogren's syndrome (Somer et al., Arthritis & Rheumatism, 49:394-398 (2003)), active type-II mixed cryoglobulinemia (Zaja et al., Blood, 101:3827-3834 (2003)), pemphigus vulgaris (Dupay et al., Arch. Dermatol., 140:91-95 (2004)), autoimmune neuropathy (Pestronk et al., J. Neurol. Neurosurg. Psychiatry 74:485-489 (2003)), paraneoplastic opsoclonus-myoclonus syndrome (Pranzatelli et al. Neurology 60 (Suppl. 1) PO5.128:A395 (2003)), and relapsing-remitting multiple sclerosis (RRMS). Cross et al. (abstract) "Preliminary Results from a Phase II Trial of Rituximab in MS" Eighth Annual Meeting of the Americas Committees for Research and Treatment in Multiple Sclerosis, 20-21 (2003).

Patents and patent publications concerning CD20 antibodies, CD20-binding molecules, and self-antigen vaccines include U.S. Pat. Nos. 5,776,456, 5,736,137, 5,843,439, 6,399,061, and 6,682,734, as well as US 2002/0197255, US 2003/0021781, US 2003/0082172, US 2003/0095963, US 2003/0147885, US 2005/0186205, and WO 1994/11526 (Anderson et al.); U.S. Pat. No. 6,455,043, US 2003/0026804, US 2003/0206903, and WO 2000/09160 (Grillo-Lopez, A.); WO 2000/27428 (Grillo-Lopez and White); US 2004/0213784 and WO 2000/27433 (Grillo-Lopez and Leonard); WO 2000/44788 (Braslawsky et al.); WO 2001/10462 (Rastetter, W.); WO 2001/10461 (Rastetter and White); WO 2001/10460 (White and Grillo-Lopez); US 2001/0018041, US 2003/0180292, US 2002/0028178, WO 2001/34194, and WO 2002/22212 (Hanna and Hariharan); US 2002/0006404 and WO 2002/04021 (Hanna and Hariharan); US 2002/0012665, US 2005/0180975, WO 2001/74388, and U.S. Pat. No. 6,896,885B5 (Hanna, N.); US 2002/0058029 (Hanna, N.); US 2003/0103971 (Hariharan and Hanna); US 2005/0123540 (Hanna et al.); US 2002/0009444 and WO 2001/80884 (Grillo-Lopez, A.); WO 2001/97858; US 2005/0112060, US 2002/0039557, and U.S. Pat. No. 6,846,476 (White, C.); US 2002/0128448 and WO 2002/34790 (Reff, M.); WO 2002/060955 (Braslawsky et al.); WO 2002/096948 (Braslawsky et al.); WO 2002/079255 (Reff and Davies); U.S. Pat. Nos. 6,171,586 and 6,991,790, and WO 1998/56418 (Lam et al.); WO 2004/0191256 and WO 1998/58964 (Raju, S.); WO 1999/22764 (Raju, S.); WO 1999/51642, U.S. Pat. No. 6,194,551, U.S. Pat. No. 6,242,195, U.S. Pat. No. 6,528,624 and U.S. Pat. No. 6,538,124 (Idusogie et al.); U.S. Pat. No. 7,122,637, US 2005/0118174, US 2005/0233382, US 2006/0194291, US 2006/0194290, US 2006/0194957, and WO 2000/42072 (Presta, L.); WO 2000/67796 (Curd et al.); WO 2001/03734 (Grillo-Lopez et al.); US 2002/0004587, US 2006/0025576, and WO 2001/77342 (Miller and Presta); US 2002/0197256 and WO 2002/078766 (Grewal, I.); US 2003/0157108 and WO 2003/035835 (Presta, L.); U.S. Pat. Nos. 5,648,267, 5,733,779, 6,017,733, and 6,159,730, and WO 1994/11523 (Reff et al.); U.S. Pat. Nos. 6,565,827, 6,090,365, 6,287,537, 6,015,542, 5,843,398, and 5,595,721 (Kaminski et al.); U.S. Pat. Nos. 5,500,362, 5,677,180, 5,721,108, 6,120,767, 6,652,852, and 6,893,625 as well as WO 1988/04936 (Robinson et al.); U.S. Pat. No. 6,410,391 (Zelsacher); U.S. Pat. No. 6,224,866 and WO00/20864 (Barbera-Guillem, E.); WO 2001/13945 (Barbera-Guillem, E.); WO 2000/67795 (Goldenberg); U.S. Pat. No. 7,074,403 (Goldenberg and Hansen); U.S. Pat. No. 7,151,164 (Hansen et al.); US 2003/0133930; WO 2000/74718 and US 2005/0191300A1 (Goldenberg and Hansen); US 2003/0219433 and WO 2003/68821 (Hansen et al.); WO 2004/058298 (Goldenberg and Hansen); WO 2000/76542 (Golay et al.); WO 2001/72333 (Wolin and Rosenblatt); U.S. Pat. No. 6,368,596 (Ghetie et al.); U.S. Pat. No. 6,306,393 and US 2002/0041847 (Goldenberg, D.); US 2003/0026801 (Weiner and Hartmann); WO 2002/102312 (Engleman, E.); US 2003/0068664 (Albitar et al.); WO 2003/002607 (Leung, S.); WO 2003/049694, US 2002/0009427, and US 2003/0185796 (Wolin et al.); WO 2003/061694 (Sing and Siegall); US 2003/0219818 (Bohen et al.); US 2003/0219433 and WO 2003/068821 (Hansen et al.); US 2003/0219818 (Bohen et al.); US 2002/0136719 (Shenoy et al.); WO 2004/032828 and US 2005/0180972 (Wahl et al.); and WO 2002/56910 (Hayden-Ledbetter). See also U.S. Pat. No. 5,849,898 and EP 330,191 (Seed et al.); EP332,865A2 (Meyer and Weiss); U.S. Pat. No. 4,861,579 (Meyer et al.); US 2001/0056066 (Bugelski et al.); WO 1995/03770 (Bhat et al.); US 2003/0219433 A1 (Hansen et al.); WO 2004/035607 and US 2004/167319 (Teeling et al.); WO 2005/103081 (Teeling et al.); US 2006/0034835, US 2006/0024300, and WO 2004/056312 (Lowman et al.); US 2004/0093621 (Shitara et al.); WO 2004/103404 (Watkins et al.); WO 2005/000901 (Tedder et al.); US 2005/0025764 (Watkins et al.); US 2006/0251652 (Watkins et al.); WO 2005/016969 (Carr et al.); US 2005/0069545 (Carr et al.); WO 2005/014618 (Chang et al.); US 2005/0079174 (Barbera-Guillem and Nelson); US 2005/0106108 (Leung and Hansen); US 2005/0123546 (Umana et al.); US 2004/0072290 (Umana et al.); US 2003/0175884 (Umana et al.); and WO 2005/044859 (Umana et al.); WO 2005/070963 (Allan et al.); US 2005/0186216 (Ledbetter and Hayden-Ledbetter); US 2005/0202534 (Hayden-Ledbetter and Ledbetter); US 2005/136049 (Ledbetter et al.); US 2003/118592 (Ledbetter et al.); US 2003/133939 (Ledbetter and Hayden-Ledbetter); US 2005/0202012 (Ledbetter and Hayden-Ledbetter); US 2005/0175614 (Ledbetter and Hayden-Ledbetter); US 2005/0180970 (Ledbetter and Hayden-Ledbetter); US 2005/0202028 (Hayden-Ledbetter and Ledbetter); US 2005/0202023 (Hayden-Ledbetter and Ledbetter); WO 2005/017148 (Ledbetter et al.); WO 2005/037989 (Ledbetter et al.); U.S. Pat. No. 6,183,744 (Goldenberg); U.S. Pat. No. 6,897,044 (Braslawski et al.); WO 2006/005477 (Krause et al.); US 2006/0029543 (Krause et al.); US 2006/0018900 (McLCCormick et al.); US 2006/0051349 (Goldenberg and Hansen); WO 2006/042240 (Iyer and Dunussi-Joannopoulos); US 2006/0121032 (Dahiyat et al.); WO 2006/064121 (Teillaud et al.); US 2006/0153838 (Watkins); CN 1718587 (Chen et al.); WO 2006/084264 (Adams et al.); US 2006/0188495 (Barron et al.); US 2004/0202658 and WO 2004/

091657 (Benynes, K.); US 2005/0095243, US 2005/ 0163775, WO 2005/00351, and WO 2006/068867 (Chan, A.); US 2006/0135430 and WO 2005/005462 (Chan et al.); US 2005/0032130 and WO 2005/017529 (Beresini et al.); US 2005/0053602 and WO 2005/023302 (Brunetta, P.); US 2006/0179501 and WO 2004/060052 (Chan et al.); WO 2004/ 060053 (Chan et al.); US 2005/0186206 and WO 2005/ 060999 (Brunetta, P.); US 2005/0191297 and WO 2005/ 061542 (Brunetta, P.); US 2006/0002930 and WO 2005/ 115453 (Brunetta et al.); US 2006/0099662 and WO 2005/ 108989 (Chuntharapai et al.); CN 1420129A (Zhongxin Guojian Pharmaceutical); US 2005/0276803 and WO 2005/ 113003 (Chan et al.); US 2005/0271658 and WO 2005/ 117972 (Brunetta et al.); US 2005/0255527 and WO 2005/ 11428 (Yang, J.); US 2006/0024295 and WO 2005/120437 (Brunetta, P.); US 2006/0051345 and WO 2005/117978 (Frohna, P.); US 2006/0062787 and WO 2006/012508 (Hitraya, E.); US 2006/0067930 and WO 2006/31370 (Lowman et al.); WO 2006/29224 (Ashkenazi, A.); US 2006/0110387 and WO 2006/41680 (Brunetta, P.); US 2006/0134111 and WO 2006/066086 (Agarwal, S.); WO 2006/069403 (Ernst and Yansura); US 2006/0188495 and WO 2006/076651 (Dummer, W.); WO 2006/084264 (Lowman, H.); WO 2006/ 093923 (Quan and Sewell); WO 2006/106959 (Numazaki et al.); WO 2006/126069 (Morawala); WO 2006/130458 (Gazit-Bornstein et al.); US 2006/0275284 (Hanna, G.); US 2007/0014785 (Golay et al.); US 2007/0014720 (Gazit-Bornstein et al.); and US 2007/0020259 (Hansen et al.); US 2007/ 0020265 (Goldenberg and Hansen); US 2007/0014797 (Hitraya); US 2007/0224189 (Lazar et al.); and WO 2008/ 003319 (Parren and Baadsgaard).

Some scientific publications concerning treatment with anti-CD20 antibodies include: Perotta and Abuel, "Response of chronic relapsing ITP of 10 years duration to rituximab" Abstract #3360 Blood, 10(1)(part 1-2):88B (1998); Perotta et al., "Rituxan in the treatment of chronic idiopathic thrombocytopaenic purpura (ITP)", Blood, 94:49 (abstract) (1999); Matthews, R., "Medical Heretics" New Scientist, (7 Apr., 2001); Leandro et al., "Clinical outcome in 22 patients with rheumatoid arthritis treated with B lymphocyte depletion" Ann Rheum Dis., supra; Leandro et al., "Lymphocyte depletion in rheumatoid arthritis: early evidence for safety, efficacy and dose response" Arthritis and Rheumatism, 44(9):S370 (2001); Leandro et al., "An open study of B lymphocyte depletion in systemic lupus erythematosus" Arthritis and Rheumatism, 46:2673-2677 (2002), wherein during a two-week period, each patient received two 500 mg infusions of antibodies of CD20, two 750 mg infusions of cyclophosphamide, and high-dose oral corticosteroids, and wherein two of the patients treated relapsed at seven and eight months, respectively, and have been retreated, although with different protocols; "Successful long-term treatment of systemic lupus erythematosus with rituximab maintenance therapy" Weide et al., Lupus, 12:779-782 (2003), wherein a patient was treated with anti-CD20 antibody (375 mg/m$^2$×4, repeated at weekly intervals), further antibody applications were made every five to six months, and then maintenance therapy was received with antibody at 375 mg/m$^2$ every three months, and a second patient with refractory SLE was treated with anti-CD20 antibody rituximab and was continuing to receive maintenance therapy every three months; Edwards and Cambridge, "Sustained improvement in rheumatoid arthritis following a protocol designed to deplete B lymphocytes" Rheumatology, 40:205-211 (2001); Cambridge et al., "B lymphocyte depletion in patients with rheumatoid arthritis: serial studies of immunological parameters" Arthritis Rheum., 46 (Suppl. 9): S1350 (2002); Cambridge et al., "Serologic changes following B lymphocyte depletion therapy for rheumatoid arthritis" Arthritis Rheum., 48:2146-2154 (2003); Edwards et al., "B-lymphocyte depletion therapy in rheumatoid arthritis and other autoimmune disorders" Biochem Soc. Trans., supra; Edwards et al., "Efficacy and safety of rituximab, a B-cell targeted chimeric monoclonal antibody: A randomized, placebo controlled trial in patients with rheumatoid arthritis," Arthritis and Rheumatism, 46(9):S197 (2002); Edwards et al., "Efficacy of B-cell-targeted therapy with rituximab in patients with rheumatoid arthritis" N Engl. J. Med., 350:2572-2582 (2004); Pavelka et al., Ann. Rheum. Dis., 63:(S1):289-290 (2004); Emery et al., Arthritis Rheum. 50 (S9):5659 (2004); Levine and Pestronk, "IgM antibody-related polyneuropathies: B-cell depletion chemotherapy using Rituximab" Neurology, 52:1701-1704 (1999); Uchida et al., "The innate mononuclear phagocyte network depletes B lymphocytes through Fc receptor-dependent mechanisms during anti-CD20 antibody immunotherapy" J. Exp. Med., 199:1659-1669 (2004); Gong et al., "Importance of cellular microenvironment and circulatory dynamics in B cell immunotherapy" J. Immunol., 174:817-826 (2005); Hamaguchi et al., "The peritoneal cavity provides a protective niche for B1 and conventional B lymphocytes during anti-CD20 immunotherapy in mice" J. Immunol., 174:4389-4399 (2005); Cragg et al. "The biology of CD20 and its potential as a target for mAb therapy" Curr. Dir. Autoimmun., 8:140-174 (2005); Eisenberg, "Mechanisms of autoimmunity" Immunol. Res., 27:203-218 (2003); DeVita et al., "Efficacy of selective B cell blockade in the treatment of rheumatoid arthritis" Arthritis & Rheum, 46:2029-2033 (2002); Higashida et al. "Treatment of DMARD-refractory rheumatoid arthritis with rituximab" Annual Scientific Meeting of the American College of Rheumatology (Abstract #LB11), New Orleans, La. (October, 2002); Tuscano, "Successful treatment of infliximab-refractory rheumatoid arthritis with rituximab" Annual Scientific Meeting of the American College of Rheumatology, New Orleans, La. (October, 2002), published as Tuscano, Arthritis Rheum. 46:3420 (2002); "Pathogenic roles of B cells in human autoimmunity; insights from the clinic" Martin and Chan, Immunity, 20:517-527 (2004); Silverman and Weisman, "Rituximab therapy and autoimmune disorders, prospects for anti-B cell therapy", Arthritis and Rheumatism, 48:1484-1492 (2003); Kazkaz and Isenberg, "Anti B cell therapy (rituximab) in the treatment of autoimmune diseases" Current Opinion in Pharmacology, 4:398-402 (2004); Virgolini and Vanda, "Rituximab in autoimmune diseases" Biomedicine & Pharmacotherapy, 58: 299-309 (2004); Klemmer et al., "Treatment of antibody mediated autoimmune disorders with an AntiCD20 monoclonal antibody Rituximab" Arthritis And Rheumatism, 48(9) (SEP):5624-5624 (2003); Kneitz et al., "Effective B cell depletion with rituximab in the treatment of autoimmune diseases" Immunobiology, 206:519-527 (2002); Arzoo et al., "Treatment of refractory antibody mediated autoimmune disorders with an anti-CD 20 monoclonal antibody (rituximab)" Annals of the Rheumatic Diseases, 61(10):922-924 (2002) Comment in Ann. Rheum. Dis. 61:863-866 (2002); "Future strategies in immunotherapy" by Lake and Dionne, in Burger's Medicinal Chemistry and Drug Discovery (John Wiley & Sons, Inc., 2003) (Chapter 2 "Antibody-Directed Immunotherapy"); Liang and Tedder, Wiley Encyclopedia of Molecular Medicine, Section: CD20 as an Immunotherapy Target (2002); Appendix 4A entitled "Monoclonal Antibodies to Human Cell Surface Antigens" by Stockinger et al., eds: Coligan et al., in Current Protocols in Immunology (John Wiley & Sons, Inc., 2003); Penichet and Morrison, "CD Antibodies/molecules: Definition; Antibody Engineering" in Wiley Encyclopedia of Molecular Medicine Section: Chimeric, Humanized and Human Antibodies (2002).

Further, see Looney, "B cells as a therapeutic target in autoimmune diseases other than rheumatoid arthritis" Rheumatology, 44 Suppl 2:ii13-ii17 (2005); Chambers and Isenberg, "Anti-B cell therapy (rituximab) in the treatment of autoimmune diseases" Lupus, 14(3):210-214 (2005); Looney et al., "B-cell depletion as a novel treatment for systemic lupus erythematosus: a phase I/II dose-escalating trial of rituximab" Arthritis Rheum., 50:2580-2589 (2004); Looney, "Treating human autoimmune disease by depleting B cells" Ann Rheum. Dis., 61:863-866 (2002); Edelbauer et al., "Rituximab in childhood systemic lupus erythematosus refractory to conventional immunosuppression Case report" Pediatr. Nephrol., 20(6): 811-813 (2005); D'Cruz and Hughes, "The treatment of lupus nephritis" BMJ, 330(7488):377-378 (2005); Looney, "B cell-targeted therapy in diseases other than rheumatoid arthritis" J. Rheumatol. Suppl., 73: 25-28-discussion 29-30 (2005); Sfikakis et al., "Remission of proliferative lupus nephritis following B cell depletion therapy is preceded by down-regulation of the T cell costimulatory molecule CD40 ligand: an open-label trial" Arthritis Rheum., 52(2):501-513 (2005); Rastetter et al., "Rituximab: expanding role in therapy for lymphomas and autoimmune diseases" Annu. Rev. Med., 55:477-503 (2004); Silverman, "Anti-CD20 therapy in systemic lupus erythematosus: a step closer to the clinic" Arthritis Rheum., 52(2):371-377 (2005), Erratum in: Arthritis Rheum. 52(4):1342 (2005); Ahn et al., "Long-term remission from life-threatening hypercoagulable state associated with lupus anticoagulant (LA) following rituximab therapy" Am. J. Hematol., 78(2): 127-129 (2005); Tahir et al., "Humanized anti-CD20 monoclonal antibody in the treatment of severe resistant systemic lupus erythematosus in a patient with antibodies against rituximab" Rheumatology, 44(4):561-562 (2005), Epub 2005, Jan. 11; Looney et al., "Treatment of SLE with anti CD20 monoclonal antibody" Curr. Dir. Autoimmun., 8:193-205 (2005); Cragg et al., "The biology of CD20 and its potential as a target for mAb therapy" Curr. Dir. Autoimmun., 8:140-174 (2005); Gottenberg et al., "Tolerance and short term efficacy of rituximab in 43 patients with systemic autoimmune diseases" Ann. Rheum. Dis., 64(6):913-920 (2005) Epub 2004 Nov. 18; Tokunaga et al., "Down-regulation of CD40 and CD80 on B cells in patients with life-threatening systemic lupus erythematosus after successful treatment with rituximab" Rheumatology 44(2): 176-182 (2005), Epub 2004 Oct. 19. See also Leandro et al., "B cell repopulation occurs mainly from naive B cells in patient with rheumatoid arthritis and systemic lupus erythematosus" Arthritis Rheum., 48 (Suppl 9): S1160 (2003).

Also see, Specks et al. "Response of Wegener's granulomatosis to anti-CD20 chimeric monoclonal antibody therapy" Arthritis & Rheumatism, 44(12):2836-2840 (2001) which disclosed use of four infusions of 375 mg/m$^2$ of anti-CD20 antibody and high-dose glucocorticoids to treat Wegener's granulomatosis. The therapy was repeated after 11 months when the cANCA recurred, but therapy was without glucocorticoids. At eight months after the second course of anti-CD20 antibody, the patients' disease remained in complete remission. In another study remission of severe ANCA-associated vasculitis was reported, when anti-CD20 antibody was used in a dose of 375 mg/m$^2$×4 along with oral prednisone at 1 mg/kg/day, which was reduced to 40 mg/day by week four, and to total discontinuation over the following 16 weeks. Four patients were re-treated with anti-CD20 antibody alone for recurring/rising ANCA titers. Keogh et al., Kidney Blood Press. Res., 26:293 (2003) reported that eleven patients with refractory ANCA-associated vasculitis went into remission upon treatment with four weekly 375 mg/m$^2$ doses of anti-CD20 antibody and high-dose glucocorticoids.

Patients with refractory ANCA-associated vasculitis were administered anti-CD20 antibody along with immunosuppressive medicaments such as intravenous cyclophosphamide, mycophenolate mofetil, azathioprine, or leflunomide. Eriksson, "Short-term outcome and safety in 5 patients with ANCA-positive vasculitis treated with rituximab" Kidney and Blood Pressure Research, 26:294 (2003) (wherein five patients with ANCA-associated vasculitis were treated with anti-CD20 antibody 375 mg/m$^2$ once a week for four weeks); Jayne et al., "B-cell depletion with rituximab for refractory vasculitis" Kidney and Blood Pressure Research, 26:294-295 (2003) (six patients with refractory vasculitis receiving four weekly infusions of anti-CD20 antibody at 375 mg/m$^2$ with cyclophosphamide along with background immunosuppression and prednisolone experienced changes in vasculitic activity). A further report of using anti-CD20 antibody along with intravenous cyclophosphamide at 375 mg/m$^2$ per dose in four doses for administering to patients with refractory systemic vasculitis is provided in Smith and Jayne, "A prospective, open label trial of B-cell depletion with rituximab in refractory systemic vasculitis" poster 998 (11th International Vasculitis and ANCA workshop), American Society of Nephrology, J. Am. Soc. Nephrol., 14:755A (2003). See also Eriksson, J. Internal Med., 257:540-548 (2005) regarding nine patients with ANCA-positive vasculitis who were treated with two or four weekly doses of 500 mg of anti-CD20 antibody; and Keogh et al., Arthritis and Rheumatism, 52:262-268 (2005), who reported that in 11 patients with refractory ANCA-associated vasculitis, treatment or re-treatment with four weekly 375 mg/m$^2$ doses of anti-CD20 antibody reportedly induced remission by B-lymphocyte depletion.

As to the activity of a humanized anti-CD20 antibody, see, for example, Vugmeyster et al., "Depletion of B cells by a humanized anti-CD20 antibody PRO70769 in *Macaca fascicularis*," J. Immunother., 28:212-219 (2005). For discussion of a human monoclonal antibody, see Baker et al., "Generation and characterization of LymphoStat-B, a human monoclonal antibody that antagonizes the bioactivities of B lymphocyte stimulator," Arthritis Rheum., 48:3253-3265 (2003). The MINT trial with anti-CD20 antibody was conducted involving treating aggressive non-Hodgkin's lymphoma in younger patients. Pfreundschuh et al., Lancet Oncology, 7(5):379-391 (2006).

Antibody-cytotoxic agent conjugates (or "ACC"), also called antibody-drug conjugates (ADC), are known to be a type of immunoconjugate that consists of cytotoxic agent covalently linked to an antibody through specialized chemical linker. The use of ACCs for the local delivery of cytotoxic or cytostatic agents, i.e., drugs to kill or inhibit tumor cells in the treatment of cancer (see Syrigos and Epenetos (1999) Anticancer Research 19:605-614; Niculescu-Duvaz and Springer (1997) Adv. Drg Del. Rev. 26:151-172; U.S. Pat. No. 4,975,278) allows targeted delivery of the drug moiety to tumors, and intracellular accumulation therein, where systemic administration of these unconjugated drug agents may result in unacceptable levels of toxicity to normal cells as well as the tumor cells sought to be eliminated (Baldwin et al., (1986) Lancet pp. (Mar. 15, 1986):603-05; Thorpe, (1985) "Antibody Carriers Of Cytotoxic Agents In Cancer Therapy: A Review," in Monoclonal Antibodies '84: Biological And Clinical Applications, A. Pinchera et al. (ed.s), pp. 475-506). Maximal efficacy with minimal toxicity is sought. Both polyclonal antibodies and monoclonal antibodies have sometimes been reported as being useful in this regard. (See Rowland et al., (1986) Cancer Immunol. Immunother., 21:183-87). Drugs that are known to be used in this regard include daunomycin, doxorubicin, methotrexate, and vindesine (Rowland et al., Cancer Immunol. Immunother. 21:183-87 (1986)). Toxins used in antibody-toxin conjugates include bacterial toxins such as diphtheria toxin, plant toxins such as ricin, small molecule toxins such as geldanamycin. Kerr et al (1997) Bioconjugate Chem. 8(6):781-784; Mandler et al (2000) Journal of the Nat. Cancer Inst. 92(19):1573-1581; Mandler et al (2000) Bioorganic & Med. Chem. Letters 10: 1025-1028; Mandler et al (2002) Bioconjugate Chem. 13:786-791), maytansinoids (EP 1391213; Liu et al., (1996) Proc. Natl. Acad. Sci. USA 93:8618-8623), and calicheamicin (Lode et al (1998) Cancer Res. 58:2928; Hinman et al (1993) Cancer Res. 53:3336-3342. Toxins may exert cytotoxic and/or cytostatic effects through diverse mechanisms including tubulin binding, DNA binding, or topoisomerase inhibition. Meyer, D. L. and Senter, P. D. "Recent Advances in Antibody Drug Conjugates for Cancer Therapy" in Annual Reports in Medicinal Chemistry, Vol 38 (2003) Chapter 23, 229-237. But many cytotoxic drugs tend to be inactive or less active when conjugated to large antibodies or protein receptor ligands.

Antibody-maytansinoid conjugates are composed of a monoclonal antibody that targets an antigen expressed on the surface of cells and a maytansine-derived compound (e.g., potent anti-mitotic drugs that inhibit microtubule polymerization) covalently linked to the antibody. Chari R V, Acc. Chem. Res. 2008 January; 41(1):98-107. With an appropriate linker, an antibody-maytansinoid conjugate (AMC) can be stable in vivo and significantly less toxic for cells that do not express the target antigen, thereby increasing the therapeutic index of the conjugate. Upon binding to the target antigen on the cell surface, an AMC is internalized, broken down in the lysosome, presumably by proteases, generating active maytansinoid metabolites which then bind and inhibit microtubules, thereby triggering cell cycle arrest and ultimately cell death, likely by apoptosis. Erickson et al, Cancer Res. 2006 Apr. 15; 66(8):4426-33. With maytansinoid conjugation, mAbs can improve targeted killing activity in vitro and in vivo.

Currently, numerous ACCs are being studied in clinical testing and pre-clinical development. Ideally, immunoconjugates could be easily administered to patients, similar to antibody therapies. One ACC in particular, called trastuzumab-SMCC-DM1 (T-DM1) has been reported to be effective in HER2-overexpressing metastatic breast cancer patients that have failed trastuzumab and chemotherapy, while also showing a favourable low toxicity profile. See Vogel C L, ASCO 2009 Abstract #1017.

Plasma clearance of antibody-maytansinoid conjugates, such as trastuzumab-SMCC-DM1 synthesized with the non-cleavable linker SMCC, is very slow vis-à-vis the clearance of antibody alone. US2005/0169933. This is in sharp contrast to plasma clearance of conjugates prepared with relatively labile disulfide bonds such as huC242-SPP-DM1. For example, the half-life for clearance of the SMCC conjugate is approximately 320 hours, while the half-life for the SPP conjugate is in the range of about 40 to 50 hours. However, the clearance of the antibody component for each type of conjugate is identical, suggesting that the difference in measured conjugate clearance rate could be due to the loss of maytansinoid from the antibody conjugate (i.e., in the case of the SPP-DM1 conjugate). The non-cleavable SMCC linkage has perhaps much more resistant maytansinoid-linker cleavage activities in vivo than the SPP-DM1 conjugate. Further, the decreased clearance rate for the SMCC linker conjugates, compared to SPP-DM1 conjugates, leads to a nearly 5-fold increase in overall maytansinoid exposure of the animal as measure by the area under the curve (AuC). This increased exposure could have a substantial impact on drug efficacy.

It has been reported that maytansinoid conjugates prepared with non-cleavable linkers such as SMCC show an unexpected increased tolerability in mice compared with conjugates prepared with cleavable disulfide linkers. US2005/0169933. For example, the tolerability of huC242-SMCC-DM1 and huC242-SPP-DM1 conjugates were compared in an acute toxicity test employing a single intravenous dose in CD-1 mice. The maximum tolerated dose (MTD) for the SMCC-DM1 conjugate was greater than the highest dose tested (150 mg/kg) while the MTD for the disulfide-linker conjugate SPP-DM1 was in the range of 45-90 mg/kg. At 150 mg/kg, all mice in the SMCC-DM1 treated group survived, while lethal toxicity was observed for all mice in the SPP-DM1 treated group by 96 hours post-treatment. Additionally, the non-reducible thioether-linked antibody-maytansinoid conjugate trastuzumab-SMCC-DM1 displayed 2 to 3-fold better tolerability in rats than the cleavable disulfide-linked trastuzumab-SPP-DM1. Lewis Phillips G D, Li G, Dugger D L, et al., Targeting HER2-positive breast cancer with trastuzumab-DM1, an antibody-cytotoxic drug conjugate, Cancer Res 2008; 68:9280-90. Therefore, it is possible that antibody drug conjugates prepared with non-cleavable linkers, such as SMCC, may exhibit favorable toxicity and pharmacokinetic parameters in preclinical models.

Although CD20 is known in the art, CD20 is not a favorable target for antibody-drug conjugation, since known anti-CD20 antibodies are very poorly internalized. Press O W, Cancer Res. 1989; 49:4906-12 and Vangeepuram N, Cancer 1997; 80 (Suppl.): 2425-30. Conjugates of CD20 antibodies have been studied previously but have not demonstrated significantly strong potency, especially when non-disulfide or acid stable linkers are used.

For example, it has been reported that non-cleavable SMCC-DM1 conjugates of an anti-CD20 antibody had the same efficacy as unconjugated antibody, while only a cleavable SPP-DM1 conjugate of the same antibody showed marginally improved efficacy in a Granta-519 xenograft model in SCID mice. Polson et al., *Cancer Res.*, 69(6):2358-2364 (2009). Similarly, it has been reported that calicheamicin conjugates of anti-CD20 antibody made with an acid-stable amide linker did not show improved in vivo efficacy over rituximab in a Ramos xenograft model in nude mice. Only calicheamicin conjugates of rituximab made with an acid-labile dimethyl hydrazide Ac-But linker showed improved in vivo efficacy in this study. DiJoseph et al., *Cancer Immunol. Immunotherapy*, 56(7):1107-1117 (2007). In a different study, it was reported that acid labile adriamycin conjugates of an anti-CD20 antibody were only moderately effective against a Daudi xenograft model. Acid stable adriamycin conjugates of the same antibody were shown to be completely ineffective. Braslawsky et al., *Cancer Immunol Immunotherapy*, 33:367-74 (1991). Rituximab conjugated to monomethyl auristatin E (MMAE) via an enzyme-cleavable peptide linkage as rituximab-vcMMAE reportedly showed in vitro and in vivo efficacy against Ramos lymphoma cells. Law et al., Clin. Cancer Res., 10(23):7842-7851 (2004); Erratum in: Clin. Cancer Res., 11(10):3969 (2005).

Another reported approach at improving the ability of monoclonal antibodies to be effective in the treatment of B-cell disorders has been to conjugate a radioactive label to the antibody such that the label is localized at the antigen site. The CD20-targeted radio-immunoconjugates Bexxar®

(131I-tositumomab) and Zevalin (90Y-ibritumomab tiuxetan) have been approved for relapsed or refractory non-Hodgkin's B-cell lymphoma patients, including patients refractory to rituximab. In a clinical setting, some rituximab-refractory patients responded to Bexxar®. Horning, J. Clin. Oncol. 2005; 23:712-9. When Zevalin and rituximab were compared in relapsed or refractory low-grade or follicular NHL, Zevalin treatment reportedly showed significantly better overall and complete response rates than rituximab treatment. Witzig, J Clin Oncol 2002; 20:2453-2463. While these clinical data suggest that anti-CD20 radio-immunoconjugates can be more effective than rituximab, they are not widely used because of additional toxicities and difficulty in administration associated with using radioactive compounds. Thus, there has been a need to develop effective anti-CD20 antibodies and conjugates that are easy to administer and have lower toxicity.

While even improved anti-CD20 antibody ofatumumab with better CDC activity than rituximab is effective and was approved for treating patients with refractory chronic lymphocytic leukemia, ofatumumab was not active on rituximab-refractory NHL patients. American Society of Hematology Meeting 2009, Abstract #935.

Thus, there continues to be a need for the development of improved and superior CD20 targeted therapeutic agents, including antibodies or antibody fragments that exhibit specificity, reduced toxicity, stability and enhanced physical and functional properties over known therapeutic agents. The instant invention addresses those needs.

SUMMARY OF THE INVENTION

Reference will now be made in detail to certain aspects of the invention, examples of which are illustrated in the accompanying structures and formulas. While the invention will be described in conjunction with the enumerated aspects, it will be understood that they are not intended to limit the invention to those aspects. On the contrary, the invention is intended to cover all alternatives, modifications, and equivalents that may be included within the scope of the present invention as defined by the claims. One skilled in the art will recognize many methods and materials similar or equivalent to those described herein, that can be used in the practice of the present invention.

In one aspect, the present invention is an anti-CD20 antibody and/or fragment thereof. In one aspect, the present invention is a cytolytic anti-CD20 antibody and/or fragment thereof. In one aspect of the invention, the anti-CD20 cytolytic antibody and fragments are useful in the treatment of medical conditions wherein B cells expressing CD20 influence the course of the condition. In one aspect, the targeted B cells are unwanted. In one aspect, the medical condition involves the activity of unwanted B cells. In one aspect, the medical condition is a B cell disease. Another aspect of the invention is an antibody or fragment thereof that specifically bind to CD20 antigen, wherein said antibody or fragment is capable of inducing antibody dependent cell mediated cytotoxicity (ADCC) and complement dependent cytotoxicity (CDC). In a preferred aspect, the medical condition is non-Hodgkin's lymphoma.

One aspect of the present invention is an antibody or fragment thereof that specifically bind to CD20, wherein said antibody or fragment is capable of inducing antibody dependent cell mediated cytotoxicity (ADCC) and complement dependent cytotoxicity (CDC), wherein the antibody or fragment is murine, non-human, humanized, chimeric, resurfaced or human. Another aspect of the invention is an antibody or fragment thereof that specifically bind to CD20, wherein the antibody or fragment is capable of inducing antibody dependent cell mediated cytotoxicity (ADCC) and complement dependent cytotoxicity (CDC), and wherein the antibody or fragment is monoclonal or single-chain.

One aspect of the present invention includes an antibody or fragment thereof that specifically bind to CD20, wherein said antibody or fragment is capable of inducing antibody dependent cell mediated cytotoxicity (ADCC) and complement dependent cytotoxicity (CDC), wherein the antibody is obtained from CHO or NS0 cells. In yet another aspect of the present invention, the antibody or fragments thereof specifically bind to at least one amino acid comprising the amino acid residues located between the third and fourth transmembrane domain of CD20.

In another aspect of the present invention, the antibody or fragments thereof specifically bind to at least one amino acid comprising the amino acids of SEQ ID NO:47, or a sequence corresponding to any one of GI 21330989, GenBank Protein ID 23110989, or the like. Another aspect of the present invention is an antibody or fragment, wherein the antibody or fragment is capable of inducing death of a cell expressing a CD20.

One aspect of the invention includes an anti-CD20 antibody or fragment wherein the antibody or fragment specifically bind to the CD20 in a Western blot, an ELISA or FACS assay.

In one aspect of the invention, the anti-CD20 antibody or fragment comprises a Fab, a Fab', a F(ab')$_2$, a Fd, a single chain Fv or scFv, a disulfide linked Fv, a V-NAR domain, a IgNar, an intrabody, an IgGDCH2, a minibiody, a F(ab')$_3$, a tetrabody, a triabody, a diabody, a (scFv)$_2$, single-domain antibody, DVD-Ig, Fcab, mAb$^2$, or a scFv-Fc. Another aspect of the present invention is an antibody or fragment and/or conjugates thereof comprising an immunoglobulin heavy chain constant domain. In one aspect of the invention, the antibody or fragment immunoglobulin heavy chain constant domain is selected from the group consisting of an IgG$_1$ constant domain, an IgG$_2$ constant domain, an IgG$_3$ constant domain and an IgG$_4$ constant domain. In one aspect of the invention, the anti-CD20 antibody is CD20-4. In another aspect of the invention, the anti-CD20 antibody is CD20-20.

In another aspect of the present invention, the antibody, fragment and/or conjugate thereof is capable of efficiently translocating CD20 into the lipid raft compartment of a cell membrane expressing CD20. In another aspect of the present invention, the antibody, fragment and/or conjugate thereof of the present invention is capable of efficiently translocating CD20 into the lipid raft compartment of the membrane of a CD20 expressing lymphoma cell and/or a CD20 expressing immuno-regulatory cell. In one aspect of the present invention, the antibody, fragment or conjugate thereof is capable of efficiently translocating CD20 into the lipid raft compartment of the membrane of Ramos lymphoma cells.

In one aspect of the present invention, the antibody, fragment and/or conjugate thereof kills Ramos lymphoma cells with an EC$_{50}$ of about 0.010 µg/mL or lower and/or kills Daudi lymphoma cells with an EC$_{50}$ of about 0.097 µg/mL or lower and/or kills Raji lymphoma cells with an EC50 of about 0.032 µg/mL or lower and/or kills SU-DHL-4 lymphoma cells with an EC50 of about 0.030 µg/mL or lower and/or kills WSU-DLCL-2 lymphoma cells with an EC$_{50}$ of about 0.10 µg/mL or lower by CDC in the presence of about 5% human serum having complement.

In another aspect of present invention, the antibody, fragment and/or conjugate thereof is capable of killing tumor cells, wherein a -SMCC-DM1 conjugate of said antibody is capable of killing Ramos cells with an EC50 of about 0.54 nM or lower and/or capable of killing Daudi cells with an EC50 of about 0.29 nM or lower.

In one aspect of the invention, the antibody, fragment or conjugate thereof binds to an epitope on CD20, which comprises or has the amino acid residue proline at position 170 and/or 172. In one aspect of the invention, the antibody, fragment or conjugate thereof binds to an epitope on CD20, which does not comprise or require the amino acid residue asparagine at position 163 and/or 166. In one aspect of the invention, the antibody, fragment or conjugate thereof binds to an epitope on CD20, which comprises or has the amino acid residue proline at position 170 and/or 172, and/or which does not comprise or require the amino acid residue asparagine at position 163 and/or 166.

In one aspect of the invention, the antibody, fragment or conjugate thereof binds to an epitope on CD20, wherein the CD20 epitope does have proline at position 170 and/or 172 and/or does not have the amino acid residue asparagine at position 163 and/or 166.

In one aspect of the invention, the antibody or fragment thereof comprises at least one complementarity-determining region having an amino acid sequence selected from the group consisting of SEQ ID NOS:23-28. In one aspect of the invention, the antibody or fragment thereof comprises at least one complementarity-determining region having an amino acid sequence selected from the group consisting of SEQ ID NOS:31-36. In one aspect of the invention, the antibody or fragment comprises at least one complementarity-determining region having an amino acid sequence selected from the group consisting of SEQ ID NOS:23-28 and 31-36, and wherein said antibody or fragment binds CD20. In one aspect of the invention, the antibody or fragment comprises at least one heavy chain and at least one light chain, wherein said heavy chain comprises three sequential complementarity-determining regions having the amino acid sequences of SEQ ID NOS:26-28 or 34, 35 and 36, and wherein said light chain comprises three sequential complementarity-determining regions having the amino acid sequences of SEQ ID NOS: 23-25 or 31-33. In one aspect of the invention, the Ab or fragment heavy chain has at least 90% sequence identity to the amino acid sequence represented by SEQ ID NO:6, 8 or 16. In one aspect of the invention, the antibody or fragment heavy chain has at least 96% to the amino acid sequence represented by SEQ ID NOs:6, 8 or 16. In one aspect of the invention, the antibody or fragment heavy chain has at least 97% to the amino acid sequence represented by SEQ ID NOs:6, 8 or 16. In one aspect of the invention, the antibody or fragment heavy chain has at least 98% to the amino acid sequence represented by SEQ ID NOs:6, 8 or 16. In one aspect of the invention, the antibody or fragment heavy chain has at least 99% to the amino acid sequence represented by SEQ ID NOs:6, 8 or 16. In one aspect of the invention, the antibody or fragment heavy chain has the amino acid sequence of SEQ ID NO:6, 8 or 16.

Sequences that form the secretory signal sequences are not present in mature polypeptide.

In a preferred aspect, the antibodies of the invention are full length antibodies wherein the VH region is joined to a human IgG heavy chain constant region. In some preferred aspects, the IgG is human $IgG_1$ or $IgG_3$.

In one aspect of the invention, the antibody or fragment thereof light chain has at least 90% sequence identity to an amino acid sequence represented by SEQ ID NO:5, 7 or 15. In one aspect of the invention, the antibody or fragment thereof light chain has at least 95% sequence identity to said amino acid sequence represented by SEQ ID NO: 5, 7 or 15. In one aspect of the invention, the antibody or fragment thereof light chain has at least 96% sequence identity to said amino acid sequence represented by SEQ ID NO: 5, 7 or 15. In one aspect of the invention, the antibody or fragment thereof light chain has at least 97% sequence identity to said amino acid sequence represented by SEQ ID NO: 5, 7 or 15. In one aspect of the invention, the antibody or fragment thereof light chain has at least 98% sequence identity to said amino acid sequence represented by SEQ ID NO: 5, 7 or 15. In one aspect of the invention, the antibody or fragment thereof light chain has at least 99% sequence identity to said amino acid sequence represented by SEQ ID NO: 5, 7 or 15. In one aspect of the invention, the antibody or fragment light chain has an amino acid sequence of SEQ ID NO: 5, 7 or 15. In one aspect, the resurfaced anti-CD20 antibody and/or conjugate thereof is CD20-4 or CD20-20, or a fragment thereof.

In one aspect of the invention, the antibody or fragment is an improved antibody or fragment that specifically bind to a CD20, prepared by: (a) providing a DNA encoding an antibody or fragment thereof comprising at least one sequence selected from the group consisting of SEQ ID NOS: 1-8, 13-16, 23-28, and 31-37; (b) introducing at least one nucleotide mutation, deletion or insertion into said DNA such that the amino acid sequence of said antibody or antibody fragment encoded by said DNA is changed; (c) expressing said antibody or antibody fragment; (d) screening said expressed antibody or antibody fragment for said improvement, whereby said improved antibody or antibody fragment is prepared. In one aspect of the invention the improvement is an increased affinity for CD20. In yet another aspect of the invention, the increased affinity results from at least one nucleotide mutation, deletion or insertion made by a known method such as oligonucleotide-mediated site-directed mutagenesis, cassette mutagenesis, error-prone PCR, DNA shuffling, and the use of mutator-strains of *E. coli*. In another aspect of the invention the improvement is an increased avidity for CD20. In another aspect of the invention the improvement is an increased cytotoxic activity for a cell expressing CD20. In another aspect of the invention, the improvement is an increased level of expression. In another aspect of the invention, the improvement is increased idiotypic activity.

In another aspect of the invention, an antibody or fragment thereof of the invention comprises one or more conservative substitutions of amino acid residues when compared to another antibody or fragment thereof of the invention. In some embodiments, such substitutions occur in framework and/or CDR and/or hypervariable sections of the heavy and/or light chains of the antibody or fragment thereof. In some embodiments, such substitutions occur only in the CDR sequences. In some embodiments, there are about 1, 2, 3, 4, 5, 6, 7, 8, 9, 10, 11, 12, 13, 14, 15, 16, 17, 18, 19, 20, 25, 30, 35, 40, 45, 50 or more such substitutions. In other embodiments, there are 1-20, 1-15, 1-10, 1-5, 1-3, 20, 19, 18, 17, 16, 15, 14, 13, 12, 11, 10, 9, 8, 7, 6, 5, 4, 3, 2 or 1 such substitutions in the heavy and/or light chains of antibodies or fragments thereof of the invention.

Thus, the present invention provides CD20 binding antibodies or functional fragments thereof and/or conjugates thereof, and their use in the treatment with CD20 expressing cells associated with diseases. In specific aspects, the antibodies that bind CD20 are more preferably resurfaced, humanized or chimeric. The humanized antibodies include those that have amino acid substitutions in the framework regions (FR) and affinity maturation antibodies with changes in the CDRs. The substituted amino acids in the CDR or FR are not limited to those present in the donor or recipient antibody. In other aspects, the anti-CD20 antibodies or functional fragments thereof and/or conjugates thereof of the invention further comprise changes in amino acid residues in the Fc region that lead to improved effector function including enhanced CDC and/or ADCC function and B-cell killing.

Other anti-CD20 antibodies or functional fragments thereof and/or conjugates thereof of the invention include those having specific changes that improve stability. In a specific aspect, the humanized CD20 antibodies or functional fragments thereof have increased stability.

Antibodies with glycosylation variation having improved ADCC function in vivo are also provided.

In one aspect of the invention, the antibody or fragment thereof is a means for specifically binding to CD20, wherein said means is capable of inducing ADCC and CDC. In one aspect of the invention, the antibody or fragment comprises at least one polypeptide comprising at least one member selected from the group consisting of SEQ ID NOs:1-8, 13-16, and 23-37.

The invention provides a resurfaced antibody that binds human CD20, or an antigen-binding fragment thereof and/or conjugate thereof, that depletes B cells in vivo. In yet another aspect, the B cells are from humans or a cynomolgus monkey.

In another aspect, the present invention is an antibody or fragment thereof produced by the hybridoma corresponding to ATCC Accession No. PTA-10485 or the hybridoma corresponding to ATCC Accession No. PTA-10561, which were deposited on Nov. 19, 2009, and Jan. 5, 2010 (respectively), with the ATCC Patent Depository, 10801 University Boulevard, Manassas, Va. 20110-2209 (USA).

For diagnostic applications, the antibodies or fragments thereof of the present invention typically will be labeled with a detectable moiety. The detectable moiety can be any one which is capable of producing, either directly or indirectly, a detectable signal. For example, the detectable moiety may be a radioisotope, such as $^3$H, $^{14}$C, $^{32}$P, $^{35}$S, or $^{131}$I; a fluorescent or chemiluminescent compound, such as fluorescein isothiocyanate, rhodamine, or luciferin; or an enzyme, such as alkaline phosphatase, beta-galactosidase or horseradish peroxidase.

In one aspect, the present invention is an anti-CD20 cytolytic antibody and/or fragment conjugate. In one aspect of the invention, the CD20-specific cytolytic antibody conjugate is useful in the treatment of medical conditions wherein B cells expressing CD20 influence the course of the condition. In one aspect, the targeted B cells are unwanted. In one aspect, the medical condition is a B cell disease. In one aspect, the medical condition involves the activity of unwanted B cells. Another aspect of the invention is an antibody conjugate that specifically bind to a CD20, wherein said antibody or fragment is capable of inducing antibody dependent cell mediated cytotoxicity (ADCC) and complement dependent cytotoxicity (CDC) in a cell expressing CD20. In one aspect, the medical condition is non-Hodgkin's lymphoma.

One aspect of the invention is a anti-CD20 antibody or fragment conjugate comprising the antibody or fragment linked to a cytotoxic agent. The cytotoxic agent used in the conjugate can be a maytansinoid and maytansinoid analogs, benzodiazepines, taxanes, CC-1065 and CC-1065 analogs, duocarmycin and duocarmycin analogs, enediynes such as calicheamicin, dolastatin and dolastatin analogs including auristatins, tomaymycin derivatives and leptomycin derivatives.

More preferred cytotoxic agents are maytansinoids and maytansinoids analogs, benzodiazepines, taxanes, CC-1065 and CC-1065 analogs.

Maytansinoids and maytansinoid analogs are among the preferred cytotoxic agents. Examples of suitable maytansinoids are known to those of skill in the art and include esters of maytansinol and maytansinol analogs. Suitable maytansinoids are disclosed in, for example, U.S. Pat. Nos. 4,424,219; 4,256,746; 4,294,757; 4,307,016; 4,313,946; 4,315,929; 4,331,598; 4,361,650; 4,362,663; 4,364,866; 4,450,254; 4,322,348; 4,371,533; 6,333,410; 5,475,092; 5,585,499; 5,846,545; 6,444,163; 6,716,821; 7,276,497, 7,473,796 and US Publication No 20050169933.

Taxanes are also preferred cytotoxic agents. Taxanes suitable for use in the present invention are disclosed in, for example, U.S. Pat. Nos. 6,372,738; 6,340,701; 6,436,931; 6,596,757; 7,441,063; 7,495,114 and 7,598,290.

One candidate for the preparation of cytotoxic conjugates are analogs of CC-1065, which is a potent anti-tumor antibiotic isolated from the culture broth of *Streptomyces zelensis*. CC-1065 is about 1000-fold more potent in vitro than are commonly used anti-cancer drugs, such as doxorubicin, methotrexate and vincristine (B. K. Bhuyan et al., *Cancer Res.*, 42, 3532-3537 (1982)). CC-1065 analogs are also preferred cytotoxic drugs for use in the present invention. CC-1065 and its analogs are disclosed in U.S. Pat. Nos. 6,756,397; 7,049,316; 7,388,026; 6,372,738; 6,340,701; 5,846,545 and 5,585,499.

Benzodiazepine derivatives are also suitable cytotoxic drugs for use in the present invention. Pyrrolobenzodiazepines, such as those described in US Patent Publication No. 20090036431 and EP Appl No. 2019104 are suitable cytotoxic drugs. Also suitable are benzodiazepine derivatives, such as those described in U.S. Provisional Application No. 61/150,201.

Cytotoxic drugs such as methotrexate, cisplatin, carboplatin, daunorubicin, doxorubicin, vincristine, vinblastine, melphalan, mitomycin C, chlorambucil and morpholino doxorubicin are also suitable for the preparation of conjugates of the present invention.

In order to link the cytotoxic agent to the antibody, a linking group is used. Suitable cleavable and non-cleavable linking groups are described herein and are well known in the art and include disulfide groups, thioether groups, acid labile groups, photolabile groups, peptidase labile groups and esterase labile groups. Preferred linking groups are disulfide groups and thioether groups, especially those described in U.S. Pat. No. 6,913,748, US Patent Publication No. 20050169933, 20090274713 and WO2009/0134976. For example, conjugates can be constructed using a disulfide exchange reaction or by forming a thioether bond between the antibody and the cytotoxic agent. Preferred linkers for modifying antibodies to give disulfide linked conjugates are N-succinimidyl 4-(2-pyridyldithio)pentanoate (SPP), N-succinimidyl 4-(2-pyridyldithio)butanoate (SPDB) or N-succinimidyl 4-(2-pyridyldithio)-2-sulfobutanoate (sulfo-SPDB).

The present invention includes aspects wherein conjugation of maytansinoids to the antibody via non-cleavable linkers enhances its potency, while allowing for the achievement of high doses in vivo such that the inherent functional activity of the anti-CD20 antibody or fragment thereof is preserved. Preferred non-cleavable linkers for modifying the antibody or antibody fragment to make a thioether bond with the maytansinoid are N-succinimidyl 4-(maleimidomethyl)cyclohexanecarboxylate (SMCC), N-sulfosuccinimidyl 4-(maleimidomethyl)cyclohexanecarboxylate (sulfoSMCC), N-succinimidyl-4-(iodoacetyl)-aminobenzoate (SIAB).

The present invention also includes aspects wherein the linkers described herein are hydrophilic (e.g., incorporating a PEG) and contribute to increasing the activity of the drug. Thus, another aspect of the invention includes improved manners in which drugs are linked to an anti-CD20 antibody such that the linker design provides conjugates that are active across a broad spectrum of tumors, particularly in low antigen expressing or drug resistant tumors. In addition incorporation of these hydrophilic linkers allows the conjugation of up to 15 molecules of a drug per antibody molecule with high yield and no aggregation or precipitation. These conjugates with hydrophilic linkers with up to 15 molecules of a drug linked per antibody molecule bind with high affinity to target CD20 antigen (similar to that of unmodified antibody). A preferred hydrophilic linker for modification of the antibody is N-succinimidyl-[(N-maleimidopropionamido)-tetraethyleneglycol]ester (NHS-PEG$_4$-maleimide).

The present invention also includes aspects wherein the linkers described herein lack a sulfur atom, such as those linkers derived from dicarboxylic acid based moeties (see US Publication No. 2005016993).

The present invention also includes aspects wherein the linkers described herein are charged, wherein the charges are retained both after modification of the anti-CD20 antibody or fragment thereof and in the resulting drug conjugate.

The present invention also includes aspects wherein about 2 to 8 drug molecules are linked to an anti-CD20 antibody or fragment thereof. A preferred aspect is a conjugate wherein about 2 to 8 drug molecules are linked to an anti-CD20 antibody or fragment thereof and the cell killing of the conjugate is more efficacious as compared to a drug load of a lesser or higher number of drugs linked to the same anti-CD20 antibody.

An even further aspect of the present invention is a method for treating cancer sensitive to treatment with said method, said method comprising parenterally administering to a patient in need thereof an effective dose of a composition comprising the conjugate of formula CB—[X$_l$—(—CH$_2$—CH$_2$—O—)$_n$—Y$_p$-D]$_m$ (formula II) or D—Y$_p$—(—CH$_2$—CH$_2$—O—)$_n$—X$_l$]$_m$—CB (formula II')
wherein,
CB represents an anti-CD20 antibody;
D represents a drug;
X represents an aliphatic, an aromatic or a heterocyclic unit bonded to the cell-binding agent via a thioether bond, an amide bond, a carbamate bond, or an ether bond;
Y represents an aliphatic, an aromatic, or a heterocyclic unit bonded to the drug via a covalent bond selected from the group consisting of a thioether bond, an amide bond, a carbamate bond, an ether bond, an amine bond, a carbon-carbon bond and a hydrazone bond;
l is 0 or 1;
p is 0 or 1;
m is an integer from 2 to 15; and
n is an integer from 1 to 2000.

Importantly, the conjugates described in this invention are highly potent or efficacious toward CD20 expressing cells that are multidrug resistant (mdr), which have poor sensitivity to treatment with cytotoxic drugs. For example, cancer therapy poses a hurdle of overcoming mechanisms of drug resistance often encountered after multiple rounds of treatment with different chemotherapeutic agents. One such mechanism observed in cancer cells is called multidrug resistance and is caused by enhanced export of drugs by ATP-binding cassette (ABC) transporters (C. Drumond, B. I. Sikic, *J. Clin. Oncology*, 1999, 17, 1061-1070, G, Szokacs et al., *Nature Reviews*, 5; 219-234, 2006). Therapies that overcome these mechanisms of drug resistance, such as interfering with or overcoming this efflux of drugs by cancer cells are of significant value.

One aspect of the invention is a composition comprising a antibody or fragment and/or conjugate thereof. Yet another aspect of the present invention is a pharmaceutical composition comprising a antibody or fragment and/or conjugate thereof and a pharmaceutically acceptable carrier. In one aspect of the invention, the antibody or fragment pharmaceutical composition comprises a conjugate and a pharmaceutically acceptable carrier. The present invention includes a composition (e.g., a pharmaceutical composition) comprising the anti-CD20 antibody or fragment conjugates and a carrier (e.g., a pharmaceutically acceptable carrier).

The present invention also includes a composition (e.g., a pharmaceutical composition) comprising the anti-CD20 antibodies or fragments thereof, conjugates and a carrier (a pharmaceutically acceptable carrier), further comprising a second therapeutic agent. The present compositions are useful for inhibiting abnormal cell growth or treating a proliferative disorder in a mammal (e.g., human). The present compositions are also useful for treating depression, anxiety, stress, phobias, panic, dysphoria, psychiatric disorders, pain, and inflammatory diseases in a mammal (e.g., human).

In one aspect of the invention, a diagnostic reagent comprises a composition having an antibody or fragment thereof and/or conjugate thereof, as described herein, wherein the antibody or fragment is labeled. In one aspect of the invention, the antibody or fragment and/or conjugate thereof label is selected from the group consisting of a radiolabel, a fluorophore, a chromophore, an imaging agent and a metal ion.

In one aspect of the invention, there is a method for specifically binding to a CD20 expressing cell. In one aspect of the invention, the CD20 is expressed by a B cell. In one aspect of the invention, the CD20 expressing cell is a cancer cell. In one aspect of the invention, the antibody or fragment binds a cancer cell selected from the group consisting of B cell lymphomas including NHL, precursor B cell lymphoblastic leukemia/lymphoma and mature B cell neoplasms, such as B cell chronic lymphocytic leukemia (CLL)/small lymphocytic lymphoma (SLL), B cell prolymphocytic leukemia, lymphoplasmacytic lymphoma, mantle cell lymphoma (MCL), follicular lymphoma (FL), including low-grade, intermediate-grade and high-grade FL, cutaneous follicle center lymphoma, marginal zone B cell lymphoma (MALT type, nodal and splenic type), hairy cell leukemia, diffuse large B cell lymphoma, Burkitt's lymphoma, plasmacytoma, plasma cell myeloma, post-transplant lymphoproliferative disorder, Waldenstrom's macroglobulinemia, and anaplastic large-cell lymphoma (ALCL).

In another aspect of the invention, the CD20 expressing cell influences an unwanted immune response. In another aspect of the invention, the CD20 expressing cell influences inflammation.

The anti-CD20 antibodies or conjugates thereof, and compositions comprising them, are useful for treating or lessening the severity of disorders, such as, characterized by abnormal growth of cells (e.g., cancer and immune disease and disorders). Other applications of this invention include, but are not limited to, co-treating osteoporosis, depression, anxiety, stress, phobias, panic, dysphoria, psychiatric disorders, and pain or as antiepileptics, antibacterials, diuretics and hypotensives, hypolipidemics, and anti-depressants.

In one aspect of the invention, there is a method for inhibiting the growth of a cancer cell comprising contacting the cell with an antibody or antibody fragment and/or conjugate thereof.

In one aspect of the invention, there is a method for treating a patient having a cancer comprising administering to the patient an effective amount of the antibody or fragment and/or conjugate thereof described herein. In one aspect of the invention, the treatment further comprises administering to said patient a therapeutic agent. In one aspect of the invention, the therapeutic agent is a cytotoxic agent.

In yet another aspect, the invention is a CD20-specific cytolytic antibody or fragment and/or conjugate thereof useful in the treatment of inflammatory diseases, such as rheumatoid arthritis and the like. In an additional aspect, the invention is a CD20-directed cytolytic antibody and/or conjugate thereof useful in the treatment of rheumatoid arthritis in combination with methotrexate. In one aspect, the invention is a CD20-specific cytolytic antibody and/or conjugate thereof useful in the treatment of rheumatoid arthritis in combination with methotrexate in patients with moderately- to severely-active rheumatoid arthritis who have inadequate response to one or more TNF antagonist therapies.

In one aspect of the invention, the antibody or fragment and/or conjugated thereof is a method for treating a patient having a cancer comprising administering to said patient an effective amount of the conjugate described herein. In one aspect of the invention, the treatable cancer is a cancer selected from the group consisting of B cell lymphomas including NHL, precursor B cell lymphoblastic leukemia/lymphoma and mature B cell neoplasms, such as B cell chronic lymphocytic leukemia (CLL)/small lymphocytic lymphoma (SLL), B cell prolymphocytic leukemia, lymphoplasmacytic lymphoma, mantle cell lymphoma (MCL), follicular lymphoma (FL), including low-grade, intermediate-grade and high-grade FL, cutaneous follicle center lymphoma, marginal zone B cell lymphoma (MALT type, nodal and splenic type), hairy cell leukemia, diffuse large B cell lymphoma, Burkitt's lymphoma, plasmacytoma, plasma cell myeloma, post-transplant lymphoproliferative disorder, Waldenstrom's macroglobulinemia, and anaplastic large-cell lymphoma (ALCL).

In one aspect of the invention, there is a method for diagnosing a subject suspected of having a cancer, said method comprising administering to a subject the diagnostic reagent; and detecting the distribution of the reagent within the subject. In one aspect of the invention, the method of diagnosis includes diagnosing a cancer selected from the group consisting of B cell lymphomas including NHL, precursor B cell lymphoblastic leukemia/lymphoma and mature B cell neoplasms, such as B cell chronic lymphocytic leukemia (CLL)/small lymphocytic lymphoma (SLL), B cell prolymphocytic leukemia, lymphoplasmacytic lymphoma, mantle cell lymphoma (MCL), follicular lymphoma (FL), including low-grade, intermediate-grade and high-grade FL, cutaneous follicle center lymphoma, marginal zone B cell lymphoma (MALT type, nodal and splenic type), hairy cell leukemia, diffuse large B cell lymphoma, Burkitt's lymphoma, plasmacytoma, plasma cell myeloma, post-transplant lymphoproliferative disorder, Waldenstrom's macroglobulinemia, and anaplastic large-cell lymphoma (ALCL).

In another aspect of the invention, there is a method for diagnosing a subject suspected of having an immune disorder said method comprising administering to a subject the diagnostic reagent; and detecting the distribution of the reagent within the subject. In one aspect of the invention, the method of diagnosis including diagnosing an immune disorder selected from the group consisting of rheumatoid arthritis, juvenile rheumatoid arthritis, systemic lupus erythematosus (SLE), Wegener's disease, inflammatory bowel disease, idiopathic thrombocytopenic purpura (ITP), thrombotic thrombocytopenic purpura (TTP), autoimmune thrombocytopenia, multiple sclerosis, psoriasis, IgA nephropathy, IgM polyneuropathies, myasthenia gravis, vasculitis, diabetes mellitus, Reynaud's syndrome, Crohn's disease, ulcerative colitis, gastritis, Hashimoto's thyroiditis, ankylosing spondylitis, hepatitis C-associated cryoglobulinemic vasculitis. A preferred aspect of the invention is a method for diagnosing a subject suspected of having an autoimmune or inflammatory disease selected from the group consisting of rheumatoid arthritis, juvenile rheumatoid arthritis, systemic lupus erythematosus (SLE), Wegener's disease, inflammatory bowel disease, idiopathic thrombocytopenic purpura (ITP), thrombotic thrombocytopenic purpura (TTP), autoimmune thrombocytopenia, multiple sclerosis, psoriasis, IgA nephropathy, IgM polyneuropathies, myasthenia gravis, vasculitis, diabetes mellitus, Reynaud's syndrome, Crohn's disease, ulcerative colitis, gastritis, Hashimoto's thyroiditis, ankylosing spondylitis, hepatitis C-associated cryoglobulinemic vasculitis, chronic focal encephalitis, bullous pemphigoid, hemophilia A, membranoproliferative glomerulnephritis, adult and juvenile dermatomyositis, adult polymyositis, chronic urticaria, primary biliary cirrhosis, neuromyelitis optica, Graves' dysthyroid disease, bullous pemphigoid, membranoproliferative glonerulonephritis, Churg-Strauss syndrome, asthma, psoriatic arthritis, dermatitis, respiratory distress syndrome, meningitis, encephalitits, uveitis, eczema, atherosclerosis, leukocyte adhesion deficiency, juvenile onset diabetes, Reiter's disease, Behcet's disease, hemolytic anemia, atopic dermatitis, pemphigus vulgaris, Wegener's granulomatosis, Omenn's syndrome, chronic renal failure, acute infectious mononucleosis, HIV and herpes-associated disease, systemic sclerosis, Sjorgen's syndrome and glomerulonephritis. Where the autoimmune disease is rheumatoid arthritis, the antibody can optionally be administered in conjunction with a second therapeutic agent, which is preferably methotrexate.

A further aspect of the invention is a method of inducing cell killing of B cells in vivo, comprising contacting B cells with an antibody and/or conjugate thereof of the present invention, thereby killing the B cells.

The invention also provides methods of treating diseases by administration of a CD20 binding antibody or fragment thereof and/or conjugate thereof to a mammal, such as a human patient suffering from a disease. In any of the methods for treating an autoimmune disease or a CD20 expressing cancer, in one aspect, the antibody is CD20-4 or CD20-20. Thus, one aspect is a method of treating a CD20 positive cancer, comprising administering to a patient suffering from the cancer, a therapeutically effective amount of a CD20 binding antibody and/or conjugate thereof of the invention. In a preferred aspect, the CD20 expressing cancer is a B cell lymphoma or leukemia expressing CD20, including non-Hodgkin's lymphoma (NHL) or lymphocyte predominant Hodgkin's disease (LPHD), chronic lymphocytic leukemia (CLL) or SLL. In one aspect of the method of treating a B cell lymphoma or leukemia, the antibody and/or conjugate thereof is administered at a dosage range of about 20-2000 mg/m$^2$. In additional aspects, the treatment method further comprises administering to the patient at least one chemotherapeutic agent, wherein for non-Hodgkin's lymphoma (NHL), the chemotherapeutic agent is selected from the group consisting of doxorubicin, cyclophosphamide, vincristine and prednisolone.

Also provided is a method of treating an autoimmune or inflammatory disease, comprising administering to a patient suffering from the autoimmune or inflammatory disease, a therapeutically effective amount of the CD20 binding antibody or fragment and/or conjugate thereof as discussed herein. The autoimmune or inflammatory disease is selected from the group consisting of rheumatoid arthritis, juvenile rheumatoid arthritis, systemic lupus erythematosus (SLE), Wegener's disease, inflammatory bowel disease, idiopathic thrombocytopenic purpura (ITP), thrombotic thrombocytopenic purpura (TTP), autoimmune thrombocytopenia, multiple sclerosis, psoriasis, IgA nephropathy, IgM polyneuropathies, myasthenia gravis, vasculitis, diabetes mellitus, Reynaud's disease, Crohn's disease, ulcerative colitis, gastritis, Hashimoto's thyroiditis, ankylosing spondylitis, hepatitis C-associated cryoglobulinemic vasculitis, chronic focal encephalitis, bullous pemphigoid, hemophilia A, membranoproliferative glomerulnephritis, adult and juvenile dermatomyositis, adult polymyositis, chronic urticaria, primary biliary cirrhosis, neuromyelitis optica, Graves' dysthyroid disease, bullous pemphigoid, membranoproliferative glonerulonephritis, Churg-Strauss syndrome, asthma, psoriatic arthritis, dermatitis, respiratory distress syndrome, meningitis, encephalitits, uveitis, eczema, atherosclerosis, leukocyte adhesion deficiency, juvenile onset diabetes, Reiter's disease, Behcet's disease, hemolytic anemia, atopic dermatitis, pemphigus vulgaris, Wegener's granulomatosis, Omenn's syndrome, chronic renal failure, acute infectious mononucleosis, HIV and herpes-associated disease, systemic sclerosis, Sjorgen's syndrome and glomerulonephritis. Where the autoimmune disease is rheumatoid arthritis, the antibody can optionally be administered in conjunction with a second therapeutic agent, which is preferably methotrexate.

In one aspect, the invention provides a method of treating an autoimmune or inflammatory disease selected from the group consisting of Dermatomyositis, Wegner's granulomatosis, ANCA, Aplastic anemia, Autoimmune hemolytic anemia (AIHA), factor VIII deficiency, hemophilia A, Autoimmune neutropenia, Castleman's syndrome, Goodpasture's syndrome, solid organ transplant rejection, graft versus host disease (GVHD), IgM mediated, thrombotic thrombocytopenic purpura (TTP), Hashimoto's Thyroiditis, autoimmune hepatitis, lymphoid interstitial pneumonitis (HIV), bronchiolitis obliterans (non-transplant) vs. NSIP, Guillain-Barre Syndrome, large vessel vasculitis, giant cell (Takayasu's) arteritis, medium vessel vasculitis, Kawasaki's Disease, polyarteritis nodosa, comprising administering to a patient suffering from the disease, a therapeutically effective amount of a CD20 binding antibody and/or conjugate. In one aspect of this method, the CD20 binding antibody is CD20-4 or CD20-20.

In Applicants' treatment methods, the CD20 binding antibodies and/or conjugate thereof can be administered alone or in conjunction with a second therapeutic agent such as a second antibody, or a chemotherapeutic agent or an immunosuppressive agent. The second antibody or fragment and/or conjugate thereof can be one that binds CD20 or a different B cell antigen, or a NK or T cell antigen. In one aspect, the second antibody or fragment and/or conjugate thereof is a radiolabeled anti-CD20 antibody. In other aspects, the CD20 binding antibody is conjugated to a cytotoxic agent including a toxin or a radioactive isotope.

The present invention includes a method of inhibiting unwanted B cells and/or abnormal cell growth or treating a proliferative disorder in a mammal (e.g., human) comprising administering to said mammal a therapeutically effective amount of the anti-CD20 antibody and/or conjugates (and/or solvates and salts thereof) or a composition thereof, alone or in combination with a second therapeutic agent.

One aspect of the present invention is a liquid formulation comprising a CD20 antibody and/or conjugate thereof at about 20 mg/mL antibody, about 10 mM histidine sulfate pH5.8, about 60 mg/ml sucrose (6%) and about 0.2 mg/ml polysorbate 20 (0.02%).

The invention also provides various isolated nucleic acids that encode any of the antibodies disclosed herein, including an expression vector for expressing the antibody and/or antibody fragments. One aspect of the present invention includes a polynucleotide(s) encoding the antibody or fragment described herein.

In one aspect of the invention, the polynucleotide encodes a light or heavy chain of the antibody or fragment and/or conjugate thereof and the polynucleotide is a DNA or RNA. In one aspect of the invention, the polynucleotide is in a vector. In another aspect of the invention, the vector is an expression vector capable of expressing said antibody or fragment.

The invention provides an isolated nucleic acid comprising the nucleotide sequence of SEQ ID NOs.:9-12 or 17-22, or a degenerate variant of these sequences, or the like. One aspect is an isolated nucleic acid comprising a sequence that encodes a polypeptide with the amino acid sequence selected from the group consisting of SEQ ID NOS.1-8, 13-16 and 23-37, optionally having conservative amino acid substitutions.

Another aspect is a vector comprising a nucleic acid described herein, including an expression vector for expression in a host cell. Included as well is a host cell containing the vector.

Another aspect of the invention includes host cells comprising nucleic acids, and host cells that produce the antibody or fragments. In a preferred aspect of the latter, the host cell is a CHO cell or NS0 cell.

A method of producing the antibodies and/or conjugate thereof is provided, the method comprising culturing the host cell that produces the antibody and recovering the antibody from the cell culture.

The present invention includes a method of synthesizing and using anti-CD20 antibodies and/or conjugates for in vitro, in situ, and in vivo diagnosis or treatment of mammalian cells, organisms, or associated pathological conditions.

The aspects of the present invention can be provided in an article of manufacture or a kit.

For use in diagnosing or treating a subject, the article of manufacture further comprises a package insert indicating that the composition is used to diagnose or treat the appropriate disease or disorder.

In a preferred aspect of all of the antibody, antibody fragments, conjugates, compositions and methods of use of this invention, the resurfaced CD20 binding antibody is CD20-4 and has a light and heavy chain amino acid sequence as described herein.

BRIEF DESCRIPTION OF THE DRAWINGS

FIGS. 1 A, C, and E) and CD20-expressing 300-19 cells (right panels; FIGS. 1 B, D, and F). Histograms are shown for staining with 10 nM muCD20-4 (top; FIGS. 1 A and B), muCD20-20 (middle; FIGS. 1 C and D) and the absence of primary antibody (bottom; FIGS. 1 E and F).

FIG. 2 depicts the binding of (A) muCD20-4 and (B) muCD20-20 to BJAB cells as assayed by flow cytometry. Each binding curve was used to determine the $EC_{50}$ of antibody binding, which corresponds to the apparent $K_d$ of the antibody.

FIG. 4 depicts a list of CD20-4 surface residues and substitutions in resurfaced versions for (A) CD20-4 VL and (B) CD20-4 VH.

FIG. 5 depicts alignments of exemplary resurfaced sequences for the CD20-4 variable region vis-à-vis a murine counterpart. FIG. 5(A) light chain variable domains (the sequence of muCD20-4LC is provided as SEQ ID NO:5; the sequence of huCD20-4 LC is provided as SEQ ID NO:15); FIG. 5(B) heavy chain variable domains (the sequence of muCD20-4HC is provided as SEQ ID NO:6; the sequence of huCD20-4HC is provided as SEQ ID NO:16). Dashes "-" denote identity with the murine sequence.

FIG. 11 depicts the results from CDC assays on WSU-DLCL-2 lymphoma cells incubated with (A) chCD20-4 or (B) chCD20-20 in comparison to rituximab or a huIgG1 isotype control antibody in the presence of 5% human serum having complement.

FIG. 12 depicts the results from CDC assays on (A) Daudi and (B) SU-DHL-4 lymphoma cells incubated with huCD20-4, rituximab, 2F2 or a huIgG1 isotype control antibody in the presence of 5% human serum having complement.

FIG. 13 depicts the results from CDC assays on (A) Raji and (B) Ramos lymphoma cells incubated with huCD20-4, rituximab, 2F2 or a huIgG1 isotype control antibody in the presence of 5% human serum having complement.

FIG. 14 depicts the results from an ADCC assay on (A) Ramos lymphoma cells and (B) Granta-519 MCL cells incubated with huCD20-4, rituximab, 2F2 or a huIgG1 isotype control antibody in the presence of purified human NK cells as effector cells.

FIG. 15 depicts the results from an ADCC assay on (A) SU-DHL-4 cells and (B) WSU-DLCL-2 DLBC lymphoma cells incubated with huCD20-4, rituximab, 2F2 or a huIgG1 isotype control antibody in the presence of purified human NK cells as effector cells.

FIG. 16 depicts the results from an ADCC assay on (A) JVM-13 CLL cells and (B) DOHH-2 follicular lymphoma cells incubated with huCD20-4, rituximab, 2F2 or a huIgG1 isotype control antibody in the presence of purified human NK cells as effector cells.

FIG. 19 depicts binding of a panel of CD20 antibodies to cells transfected with human the CD20 antigen variant CD20-A170S P172S as assayed by flow cytometry. (A) huCD20-4, rituximab, 2F2, GA101-F and (B) chCD20-20, 2F2 were tested for binding.

FIG. 21 depicts binding of huCD20-4 in comparison with (A) huCD20-4-SMCC-DM1 or (B) huCD20-4-SPP-DM1 conjugates to BJAB lymphoma cells by flow cytometry.

FIG. 22 depicts the results from an Annexin-V assay to measure induction of apoptosis on (A) Ramos and (B) WSU-DLCL-2 lymphoma cells incubated with rituximab, huCD20-4, huCD20-4-SMCC-DM1, or huCD20-4-SPDB-DM4 at concentrations ranging from $3 \times 10^{-8}$ M to $1 \times 10^{-11}$ M. Ramos cells were treated with the same concentrations of non-binding huIgG1-SMCC-DM1 and huIgG1-SPDB-DM4 conjugates for comparison.

FIG. 23 depicts the results from CDC assays on (A) Daudi and (B) WSU-DLCL-2 lymphoma cells incubated with huCD20-4, huCD20-4-SMCC-DM1, huCD20-4-SPDB-DM4, rituximab or a huIgG1 isotype control antibody in the presence of 5% human serum as a source of complement.

FIG. 24 depicts the results from ADCC assays on (A) JVM-13 CLL and (B) SU-DHL-4 lymphoma cells incubated with huCD20-4, huCD20-4-SMCC-DM1, rituximab or a huIgG1 isotype control antibody in the presence of purified human NK cells as effector cells.

FIG. 25 depicts the results from an exemplary WST-8 cytotoxicity assay on (A) Ramos and (B) Daudi cells incubated with huCD20-4, huCD20-4-SMCC-DM1, rituximab or a non-binding huIgG1-SMCC-DM1 control conjugate at concentrations ranging from $3 \times 10^{-8}$ M to $1 \times 10^{-11}$ M for 5 days.

FIG. 26 depicts the results from an exemplary WST-8 cytotoxicity assay on (A) Granta-519 and (B) SC-1 cells incubated with huCD20-4, huCD20-4-SMCC-DM1, rituximab or a non-binding huIgG1-SMCC-DM1 control conjugate at concentrations ranging from $3 \times 10^{-8}$ M to $1 \times 10^{-11}$ M for 5 days.

FIG. 27 depicts the results from an exemplary WST-8 cytotoxicity assay on (A) DOHH-2 B-cell lymphoma cells and (B) Molt-4 T-cell leukemia cells incubated with huCD20-4, huCD20-4-SMCC-DM1, rituximab or a non-binding huIgG1-SMCC-DM1 control conjugate at concentrations ranging from $3 \times 10^{-8}$ M to $1 \times 10^{-11}$ M for 5 days. Molt-4 cells are used as a CD20 antigen negative cell line.

FIG. 28 depicts the results from an exemplary WST-8 cytotoxicity assay on (A) Ramos and (B) Daudi cells incubated with huCD20-4-SMCC-DM1, rituximab-SMCC-DM1 or a non-binding huIgG-SMCC-DM1 control conjugate at concentrations ranging from $3\times10^{-8}$ M to $1\times10^{-11}$ M for 5 days.

FIG. 29 depicts results from an exemplary WST-8 cytotoxicity assay on (A) Ramos and (B) Daudi cells incubated with huCD20-4, huCD20-4-SMCC-DM1, huCD20-4-SPDB-DM4, huCD20-4-SPP-DM1 or the non-binding huIgG-SPP-DM1 control conjugates at concentrations ranging from $3\times10^{-8}$ M to $1\times10^{-11}$ M for 5 days.

Figure 30:
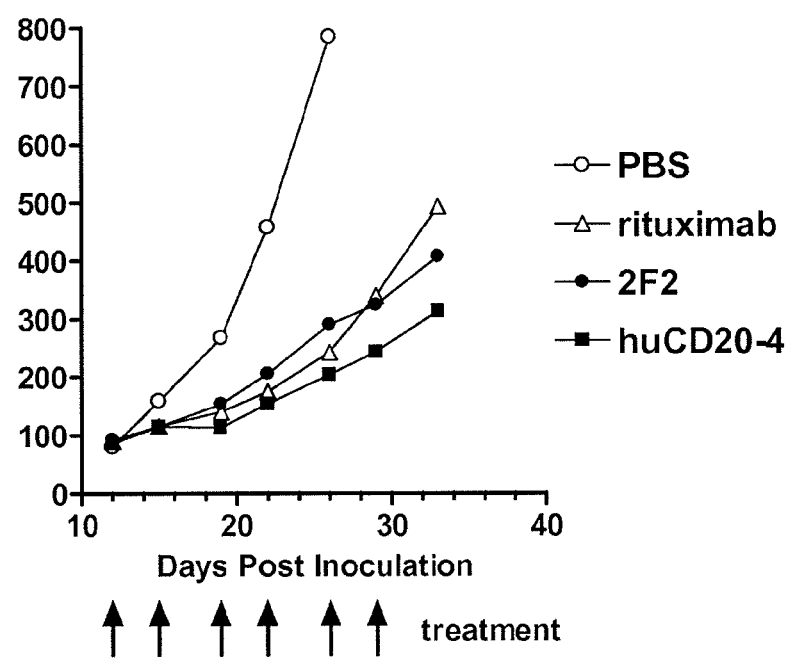

FIG. 30 depicts results from an experiment using an established xenograft model of Raji lymphoma cells implanted subcutaneous into SCID mice. Animals were treated twice per week for 3 weeks on days 12, 15, 19, 22, 26 and 29 post cell inoculation with either PBS as a control, 10 mg/kg of huCD20-4, rituximab or 2F2. The median tumor volume of the different treatment groups is plotted against time in days post tumor cell inoculation.

Figure 31:
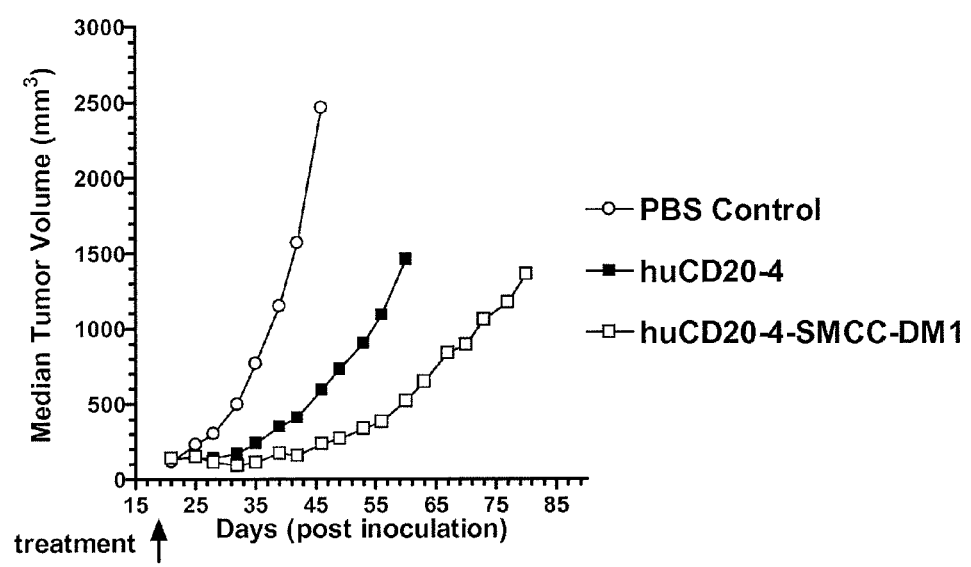

FIG. 31 depicts results from an experiment using a xenograft model of SU-DHL-4 DLBC lymphoma cells implanted subcutaneous into SCID mice. Animals were treated once on day 19 post cell inoculation with either PBS as a control, 10 mg/kg of huCD20-4, or 10 mg/kg huCD20-4-SMCC-DM1. The median tumor volume of the different treatment groups is plotted against time in days post tumor cell inoculation.

Figure 32:
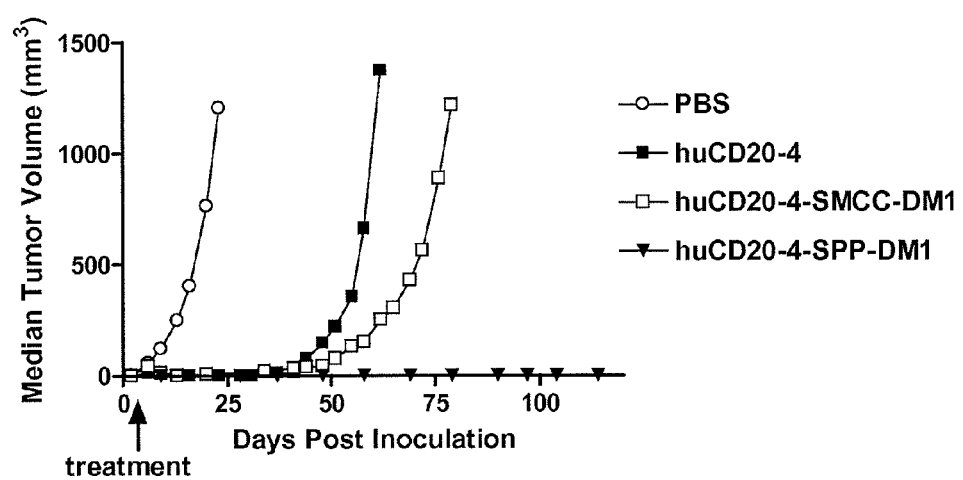

FIG. 32 depicts the results of an exemplary xenograft study using DOHH-2 follicular lymphoma cells implanted subcutaneous into SCID mice. Animals were treated once on day 3 post cell inoculation with either PBS as a control, 10 mg/kg of huCD20-4, 10 mg/kg of huCD20-4-SMCC-DM1 or 5 mg/kg of huCD20-4-SPP-DM1. The median tumor volume of the different treatment groups is plotted against time in days post tumor cell inoculation.

Figure 33:
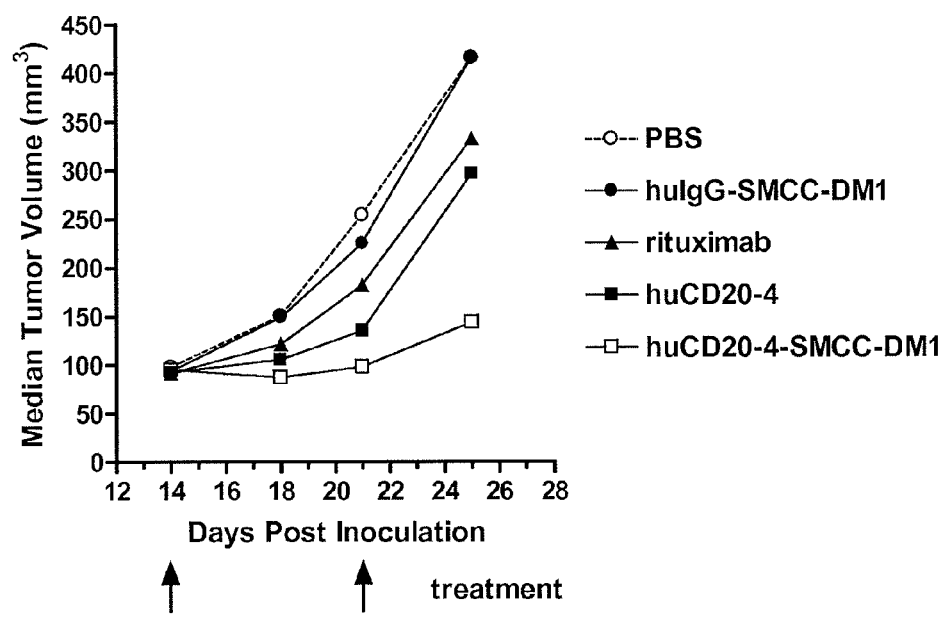

FIG. 33 depicts results from an experiment using a xenograft model of JVM-13 CLL cells implanted subcutaneous into SCID mice. Animals were treated twice on days 14 and 21 post cell inoculation with either PBS as a control, or 10 mg/kg of either rituximab, huCD20-4, huCD20-4-SMCC-DM1 or a non-targeted huIgG-SMCC-DM1 conjugate. The median tumor volume of the different treatment groups is plotted against time in days post tumor cell inoculation.

DETAILED DESCRIPTION OF THE INVENTION

The present invention provides improved anti-CD20 antibodies having high potency in mediating CDC activities against CD20 expressing (e.g., positive) cells. In addition, these antibodies have ADCC activities against the same cells. Further, conjugates of anti-CD20 antibodies with SMCC-DM1 kill CD20 expressing cells unexpectedly well, as demonstrated using in vivo tumor models.

Definitions

In all aspects, an "aliphatic group" is defined as an alkyl, alkenyl or alkynyl group. An alkyl group is an aliphatic hydrocarbon group which may be straight or branched, preferably having 1 to 20 carbon atoms in the chain or cyclic, preferably having 3 to 10 carbon atoms. More preferred alkyl groups have 1 to 12 carbon atoms in the chain. "Branched" means that one or more lower alkyl groups such as methyl, ethyl or propyl are attached to a linear alkyl chain. Exemplary alkyl groups include methyl, ethyl, n-propyl, i-propyl, n-butyl, t-butyl, n-pentyl, 3-pentyl, octyl, nonyl, decyl, cyclopentyl and cyclohexyl.

An alkenyl group is an aliphatic hydrocarbon group containing a carbon-carbon double bond and which may be straight or branched, preferably having 2 to 15 carbon atoms in the chain. More preferred alkenyl groups have 2 to 12 carbon atoms in the chain; and more preferably about 2 to 4 carbon atoms in the chain. Exemplary alkenyl groups include ethenyl, propenyl, n-butenyl, i-butenyl, 3-methylbut-2-enyl, n-pentenyl, heptenyl, octenyl, nonenyl, and decenyl.

An alkynyl group is an aliphatic hydrocarbon group containing a carbon-carbon triple bond and which may be straight or branched, preferably having 2 to 15 carbon atoms in the chain. More preferred alkynyl groups have 2 to 12 carbon atoms in the chain; and more preferably 2 to 4 carbon atoms in the chain. Exemplary alkynyl groups include ethynyl, propynyl, n-butynyl, 2-butynyl, 3-methylbutynyl, n-pentynyl, heptynyl, octynyl and decynyl.

As used herein, the term "aromatic group" means a substituted or unsubstituted aryl group consisting of an aromatic monocyclic or multicyclic hydrocarbon ring system of 6 to 14 carbon atoms, preferably of 6 to 10 carbon atoms. Exemplary aryl groups include phenyl and naphthyl. Substituents include, but are not limited to, alkyl groups, halogens, nitro, amino, hydroxyl and $C_1$-$C_3$ alkoxy groups, such as methoxy, ethoxy and propoxy.

The terms "heterocycle," "heterocyclyl" and "heterocyclic group" refer to a saturated, partially unsaturated or unsaturated, non-aromatic stable 3 to 14, preferably 5 to 10 membered mono, bi or multicyclic rings wherein at least one member of the ring is a hetero atom, or an aromatic, preferably 5 to 10 membered mono-, bi- or multicyclic ring having at least one hetero atom. Typically, hetero atoms include, but are not limited to, oxygen, nitrogen, sulfur, selenium, and phosphorus atoms. Preferable hetero atoms are oxygen, nitrogen and sulfur. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. "Heterocyclyl" also includes radicals where heterocycle radicals are fused with a saturated, partially unsaturated ring, or aromatic carbocyclic or heterocyclic ring.

The aliphatic, aromatic and heterocyclic units can also possess a charged substituent. The charged substituent can be a negatively charged group selected from, but not limited to carboxylate, sulfonate and phosphate, or a positively charged group selected from a tertiary or quaternary amino group.

The term "heteroaryl" refers to a monovalent aromatic radical of 5- or 6-membered rings, and includes fused ring systems (at least one of which is aromatic) of 5-18 atoms, containing one or more heteroatoms independently selected from nitrogen, oxygen, and sulfur. Examples of heteroaryl groups are pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl.

The heterocycle or heteroaryl groups may be carbon (carbon-linked) or nitrogen (nitrogen-linked) attached where such is possible. By way of example and not limitation, carbon bonded heterocycles and heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline.

By way of example and not limitation, nitrogen bonded heterocycles and heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or O-carboline.

The heteroatoms present in heteroaryl and heterocyclyl groups include the oxidized forms such as NO, SO, and $SO_2$. Substituents of heteroaryls or heterocyclyls include, but are not limited to, alkyl groups, halogens, nitro, amino, hydroxyl and $C_1$-$C_3$ alkoxy groups, such as methoxy, ethoxy and propoxy.

"Halogens" include fluorine, chlorine, bromine and iodine atoms. Fluorine and chlorine atoms are preferred.

The term "conjugate" as used herein refers to a compound or a derivative thereof that is linked to a cell binding agent (i.e., an anti-CD20 antibody or fragment thereof) and is defined by a generic formula: C-L-CBA, wherein C=compound, L=linker, and CBA=cell binding agent or anti-CD20 antibody or fragment. In some embodiments, the generic formula: D-L-CBA, wherein D=drug, L=linker and CBA=cell binding agent or anti-CD20 antibody or fragment, may also be used in the same manner.

A linker is any chemical moiety that is capable of linking a compound, usually a drug, such as a maytansinoid, to a cell-binding agent such as an anti-CD20 antibody or a fragment thereof in a stable, covalent manner. Linkers can be susceptible to or be substantially resistant to acid-induced cleavage, light-induced cleavage, peptidase-induced cleavage, esterase-induced cleavage, and disulfide bond cleavage, at conditions under which the compound or the antibody remains active. Suitable linkers are well known in the art and include, for example, disulfide groups, thioether groups, acid labile groups, photolabile groups, peptidase labile groups and esterase labile groups. Linkers also include charged linkers, and hydrophilic forms thereof as described herein and know in the art.

"Abnormal cell growth", as used herein, unless otherwise indicated, refers to cell growth that is independent of normal regulatory mechanisms (e.g., loss of contact inhibition). This includes, for example, the abnormal growth of: (1) tumor cells (tumors) that proliferate by expressing a mutated tyrosine kinase or overexpression of a receptor tyrosine kinase; (2) benign and malignant cells of other proliferative diseases in which aberrant tyrosine kinase activation occurs; (3) any tumors that proliferate by receptor tyrosine kinases; (4) any tumors that proliferate by aberrant serine/threonine kinase activation; and (5) benign and malignant cells of other proliferative diseases in which aberrant serine/threonine kinase activation occurs.

The present invention can be used to treat and/or prevent a variety of diseases involving cells expressing CD20 including tumorigenic diseases and immune diseases, e.g., autoimmune or inflammatory diseases.

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. Examples of "tumorigenic" diseases which can be treated and/or prevented include B cell lymphomas including NHL, precursor B cell lymphoblastic leukemia/lymphoma and mature B cell neoplasms, such as B cell chronic lymphocytic leukemia (CLL)/small lymphocytic lymphoma (SLL), B cell prolymphocytic leukemia, lymphoplasmacytic lymphoma, mantle cell lymphoma (MCL), follicular lymphoma (FL), including low-grade, intermediate-grade and high-grade FL, cutaneous follicle center lymphoma, marginal zone B cell lymphoma (MALT type, nodal and splenic type), hairy cell leukemia, diffuse large B cell lymphoma, Burkitt's lymphoma, plasmacytoma, plasma cell myeloma, post-transplant lymphoproliferative disorder, Waldenstrom's macroglobulinemia, and anaplastic large-cell lymphoma (ALCL).

Examples of "immune disorders" and diseases in which CD20 expressing B cells are involved which can be treated and/or prevented include psoriasis, psoriatic arthritis, dermatitis, systemic scleroderma and sclerosis, inflammatory bowel disease (IBD), Crohn's disease, ulcerative colitis, respiratory distress syndrome, meningitis, encephalitis, uveitis, glomerulonephritis, eczema, asthma, atherosclerosis, leukocyte adhesion deficiency, multiple sclerosis, Reynaud's syndrome, Sjogren's syndrome, juvenile onset diabetes, Reiter's disease, Behcet's disease, immune complex nephritis, IgA nephropathy, IgM polyneuropathies, immune-mediated thrombocytopenias, such as acute idiopathic thrombocytopenic purpura and chronic idiopathic thrombocytopenic purpura, hemolytic anemia, myasthenia gravis, lupus nephritis, systemic lupus erythematosus, rheumatoid arthritis (RA), atopic dermatitis, pemphigus, Graves' disease, Hashimoto's thyroiditis, Wegener's granulomatosis, Omenn's syndrome, chronic renal failure, acute infectious mononucleosis, HN, and herpes virus associated diseases. Further examples are severe acute respiratory distress syndrome and choreoretinitis. Yet further examples are diseases and disorders caused by infection of B-cells with virus, such as Epstein-Barr virus (EBV).

A "therapeutic agent" encompasses both a biological agent such as an antibody, a peptide, a protein, an enzyme or a chemotherapeutic agent.

A "chemotherapeutic agent" is a chemical compound useful in the treatment of cancer. Examples of chemotherapeutic agents include Erlotinib (TARCEVA®, Genentech/OSI Pharm.), Bortezomib (VELCADE®, Millennium Pharm.), Fulvestrant (FASLODEX®, AstraZeneca), Sutent (SU11248, Pfizer), Letrozole (FEMARA®, Novartis), Imatinib mesylate (GLEEVEC®, Novartis), PTK787/ZK 222584 (Novartis), Oxaliplatin (Eloxatin®, Sanofi), 5-FU (5-fluorouracil), Leucovorin, Rapamycin (Sirolimus, RAPAMUNE®, Wyeth), Lapatinib (TYKERB®, GSK572016, Glaxo Smith Kline), Lonafarnib (SCH 66336), Sorafenib (BAY43-9006, Bayer Labs), and Gefitinib (IRESSA®, AstraZeneca), AG1478, AG1571 (SU 5271; Sugen), alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaI1 and calicheamicin omegaI1 (Angew Chem. Intl. Ed. Engl. (1994) 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamniprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2''-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (doxetaxel; Rhone-Poulenc Rorer, Antony, France); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; a topoisomerase 1 inhibitor such as LURTOTECAN®; ABARELIX® rmRH; (ix) anti-angiogenic agents such as bevacizumab (AVASTIN®, Genentech); and (x) pharmaceutically acceptable salts, acids and derivatives of any of the above. Other anti-angiogenic agents include MMP-2 (matrix-metalloproteinase 2) inhibitors, MMP-9 (matrix-metalloproteinase 9) inhibitors, COX-II (cyclooxygenase II) inhibitors, and VEGF receptor tyrosine kinase inhibitors. Examples of such useful matrix metalloproteinase inhibitors that can be used in combination with the present compounds/compositions are described in WO 96/33172, WO 96/27583, EP 818442, EP 1004578, WO 98/07697, WO 98/03516, WO 98/34918, WO 98/34915, WO 98/33768, WO 98/30566, EP 606,046, EP 931,788, WO 90/05719, WO 99/52910, WO 99/52889, WO 99/29667, WO 99/07675, EP 945864, U.S. Pat. No. 5,863,949, U.S. Pat. No. 5,861,510, and EP 780,386, all of which are incorporated herein in their entireties by reference. Examples of VEGF receptor tyrosine kinase inhibitors include 4-(4-bromo-2-fluoroanilino)-6-methoxy-7-(1-methylpiperidin-4-ylmethoxy)quinazoline (ZD6474; Example 2 within WO 01/32651), 4-(4-fluoro-2-methylindol-5-yloxy)-6-methoxy-7-(3-pyrrolidin-1-ylpropoxy)-quinazoline (AZD2171; Example 240 within WO 00/47212), vatalanib (PTK787; WO 98/35985) and SU11248 (sunitinib; WO 01/60814), and compounds such as those disclosed in PCT Publication Nos. WO 97/22596, WO 97/30035, WO 97/32856, and WO 98/13354).

Other examples of chemotherapeutic agents include inhibitors of PI3K (phosphoinositide-3 kinase), such as those reported in Yaguchi et al (2006) Jour. of the Nat. Cancer Inst. 98(8):545-556; U.S. Pat. No. 7,173,029; U.S. Pat. No. 7,037,915; U.S. Pat. No. 6,608,056; U.S. Pat. No. 6,608,053; U.S. Pat. No. 6,838,457; U.S. Pat. No. 6,770,641; U.S. Pat. No. 6,653,320; U.S. Pat. No. 6,403,588; WO 2006/046031; WO 2006/046035; WO 2006/046040; WO 2007/042806; WO 2007/042810; WO 2004/017950; US 2004/092561; WO 2004/007491; WO 2004/006916; WO 2003/037886; US 2003/149074; WO 2003/035618; WO 2003/034997; US 2003/158212; EP 1417976; US 2004/053946; JP 2001247477; JP 08175990; JP 08176070; U.S. Pat. No. 6,703,414; and WO 97/15658, all of which are incorporated herein in their entireties by reference. Specific examples of such PI3K inhibitors include SF-1126 (PI3K inhibitor, Semafore Pharmaceuticals), BEZ-235 (PI3K inhibitor, Novartis), XL-147 (PI3K inhibitor, Exelixis, Inc.).

As used herein, the term "CD20" or "CD20 antigen" refers to polypeptides and any variants, isoforms and species homologs of CD20 that are naturally expressed or are expressed on cells transfected with the CD20 gene, or the like. Human CD20 is also known as MS4A1, the membrane-spanning 4-domains, subfamily A, member 1. Additional synonyms for CD20, as recognized in the art, include CD20 antigen, CD20 receptor, B-lymphocyte surface antigen B1, B1, Bp35, LEU-16, MGC3969, MS4A2 and S7. Two transcript variants have been described for human CD20. Variant 1 represents a longer transcript variant and corresponds to GenBank ID (GI) 68348720. Variant 3 lacks a portion of the 5' UTR, compared to variant 1 and corresponds to GenBank ID (GI) 68348721. Variants 1 and 3 encode the same protein. The major form of human CD20 comprises a 297 amino acid protein described by GenBank Protein ID 23110989.

The term "epitope" refers to a protein determinant capable of specific binding to an antibody. Epitopes usually consist of chemically active surface groupings of molecules such as amino acids or sugar side chains and usually have specific three dimensional structural characteristics, as well as specific charge characteristics.

The term "raft" refers to the sphingolipid- and cholesterol-rich membrane microdomains located in the outer leaflet area of the plasma membrane of a cell. The ability of certain proteins to associate within such domains can affect the protein's function. For example, the translocation of CD20 molecules into lipid rafts, after being bound by the antibodies and/or fragments thereof of the present invention, creates a high density of CD20 antigen-antibody complex in the plasma membranes. Such a high density of CD20 antigen-antibody complexes can enable efficient activation of the complement system during CDC.

As used herein, an "antibody" or fragment and the like includes any protein or peptide containing molecule that comprises at least a portion of an immunoglobulin molecule, such as but not limited to, at least one complementarity determining region (CDR) of a heavy or light chain or a ligand binding portion thereof, a heavy chain or light chain variable region, a heavy chain or light chain constant region, a framework region, or any portion thereof, or at least one portion of an antigen or antigen receptor or binding protein, which can be incorporated into an antibody to CD20 of the present invention. Such antibody optionally further affects a specific ligand, such as but not limited to, where such antibody modulates, decreases, increases, antagonizes, agonizes, mitigates, aleviates, blocks, inhibits, abrogates and/or interferes with at least one antigen activity or binding, or with antigen receptor activity or binding, in vitro, in situ, in vivo and ex vivo. As a non-limiting example, various CD20 specific antibodies are disclosed, wherein a specified portion or variant can bind at least one antigen molecule, or specified portions, variants or domains thereof. A suitable antigen specific antibody, specified portion, or variant can also optionally affect at least one activity or function, such as but not limited to, RNA, DNA or protein synthesis, release, receptor signaling, membrane association, binding activity, protein production and/or synthesis.

Antibodies are heterotetrameric glycoproteins, composed of two identical light chains (LC) and two identical heavy chains (HC). Typically, each light chain is linked to a heavy chain by one covalent disulfide bond, while the number of disulfide linkages varies between the heavy chains of different immunoglobulin isotypes. Each heavy and light chain also has spaced intrachain disulfide bridges. Each heavy chain has at one end a variable domain (VH) followed by a number of constant domains. Each light chain has a variable domain at one end (VL) and a constant domain at its other end; the constant domain of the light chain is aligned with the first constant domain of the heavy chain and the light chain variable domain is aligned with the variable domain of the heavy chain. Antibody light chains of any vertebrate species can be assigned to one of two clearly distinct types, namely kappa and lambda, based on the amino acid sequences of their constant domains. Immunoglobulins can be assigned to five major classes, namely IgA, IgD, IgE, IgG and IgM, depending on the heavy chain constant domain amino acid sequence. IgA and IgG are further sub-classified as the isotypes IgA1, IgA2, IgG1, IgG2, IgG3 and IgG4.

Antibody fragments include any protein or peptide containing molecule that comprises at least a portion of an immunoglobulin molecule, such as but not limited to, at least one complementarity determining region (CDR) of a heavy or light chain or a ligand binding portion thereof, a heavy chain or light chain variable region, a heavy chain or light chain constant region, a framework region, or any portion thereof, or at least one portion of an antigen or antigen receptor or binding protein, which can be incorporated into an antibody to CD20 of the present invention.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and the heavy-chain variable domains. The more highly conserved portions of variable domains are called the framework (FR). The variable domains of native heavy and light chains each comprise four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen-binding site of antibodies (see Kabat et al., Sequences of Proteins of Immunological Interest, Fifth Edition, National Institute of Health, Bethesda, Md. (1991)). The constant domains are not involved directly in binding an antibody to an antigen, but exhibit various effector functions, such as participation of the antibody in antibody-dependent cellular toxicity.

The term "antibody" also includes digestion fragments, specified portions and variants thereof, including antibody mimetics or comprising portions of antibodies that mimic the structure and/or function of an antibody or specified fragment or portion thereof, including single chain antibodies and fragments thereof. Functional fragments include antigen-binding fragments that bind to a mammalian antigens, such as CD20, alone or in combination with other antigens, such as, for example, human epidermal growth factor receptor (HER1), IgE, vascular endothelial growth factor, HER dimerization inhibitors, Bcl-2 family proteins, MET, IL-13, IFN alpha, EGFL7, CD40, DR4 and DR5, PI3 kinase, lymphotoxin alpha, beta 7 integrin, amyloid beta, CRIg, TNF, complement (C5), CBL, CD147, IL-8, gp120, VLA-4, CD11a, CD18, VEGF, CD40L, Id, ICAM-1, CD2, EGFR, TGF-beta, TNF-alpha, E-selectin, Fact VII, TNF, Her2/neu, F gp, CD11/18, CD14, ICAM-3, CD80, CD40L, CD4, CD23, beta2-integrin, alpha4beta7, CD52, HLA DR, CD22, CD64 (FcR), TCR alpha beta, CD2, CD3, Hep B, CA 125, EpCAM, gp120, CMV, gpIIbIIIa, IgE, IL5, IL-4, CD25, CD3, CD33, CD19, CD22, CD28, CD36, CD37, CD44, CD55, CD59, CD70, CD79, CD80, CD103, CD134, CD137, CD138, CD152, CD30, HLA, VNRintegrin, CD25, IL-23 and IL-12. For example, antibody fragments capable of binding to antigen or portions thereof, include, but are not limited to, Fab (e.g., by papain digestion), Fab' (e.g., by pepsin digestion and partial reduction) and F(ab')2 (e.g., by pepsin digestion), facb (e.g., by plasmin digestion), pFc' (e.g., by pepsin or plasmin digestion), Fd (e.g., by pepsin digestion, partial reduction and reaggregation), Fv or scFv (e.g., by molecular biology techniques) fragments, are encompassed by the present invention (see, e.g., Colligan, Immunology).

Such fragments can be produced by enzymatic cleavage, synthetic or recombinant techniques, as known in the art and/or as described herein. Antibodies can also be produced in a variety of truncated forms using antibody genes in which one or more stop codons have been introduced upstream of the natural stop site. For example, a combination gene encoding a F(ab')2 heavy chain portion can be designed to include DNA sequences encoding the CH1 domain and/or hinge region of the heavy chain. The various portions of antibodies can be joined together chemically by conventional techniques, or can be prepared as a contiguous protein using genetic engineering techniques.

"Blocking" antibody or an "antagonist" antibody is one which inhibits or reduces biological activity of the antigen it binds such as CD20. Preferred blocking antibodies or antagonist antibodies substantially or completely inhibit the biological activity of the antigen. Desirably, the biological activity is reduced by 10%, 20%, 30%, 50%, 70%, 80%, 90%, 95%, or even 100%.

An "agonist antibody", as used herein, is an antibody which mimics at least one of the functional activities of a reference polypeptide of interest.

An "anti-idiotypic (anti-Id) antibody" is an antibody which recognizes unique determinants generally associated with the antigen-binding site of an antibody. An Id antibody can be prepared by immunizing an animal of the same species and genetic type (e.g., mouse strain) as the source of the mAb with the mAb to which an anti-Id is being prepared. The immunized animal will recognize and respond to the idiotypic determinants of the immunizing antibody by producing an antibody to these idiotypic determinants (the anti-Id antibody). See, for example, U.S. Pat. No. 4,699,880, which is herein entirely incorporated by reference. The anti-Id antibody may also be used as an "immunogen" to induce an immune response in yet another animal, producing a so-called anti-anti-Id antibody. The anti-anti-Id may be epitopically identical to the original mAb which induced the anti-Id. Thus, by using antibodies to the idiotypic determinants of a mAb, it is possible to identify other clones expressing antibodies of identical specificity.

An "isolated" antibody is one separated and/or recovered from its natural environment. Contaminant components of its natural environment are materials which would interfere with diagnostic or therapeutic uses for the antibody, and may include enzymes, hormones, and other proteinaceous or non-proteinaceous solutes. In preferred aspects, the antibody will be purified (1) to greater than 95% by weight of antibody as determined by, for example, the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE (sodium dodecyl sulfate polyacrylamide gel electrophoresis) under reducing or nonreducing conditions using Coomassie blue or, preferably, silver stain. Isolated antibody includes the CD20 antibody in situ within recombinant cells since at least one component of the antibody's natural environment will not be present. Ordinarily, however, isolated antibody will be prepared by at least one purification step.

The term "rituximab" or "RITUXAN®" refers to the commercially available chimeric anti-CD20 antibody described as "C2B8" in U.S. Pat. No. 5,736,137 (Anderson et al.). The term "2F2" or "ofatumumab" refers to the fully human anti-CD20 antibody as described in WO 2004/035607 (Teeling et al. (2004)). The term "GA101" or "afutuzumab" refers to the humanized and glyco-engineered anti-CD20 antibody consisting of the heavy chain B-HH6 and light chain B-KV1 as described in WO 2005/0448959 (Umana, U.S. Pat. No. 5,639,641 (2005)). The term "B1" refers to the murine anti-CD20 antibody tositumomab, which corresponds to the unlabeled antibody component of Bexxar®.

As used herein, the term "engineered antibody" or "altered antibody" includes an antibody with significant human frameworks and constant regions (CL, CH domains (e.g., CH1, CH2, CH3), and hinge), and CDRs derived from antigen binding antibodies such as anti-CD20 antibodies or fragments thereof. Fully human frameworks comprise frameworks that correspond to human germline sequences as well as sequences with somatic mutations. CDRs may be derived from one or more CDRs that associate with or bind to antigen in or outside of the context of any antibody framework. For example, the CDRs of the human engineered antibody of the present invention directed to CD20 may be derived from CDRs that bind antigen in the context of a mouse antibody framework and then are engineered to bind antigen in the context of a human framework. Often, the human engineered antibody is substantially non-immunogenic in humans.

Similarly, antibodies designated primate (monkey, baboon, chimpanzee, etc.), rodent (mouse, rat, rabbit, guinea pig, hamster, and the like) and other mammals designate such species, sub-genus, genus, sub-family, and family specific antibodies. Further, chimeric antibodies can include any combination of the above. Such changes or variations optionally and preferably retain or reduce the immunogenicity in humans or other species relative to non-modified antibodies. A human engineered antibody is distinct from a chimeric or humanized antibody.

An engineered antibody can be produced by a non-human animal or prokaryotic or eukaryotic cell that is capable of expressing functionally rearranged human or human engineered immunoglobulin (e.g., heavy chain and/or light chain) genes. Further, when a engineered antibody is a single chain antibody, it can comprise a linker peptide that is not found in native human or non-human antibodies. For example, an Fv can comprise a linker peptide, such as two to about eight glycine or other amino acid residues, which connects the variable region of the heavy chain and the variable region of the light chain. Such linker peptides are considered to be of human origin.

Bispecific, heterospecific, heteroconjugate or similar antibodies can also be used that are monoclonal, preferably, human, human engineered, resurfaced or humanized, antibodies that have binding specificities for at least two different antigens such as CD20 and a non-CD20 antigen. In the present case, one of the binding specificities is for at least one antigenic protein, the other one is for another antigenic protein. Methods for making bispecific antibodies are known in the art. Traditionally, the recombinant production of bispecific antibodies is based on the co-expression of two immunoglobulin heavy chain-light chain pairs, where the two heavy chains have different specificities (Milstein and Cuello, Nature 305:537 (1983)). Because of the random assortment of immunoglobulin heavy and light chains, these hybridomas (quadromas) produce a potential mixture of about 10 different antibody molecules, of which only one has the correct bispecific structure. The purification of the correct molecule is usually done by affinity chromatography steps or as otherwise described herein. Similar procedures are disclosed, e.g., in WO 93/08829, U.S. Pat. Nos. 6,210,668, 6,193,967, 6,132,992, 6,106,833, 6,060,285, 6,037,453, 6,010,902, 5,989,530, 5,959,084, 5,959,083, 5,932,448, 5,833,985, 5,821,333, 5,807,706, 5,643,759, 5,601,819, 5,582,996, 5,496,549, 4,676,980, WO 91/00360, WO 92/00373, EP 03089, Traunecker et al., EMBO J. 10:3655 (1991), Suresh et al., Methods in Enzymology 121:210 (1986), U.S. 20090258026, U.S. 20060140946 and U.S. 20070298040, each entirely incorporated herein by reference.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

"Human effector cells" are leukocytes which express one or more FcRs and perform effector functions. In certain aspects, the cells express at least FcγRIII and perform ADCC effector function(s). Examples of human leukocytes which mediate ADCC include peripheral blood mononuclear cells (PBMC), natural killer (NK) cells, monocytes, cytotoxic T cells and neutrophils. The effector cells may be isolated from a native source, e.g., from blood.

Anti-CD20 Antibodies

Based on Applicants' discovery, inter alia, the anti-CD20 antibodies and fragments thereof, conjugates, compositions and methods of the invention can be mutant antibodies and the like. The anti-CD20 antibody can be an "engineered antibody" or an altered antibody such as an amino acid sequence variant of the anti-CD20 antibody wherein one or more of the amino acid residues of the anti-CD20 antibody have been modified. The modifications to the amino acid sequence of the anti-CD20 antibody include modifications to the polypeptide and/or polynucleotide sequence to improve affinity or avidity of the antibody or fragment for its antigen, and/or modifications to the Fc portion of the antibody to improve effector function unless otherwise indicated herein or known. The modifications may be made to any known anti-CD20 antibodies or anti-CD20 antibodies identified as described herein. Such altered antibodies necessarily have less than 100% sequence identity or similarity with a reference anti-CD20 antibody. In a preferred aspect, the altered antibody will have an amino acid sequence having at least 20%, 25%, 35%, 45%, 55%, 65%, or 75% amino acid sequence identity or similarity with the amino acid sequence of either the heavy or light chain variable domain of the anti-CD20 antibody, more preferably at least 80%, more preferably at least 85%, more preferably at least 90%, and most preferably at least 95%. In a preferred aspect, the altered antibody will have an amino acid sequence having at least 25%, 35%, 45%, 55%, 65%, or 75% amino acid sequence identity or similarity with the amino acid sequence of the heavy chain CDR1, CDR2, or CDR3 of the anti-CD20 antibody, more preferably at least 80%, more preferably at least 85%, more preferably at least 90%, and most preferably at least 95%. In a preferred aspect, the altered antibody will maintain human CD20 binding capability. In certain aspects, the anti-CD20 antibody of the invention comprises a heavy chain that is about 10%, 15%, 20%, 25%, 30%, 35%, 40%, 45%, 50%, 55%, 60%, 65%, 70%, 75%, 80%, 85%, 90%, 95%, 96%, 97%, 98%, 99% or more identical to the amino acid sequences of SEQ ID NOs:6, 8 or 16. In certain aspects, the anti-CD20 antibody of the invention comprises a light chain that is about 10%, 15%, 20%, 25%, 30%, 35%, 40%, 45%, 50%, 55%, 60%, 65%, 70%, 75%, 80%, 85%, 90%, 95%, 96%, 97%, 98%, 99% or more identical to the amino acid sequences of SEQ ID NOs:5, 7 or 15. In a preferred aspect, the altered antibody will have an amino acid sequence having at least 25%, 35%, 45%, 55%, 65%, or 75% amino acid sequence identity or similarity with the amino acid sequence of light chain CDR1, CDR2, or CDR3 of the anti-CD20 antibody, more preferably at least 80%, more preferably at least 85%, more preferably at least 90%, and most preferably at least 95%, 96%, 97%, 98%, 99%.

In some embodiments of the invention, the anti-CD20 antibody can be an "engineered antibody" or an altered antibody such as an amino acid sequence variant of the anti-CD20 antibody wherein one or more of the amino acid residues of the anti-CD20 antibody have been modified. The modifications to the amino acid sequence of the anti-CD20 antibody include modifications to the polypeptide and/or polynucleotide sequence to improve affinity or avidity of the antibody or fragment for its antigen, and/or modifications to the Fc portion of the antibody to improve effector function unless otherwise indicated herein or known. The modifications may be made to any known anti-CD20 antibodies or anti-CD20 antibodies identified as described herein. Such altered antibodies necessarily have less than 100% sequence identity or similarity with a reference anti-CD20 antibody. In a preferred aspect, the altered antibody will have an amino acid sequence having at least 1-5, 1-3, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45 or 50 conservative amino acid substitutions when compared with the amino acid sequence of either the heavy or light chain variable domain of the anti-CD20 antibody. In a preferred aspect, the altered antibody will have an amino acid sequence having at least 1-20, 1-15, 1-10, 1-5, 1-3, 20, 19, 18, 17, 16, 15, 14, 13, 12, 11, 10, 9, 8, 7, 6, 5, 4, 3, 2 or 1 conservative amino acid substitutions when compared with the amino acid sequence of the heavy chain CDR1, CDR2, or CDR3 of the anti-CD20 antibody. In a preferred aspect, the altered antibody will maintain human CD20 binding capability. In certain aspects, the anti-CD20 antibody of the invention comprises a heavy chain having an amino acid sequence that has about 1-20, 1-15, 1-10, 1-5, 1-3, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45 or 50 conservative amino acid substitutions when compared with the amino acid sequence of the amino acid sequences of SEQ ID NOs:6, 8 or 16. In certain aspects, the anti-CD20 antibody of the invention comprises a heavy chain having an amino acid sequence that has about 1-20, 1-15, 1-10, 1-5, 1-3, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45 or 50 conservative amino acid substitutions when compared with the amino acid sequence of the amino acid sequences of SEQ ID NOs:5, 7 or 15. In a preferred aspect, the altered antibody will have an amino acid sequence having at least 1-20, 1-15, 1-10, 1-5, 1-3, 20, 19, 18, 17, 16, 15, 14, 13, 12, 11, 10, 9, 8, 7, 6, 5, 4, 3, 2 or 1 conservative amino acid substitutions when compared with the amino acid sequence of the light chain CDR1, CDR2, or CDR3 of the anti-CD20 antibody.

Hybridomas producing the anti-CD20 antibodies CD20-4 and CD20-20 have been deposited under ATCC deposit nos. PTA-10485 and PTA-10561.

"% identity", as known in the art, is a measure of the relationship between two polynucleotides or two polypeptides, as determined by comparing their sequences. Identity or similarity with respect to a sequence is defined herein as the percentage of amino acid residues in the candidate sequence that are identical (i.e., same residue) or similar (i.e., amino acid residue from the same group based on common side-chain properties, see below) to anti-CD20 antibody residues, after aligning the sequences and introducing gaps, if necessary, to achieve the maximum percent sequence identity. None of N-terminal, C-terminal, or internal extensions, deletions, or insertions into the antibody sequence outside of the variable domain shall be construed as affecting sequence identity or similarity. In general, the two sequences to be compared are aligned to give a maximum correlation between the sequences. The alignment of the two sequences is examined and the number of positions giving an exact amino acid or nucleotide correspondence between the two sequences determined, divided by the total length of the alignment and multiplied by 100 to give a % identity figure. This % identity figure may be determined over the whole length of the sequences to be compared, which is particularly suitable for sequences of the same or very similar length and which are highly homologous, or over shorter defined lengths, which is more suitable for sequences of unequal length or which have a lower level of homology.

For example, sequences can be aligned with the software clustalW under Unix which generates a file with an ".aln" extension, this file can then be imported into the Bioedit program (Hall, T. A. 1999, BioEdit: a user-friendly biological sequence alignment editor and analysis program for Windows 95/98/NT. Nucl. Acids. Symp. Ser. 41:95-98) which opens the .aln file. In the Bioedit window, one can choose individual sequences (two at a time) and align them. This method allows for comparison of the entire sequence.

Methods for comparing the identity of two or more sequences are well-known in the art. Thus for instance, programs are available in the Wisconsin Sequence Analysis Package, version 9.1 (Devereux J. et al., Nucleic Acids Res., 12:387-395, 1984, available from Genetics Computer Group, Madison, Wis., USA). The determination of percent identity between two sequences can be accomplished using a mathematical algorithm. For example, the programs BESTFIT and GAP, may be used to determine the % identity between two polynucleotides and the % identity between two polypeptide sequences. BESTFIT uses the "local homology" algorithm of Smith and Waterman (Advances in Applied Mathematics, 2:482-489, 1981) and finds the best single region of similarity between two sequences. BESTFIT is more suited to comparing two polynucleotide or two polypeptide sequences which are dissimilar in length, the program assuming that the shorter sequence represents a portion of the longer. In comparison, GAP aligns two sequences finding a "maximum similarity" according to the algorithm of Neddleman and Wunsch (J. Mol. Biol., 48:443-354, 1970). GAP is more suited to comparing sequences which are approximately the same length and an alignment is expected over the entire length. Preferably the parameters "Gap Weight" and "Length Weight" used in each program are 50 and 3 for polynucleotides and 12 and 4 for polypeptides, respectively. Preferably % identities and similarities are determined when the two sequences being compared are optimally aligned.

Other programs for determining identity and/or similarity between sequences are also known in the art, for instance the BLAST family of programs (Karlin & Altschul, 1990, Proc. Natl. Acad. Sci. USA, 87:2264-2268, modified as in Karlin & Altschul, 1993, Proc. Natl. Acad. Sci. USA, 90:5873-5877, available from the National Center for Biotechnology Information (NCB), Bethesda, Md., USA). These programs exemplify a preferred, non-limiting example of a mathematical algorithm utilized for the comparison of two sequences. Such an algorithm is incorporated into the NBLAST and XBLAST programs of Altschul et al., 1990, J. Mol. Biol., 215:403-410. BLAST nucleotide searches can be performed with the NBLAST program, score=100, wordlength=12 to obtain nucleotide sequences homologous to a nucleic acid molecule encoding all or a portion of any anti-CD20 antibody of the invention. BLAST protein searches can be performed with the XBLAST program, score=50, wordlength=3 to obtain amino acid sequences homologous to a protein molecule of the invention. To obtain gapped alignments for comparison purposes, Gapped BLAST can be utilized as described in Altschul et al., 1997, Nucleic Acids Res., 25:3389-3402. Alternatively, PSI-Blast can be used to perform an iterated search which detects distant relationships between molecules (Id.). When utilizing BLAST, Gapped BLAST, and PSI-Blast programs, the default parameters of the respective programs (XBLAST and NBLAST) can be used. Another preferred, non-limiting example of a mathematical algorithm utilized for the comparison of sequences is the algorithm of Myers and Miller, 1988, CABIOS 4:11-17. Such an algorithm is incorporated into the ALIGN program (version 2.0) which is part of the GCG sequence alignment software package. When utilizing the ALIGN program for comparing amino acid sequences, a PAM 120 weight residue table, a gap length penalty of 12, and a gap penalty of 4 can be used.

Another non-limiting example of a program for determining identity and/or similarity between sequences known in the art is FASTA (Pearson W. R. and Lipman D. J., Proc. Nat. Acad. Sci. USA, 85:2444-2448, 1988, available as part of the Wisconsin Sequence Analysis Package). Preferably the BLOSUM62 amino acid substitution matrix (Henikoff S. and Henikoff J. G., Proc. Nat. Acad. Sci. USA, 89:10915-10919, 1992) is used in polypeptide sequence comparisons including where nucleotide sequences are first translated into amino acid sequences before comparison.

Yet another non-limiting example of a program known in the art for determining identity and/or similarity between amino acid sequences is SeqWeb Software (a web-based interface to the GCG Wisconsin Package: Gap program) which is utilized with the default algorithm and parameter settings of the program: blosum62, gap weight 8, length weight 2.

The percent identity between two sequences can be determined using techniques similar to those described above, with or without allowing gaps. In calculating percent identity, typically exact matches are counted.

The program BESTFIT can be used to determine the % identity of a query polynucleotide or a polypeptide sequence with respect to a polynucleotide or a polypeptide sequence of the present invention, the query and the reference sequence being optimally aligned and the parameters of the program set at the default value.

To generate an altered antibody, one or more amino acid alterations (e.g., substitutions) are introduced in one or more of the hypervariable regions of an antibody. Alternatively, or in addition, one or more alterations (e.g., substitutions) of framework region residues may be introduced in an anti-CD20 antibody where these result in an improvement in the binding affinity of the antibody mutant for the antigen. Examples of framework region residues to modify include those which non-covalently bind antigen directly (Amit et al., Science, 233:747-753 (1986)); interact with/effect the conformation of a CDR (Chothia et al., J. Mol. Biol., 196:901-

917 (1987)); and/or participate in the VL VH interface. In certain aspects, modification of one or more of such framework region residues results in an enhancement of the binding affinity of the antibody for the antigen. For example, from about one to about five framework residues (e.g., 1, 2, 3, 4 or 5) may be altered in this aspect of the invention. Sometimes, this may be sufficient to yield an antibody with an enhancement of the binding affinity, even where none of the hypervariable region residues have been altered. Normally, however, an altered antibody will comprise additional hypervariable region alteration(s).

The hypervariable region residues which are altered may be changed randomly, especially where the starting binding affinity of an anti-CD20 antibody for the antigen is such that such randomly produced altered antibody can be readily screened.

One useful procedure for generating such an altered antibody is called "alanine scanning mutagenesis" (Cunningham and Wells, Science, 244:1081-1085 (1989)). One or more of the hypervariable region residue(s) are replaced by alanine or polyalanine residue(s) to affect the interaction of the amino acids with the antigen. Those hypervariable region residue(s) demonstrating functional sensitivity to the substitutions then are refined by introducing additional or other mutations at or for the sites of substitution. Thus, while the site for introducing an amino acid sequence variation is predetermined, the nature of the mutation per se need not be predetermined. The Ala-mutants produced this way are screened for their biological activity as described herein and/or as known in the art.

Another procedure for generating such an altered antibody involves affinity maturation using phage display (Hawkins et al., J. Mol. Biol., 254:889-896 (1992) and Lowman et al., Biochemistry, 30(45):10832-10837 (1991)). Briefly, several hypervariable region sites (e.g., 6-7 sites) are mutated to generate all possible amino acid substitutions at each site. The antibody mutants thus generated are displayed in a monovalent fashion from filamentous phage particles as fusions to the gene III product of M13 packaged within each particle. The phage-displayed mutants are then screened for their biological activity (e.g., binding affinity) as herein disclosed and/or as known in the art.

Mutations in antibody sequences may include substitutions, deletions, including internal deletions, additions, including additions yielding fusion proteins, or conservative substitutions of amino acid residues within and/or adjacent to the amino acid sequence, but that result in a "silent" change, in that the change produces a functionally equivalent anti-CD20 antibody or fragment. Conservative amino acid substitutions may be made on the basis of similarity in polarity, charge, solubility, hydrophobicity, hydrophilicity, and/or the amphipathic nature of the residues involved. For example, non-polar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. In addition, glycine and proline are residues can influence chain orientation. Non-conservative substitutions will entail exchanging a member of one of these classes for a member of another class. Furthermore, if desired, non-classical amino acids or chemical amino acid analogs can be introduced as a substitution or addition into the antibody sequence. Non-classical amino acids include, but are not limited to, the D-isomers of the common amino acids, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosine, citrulline, cysteic acid, t-butylglycine, t-butylalanine, phenylglycine, cyclohexylalanine, β-alanine, fluoro-amino acids, designer amino acids such as β-methyl amino acids, C α-methyl amino acids, N α-methyl amino acids, and amino acid analogs generally.

In another aspect, the sites selected for modification are affinity matured using phage display (see above).

Any technique for mutagenesis known in the art can be used to modify individual nucleotides in a DNA sequence, for purposes of making amino acid substitution(s) in the antibody sequence, or for creating/deleting restriction sites to facilitate further manipulations. Such techniques include, but are not limited to, chemical mutagenesis, in vitro site-directed mutagenesis (Kunkel, Proc. Natl. Acad. Sci. USA, 82:488 (1985); Hutchinson, C. et al., J. Biol. Chem., 253:6551 (1978)), oligonucleotide-directed mutagenesis (Smith, Ann. Rev. Genet., 19:423-463 (1985); Hill et al., Methods Enzymol., 155:558-568 (1987)), PCR-based overlap extension (Ho et al., Gene, 77:51-59 (1989)), PCR-based megaprimer mutagenesis (Sarkar et al., Biotechniques, 8:404-407 (1990)), etc. Modifications can be confirmed by double-stranded dideoxy DNA sequencing.

The isolated nucleic acids of the present invention can be used for production of at least one CD20 specific antibody or fragment or specified variant thereof, which can be used to measure or effect in a cell, tissue, organ or animal (including mammals and humans), to diagnose, monitor, modulate, treat, alleviate, help prevent the incidence of, or reduce the symptoms of, at least one condition, selected from, but not limited to, at least one of an immune disorder or disease, a cardiovascular disorder or disease, an infectious, malignant, and/or neurologic disorder or disease, or other known or specified antigen related condition.

Significantly human engineered antibodies that are specific for human proteins or fragments thereof, such as CD20, can be engineered for other immunogenic antigens or isoforms, such as a CD20 protein and/or a portion thereof (including synthetic molecules, such as synthetic peptides) or any one of or combination of antigens, such as CD56, human epidermal growth factor receptor (HER1), IgE, vascular endothelial growth factor, HER dimerization inhibitors, Bcl-2 family proteins, MET, IL-13, IFN alpha, EGFL7, CD40, DR4 and DR5, PI3 kinase, lymphotoxin alpha, beta 7 integrin, amyloid beta, CRIg, TNF, complement (C5), CBL, CD147, IL-8, gp120, VLA-4, CD11a, CD18, VEGF, CD40L, Id, ICAM-1, CD2, EGFR, TGF-beta, TNF-alpha, E-selectin, Fact VII, TNF, Her2/neu, F gp, CD11/18, CD14, ICAM-3, CD80, CD40L, CD4, CD23, beta2-integrin, alpha4beta7, CD52, HLA DR, CD22, CD64 (FcR), TCR alpha beta, CD2, CD3, Hep B, CA 125, EpCAM, gp120, CMV, gpIIbIIIa, IgE, IL-5, IL-4, CD25, CD3, CD33, CD30, CD19, CD22, CD28, CD36, CD37, CD44, CD55, CD59, CD70, CD79, CD80, CD103, CD134, CD137, CD138, CD152, HLA, VNRintegrin, CD25, IL-23 and IL-12, for example.

Antibody Production

At least one antigen specific antibody of the present invention, such as an anti-CD20 antibody, can be optionally produced by a cell line, a mixed cell line, an immortalized cell or clonal population of immortalized cells, as well known in the art. See, e.g., Ausubel, et al., ed., Current Protocols in Molecular Biology, John Wiley & Sons, Inc., NY, N.Y. (1987-2001); Sambrook, et al., Molecular Cloning: A Laboratory Manual, 2 nd Edition, Cold Spring Harbor, N.Y. (1989); Harlow and Lane, Antibodies, a Laboratory Manual, Cold Spring Harbor, N.Y. (1989); Colligan, et al., eds., Current Protocols in Immunology, John Wiley & Sons, Inc., NY (1994-2001); Colligan et al., Current Protocols in Protein Science, John Wiley & Sons, NY, N.Y., (1997-2001).

In one approach, a hybridoma is produced by fusing a suitable immortal cell line (e.g., a myeloma cell line, such as, but not limited to, Sp2/0, Sp2/0-AG14, NSO, NS1, NS2, AE-1, L.5, L243, P3X63Ag8.653, Sp2 SA3, Sp2 MAI, Sp2 SS1, Sp2 SA5, U937, MLA 144, ACT IV, MOLT4, DA-1, JURKAT, WEHI, K-562, COS, RAJI, NIH 3T3, HL-60, MLA 144, NAMALWA, NEURO 2A, or the like, or heteromylomas, fusion products thereof, or any cell or fusion cell derived therefrom, or any other suitable cell line as known in the art), with antibody producing cells, such as, but not limited to, isolated or cloned spleen, peripheral blood, lymph, tonsil, or other immune or B cell containing cells, or any other cells expressing heavy or light chain constant or variable or framework or CDR sequences, either as endogenous or heterologous nucleic acid, as recombinant or endogenous, viral, bacterial, algal, prokaryotic, amphibian, insect, reptilian, fish, mammalian, rodent, equine, ovine, goat, sheep, primate, eukaryotic, genomic DNA, cDNA, rDNA, mitochondrial DNA or RNA, chloroplast DNA or RNA, hnRNA, mRNA, tRNA, single, double or triple stranded, hybridized, and the like or any combination thereof. See, e.g., Ausubel, supra, and Colligan, *Immunology*, supra, chapter 2, entirely incorporated herein by reference.

Antibody producing cells can also be obtained from the peripheral blood or, preferably, the spleen or lymph nodes, of humans or other suitable animals that have been immunized with the antigen of interest. Any other suitable host cell can also be used for expressing heterologous or endogenous nucleic acid encoding an antibody, specified fragment or variant thereof, of the present invention. The fused cells (hybridomas) or recombinant cells can be isolated using selective culture conditions or other suitable known methods, and cloned by limiting dilution or cell sorting, or other known methods. Cells which produce antibodies with the desired specificity can be selected by a suitable assay (e.g., ELISA, and more specifically a CD20 ELISA).

A human antigen specific antibody can additionally be generated by immunization of a transgenic animal (e.g., mouse, rat, hamster, non-human primate, and the like) capable of producing a repertoire of human antibodies, as described herein and/or as known in the art. Cells that produce a antigen specific antibody can be isolated from such animals and immortalized using suitable methods, such as the methods described herein.

Transgenic mice that can produce a repertoire of human antibodies that bind to human antigens such as CD20 can be produced by known methods (e.g., but not limited to, U.S. Pat. Nos. 5,770,428, 5,569,825, 5,545,806, 5,625,126, 5,625,825, 5,633,425, 5,661,016 and 5,789,650 issued to Lonberg et al.; Jakobovits et al. WO 98/50433, Jakobovits et al. WO 98/24893, Lonberg et al. WO 98/24884, Lonberg et al. WO 97/13852, Lonberg et al. WO 94/25585, Kucherlapate et al. WO 96/34096, Kucherlapate et al. EP 0463 151 B1, Kucherlapet al. EP 0710 719 A1, Surani et al. U.S. Pat. No. 5,545,807, Bruggemann et al. WO 90/04036, Bruggemann et al. EP 0438 474 B1, Lonberg et al. EP 0814 259 A2, Lonberg et al. GB 2 272 440 A, Lonberg et al. Nature 368:856-859 (1994), Taylor et al., Int. Immunol. 6(4)579-591 (1994), Green et al, Nature Genetics 7:13-21 (1994), Mendez et al., Nature Genetics 15:146-156 (1997), Taylor et al., Nucleic Acids Research 20(23):6287-6295 (1992), Tuaillon et al., Proc Natl Acad Sci USA 90(8)3720-3724 (1993), Lonberg et al., Int Rev Immunol 13(1):65-93 (1995) and Fishwald et al., Nat Biotechnol 14(7):845-851 (1996), which are each entirely incorporated herein by reference). Generally, these mice comprise at least one transgene comprising DNA from at least one human immunoglobulin locus that is functionally rearranged, or which can undergo functional rearrangement. The endogenous immunoglobulin loci in such mice can be disrupted or deleted to eliminate the capacity of the animal to produce antibodies encoded by endogenous genes.

Screening antibodies for specific binding to similar proteins or fragments can be conveniently achieved using peptide display libraries, phage display and other known methods. Peptide display method involves the screening of large collections of peptides for individual members having the desired function or structure. Antibody screening of peptide display libraries is well known in the art. The displayed peptide sequences can be from 3 to 5000 or more amino acids in length, frequently from 5-100 amino acids long, and often from about 8 to 25 amino acids long. In addition to direct chemical synthetic methods for generating peptide libraries, several recombinant DNA methods have been described. One type involves the display of a peptide sequence on the surface of a bacteriophage or cell. Each bacteriophage or cell contains the nucleotide sequence encoding the particular displayed peptide sequence. Such methods are described in PCT Patent Publication Nos. 91/17271, 91/18980, 91/19818, and 93/08278.

Other systems for generating libraries of peptides have aspects of both in vitro chemical synthesis and recombinant methods. Examples of these systems are described in, for example, PCT Patent Publication Nos. 92/05258, 92/14843, and 96/19256. See also, U.S. Pat. Nos. 5,658,754; and 5,643,768. Peptide display libraries, vector, and screening kits are commercially available from such suppliers as Invitrogen (Carlsbad, Calif.), and Cambridge Antibody Technologies (Cambridgeshire, UK). Examples of these systems are described in, for example, U.S. Pat. Nos. 4,704,692; 4,939,666; 4,946,778; 5,260,203; 5,455,030; 5,518,889; 5,534,621; 5,656,730; 5,763,733; 5,767,260; 5,856,456 assigned to Enzon; U.S. Pat. Nos. 5,223,409; 5,403,484; 5,571,698; 5,837,500 assigned to Dyax; U.S. Pat. Nos. 5,427,908; 5,580,717 assigned to Affymax; U.S. Pat. No. 5,885,793 assigned to Cambridge Antibody Technologies; U.S. Pat. No. 5,750,373 assigned to Genentech; U.S. Pat. Nos. 5,618,920; 5,595,898; 5,576,195; 5,698,435; 5,693,493; 5,698,417 assigned to Xoma, et al.; and Sambrook, supra. CD20 antibodies of the present invention can also be prepared using at least one antigen specific antibody encoding nucleic acid to provide transgenic animals or mammals, such as goats, cows, horses, sheep, rabbits and the like, that produce such antibodies in their milk. Such animals can be provided using known methods. Examples of these methods are described in, for example, but not limited to, U.S. Pat. Nos. 5,827,690; 5,849,992; 4,873,316; 5,849,992; 5,994,616; 5,565,362; 5,304,489, and the like. Each reference referred to herein is entirely incorporated by reference.

Anti-CD20 antibodies of the present invention can additionally be prepared using at least one antigen specific antibody encoding nucleic acid to provide transgenic plants and cultured plant cells (e.g., but not limited to, tobacco and maize) that produce such antibodies, specified portions or variants in the plant parts or in cells cultured therefrom. As a non-limiting example, transgenic tobacco leaves expressing recombinant proteins are successfully used to provide large amounts of recombinant proteins, e.g., using an inducible promoter. See, e.g., Cramer et al., Curr. Top. Microbol. Immunol. 240:95-118 (1999) and references cited therein. Also, transgenic maize are used to express mammalian proteins at commercial production levels, with biological activities equivalent to those produced in other recombinant systems or purified from natural sources. See, e.g., Hood et al., Adv. Exp. Med. Biol. 464:127-147 (1999) and references cited therein. Antibodies (including antibody fragments, such as single chain antibodies (ScFvs)) are produced in large amounts from transgenic plant seeds, including tobacco seeds and potato tubers. See, e.g., Conrad et al., Plant Mol. Biol. 38:101-109 (1998) and references cited therein. Thus, CD20 antibodies of the present invention are produced using transgenic plants, according to known methods. See also, e.g., Fischer et al., Biotechnol. Appl. Biochem. 30:99-108 (October, 1999), Ma et al., Trends Biotechnol. 13:522-7 (1995); Ma et al., Plant Physiol. 109:341-6 (1995); Whitelam et al., Biochem. Soc. Trans. 22:940-944 (1994); and references cited therein.

Antibody Engineering, Humanization and Resurfacing

Methods for engineering, humanizing or resurfacing non-human or human antibodies can also be used and are well known in the art. A humanized, resurfaced or similarly engineered antibody may have one or more amino acid residues from a source that is non-human, e.g., but not limited to, mouse, rat, rabbit, non-human primate or other mammal. These non-human amino acid residues are replaced by residues that are often referred to as "import" residues, which are typically taken from an "import" variable, constant or other domain of a known human sequence.

Known human Ig sequences are disclosed, e.g., in Kabat et al., Sequences of Proteins of Immunological Interest, U.S. Dept. Health (1983), which is incorporated herein in its entirety by reference.

Such imported sequences can be used to reduce immunogenicity or reduce, enhance or modify binding, affinity, on-rate, off-rate, avidity, specificity, half-life, or any other suitable characteristic, as known in the art. In general, the CDR residues are directly and most substantially involved in influencing CD20 binding. Accordingly, part or all of the non-human or human CDR sequences are maintained while the non-human sequences of the variable and constant regions may be replaced with human or other amino acids.

Antibodies can also optionally be humanized, resurfaced, engineered or human antibodies engineered with retention of high affinity for the antigen CD20 and other favorable biological properties. To achieve this goal, humanized (or human) or engineered anti-CD20 antibodies and resurfaced antibodies can be optionally prepared by a process of analysis of the parental sequences and various conceptual humanized and engineered products using three-dimensional models of the parental, engineered, and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen, such as CD20. In this way, framework (FR) residues can be selected and combined from the consensus and import sequences so that the desired antibody characteristic, such as increased affinity for the target antigen(s), is achieved.

Humanization, resurfacing or engineering of antibodies of the present invention can be performed using any known method, such as but not limited to those described in, Winter (Jones et al., Nature 321:522 (1986); Riechmann et al., Nature 332:323 (1988); Verhoeyen et al., Science 239:1534 (1988)), Sims et al., J. Immunol. 151: 2296 (1993); Chothia and Lesk, J. Mol. Biol. 196:901 (1987), Carter et al., Proc. Natl. Acad. Sci. U.S.A. 89:4285 (1992); Presta et al., J. Immunol. 151:2623 (1993), U.S. Pat. Nos. 5,639,641, 5,723,323; 5,976,862; 5,824,514; 5,817,483; 5,814,476; 5,763,192; 5,723,323; 5,766,886; 5,714,352; 6,204,023; 6,180,370; 5,693,762; 5,530,101; 5,585,089; 5,225,539; 4,816,567; PCT/: US98/16280; US96/18978; US91/09630; US91/05939; US94/01234; GB89/01334; GB91/01134; GB92/01755; WO90/14443; WO90/14424; WO90/14430; EP 229246; 7,557,189; 7,538,195; and 7,342,110, each of which is entirely incorporated herein by reference, including the references cited therein.

Fc Regions

In certain aspects, the antibody comprises an altered (e.g., mutated) Fc region. For example, in some aspects, the Fc region has been altered to reduce or enhance the effector functions of the antibody. In some aspects, the Fc region is an isotype selected from IgM, IgA, IgG, IgE, or other isotype.

Alternatively or additionally, it may be useful to combine amino acid modifications with one or more further amino acid modifications that alter C1q binding and/or the complement dependent cytotoxicity (CDC) function of the Fc region of an antigen binding molecule. The starting polypeptide of particular interest may be one that binds to C1q and displays complement dependent cytotoxicity. Polypeptides with pre-existing C1q binding activity, optionally further having the ability to mediate CDC, may be modified such that one or both of these activities are enhanced. Amino acid modifications that alter C1q and/or modify its complement dependent cytotoxicity function are described, for example, in WO0042072, which is hereby entirely incorporated by reference.

One can design an Fc region of an antibody of the present invention with altered effector function, e.g., by modifying C1q binding and/or FcγR binding and thereby changing CDC activity and/or ADCC activity. "Effector functions" are responsible for activating or diminishing a biological activity (e.g., in a subject). Examples of effector functions include, but are not limited to: C1q binding; complement dependent cytotoxicity (CDC); Fc receptor binding; antibody-dependent cell-mediated cytotoxicity (ADCC); phagocytosis; down regulation of cell surface receptors (e.g., B cell receptor; BCR), etc. Such effector functions may require the Fc region to be combined with a binding domain (e.g., an antibody variable domain) and can be assessed using various assays (e.g., Fc binding assays, ADCC assays, CDC assays, etc.).

For example, one can generate a variant Fc region of the engineered anti-CD20 antibody with improved C1q binding and improved FcγRIII binding (e.g., having both improved ADCC activity and improved CDC activity). Alternatively, if it is desired that effector function be reduced or ablated, a variant Fc region can be engineered with reduced CDC activity and/or reduced ADCC activity. In other aspects, only one of these activities may be increased, and, optionally, also the other activity reduced (e.g., to generate an Fc region variant with improved ADCC activity, but reduced CDC activity, and vice versa). An exemplary Fc mutant is the triple residue change, S239D, A330L, and I332D (EU numbering system) in which ADCC is enhanced and CDC activity is diminished. Non-limiting methods for designing such mutants can be found, for example, in Lazar et al. (2006, Proc. Natl. Acad. Sci. U.S.A. 103(11): 4005-4010) and Okazaki et al. (2004, J. Mol. Biol. 336(5):1239-49). See also WO 03/074679, WO 2004/029207, WO 2004/099249, WO2006/047350, WO 2006/019447, WO 2006/105338, WO 2007/041635.

Fc mutations can also be introduced in engineered antibodies to alter their interaction with the neonatal Fc receptor (FcRn) and improve their pharmacokinetic properties. A collection of human Fc variants with improved binding to the FcRn have been described and include, for example, Shields et al., 2001. High resolution mapping of the binding site on human IgG1 for FcγRI, FcγRII, FcγRIII, and FcRn and design of IgG1 variants with improved binding to the FcγR, J. Biol. Chem. 276:6591-6604), which is hereby entirely incorporated by reference.

Another type of amino acid substitution serves to alter the glycosylation pattern of the Fc region of an antibody. Glycosylation of an Fc region is typically either N-linked or O-linked. N-linked generally refers to the attachment of the carbohydrate moiety to the side chain of an asparagine residue. The recognition sequences for enzymatic attachment of the carbohydrate moiety to the asparagine side chain peptide sequences are asparagine-X-serine and asparagine-X-threonine, where X is any amino acid except proline. Thus, the presence of either of these peptide sequences in a polypeptide creates a potential glycosylation site. O-linked glycosylation generally refers to the attachment of one of the sugars N-aceylgalactosamine, galactose, or xylose to a hydroxyamino acid, most commonly serine or threonine, although 5-hydroxyproline or 5-hydroxylysine may also be used.

The glycosylation pattern of an antibody or fragment thereof may be altered, for example, by deleting one or more glycosylation site(s) found in the polypeptide, and/or adding one or more glycosylation site(s) that are not present in the polypeptide. Removal of glycosylation sites in the Fc region of a antibody or antibody fragment is conveniently accomplished by altering the amino acid sequence such that it eliminates one or more of the above-described tripeptide sequences (for N-linked glycosylation sites). An exemplary glycosylation variant has an amino acid substitution of residue N297 to A297 (EU numbering system) of the heavy chain. The removal of an O-linked glycosylation site may also be achieved by the substitution of one or more glycosylated serine or threonine residues with any amino acid besides serine or threonine.

Where the antibody comprises an Fc region, the carbohydrate attached thereto may be altered. For example, antibodies with a mature carbohydrate structure that lacks fucose attached to an Fc region of the antibody are described in, for example, US Pat. Appl. No. US 2003/0157108 (Presta, L.) and US 2004/0093621 (Kyowa Hakko Kogyo Co., Ltd). Antibodies with a bisecting N-acetylglucosamine (GlcNAc) in the carbohydrate attached to an Fc region of the antibody are referenced in, for example, WO 2003/011878, Jean-Mairet et al. and U.S. Pat. No. 6,602,684, Umana et al. Antibodies with at least one galactose residue in the oligosaccharide attached to an Fc region of the antibody are reported in, for example, WO 1997/30087, Patel et al. See also, WO 1998/58964 and WO 1999/22764 (Raju, S.) concerning antibodies with altered carbohydrate attached to the Fc region thereof. See also, for example, US 2005/0123546 (Umana et al.) regarding antigen-binding molecules with modified glycosylation.

In certain aspects, a glycosylation variant comprises an Fc region, wherein a carbohydrate structure attached to the Fc region lacks fucose. Such variants have improved ADCC function. Examples of publications related to "defucosylated" or "fucose-deficient" antibodies include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; Okazaki et al., J. Mol. Biol., 336:1239-1249 (2004); Yamane Ohnuki et al., Biotech. Bioeng., 87: 614 (2004). Non-limiting examples of cell lines producing defucosylated antibodies include Lec13 CHO cells deficient in protein fucosylation (Ripka et al. Arch. Biochem. Biophys. 249:533-545 (1986); US Pat. Appl. No. US 2003/0157108 AI, Presta, L; and WO 2004/056312 AI, Adams et al., especially at Example 11), knockout cell lines, such as alpha-1,6-fucosyltransferase gene, FUT8, knockout CHO cells (Yamane-Ohnuki et al., Biotech. Bioeng., 87: 614 (2004)), and through the use of fucosylation pathway inhibitors such as, for example, castanospermine in cell culture media (US Pat. Appl. No. 2009/0041765).

In certain aspects, the antibody of the present invention is expressed in cells that express beta (1,4)-N-acetylglucosaminyltransferase III (GnT III), such that GnT III adds GlcNAc to the human engineered antigen specific antibody. Methods for producing antibodies in such a fashion are provided in WO/9954342, WO/03011878, patent publication 20030003097A1, and Umana et al., Nature Biotechnology, 17:176-180, February 1999.

Antibody Affinity

The antibodies of the invention bind human CD20, with a wide range of affinities ($K_D$). In a preferred aspect, at least one mAb of the present invention can optionally bind human antigen with high affinity. For example, a human or human engineered or humanized or resurfaced mAb can bind human antigen with a $K_D$ equal to or less than about $10^{-7}$ M, such as but not limited to, 0.1-9.9 (or any range or value therein)$\times 10^{-7}$, $10^{-8}$, $10^{-9}$, $10^{-10}$, $10^{-11}$, $10^{-12}$, $10^{-13}$, $10^{-14}$, $10^{-15}$ or any range or value therein, as determined by enzyme-linked immunoabsorbent assay (ELISA), surface plasmon resonance (SPR) or the KinExA® method, as practiced by those of skill in the art. The anti-CD20 antibodies bind with a Kd of about $10^{-9}$ M or less, more specifically about $10^{-9}$ to $10^{-10}$ M.

The affinity or avidity of an antibody for an antigen is determined experimentally using any suitable method well known in the art, e.g. enzyme-linked immunoabsorbent assay (ELISA), or radioimmunoassay (RIA), or kinetics (e.g., BIACORE™ analysis) or flow cytometry based assays. Direct binding assays as well as competitive binding assay formats can be readily employed. (See, for example, Berzofsky, et al., "Antibody-Antigen Interactions," In Fundamental Immunology, Paul, W. E., Ed., Raven Press: New York, N.Y. (1984); Kuby, Janis Immunology, W. H. Freeman and Company: New York, N.Y. (1992); and methods described herein. The measured affinity of a particular antibody-antigen interaction can vary if measured under different conditions (e.g., salt concentration, pH, temperature). Thus, measurements of affinity and other antigen-binding parameters (e.g., KD or $K_d$, $K_{on}$, $K_{off}$) are preferably made with standardized solutions of antibody and antigen, and a standardized buffer, as known in the art and such as the buffer described herein.

In one aspect, binding assays can be performed using flow cytometry on cells expressing the CD20 antigen on the surface. For example, such CD20-positive cells were incubated with varying concentrations of anti-CD20 antibodies using $1\times 10^5$ cells per sample in 100 μL FACS buffer (RPMI-1640 medium supplemented with 2% normal goat serum). Then, the cells were pelleted, washed, and incubated for 1 h with 100 μL of FITC-conjugated goat anti-mouse IgG-antibody (such as is obtainable from, for example Jackson Laboratory, 6 μg/mL in FACS buffer). The cells were pelleted again, washed with FACS buffer and resuspended in 200 μL of PBS containing 1% formaldehyde. Samples were acquired, for example, using a FACSCalibur flow cytometer with the HTS multiwell sampler and analyzed using CellQuest Pro (all from BD Biosciences, San Diego, US). For each sample the mean fluorescence intensity for FL1 (MFI) was exported and plotted against the antibody concentration in a semi-log plot to generate a binding curve. A sigmoidal dose-response curve is fitted for binding curves and EC50 values are calculated using programs such as GraphPad Prism v4 with default parameters (GraphPad software, San Diego, Calif.). EC50 values can be used as a measure for the apparent dissociation constant "Kd" or "KD" for each antibody.

Percent (%) amino acid sequence identity with respect to a peptide or polypeptide sequence is also defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, those discussed herein, such as by using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. In situations where ALIGN-2 is available and can be employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

Desirably, two or more amino acid sequences are at least 50%, 60%, 70%, 80%, or 90% identical. More desirably, two or more amino acid sequences are at least 95%, 96%, 97%, 98%, 99%, or even 100% identical. Unless specifically stated otherwise, all % amino acid sequence identity values used herein are obtained as described in the immediately preceding paragraph using, for example, the ALIGN-2 or BLAST computer programs.

Antibody Use

Generally, some forms of the antigen specific antibodies useful in the methods and compositions of the present invention can optionally be characterized by high affinity binding to antigen and, optionally and preferably, as having low toxicity and adverse consequences on the recipient. In particular, an antibody, specified fragment or variant of the invention, where the individual components, such as the variable region, constant region and framework, individually and/or collectively, optionally and preferably possess low immunogenicity, is useful in the present invention. The antibodies that can be used in the invention are optionally characterized by their ability to treat patients for extended periods with measurable alleviation of symptoms and low and/or acceptable toxicity. Low or acceptable immunogenicity and/or high affinity, as well as other suitable properties, can contribute to the therapeutic results achieved. "Low immunogenicity" is defined herein as at least the incidence of titrable levels of antibodies to an antigen in patients treated with an antibody as occurring in less than 25% of patients treated, preferably, in less than 10% of patients treated with the recommended dose for the recommended course of therapy during the treatment period.

The isolated nucleic acids of the present invention can be used for production of at least one CD20 specific antibody fragment thereof or specified variant thereof, which can be used to measure or effect in an cell, tissue, organ or animal (including mammals and humans), to diagnose, monitor, modulate, treat, alleviate, help prevent the incidence of, or reduce the symptoms of, at least one condition, selected from, but not limited to, at least one of an immune disorder or disease, a cardiovascular disorder or disease, an infectious, malignant, and/or neurologic disorder or disease, or other known or specified antigen related condition.

Such a method can comprise administering an effective amount of a composition or a pharmaceutical composition comprising at least one antigen specific antibody, such as an anti-CD20 antibody or fragment, to a cell, tissue, organ, animal or patient in need of such modulation, treatment, alleviation, prevention, or reduction in symptoms, effects or mechanisms. The effective amount can comprise an amount of about 0.001 to 500 mg/kg per single (e.g., bolus), multiple or continuous administration, or to achieve a serum concentration of about 0.01-5000 μg/ml serum concentration per single, multiple, or continuous administration, or any effective range or value therein, as done and determined using known methods, as described herein or known in the relevant arts.

Exemplary Antibodies

Preferred antigen specific CD20 antibodies of the invention have the sequences shown. For example, an antigen specific antibody of the invention includes one of the light chain CDR sequences shown in Table 1 (i.e., CDRL1, CDRL2, and CDRL3) and/or one of the heavy chain CDR sequences shown in Table 1 (i.e., CDRH1, CDRH2, and CDRH3). More specifically, an antiCD20-20 antibody has the CDRL1 of SEQ ID NO:31, CDRL2 of SEQ ID NO: 32, CDRL3 of SEQ ID NO: 33, CDRH1 of SEQ ID NO: 34, CDRH2 of SEQ ID NO: 35, CDRH3 of SEQ ID NO: 37. And an anti-CD20-4 antibody has the CDRL1 of SEQ ID NO: 23, CDRL2 of SEQ ID NO: 24, CDRL3 of SEQ ID NO: 25, CDRH1 of SEQ ID NO: 26, CDRH2 of SEQ ID NO: 27, CDRH3 of SEQ ID NO: 28.

Exemplary aspects of the present invention include:
Murine Amino Acid Sequences

```
muCD20-4LC
                                          [SEQ ID NO: 1]
DIVMTQSQKFMSTSVGDRVSVNCKASQNVGTNVAWYQQKPRQSPKGLIYS

ASFRYSGVPDRFTGSGSGTDFTLTIFNVQSDDLAEYFCQQYNNYPLTFGG

GTKLEIKRADAAPTVSIFPPSSEQLTSGGASVVCFLNNFYPKDINVKWKI

DGSERQNGVLNSWTDQDSKDSTYSMSSTLTLTKDEYERHNSYTCEATHKT

STSPIVKSFNRNEC;

muCD20-4HC
                                          [SEQ ID NO: 2]
EVKVEESGGGLVKTGGSMKLSCVASGFSFNNYWMNWVRQSPEKGLEWVAE

IRLKSNNYATHYVESVKGRFTISRDDSKSSVYLQMNNLRAEDTGIYYCTG

WDDYAMDHWGQGISVTVSSAKTTAPSVYPLAPVCGDTTGSSVTLGCLVKG

YFPEPVTLTWNSGSLSSGVHTFPAVLQSDLYTLSSSVTVTSSTWPSQSIT

CNVAHPASSTKVDKKIEPRGPTIKPCPPCKCPAPNLLGGPSVFIFPPKIK

DVLMISLSPIVTCVVVDVSEDDPDVQISWFVNNVEVHTAQTQTHREDYNS
```

TLRVVSALPIQHQDWMSGKEFKCKVNNKDLPAPIERTISKPKGSVRAPQV
YVLPPPEEEMTKKQVTLTCMVTDFMPEDIYVEWTNNGKTELNYKNTEPVL
DSDGSYFMYSKLRVEKKNWVERNSYSCSVVHEGLHNHHTTKSFSRTPGK;

muCD20-20LC
[SEQ ID NO: 3]
DIKMTQSPSSMYTSLGERVTITCKASQDINSFLSWFQQKPGKSPKTLIYR
AYRLVDGVPSRFSGSGSGQDYSLTISSLEFEDMGIYYCLQSGAFPLTFGA
GTKLELKRADAAPTVSIFPPSSEQLTSGGASVVCFLNNFYPKDINVKWKI
DGSERQNGVLNSWTDQDSKDSTYSMSSTLTLTKDEYERHNSYTCEATHKT
STSPIVKSFNRNEC muCD20-20HC
[SEQ ID NO: 4]
QVQLQQSGAELARPGASVKLSCKASGYTFTSYWMHWVKQRPGQGLEWIGA
IYPGDGDTRYTQKFKGKATLTADKSSYTAYMQLSSLASEDSAVYYCARSP
DFYGSGYDFDYWGQGTTLTVSSAKTTPPSVYPLAPGSAAQTNSMVTLGCL
VKGYFPEPVTVTWNSGSLSSGVHTFPAVLESDLYTLSSSVTVPSSMRPSE
TVTCNVAHPASSTKVDKKIVPRDCGCKPCICTVPEVSSVFIFPPKPKDVL
TITLTPKVTCVVVDISKDDPEVQFSWFVDDVEVHTAQTQPREEQFNSTFR
SVSELPIMHQDWLNGKEFKCRVNSAAFPAPIEKTISKTKGRPKAPQVYTI
PPPKEQMAKDKVSLTCMITDFFPEDITVEWQWNGQPAENYKNTQPIMNTN
GSYFVYSKLNVQKSNWEAGNTFTCSVLHEGLHNHHTEKSLSHSPGK;

Murine Variable Region Amino Acid Sequences muCD20-4VL
[SEQ ID NO: 5]
DIVMTQSQKFMSTSVGDRVSVNCKASQNVGTNVAWYQQKPRQSPKGLIYS
ASFRYSGVPDRFTGSGSGTDFTLTIFNVQSDDLAEYFCQQYNNYPLTFGG
GTKLEIKR;

muCD20-4VH
[SEQ ID NO: 6]
EVKVEESGGGLVKTGGSMKLSCVASGFSFNNYWMNWVRQSPEKGLEWVAE
IRLKSNNYATHYVESVKGRFTISRDDSKSSVYLQMNNLRAEDTGIYYCTG
WDDYAMDHWGQGISVTVSS;

muCD20-20VL
[SEQ ID NO: 7]
DIKMTQSPSSMYTSLGERVTITCKASQDINSFLSWFQQKPGKSPKTLIYR
AYRLVDGVPSRFSGSGSGQDYSLTISSLEFEDMGIYYCLQSGAFPLTFGA
GTKLELKR;

muCD20-20VH
[SEQ ID NO: 8]
QVQLQQSGAELARPGASVKLSCKASGYTFTSYWMHWVKQRPGQGLEWIGA
IYPGDGDTRYTQKFKGKATLTADKSSYTAYMQLSSLASEDSAVYYCARSP
DFYGSGYDFDYWGQGTTLTVSS;

Murine Variable Region DNA Sequences muCD20-4VL
[SEQ ID NO: 9]
gacattgtgatgacccagtctcaaaaattcatgtccacatcagtaggaga
cagggtcagcgtcaactgcaaggccagtcagaatgtgggcactaatgtag
cctggtatcaacagaaaccaaggcaatctcctaaaggattgatttattcg
gcatccttccggtacagtggagtccctgatcgcttcacaggcagtggatc
tgggacagatttcactctcaccatcttcaatgtgcagtctgacgacttgg
cagagtatttctgtcagcaatataataattatcctctgacgttcggtgga
ggcaccaagctggaaatcaaacgg;

muCD20-4VH
[SEQ ID NO: 10]
gaagtgaaggttgaggagtctggaggaggcttggtgaaaactggaggatc
catgaaactctcctgtgttgcctctggattcagtttcaataactattgga
tgaactgggtccgccagtctccagagaagggcttgagtgggttgctgaa
atcagattgaaatctaataattatgcgacacattatgtggagtctgtgaa
agggaggttcaccatctcaagagatgattccaaaagtagtgtctacctgc
aaatgaataacttaagagctgaagacactggcatttattactgtactggc
tgggacgattatgctatggaccactggggtcaaggaatctcagtcaccgt
ctcctcag;

muCD20-20VL
[SEQ ID NO: 11]
gacatcaagatgacccagtctccatcttccatgtatacatctctaggaga
gagagtcactatcacttgcaaggcgagtcaggacattaatagcttttttaa
gctggttccaacagaaaccagggaaatctcctaagaccctgatctatcgt
gcatacagattggtagatgggtcccatcaaggttcagtggcagtggatc
tggacaagattattctctcaccatcagcagcctggagtttgaagatatgg
gaatttattattgtctacagtctggtgcgtttccgctcacgttcggtgct
gggaccaagctggaactgaaacgg;

muCD20-20VH
[SEQ ID NO: 12]
caggttcagctccagcagtctggggctgagctggcaagacctggggcttc
agtgaagttgtcctgcaaggcttctggctacacttttactagctactgga
tgcattgggtaaaacagaggcctggacagggtctggaatggattgggct
atttatcctggagatggtgatactaggtacactcagaagtttaagggcaa
ggccacattgactgcagataaatcctcctacacagcctacatgcaactca
gtagcttggcatctgaagactctgcggtctattactgtgcaagatcaccc
gatttctacggtagtggctacgactttgactactggggccaaggcaccac
tctcacagtctcctca;

Humanized CD20-4 Amino Acid Sequences huCd20-4LC
[SEQ ID NO: 13]
DIQMTQSPSTMSTSVGDRVSVNCKASQNVGTNVAWYQQKPGKSPKGLIYS
ASFRYSGVPSRFTGSGSGTDFTLTIFNVQPDDLAEYFCQQYNNYPLTFGG
GTKLEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC;

huCD20-4HC

[SEQ ID NO: 14]
EVQVEESGGGLVQPGGSMRLSCVASGFSFNNYWMNWVRQSPGKGLEWVAE
IRLKSNNYATHYVDSVKGRFTISRDDSKSSVYLQMNNLRAEDTGIYYCTG
WDDYAMDHWGQGISVTVSSASTKGPSVFPLAPSSKSTSGGTAALGCLVKD
YFPEPVTVSWNSGALTSGVHTFPAVLQSSGLYSLSSVVTVPSSSLGTQTY
ICNVNHKPSNTKVDKKVEPKSCDKTHTCPPCPAPELLGGPSVFLFPPKPK
DTLMISRTPEVTCVVVDVSHEDPEVKFNWYVDGVEVHNAKTKPREEQYNS
TYRVVSVLTVLHQDWLNGKEYKCKVSNKALPAPIEKTISKAKGQPREPQV
YTLPPSRDELTKNQVSLTCLVKGFYPSDIAVEWESNGQPENNYKTTPPVL
DSDGSFFLYSKLTVDKSRWQQGNVFSCSVMHEALHNHYTQKSLSLSPGK;

Humanized CD20-4 Variable Region Amino Acid Sequences huCD20-4VL
[SEQ ID NO: 15]
DIQMTQSPSTMSTSVGDRVSVNCKASQNVGTNVAWYQQKPGKSPKGLIYS
ASFRYSGVPSRFTGSGSGTDFTLTIFNVQPDDLAEYFCQQYNNYPLTFGG
GTKLEIKR;

huCD20-4VH
[SEQ ID NO: 16]
EVQVEESGGGLVQPGGSMRLSCVASGFSFNNYWMNWVRQSPGKGLEWVAE
IRLKSNNYATHYVDSVKGRFTISRDDSKSSVYLQMNNLRAEDTGIYYCTG
WDDYAMDHWGQGISVTVSS;

Humanized and Chimeric Variable Region DNA Sequences huCD20-4VL
[SEQ ID NO: 17]
gaattcgccaccatggggtggtcatgtataatccttttcttggttgctac
cgctaccggggttcactccgacatccagatgacccaatctccctccacca
tgtctacttccgtcggggacagggtgtcagtgaattgcaaagccagccaa
aacgtcggcaccaatgtcgcttggtaccagcagaagcccggtaaaagccc
taagggactgatctacagcgctagcttccgttacagtggtgtcccttctc
gcttcacagggtctggatctggaaccgacttcactctcactattttcaat
gttcaaccagatgacctcgcagaatacttttgccagcagtacaacaatta
tccccttaccttcggtggcggcaccaagctggaaatcaagcgtacg;

huCD20-4VH
[SEQ ID NO: 18]
aagcttgccaccatgggatggtcttgcatcatactgttcctggttgcaac
cgctacaggagtgcatagcgaggtgcaggtggaggagtcaggaggggggac
tggtacagcccggcggttctatgagactcagttgcgtcgccagtggcttc
agctttaataactactggatgaattgggtgagacagtcacccggaaaagg
ccttgaatgggtagctgagattcggcttaagtccaataattacgctaccc
attatgtggactctgttaaaggccgttttactatttctagggacgactct
aaatctagcgtctcttgcagatgaacaaccttcgtgccgaggacacagg
aatctactattgtaccggttgggacgattacgcaatggaccactggggcc
agggtatcagcgtaacagtgtctagcgcatctacaaagggccc;

chCD20-4VL
[SEQ ID NO: 19]
gaattcgccaccatggggctggagttgtatcatcctcttcctggtagccac
agccacaggagttcactcagacattgtcatgacccagtctcagaagttca
tgtctacatccgtcggcgaccgggtgagcgtgaactgtaaggcaagccaa
aatgtggggactaacgtcgcctggtatcaacagaagcctaggcaatcccc
caaaggctcatatattccgcaagtttccgttattccggggtacctgaca
ggtttactggttcagggtctggcaccgattttaccctgaccatcttcaat
gtacagagtgacgatctcgccgagtacttttgccaacagtataacaacta
tcctctcactttcggggggaggtaccaagctggagattaaacgtacg;

chCD20-4VH
[SEQ ID NO: 20]
aagcttgccaccatgggctggtcctgcatcatcctcttctggtggccac
agctaccggcgttcacagcgaggtgaaggtcgaagaatctggcggggac
tggttaaaacaggcggctctatgaagctctcttgtgtggcttccggcttc
agcttcaacaattattggatgaattgggtgcgccagtctccagagaaggg
gttggaatgggtcgcagaaatacgactgaagagcaataattatgccaccc
attatgtggaaagcgttaaaggcagatttaccatctcaagggacgatagt
aaatctccgtgtaccttcagatgaacaatcttagagccgaggataccgg
gatctactattgcactggatgggacgactatgctatggatcactggggcc
agggcattagcgtgaccgttagctctgctagtaccaagggccc;

chCD20-20VH
[SEQ ID NO: 21]
aagcttgccaccatgggggtggagttgtataatcctgtttcttgtggcaac
agccacaggagtccactcccaggtacagctgcagcagtctggcgctgagc
tggcccgccccggagcatccgtgaagttgagctgcaaagcaagtgggtac
accttcaccagttattggatgcattgggtgaagcagagacctggacaggg
tctggagtggattggcgctatctatcccggagatggcgatacacggtaca
cacagaaatttaagggcaaggccactcttactgcagataaatccagctac
acagcttacatgcaactctcttctctggcttccgaagactctgcagtgta
ttattgcgctaggtccccagatttctacggggagtggggtacgacttcgatt
actggggacaaggaactacacttactgtgagttccgcctcaacaaagggc
cc;

chCD20-20VL
[SEQ ID NO: 22]
gaattcgccaccatgggctggtcttgtattatactgttcctggtcgctac
tgccaccggggtgcacagcgatattaagatgacccagagtccatcaagca
tgtatacatcccttggagagagagtgactataacctgcaaagcatcacaa
gacattaacagcttcctcagctggttccagcagaagcccgggaagagtcc
caaaacacttatctatagagcataccggctggtcgacggtgtacctagtc
gcttcagcggctccggaagtgggcaggattactcacttacaatctctagt
ctggagttcgaggacatgggggattactactgtcttcaaagtggagcatt
tccactcacatttggggcaggcaccaagctggagctgaaacgtacg;

Murine and Human CD20-4 Resurfacing CDR's

```
Light chain
CD20-4_LC_CDR1
KASQNVGTNVA                          [SEQ ID NO: 23]

CD20-4_LC_CDR2
SASFRYS                              [SEQ ID NO: 24]

CD20-4_LC_CDR3
QQYNNYPLT                            [SEQ ID NO: 25]

Heavy Chain
CD20-4_HC_CDR1
NYWMN                                [SEQ ID NO: 26]

CD20-4_HC_CDR2-AbM
EIRLKSNNYATH                         [SEQ ID NO: 27]

CD20-4_HC_CDR3
WDDYAMDH                             [SEQ ID NO: 28]

Kabat Defined murine and humanized CD20-4 HC CDR2
murine-HC-CDR2-Kabat
EIRLKSNNYATHYVESVKG                  [SEQ ID NO: 29]

human-HC-CDR2-Kabat
EIRLKSNNYATHYVDSVKG                  [SEQ ID NO: 30]
```

Murine and Chimeric CD20-20 CDR Sequences

```
   Light Chain
   CD20-20_LC_CDR1
   KASQDINSFLS                       [SEQ ID NO: 31]

CD20-20_LC_CDR2
   RAYRLVD                           [SEQ ID NO: 32]

CD20-20_LC_CDR3
   LQSGAFPLT                         [SEQ ID NO: 33]

Heavy Chain
   CD20-20_HC_CDR1
   SYWMH                             [SEQ ID NO: 34]

CD20-20_HC_CDR2
   AIYPGDGDTR                        [SEQ ID NO: 35]

CD20-20_HC_CDR3
   SPDFYGSGYDFDY                     [SEQ ID NO: 37]

Kabat Defined murine CD20-20 HC CDR2
   CD20-20_HC_CDR2-Kabat
   AIYPGDGTRYTQKFKG                  [SEQ ID NO: 36]
```

One having ordinary skill in the art understands that the sequences in the present application are non-limiting examples.

Functional Equivalents, Antibody Variants and Derivatives

Functional equivalents further include fragments of antibodies that have the same, or comparable binding characteristics to those of the whole or intact antibody. Such fragments may contain one or both Fab fragments or the F(ab')$_2$ fragment. Preferably the antibody fragments contain all six complementarity determining regions of the whole antibody, although fragments containing fewer than all of such regions, such as one, two, three, four or five CDRs, are also functional. Further, the functional equivalents may be or may combine members of any one of the following immunoglobulin classes: IgG, IgM, IgA, IgD, or IgE, and the subclasses thereof.

In certain aspects of the invention, the anti-CD20 antibodies can be modified to produce fusion proteins; i.e., the antibody, or a fragment fused to a heterologous protein, polypeptide or peptide. In certain aspects, the protein fused to the portion of an anti-CD20 antibody is an enzyme component of ADEPT. Examples of other proteins or polypeptides that can be engineered as a fusion protein with an anti-CD20 antibody include, but are not limited to toxins such as ricin, abrin, ribonuclease, DNase I, Staphylococcal enterotoxin-A, pokeweed anti-viral protein, gelonin, diphtherin toxin, *Pseudomonas* exotoxin, and *Pseudomonas* endotoxin. See, for example, Pastan et al., Cell, 47:641 (1986); and Goldenberg et al., Cancer Journal for Clinicians, 44:43 (1994). Enzymatically active toxins and fragments thereof which can be used include diphtheria A chain, non-binding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin and the tricothecenes. Non-limiting examples are included in, for example, WO 93/21232 published Oct. 28, 1993 incorporated entirely herein by reference.

Additional fusion proteins may be generated through the techniques of gene-shuffling, motif-shuffling, exon-shuffling, and/or codon-shuffling (collectively referred to as "DNA shuffling"). DNA shuffling may be employed to alter the activities of the antibodies or fragments thereof (e.g., an antibody or a fragment thereof with higher affinities and lower dissociation rates). See, generally, U.S. Pat. Nos. 5,605,793; 5,811,238; 5,830,721; 5,834,252; and 5,837,458, and Patten et al., 1997, Curr. Opinion Biotechnol., 8:724-33; Harayama, 1998, Trends Biotechnol., 16(2):76-82; Hansson et al., 1999, J. Mol. Biol., 287:265-76; and Lorenzo and Blasco, 1998, Biotechniques, 24(2):308-313, each of which is hereby incorporated by reference in its entirety. The antibody can further be a binding-domain immunoglobulin fusion protein as described in U.S. Publication 20030118592, U.S. Publication 200330133939, and PCT Publication WO 02/056910, all to Ledbetter et al., which are incorporated herein by reference in their entireties.

Domain Antibodies. The anti-CD20 antibodies of the compositions and methods of the invention can be domain antibodies, e.g., antibodies containing the small functional binding units of antibodies, corresponding to the variable regions of the heavy (VH) or light (VL) chains of human antibodies. Examples of domain antibodies include, but are not limited to, those available from Domantis Limited (Cambridge, UK) and Domantis Inc. (Cambridge, Mass., USA), that are specific to therapeutic targets (see, for example, WO04/058821; WO04/003019; U.S. Pat. Nos. 6,291,158; 6,582,915; 6,696,245; and 6,593,081). Commercially available libraries of domain antibodies can be used to identify anti-CD20 domain antibodies. In certain aspects, the anti-CD20 antibodies of the invention comprise a CD20 functional binding unit and a Fc gamma receptor functional binding unit.

Diabodies. The term "diabodies" refers to small antibody fragments with two antigen-binding sites, which fragments comprise a heavy chain variable domain (VH) connected to a light chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA, 90:6444-6448 (1993).

Vaccibodies. In certain aspects of the invention, the anti-CD20 antibodies are vaccibodies. Vaccibodies are dimeric polypeptides. Each monomer of a vaccibody consists of a scFv with specificity for a surface molecule on an APC connected through a hinge region and a Cg3 domain to a second scFv. In other aspects of the invention, vaccibodies containing as one of the scFv's an anti-CD20 antibody fragment may be used to juxtapose B cells to be destroyed and an effector cell that mediates ADCC. For example, see, Bogen et al., U.S. Patent Application Publication No. 20040253238.

Linear Antibodies. In certain aspects of the invention, the anti-CD20 antibodies are linear antibodies. Linear antibodies comprise a pair of tandem Fd segments (VH-CH1-VH-CH1) which form a pair of antigen-binding regions. Linear antibodies can be bispecific or monospecific. Non-limiting examples of linear antibodies are disclosed in, for example, Zapata et al., Protein Eng., 8(10): 1057-1062 (1995).

Parent Antibody. In certain aspects of the invention, the anti-CD20 antibody is a parent antibody. A "parent antibody" is an antibody comprising an amino acid sequence which lacks, or is deficient in, one or more amino acid residues in or adjacent to one or more hypervariable regions thereof compared to an altered/mutant antibody as herein disclosed. Thus, the parent antibody has a shorter hypervariable region than the corresponding hypervariable region of an antibody mutant as herein disclosed. The parent polypeptide may comprise a native sequence (i.e., a naturally occurring) antibody (including a naturally occurring allelic variant) or an antibody with pre-existing amino acid sequence modifications (such as other insertions, deletions and/or substitutions) of a naturally occurring sequence. Preferably the parent antibody is a humanized antibody or a human antibody.

Antibody Fragments. "Antibody fragments" comprise a portion of a full-length antibody, generally the antigen binding or variable region thereof. Examples of antibody fragments include Fab, Fab', F(ab')2, and Fv fragments; diabodies; linear antibodies; single-chain antibody molecules; and multispecific antibodies formed from antibody fragments, among others.

Traditionally, fragments were derived via proteolytic digestion of intact antibodies (see, e.g., Morimoto et al., Journal of Biochemical and Biophysical Methods, 24:107-117 (1992) and Brennan et al., Science, 229:81 (1985)). However, fragments can now be produced directly by recombinant host cells. For example, the antibody fragments can be isolated from the antibody phage libraries as discussed herein. Alternatively, Fab'-SH fragments can be directly recovered from *E. coli* and chemically coupled to form F(ab')2 fragments (Carter et al., Bio Technology, 10:163-167 (1992)). According to another approach, F(ab')2 fragments can be isolated directly from recombinant host cell culture. Other techniques for the production of antibody fragments are apparent to the skilled practitioner given the detailed teachings in the present specification. In other aspects, the antibody of choice is a single-chain Fv fragment (scFv). See, for example, WO 93/16185. In certain aspects, the antibody is not a Fab fragment.

Bispecific Antibodies. Bispecific antibodies are antibodies that have binding specificities for at least two different epitopes. Exemplary bispecific antibodies may bind to two different epitopes of CD20. Other such antibodies may bind CD20 and further bind a second antigen. Alternatively, a CD20 binding arm may be combined with an arm which binds to a triggering molecule on a leukocyte such as a T cell receptor molecule (e.g., CD2 or CD3), or Fc receptors for IgG (FcγR), so as to focus cellular defense mechanisms to the target. Bispecific antibodies may also be used to localize cytotoxic agents to the target. These antibodies possess a cell marker-binding arm and an arm which binds the cytotoxic agent (e.g., saporin, anti-interferonα, vinca alkaloid, ricin A chain, methola-exate or radioactive isotope hapten). Bispecific antibodies can be prepared as full-length antibodies or antibody fragments (e.g., F(ab'): bispecific antibodies).

Methods for making bispecific antibodies are known in the art. See, for example, Millstein et al., Nature, 305:537-539 (1983); Traunecker et al., EMBO J., 10:3655-3659 (1991); Suresh et al., Methods in Enzymology, 121:210 (1986); Kostelny et al., J. Immunol., 148(5):1547-1553 (1992); Hollinger et al., Proc. Natl. Acad. Sci. USA, 90:6444-6448 (1993); Gruber et al., J. Immunol., 152:5368 (1994); U.S. Pat. Nos. 4,474,893; 4,714,681; 4,925,648; 5,573,920; 5,601,81; 95,731,168; 4,676,980; and 4,676,980, WO 94/04690; WO 91/00360; WO 92/200373; WO 93/17715; WO 92/08802; EP 03089 and US 2009/0048122.

In certain aspects of the invention, the compositions and methods comprise a bispecific murine antibody or fragment thereof and/or conjugates thereof with specificity for human CD20 and the CD3 epsilon chain of the T cell receptor, such as the bispecific antibody described by Daniel et al., Blood, 92:4750-4757 (1998). In preferred aspects, where the anti-CD20 antibody or fragments thereof and/or conjugates thereof of the compositions and methods of the invention is bispecific, the anti-CD20 antibody is human or humanized and has specificity for human CD20 and an epitope on a T cell or is capable of binding to a human effector-cell such as, for example, a monocyte/macrophage and/or a natural killer cell to effect cell death.

Antibody Binding Affinity

In certain aspects of the invention, the anti-CD20 antibodies can be modified to alter their binding affinity for the CD20 and antigenic fragments thereof. Binding properties may be determined by a variety of in vitro assay methods known in the art, e.g. enzyme-linked immunoabsorbent assay (ELISA), or radioimmunoassay (RIA)), or kinetics (e.g. BIACORE™ analysis) or flow cytometry based assays. It is generally understood that a binding molecule having a low KD is preferred.

In one aspect of the present invention, antibodies or antibody fragments specifically bind CD20 and antigenic fragments thereof with a dissociation constant or KD or Kd ($k_{off}/k_{on}$) of less than $10^{-5}$ M, or of less than $10^{-6}$ M, or of less than $10^{-7}$ M, or of less than $10^{-8}$ M, or of less than $10^{-9}$ M, or of less than $10^{-10}$ M, or of less than $10^{-11}$ M, or of less than $10^{-12}$ M, or of less than $10^{-13}$ M.

In another aspect, the antibody or fragment of the invention binds to CD20 and/or antigenic fragments thereof with a $K_{off}$ of less than $1\times10^{-3}$ s$^{-1}$, or less than $3\times10^{-3}$ s$^{-1}$. In other aspects, the antibody binds to CD20 and antigenic fragments thereof with a $K_{off}$ less than $10^{-3}$ s$^{-1}$ less than $5\times10^{-3}$ s$^{-1}$, less than $10^{-4}$ s$^{-1}$, less than $5\times10^{-4}$ s$^{-1}$, less than $10^{-5}$ s$^{-1}$, less than $5\times10^{-5}$ s$^{-1}$, less than $10^{-6}$ s$^{-1}$, less than $5\times10^{-6}$ s$^{-1}$, less than $10^{-7}$ s$^{-1}$, less than $5\times10^{-7}$ s$^{-1}$, less than $10^{-8}$ s$^{-1}$, less than $5\times10^{-8}$ s$^{-1}$, less than $10^{-9}$ s$^{-1}$, less than $5\times10^{-9}$ s$^{-1}$, or less than $10^{-10}$ s$^{-1}$.

In another aspect, the antibody or fragment of the invention binds to CD20 and/or antigenic fragments thereof with an association rate constant or $k_{on}$ rate of at least $10^5$ M$^{-1}$ s$^{-1}$, at least $5\times10^5$ M$^{-1}$ s$^{-1}$, at least $10^6$ M$^{-1}$ s$^{-1}$, at least $5\times10^6$ M$^{-1}$ s$^{-1}$, at least $10^7$ M$^{-1}$ s$^{-1}$, at least $5\times10^7$ M$^{-1}$ s$^{-1}$, or at least $10^8$ M$^{-1}$ s$^{-1}$, or at least $10^9$ M$^{-1}$ s$^{-1}$.

One of skill understands that the conjugates of the invention have the same properties as those described herein.

Antibody pI and Tm

In certain aspects of the invention, the anti-CD20 antibodies can be modified to alter their isoelectric point (pI). Antibodies, like all polypeptides, have a pI, which is generally defined as the pH at which a polypeptide carries no net charge. It is known in the art that protein solubility is typically lowest when the pH of the solution is equal to the isoelectric point (pI) of the protein. As used herein the pI value is defined as the pI of the predominant charge form. The pI of a protein may be determined by a variety of methods including but not limited to, isoelectric focusing and various computer algorithms (see, e.g., Bjellqvist et al., 1993, Electrophoresis, 14:1023). In addition, the thermal melting temperatures (Tm) of the Fab domain of an antibody, can be a good indicator of the thermal stability of an antibody and may further provide an indication of the shelf-life. A lower Tm indicates more aggregation/less stability, whereas a higher Tm indicates less aggregation/more stability. Thus, in certain aspects antibodies having higher Tm are preferable. Tm of a protein domain (e.g., a Fab domain) can be measured using any standard method known in the art, for example, by differential scanning calorimetry (see, e.g., Vermeer et al., 2000, Biophys. J. 78:394-404; Vermeer et al., 2000, Biophys. J. 79: 2150-2154).

Accordingly, an additional nonexclusive aspect of the present invention includes modified antibodies that have certain preferred biochemical characteristics, such as a particular isoelectric point (pI) or melting temperature (Tm).

More specifically, in one aspect, the modified antibodies of the present invention have a pI ranging from 5.5 to 9.5. In still another specific aspect, the modified antibodies of the present invention have a pI that ranges from about 5.5 to about 6.0, or about 6.0 to about 6.5, or about 6.5 to about 7.0, or about 7.0 to about 7.5, or about 7.5 to about 8.0, or about 8.0 to about 8.5, or about 8.5 to about 9.0, or about 9.0 to about 9.5. In other specific aspects, the modified antibodies of the present invention have a pI that ranges from 5.5-6.0, or 6.0 to 6.5, or 6.5 to 7.0, or 7.0-7.5, or 7.5-8.0, or 8.0-8.5, or 8.5-9.0, or 9.0-9.5. Even more specifically, the modified antibodies of the present invention have a pI of at least 5.5, or at least 6.0, or at least 6.3, or at least 6.5, or at least 6.7, or at least 6.9, or at least 7.1, or at least 7.3, or at least 7.5, or at least 7.7, or at least 7.9, or at least 8.1, or at least 8.3, or at least 8.5, or at least 8.7, or at least 8.9, or at least 9.1, or at least 9.3, or at least 9.5. In other specific aspects, the modified antibodies of the present invention have a pI of at least about 5.5, or at least about 6.0, or at least about 6.3, or at least about 6.5, or at least about 6.7, or at least about 6.9, or at least about 7.1, or at least about 7.3, or at least about 7.5, or at least about 7.7, or at least about 7.9, or at least about 8.1, or at least about 8.3, or at least about 8.5, or at least about 8.7, or at least about 8.9, or at least about 9.1, or at least about 9.3, or at least about 9.5.

It is possible to optimize solubility by altering the number and location of ionizable residues in the antibody to adjust the pI. For example the pI of a polypeptide can be manipulated by making the appropriate amino acid substitutions (e.g., by substituting a charged amino acid such as a lysine, for an uncharged residue such as alanine). Without wishing to be bound by any particular theory, amino acid substitutions of an antibody that result in changes of the pI of said antibody may improve solubility and/or the stability of the antibody. One skilled in the art would understand which amino acid substitutions would be most appropriate for a particular antibody to achieve a desired pI. In one aspect, a substitution is generated in an antibody of the invention to alter the pI. It is specifically contemplated that the substitution(s) of the Fc region that result in altered binding to FcγR (described supra) may also result in a change in the pI. In another aspect, substitution(s) of the Fc region are specifically chosen to effect both the desired alteration in FcγR binding and any desired change in pI.

In one aspect, the modified antibodies of the present invention have a Tm ranging from 65° C. to 120° C. In specific aspects, the modified antibodies of the present invention have a Tm ranging from about 75° C. to about 120° C., or about 75° C. to about 85° C., or about 85° C. to about 95° C., or about 95° C. to about 105° C., or about 105° C. to about 115° C., or about 115° C. to about 120° C. In other specific aspects, the modified antibodies of the present invention have a Tm ranging from 75° C. to 120° C., or 75° C. to 85° C., or 85° C. to 95° C., or 95° C. to 105° C., or 105° C. to 115° C., or 115° C. to 120° C. In still other specific aspects, the modified antibodies of the present invention have a Tm of at least about 65° C., or at least about 70° C., or at least about 75° C., or at least about 80° C., or at least about 85° C., or at least about 90° C., or at least about 95° C., or at least about 100° C., or at least about 105° C., or at least about 110° C., or at least about 115° C., or at least about 120° C. In yet other specific aspects, the modified antibodies of the present invention have a Tm of at least 65° C., or at least 70° C., or at least 75° C., or at least 80° C., or at least 85° C., or at least 90° C., or at least 95° C., or at least 100° C., or at least 105° C., or at least 110° C., or at least 115° C., or at least 120° C.

Engineered Effector Function

It may be desirable to modify the anti-CD20 antibody of the invention with respect to effector function, so as to enhance the effectiveness of the antibody in treating an B-cell associated disease, a cancer, a GVHD or rejection, for example. For example, cysteine residue(s) may be introduced in the Fc region, thereby allowing interchain disulfide bond formation in this region. The homodimeric antibody thus generated may have improved internalization capability and/or increased complement-mediated cell killing and/or antibody-dependent cellular cytotoxicity (ADCC). See, Caron et al., J. Exp Med., 176:1191-1195 (1992) and Shopes, B., J. Immunol., 148:2918-2922 (1992). Homodimeric antibodies with enhanced activity may also be prepared using heterobifunctional cross-linkers as described in Wolff et al., Cancer Research, 53:2560-2565 (1993). Alternatively, an antibody can be engineered which has dual Fc regions and may thereby have enhanced complement lysis and ADCC capabilities. See, Stevenson et al., Anti-Cancer Drug Design, 3:219-230 (1989).

Other methods of engineering Fc regions of antibodies so as to alter effector functions are known in the art (e.g., U.S. Patent Publication No. 20040185045 and PCT Publication No. WO 2004/016750, both to Koenig et al., which describe altering the Fc region to enhance the binding affinity for FcγRIIB as compared with the binding affinity for FCγRIIA; see, also, PCT Publication Nos. WO 99/58572 to Amour et al.; WO 99/51642 to Idusogie et al.; and U.S. Pat. No. 6,395,272 to Deo et al.; the disclosures of which are incorporated herein in their entireties). Methods of modifying the Fc region to decrease binding affinity to FcγRIIB are also known in the art (e.g., U.S. Patent Publication No. 20010036459 and PCT Publication No. WO 01/79299, both to Ravetch et al., the disclosures of which are incorporated herein in their entireties). Modified antibodies having variant Fc regions with enhanced binding affinity for FcγRIIIA and/or FcγRIIA as compared with a wild type Fc region are known (e.g., PCT Publication Nos. WO 2004/063351, to Stavenhagen et al.; the disclosure of which is incorporated herein in its entirety).

In vitro assays known in the art can be used to determine whether the anti-CD20 antibodies, compositions, conjugates and methods of the invention, for example, are capable of mediating ADCC, such as those described herein.

Variant Fc Regions. The present invention provides formulation of proteins comprising a variant Fc region. That is, a non-naturally occurring Fc region, for example an Fc region comprising one or more non-naturally occurring amino acid residues. Also encompassed by the variant Fc regions of the present invention are Fc regions which comprise amino acid deletions, additions and/or modifications.

It will be understood that Fc region as used herein includes the polypeptides comprising the constant region of an antibody excluding the first constant region immunoglobulin domain. Thus Fc refers to the last two constant region immunoglobulin domains of IgA, IgD, and IgG, and the last three constant region immunoglobulin domains of IgE and IgM, and the flexible hinge N-terminal to these domains. For IgA and IgM Fc may include the J chain. For IgG, Fc comprises immunoglobulin domains Cγ2 and Cγ3 (Cγ2 and Cγ3) and the hinge between Cγ1 (Cγ1) and Cγ2 (Cγ2). Although the boundaries of the Fc region may vary, the human IgG heavy chain Fc region is usually defined to comprise residues C226 or P230 to its carboxyl-terminus, wherein the numbering is according to the EU index as in Kabat et al. (1991, NIH Publication 91-3242, National Technical Information Service, Springfield, Va.). The "EU index as set forth in Kabat" refers to the residue numbering of the human IgG1 EU antibody as described in Kabat et al., supra. Fc may refer to this region in isolation, or this region in the context of an antibody, antibody fragment, or Fc fusion protein. An Fc variant protein may be an antibody, Fc fusion, or any protein or protein domain that comprises an Fc region. Particularly preferred are proteins comprising variant Fc regions, which are non-naturally occurring variants of an Fc. Polymorphisms have been observed at a number of Fc positions, including but not limited to Kabat 270, 272, 312, 315, 356, and 358, and thus slight differences between the presented sequence and sequences in the prior art may exist and would be known to one of skill in the art based on the present teachings.

The present invention encompasses Fc variant proteins which have altered binding properties for an Fc ligand (e.g., an Fc receptor, C1q) relative to a comparable molecule (e.g., a protein having the same amino acid sequence except having a wild type Fc region). Examples of binding properties include, but are not limited to, binding specificity, equilibrium dissociation constant ($K_D$), dissociation and association rates ($K_{off}$ and $K_{on}$), binding affinity and/or avidity. It is generally understood that a binding molecule (e.g., a Fc variant protein such as an antibody) with a low KD is preferable to a binding molecule with a high KD. However, in some instances the value of the $K_{on}$ or $K_{off}$ may be more relevant than the value of the KD. One skilled in the art can determine which kinetic parameter is most important for a given antibody application.

The affinities and binding properties of an Fc domain for its ligand, may be determined by a variety of in vitro assay methods (biochemical or immunological based assays) known in the art for determining Fc-FcγR interactions, i.e., specific binding of an Fc region to an FcγR including but not limited to, equilibrium methods (e.g., enzyme-linked immunoabsorbent assay (ELISA), or radioimmunoassay (RIA)), or kinetics (e.g., BIACORE.™ analysis), and other methods such as indirect binding assays, competitive inhibition assays, fluorescence resonance energy transfer (FRET), gel electrophoresis and chromatography (e.g., gel filtration). These and other methods may utilize a label on one or more of the components being examined and/or employ a variety of detection methods including but not limited to chromogenic, fluorescent, luminescent, or isotopic labels. A detailed description of binding affinities and kinetics can be found in, for example, Paul, W. E., ed., Fundamental Immunology, 4th Ed., Lippincott-Raven, Philadelphia (1999).

For example, a modification that enhances Fc binding to one or more positive regulators (e.g., FcγRIIIA) while leaving unchanged or even reducing Fc binding to the negative regulator FcγRIIB would be more preferable for enhancing ADCC activity. Alternatively, a modification that reduced binding to one or more positive regulator and/or enhanced binding to FcγRIIB would be preferable for reducing ADCC activity. Accordingly, the ratio of binding affinities (e.g., equilibrium dissociation constants (KD)) can indicate if the ADCC activity of an Fc variant is enhanced or decreased. For example, a decrease in the ratio of FcγRIIIA/FcγRIIB equilibrium dissociation constants (KD), will correlate with improved ADCC activity, while an increase in the ratio will correlate with a decrease in ADCC activity. Additionally, modifications that enhanced binding to C1q would be preferable for enhancing CDC activity while modification that reduced binding to C1q would be preferable for reducing or eliminating CDC activity.

In one aspect, the Fc variants of the invention bind FcγRIIIA with increased affinity relative to a comparable molecule. In another aspect, the Fc variants of the invention bind FcγRIIIA with increased affinity and bind FcγRIIB with a binding affinity that is unchanged relative to a comparable molecule. In still another aspect, the Fc variants of the invention bind FcγRIIIA with increased affinity and bind FcγRIIB with a decreased affinity relative to a comparable molecule. In yet another aspect, the Fc variants of the invention have a ratio of FcγRIIIA/FcγRIIB equilibrium dissociation constants (KD) that is decreased relative to a comparable molecule.

In one aspect, the Fc variant protein has enhanced binding to one or more Fc ligand relative to a comparable molecule. In another aspect, the Fc variant protein has an affinity for an Fc ligand that is at least 2 fold, or at least 3 fold, or at least 5 fold, or at least 7 fold, or a least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold greater than that of a comparable molecule. In a specific aspect, the Fc variant protein has enhanced binding to an Fc receptor. In another specific aspect, the Fc variant protein has enhanced binding to the Fc receptor FcγRIIIA. In still another specific aspect, the Fc variant protein has enhanced binding to the Fc receptor FcRn. In yet another specific aspect, the Fc variant protein has enhanced binding to C1q relative to a comparable molecule.

In another aspect, an Fc variant of the invention has an equilibrium dissociation constant (KD) that is decreased between about 2 fold and about 10 fold, or between about 5 fold and about 50 fold, or between about 25 fold and about 250 fold, or between about 100 fold and about 500 fold, or between about 250 fold and about 1000 fold relative to a comparable molecule. In another aspect, an Fc variant of the invention has an equilibrium dissociation constant (KD) that is decreased between 2 fold and 10 fold, or between 5 fold and 50 fold, or between 25 fold and 250 fold, or between 100 fold and 500 fold, or between 250 fold and 1000 fold relative to a comparable molecule. In a specific aspect, the Fc variants have an equilibrium dissociation constants (KD) for FcγRIIIA that is reduced by at least 2 fold, or at least 3 fold, or at least 5 fold, or at least 7 fold, or a least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold, or at least 400 fold, or at least 600 fold, relative to a comparable molecule.

The serum half-life of proteins comprising Fc regions may be increased by increasing the binding affinity of the Fc region for FcRn. In one aspect, the Fc variant protein has enhanced serum half life relative to comparable molecule.

"Antibody-dependent cell-mediated cytotoxicity" or "ADCC" refers to a form of cytotoxicity in which secreted Ig bound onto Fc receptors (FcRs) present on certain cytotoxic cells (e.g., Natural Killer (NK) cells, neutrophils, and macrophages) enables these cytotoxic effector cells to bind specifically to an antigen-bearing target cell and subsequently kill the target cell with cytotoxins. High-affinity IgG antibodies, for example, directed to the surface of target cells "arm" the cytotoxic cells and afford such killing. Lysis of the target cell is extracellular, requires direct cell-to-cell contact, and does not involve complement. It is contemplated that, in addition to antibodies, other proteins comprising Fc regions, specifically Fc fusion proteins, having the capacity to bind specifically to an antigen-bearing target cell will be able to effect cell-mediated cytotoxicity. For simplicity, the cell-mediated cytotoxicity resulting from the activity of an Fc fusion protein is also referred to herein as ADCC activity.

The ability of any particular Fc variant protein to mediate lysis of the target cell by ADCC can be assayed. To assess ADCC activity an Fc variant protein of interest is added to target cells in combination with immune effector cells, which may be activated by the antigen antibody complexes resulting in cytolysis of the target cell. Cytolysis is generally detected by the release of label (e.g., radioactive substrates, fluorescent dyes or natural intracellular proteins) from the lysed cells. Useful effector cells for such assays include peripheral blood mononuclear cells (PBMC) and Natural Killer (NK) cells. Specific examples of in vitro ADCC assays are described in Wisecarver et al., 1985, 79:277-282; Bruggemann et al., 1987, J Exp Med, 166:1351-1361; Wilkinson et al., 2001, J Immunol Methods, 258:183-191; and Patel et al., 1995, J Immunol Methods, 184:29-38. Alternatively, or additionally, ADCC activity of the Fc variant protein of interest may be assessed in vivo, e.g., in a animal model such as that disclosed in Clynes et al., 1998, PNAS USA, 95:652-656.

In one aspect, an Fc variant protein has enhanced ADCC activity relative to a comparable molecule. In a specific aspect, an Fc variant protein has ADCC activity that is at least 2 fold, or at least 3 fold, or at least 5 fold, or at least 10 fold, or at least 50 fold, or at least 100 fold greater than that of a comparable molecule. In another specific aspect, an Fc variant protein has enhanced binding to the Fc receptor FcγRIIIA and has enhanced ADCC activity relative to a comparable molecule. In other aspects, the Fc variant protein has both enhanced ADCC activity and enhanced serum half life relative to a comparable molecule.

"Complement dependent cytotoxicity" and "CDC" refer to the lysing of a target cell in the presence of complement. The complement activation pathway is initiated by the binding of the first component of the complement system (C1q) to a molecule, an antibody for example, complexed with a cognate antigen. To assess complement activation, a CDC assay, e.g. as described in Gazzano-Santoro et al., 1996, J. Immunol. Methods, 202:163, may be performed. In one aspect, an Fc variant protein has enhanced CDC activity relative to a comparable molecule. In a specific aspect, an Fc variant protein has CDC activity that is at least 2 fold, or at least 3 fold, or at least 5 fold, or at least 10 fold, or at least 50 fold, or at least 100 fold greater than that of a comparable molecule. In other aspects, the Fc variant protein has both enhanced CDC activity and enhanced serum half life relative to a comparable molecule.

In one aspect, the present invention provides formulations, wherein the Fc region comprises a non-naturally occurring amino acid residue at one or more positions selected from the group consisting of 234, 235, 236, 239, 240, 241, 243, 244, 245, 247, 252, 254, 256, 262, 263, 264, 265, 266, 267, 269, 296, 297, 298, 299, 313, 325, 326, 327, 328, 329, 330, 332, 333, and 334 as numbered by the EU index as set forth in Kabat. Optionally, the Fc region may comprise a non-naturally occurring amino acid residue at additional and/or alternative positions known to one skilled in the art (see, e.g., U.S. Pat. Nos. 5,624,821; 6,277,375; 6,737,056; PCT Patent Publications WO 01/58957; WO 02/06919; WO 04/016750; WO 04/029207; WO 04/035752 and WO 05/040217) or as disclosed herein.

In a specific aspect, the present invention provides an Fc variant protein formulation, wherein the Fc region comprises at least one non-naturally occurring amino acid residue selected from the group consisting of 234D, 234E, 234N, 234Q, 234T, 234H, 234Y, 234I, 234V, 234F, 235A, 235D, 235R, 235W, 235P, 235S, 235N, 235Q, 235T, 235H, 235Y, 235I, 235V, 235F, 236E, 239D, 239E, 239N, 239Q, 239F, 239T, 239H, 239Y, 240I, 240A, 240T, 240M, 241W, 241L, 241Y, 241E, 241R, 243W, 243L 243Y, 243R, 243Q, 244H, 245A, 247V, 247G, 252Y, 254T, 256E, 262I, 262A, 262T, 262E, 263I, 263A, 263T, 263M, 264L, 264I, 264W, 264T, 264R, 264F, 264M, 264Y, 264E, 265G, 265N, 265Q, 265Y, 265F, 265V, 265I, 265L, 265H, 265T, 266I, 266A, 266T, 266M, 267Q, 267L, 269H, 269Y, 269F, 269R, 296E, 296Q, 296D, 296N, 296S, 296T, 296L, 296I, 296H, 269G, 297S, 297D, 297E, 298H, 298I, 298T, 298F, 299I, 299L, 299A, 299S, 299V, 299H, 299F, 299E, 313F, 325Q, 325L, 325I, 325D, 325E, 325A, 325T, 325V, 325H, 327G, 327W, 327N, 327L, 328S, 328M, 328D, 328E, 328N, 328Q, 328F, 328I, 328V, 328T, 328H, 328A, 329F, 329H, 329Q, 330K, 330G, 330T, 330C, 330L, 330Y, 330V, 330I, 330F, 330R, 330H, 332D, 332S, 332W, 332F, 332E, 332N, 332Q, 332T, 332H, 332Y, and 332A as numbered by the EU index as set forth in Kabat. Optionally, the Fc region may comprise additional and/or alternative non-naturally occurring amino acid residues known to one skilled in the art (see, e.g., U.S. Pat. Nos. 5,624,821; 6,277,375; 6,737,056; PCT Patent Publications WO 01/58957; WO 02/06919; WO 04/016750; WO 04/029207; WO 04/035752 and WO 05/040217).

In another aspect, the present invention provides an Fc variant protein formulation, wherein the Fc region comprises at least a non-naturally occurring amino acid at one or more positions selected from the group consisting of 239, 330 and 332, as numbered by the EU index as set forth in Kabat. In a specific aspect, the present invention provides an Fc variant protein formulation, wherein the Fc region comprises at least one non-naturally occurring amino acid selected from the group consisting of 239D, 330L and 332E, as numbered by the EU index as set forth in Kabat. Optionally, the Fc region may further comprise an additional non-naturally occurring amino acid at one or more positions selected from the group consisting of 252, 254, and 256, as numbered by the EU index as set forth in Kabat. In a specific aspect, the present invention provides an Fc variant protein formulation, wherein the Fc region comprises at least one non-naturally occurring amino acid selected from the group consisting of 239D, 330L and 332E, as numbered by the EU index as set forth in Kabat, and at least one non-naturally occurring amino acid at one or more positions are selected from the group consisting of 252Y, 254T and 256E, as numbered by the EU index as set forth in Kabat.

In one aspect, the Fc variants of the present invention may be combined with other known Fc variants such as those disclosed in Ghetie et al., 1997, Nat. Biotech. 15:637-40; Duncan et al, 1988, Nature 332:563-564; Lund et al., 1991, J. Immunol., 147:2657-2662; Lund et al, 1992, Mol. Immunol., 29:53-59; Alegre et al, 1994, Transplantation 57:1537-1543; Hutchins et al., 1995, Proc Natl. Acad Sci USA, 92:11980-

11984; Jefferis et al, 1995, Immunol Lett., 44:111-117; Lund et al., 1995, Faseb J., 9:115-119; Jefferis et al, 1996, Immunol Lett., 54:101-104; Lund et al, 1996, J. Immunol., 157:4963-4969; Armour et al., 1999, Eur J Immunol 29:2613-2624; Idusogie et al, 2000, J. Immunol., 164:4178-4184; Reddy et al, 2000, J. Immunol., 164:1925-1933; Xu et al., 2000, Cell Immunol., 200:16-26; Idusogie et al, 2001, J. Immunol., 166: 2571-2575; Shields et al., 2001, J. Biol. Chem., 276:6591-6604; Jefferis et al, 2002, Immunol Lett., 82:57-65; Presta et al., 2002, Biochem Soc Trans., 30:487-490); U.S. Pat. Nos. 5,624,821; 5,885,573; 5,677,425; 6,165,745; 6,277,375; 5,869,046; 6,121,022; 5,624,821; 5,648,260; 6,528,624; 6,194,551; 6,737,056; 6,821,505; 6,277,375; U.S. Patent Publication Nos. 2004/0002587 and PCT Publications WO 94/29351; WO 99/58572; WO 00/42072; WO 02/060919; WO 04/029207; WO 04/099249; and WO 04/063351 which disclose exemplary Fc variants. Also encompassed by the present invention are Fc regions which comprise deletions, additions and/or modifications. Still other modifications/substitutions/additions/deletions of the Fe domain will be readily apparent to one skilled in the art.

Methods for generating non-naturally occurring Fc regions are known in the art. For example, amino acid substitutions and/or deletions can be generated by mutagenesis methods, including, but not limited to, site-directed mutagenesis (e.g., Kunkel, Proc. Natl. Acad. Sci. USA, 82:488-492 (1985)), PCR mutagenesis (e.g., Higuchi, in "PCR Protocols: A Guide to Methods and Applications", Academic Press, San Diego, pp. 177-183 (1990)), and cassette mutagenesis (e.g., Wells et al., Gene, 34:315-323 (1985)). Preferably, site-directed mutagenesis is performed by the overlap-extension PCR method (e.g., Higuchi, in "PCR Technology: Principles and Applications for DNA Amplification", Stockton Press, New York, pp. 61-70 (1989)). Alternatively, the technique of overlap-extension PCR (e.g., Higuchi, supra.) can be used to introduce any desired mutation(s) into a target sequence (the starting DNA). For example, the first round of PCR in the overlap-extension method involves amplifying the target sequence with an outside primer (primer 1) and an internal mutagenesis primer (primer 3), and separately with a second outside primer (primer 4) and an internal primer (primer 2), yielding two PCR segments (segments A and B). The internal mutagenesis primer (primer 3) is designed to contain mismatches to the target sequence specifying the desired mutation(s). In the second round of PCR, the products of the first round of PCR (segments A and B) are amplified by PCR using the two outside primers (primers 1 and 4). The resulting full-length PCR segment (segment C) is digested with restriction enzymes and the resulting restriction fragment is cloned into an appropriate vector. As the first step of mutagenesis, the starting DNA (e.g., encoding an Fc fusion protein, an antibody or simply an Fc region), is operably cloned into a mutagenesis vector. The primers are designed to reflect the desired amino acid substitution. Other exemplary methods useful for the generation of variant Fc regions are known in the art (see, e.g., U.S. Pat. Nos. 5,624,821; 5,885,573; 5,677, 425; 6,165,745; 6,277,375; 5,869,046; 6,121,022; 5,624,821; 5,648,260; 6,528,624; 6,194,551; 6,737,056; 6,821,505; 6,277,375; U.S. Patent Publication Nos. 2004/0002587 and PCT Publications WO 94/29351; WO 99/58572; WO 00/42072; WO 02/060919; WO 04/029207; WO 04/099249; WO 04/063351, the entire contents of which are incorporated herein by reference).

In some aspects, an Fc variant protein comprises one or more engineered glycoforms, i.e., a carbohydrate composition that is covalently attached to the molecule comprising an Fc region. Engineered glycoforms may be useful for a variety of purposes, including but not limited to enhancing or reducing effector function. Engineered glycoforms may be generated by methods disclosed herein and any method known to one skilled in the art, for example by using engineered or variant expression strains, by using growth conditions or media affecting glycosylation, by co-expression with one or more enzymes, for example DI N-acetylglucosaminyltransferase III (GnTI11), by expressing a molecule comprising an Fc region in various organisms or cell lines from various organisms, or by modifying carbohydrate(s) after the molecule comprising Fc region has been expressed. Methods for generating engineered glycoforms are known in the art, and include but are not limited to those described in Umana et al., 1999, Nat. Biotechnol., 17:176-180; Davies et al., 20017 Biotechnol Bioeng., 74:288-294; Shields et al., 2002, J Biol. Chem., 277:26733-26740; Shinkawa et al., 2003, J Biol. Chem., 278:3466-3473) U.S. Pat. No. 6,602,684; U.S. application Ser. No. 10/277,370; U.S. application Ser. No. 10/113, 929; PCT WO 00/61739A1; PCT WO 01/292246A1; PCT WO 02/311140A1; PCT WO 02/30954A1; Potillegent™ technology (Biowa, Inc., Princeton, N.J.); GlycoMAb™ glycosylation engineering technology (GLYCART™ biotechnology AG, Zurich, Switzerland). See also, e.g., WO 00061739; EA01229125; US 20030115614; Okazaki et al., 2004, JMB, 336: 1239-49.

Polynucleotides, Vectors, Host Cells and Recombinant Methods

The present invention further provides polynucleotides comprising a nucleotide sequence encoding an antibody of the invention or epitope-binding fragments thereof.

The present invention also encompasses polynucleotides encoding a polypeptide that can bind CD20 and that hybridizes under stringent hybridization conditions to polynucleotides that encode an antibody of the present invention, wherein said stringent hybridization conditions include: prehybridization for 2 hours at 60° C. in 6×SSC, 0.5% SDS, 5×Denhardt's solution, and 100 µg/ml heat denatured salmon sperm DNA; hybridization for 18 hours at 60° C.; washing twice in 4×SSC, 0.5% SDS, 0.1% sodium pyrophosphate, for 30 min at 60° C. and twice in 2×SSC, 0.1% SDS for 30 min at 60° C.

The polynucleotides may be obtained, and the nucleotide sequence of the polynucleotides determined, methods known in the art. For example, if the nucleotide sequence of the antibody is known, a polynucleotide encoding the antibody may be assembled from chemically synthesized oligonucleotides (e.g., as described in Kutmeier et al., 1994, *BioTechniques* 17:242) which, briefly, involves the synthesis of overlapping oligonucleotides containing portions of the sequence encoding the antibody, annealing and ligation of those oligonucleotides, and then amplification of the ligated oligonucleotides by PCR.

Methods for the construction of recombinant vectors containing antibody coding sequences and appropriate transcriptional and translational control signals are well known in the art. These methods include, for example, in vitro recombinant DNA techniques, synthetic techniques, and in vivo genetic recombination. The invention, thus, provides replicable vectors comprising a nucleotide sequence encoding an antibody molecule of the present invention, or a heavy or light chain thereof, or a heavy or light chain variable domain, or an epitope-binding fragment of any of these, operably linked to a promoter.

The recombinant vector is transferred to a host cell by conventional techniques and the transfected cells are then cultured by conventional techniques to produce an antibody of the invention. Thus, the invention includes host cells containing a polynucleotide encoding an antibody of the invention, or an epitope-binding fragment thereof, operably linked to a heterologous promoter. In preferred aspects, vectors encoding both the heavy and light chains may be co-expressed in the host cell for expression of an entire immunoglobulin molecule.

A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *E. coli* and *B. subtilis*) transformed with recombinant bacteriophage DNA, plasmid DNA or cosmid DNA expression vectors containing antibody coding sequences; yeast (e.g., *Saccharomyces* and *Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus (CaMV); tobacco mosaic virus (TMV) or transformed with recombinant plasmid expression vectors (e.g., Ti plasmid) containing antibody coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter).

Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (for example, as disclosed in Foecking et al., 1986, Gene 45:101; Cockett et al., 1990, Bio/Technology 8:2).

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoters, enhancers, transcription terminators, polyadenylation sites, etc.) and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compounds that interact directly or indirectly with the antibody molecule.

Once an antibody molecule of the invention has been recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. In this regard, U.S. Pat. No. 7,538,195 has been referred to in the present disclosure, the teachings of which are hereby incorporated in its entirety by reference.

In another aspect, diverse antibodies and antibody fragments, as well as antibody mimics may be readily produced by mutation, deletion and/or insertion within the variable and constant region sequences that flank a particular set of CDRs. Thus, for example, different classes of Ab are possible for a given set of CDRs by substitution of different heavy chains, whereby, for example, IgG1-4, IgM, IgA1-2, IgD, IgE antibody types and isotypes may be produced. Similarly, artificial antibodies within the scope of the invention may be produced by embedding a given set of CDRs within an entirely synthetic framework. The teem "variable" is used herein to describe certain portions of the variable domains that differ in sequence among antibodies and are used in the binding and specificity of each particular antibody for its antigen. However, the variability is not usually evenly distributed through the variable domains of the antibodies. It is typically concentrated in three segments called complementarity determining regions (CDRs) or hypervariable regions both in the light chain and the heavy chain variable domains. The more highly conserved portions of the variable domains are called the framework (FR). The variable domains of heavy and light chains each comprise four framework regions, largely adopting a beta-sheet configuration, connected by three CDRs, which form loops connecting, and in some cases forming part of the beta-sheet structure. The CDRs in each chain are held together in close proximity by the FR regions and, with the CDRs from the other chain, contribute to the formation of the antigen binding site of antibodies (see, for example, E. A. Kabat et al. *Sequences of Proteins of Immunological Interest*, fifth edition, 1991, NIH). The constant domains are not involved directly in binding an antibody to an antigen, but exhibit various effector functions, such as participation of the antibody in antibody-dependent cellular toxicity.

Humanized antibodies, or antibodies adapted for non-rejection by other mammals, may be produced using several technologies such as resurfacing and CDR grafting. In the resurfacing technology, molecular modeling, statistical analysis and mutagenesis are combined to adjust the non-CDR surfaces of variable regions to resemble the surfaces of known antibodies of the target host. Strategies and methods for the resurfacing of antibodies, and other methods for reducing immunogenicity of antibodies within a different host, are disclosed in, for example, U.S. Pat. No. 5,639,641, which is hereby incorporated in its entirety by reference. In the CDR grafting technology, the murine heavy and light chain CDRs are grafted into a fully human framework sequence.

The invention also includes functional equivalents of the antibodies described in this specification. Functional equivalents have binding characteristics that are comparable to those of the antibodies, and include, for example, chimerized, humanized and single chain antibodies as well as fragments thereof. Exemplary methods of producing such functional equivalents are disclosed in PCT Application WO 93/21319, European Patent Application No. 239,400; PCT Application WO 89/09622; European Patent Application 338,745; and European Patent Application EP 332,424, which are incorporated in their respective entireties by reference.

Functional equivalents include polypeptides with amino acid sequences substantially the same as the amino acid sequence of the variable or hypervariable regions of the antibodies of the invention. "Substantially the same" as applied to an amino acid sequence is defined herein as a sequence with at least about 90%, and more preferably at least about 95%, 96%, 97%, 98%, and 99% sequence identity to another amino acid sequence, as determined by the FASTA search method in accordance with Pearson and Lipman, Proc. Natl. Acad. Sci. USA 85, 2444-2448 (1988).

Chimerized antibodies preferably have constant regions derived substantially or exclusively from human antibody constant regions and variable regions derived substantially or exclusively from the sequence of the variable region from a mammal other than a human. Humanized forms of the antibodies are made by substituting the complementarity determining regions of, for example, a mouse antibody, into a human framework domain, e.g., PCT Pub. No. WO92/22653. Humanized antibodies preferably have constant regions and variable regions other than the complementarity determining regions (CDRs) derived substantially or exclusively from the corresponding human antibody regions and CDRs derived substantially or exclusively from a mammal other than a human.

Functional equivalents also include single-chain antibody fragments, also known as single-chain antibodies (scFvs). These fragments contain at least one fragment of an antibody variable heavy-chain amino acid sequence ($V_H$) tethered to at least one fragment of an antibody variable light-chain sequence ($V_L$) with or without one or more interconnecting linkers. Such a linker may be a short, flexible peptide selected to assure that the proper three-dimensional folding of the ($V_L$) and ($V_H$) domains occurs once they are linked so as to maintain the target molecule binding-specificity of the whole antibody from which the single-chain antibody fragment is derived. Generally, the carboxyl terminus of the ($V_L$) or ($V_H$) sequence may be covalently linked by such a peptide linker to the amino acid terminus of a complementary ($V_L$) and ($V_H$) sequence. Single-chain antibody fragments may be generated by molecular cloning, antibody phage display library or similar techniques. These proteins may be produced either in eukaryotic cells or prokaryotic cells, including bacteria.

Single-chain antibody fragments contain amino acid sequences having at least one of the variable or complementarity determining regions (CDRs) of the intact antibodies described in this specification, but are lacking some or all of the constant domains of those antibodies. These constant domains are not necessary for antigen binding, but constitute a major portion of the structure of intact antibodies. Single-chain antibody fragments may therefore overcome some of the problems associated with the use of antibodies containing a part or all of a constant domain. For example, single-chain antibody fragments tend to be free of undesired interactions between biological molecules and the heavy-chain constant region, or other unwanted biological activity. Additionally, single-chain antibody fragments are considerably smaller than intact or whole antibodies and may therefore have greater capillary permeability than intact antibodies, allowing single-chain antibody fragments to localize and bind to target antigen-binding sites more efficiently. Also, antibody fragments can be produced on a relatively large scale in prokaryotic cells, thus facilitating their production. Furthermore, the relatively small size of single-chain antibody fragments makes them less likely to provoke an immune response in a recipient than intact antibodies.

The knowledge of the amino acid and nucleic acid sequences for the anti-CD20 antibody and its resurfaced or humanized variants, which are described herein, can be used to develop many antibodies which also bind to human CD20. Several studies have surveyed the effects of introducing one or more amino acid changes at various positions in the sequence of an antibody, based on the knowledge of the primary antibody sequence, on its properties such as binding and level of expression (e.g., Yang, W. P. et al., 1995, *J. Mol. Biol.*, 254, 392-403; Rader, C. et al., 1998, *Proc. Natl. Acad. Sci. USA*, 95, 8910-8915; Vaughan, T. J. et al., 1998, *Nature Biotechnology*, 16, 535-539).

In these studies, variants of the primary antibody have been generated by changing the sequences of the heavy and light chain genes in the CDR1, CDR2, CDR3, or framework regions, using methods such as oligonucleotide-mediated site-directed mutagenesis, cassette mutagenesis, error-prone PCR, DNA shuffling, or mutator-strains of *E. coli* (Vaughan, T. J. et al., 1998, *Nature Biotechnology*, 16, 535-539; Adey, N. B. et al., 1996, Chapter 16, pp. 277-291, in "*Phage Display of Peptides and Proteins*", Eds. Kay, B. K. et al., Academic Press). These methods of changing the sequence of the primary antibody have resulted in improved affinities of the secondary antibodies (e.g., Gram, H. et al., 1992, *Proc. Natl. Acad. Sci. USA*, 89, 3576-3580; Boder, E. T. et al., 2000, *Proc. Natl. Acad. Sci. USA*, 97, 10701-10705; Davies, J. and Riechmann, L., 1996, *Immunotechnolgy*, 2, 169-179; Thompson, J. et al., 1996, *J. Mol. Biol.*, 256, 77-88; Short, M. K. et al., 2002, *J. Biol. Chem.*, 277, 16365-16370; Furukawa, K. et al., 2001, *J. Biol. Chem.*, 276, 27622-27628).

By a similar directed strategy of changing one or more amino acid residues of the antibody, the antibody sequences described in this invention can be used to develop anti-CD20 antibodies with improved functions, such as those methods described in patent application publication 20090246195, the contents of which is incorporated in its entirety herein by reference.

Immunoconjugates

The present invention is also directed to conjugates (also referred to herein as immunoconjugates), comprising the anti-CD20 antibodies, antibody fragments, functional equivalents, improved antibodies and their aspects as disclosed herein, linked or conjugated to a drug or prodrug. Suitable drugs or prodrugs are known in the art. Preferred drugs or prodrugs are cytotoxic agents. The cytotoxic agent used in the cytotoxic conjugate of the present invention may be any compound that results in the death of a cell, or induces cell death, or in some manner decreases cell viability, and includes, for example, maytansinoids and maytansinoid analogs, benzodiazepines, taxoids, CC-1065 and CC-1065 analogs, duocarmycins and duocarmycin analogs, enediynes, such as calicheamicins, dolastatin and dolastatin analogs including auristatins, tomaymycin derivatives, leptomycin derivatives, methotrexate, cisplatin, carboplatin, daunorubicin, doxorubicin, vincristine, vinblastine, melphalan, mitomycin C, chlorambucil and morpholino doxorubicin. More preferred cytotoxic agents are maytansinoids and maytansinoids analogs, benzodiazepines, taxanes, CC-1065 and CC-1065 analogs. Especially preferred are maytansinoids and maytansinoid analogs, many of which are described in U.S. Patent Publication Nos. 20070048314, 20060233814, 20080003652, 20060155110, 20060128970, 20090182038, 20090042837, 20080233618, 20080119558, 20060099235, 20050272727, 20050203174, 20050112726, 20060182750, 20090202536, 20090142361, 20080249085, 20080226659, 20080171865, 20080171856, 20080171040, 20080145374, 20080114153, 20070270585, 20070269447, 20070264266, 20070009541, 20070009540, 20070009539, 20060167245, 20060127407, 20060084141, 20050276812, 20050169933, 20050152913, 20050113571, 20050003513, 20040241174, 20040235840, 20040120949, 20040014980, 20030157694, 20020156318, 20020156274, 20020001587, the contents of which are herein incorporated by reference in their entireties.

Such conjugates can be prepared by using a linking group in order to link a drug or prodrug to the antibody or functional equivalent. Suitable linking groups are well known in the art and include, for example, disulfide groups, thioether groups, acid labile groups, photolabile groups, peptidase labile groups and esterase labile groups.

The drug or prodrug can, for example, be linked to the anti-CD20 antibody or fragment thereof through a disulfide bond. The linker molecule or crosslinking agent comprises a reactive chemical group that can react with the anti-CD20 antibody or fragment thereof. Preferred reactive chemical groups for reaction with the cell-binding agent are N-succinimidyl esters and N-sulfosuccinimidyl esters. Additionally the linker molecule comprises a reactive chemical group, preferably a dithiopyridyl group that can react with the drug to form a disulfide bond. Particularly preferred linker molecules include, for example, N-succinimidyl 3-(2-pyridyldithio) propionate (SPDP) (see, e.g., Carlsson et al., *Biochem. J*, 173: 723-737 (1978)), N-succinimidyl 4-(2-pyridyldithio)butanoate (SPDB) (see, e.g., U.S. Pat. No. 4,563,304), N-succinimidyl 4-(2-pyridyldithio)2-sulfobutanoate (sulfo-SPDB) (see US Publication No. 20090274713), N-succinimidyl 4-(2-pyridyldithio)pentanoate (SPP) (see, e.g., CAS Registry number 341498-08-6), 2-iminothiolane, or acetylsuccinic anhydride and other reactive cross-linkers, such as those described in U.S. Pat. No. 6,913,748, which is incorporated herein in its entirety by reference, using known methods. See, for example, U.S. Pat. No. 4,563,304; Carlsson et al, Biochem. J., 173:723-737 (1978); Blattler et al, Biochem., 24:1517-1524 (1985); Lambert et al, Biochem., 22:3913-3920 (1983); Klotz et al, Arch. Biochem. Biophys., 96:605 (1962); and Liu et al, Biochem., 18:690 (1979), Blakey and Thorpe, Antibody, Immunoconjugates and Radiopharmaceuticals, 1:1-16 (1988); Worrell et al, Anti-Cancer Drug Design, 1:179-184 (1986), the disclosures of which are incorporated by reference herein in their entirety. For example, the antibody or cell binding agent can be modified with crosslinking reagents and the antibody or cell binding agent containing free or protected thiol groups thus derived is then reacted with a disulfide- or thiol-containing maytansinoid to produce conjugates. The conjugates can be purified by chromatography, including but not limited to HPLC, size-exclusion, adsorption, ion exchange and affinity capture, dialysis or tangential flow filtration.

In another aspect of the present invention, the anti-CD20 antibody is linked to cytotoxic drugs via disulfide bonds and a polyethylene glycol spacer in enhancing the potency, solubility or the efficacy of the immunoconjugate. Such cleavable hydrophilic linkers are described in WO2009/0134976. The additional benefit of this linker design is the desired high monomer ratio and the minimal aggregation of the antibody-drug conjugate. Specifically contemplated in this aspect are conjugates of cell-binding agents and drugs linked via disulfide group (—S—S—) bearing polyethylene glycol spacers ($(CH_2CH_2O)_{n=1-14}$) with a narrow range of drug load of 2-8 are described that show relatively high potent biological activity toward cancer cells and have the desired biochemical properties of high conjugation yield and high monomer ratio with minimal protein aggregation.

Specifically contemplated in this aspect is an anti-CD20 antibody drug conjugate of formula (I) or a conjugate of formula (I'):

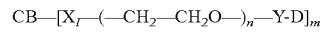  (I)

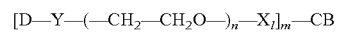  (I')

wherein:
CB represents an anti-CD20 antibody or fragment;
D represents a drug;
X represents an aliphatic, an aromatic or a heterocyclic unit attached to the cell-binding agent via a thioether bond, an amide bond, a carbamate bond, or an ether bond;
Y represents an aliphatic, an aromatic or a heterocyclic unit attached to the drug via a disulfide bond;
l is 0 or 1;
m is an integer from 2 to 8; and
n is an integer from 1 to 24.
More preferably, m is an integer from 2 to 6.
Also, even more preferably, m is an integer from 3 to 5.
Also, more preferably, n is an integer form 2 to 8. Alternatively, as disclosed in, for example, U.S. Pat. Nos. 6,441,163 and 7,368,565, the drug can be first modified to introduce a reactive ester suitable to react with a cell-binding agent. Reaction of these drugs containing an activated linker moiety with a cell-binding agent provides another method of producing a cell-binding agent drug conjugate. Maytansinoids may also be linked to anti-CD20 antibody or fragment using PEG linking groups, as set forth for example in U.S. Pat. No. 6,716,821. These PEG non-cleavable linking groups are soluble both in water and in non-aqueous solvents, and can be used to join one or more cytotoxic agents to a cell binding agent. Exemplary PEG linking groups include heterobifunctional PEG linkers that react with cytotoxic agents and cell binding agents at opposite ends of the linkers through a functional sulfhydryl or disulfide group at one end, and an active ester at the other end. As a general example of the synthesis of a cytotoxic conjugate using a PEG linking group, reference is again made to U.S. Pat. No. 6,716,821 which is incorporated entirely by reference herein. Synthesis begins with the reaction of one or more cytotoxic agents bearing a reactive PEG moiety with a cell-binding agent, resulting in displacement of the terminal active ester of each reactive PEG moiety by an amino acid residue of the cell binding agent, to yield a cytotoxic conjugate comprising one or more cytotoxic agents covalently bonded to a cell binding agent through a PEG linking group. Alternatively, the cell binding can be modified with the bifunctional PEG crosslinker to introduce a reactive disulfide moiety (such as a pyridyldisulfide), which can then be treated with a thiol-containing maytansinoid to provide a conjugate. In another method, the cell binding can be modified with the bifunctional PEG crosslinker to introduce a thiol moiety which can then can be treated with a reactive disulfide-containing maytansinoid (such as a pyridyldisulfide), to provide a conjugate.

Antibody-drug conjugates with non-cleavable links can also be prepared. Such crosslinkers are described in the art (see, e.g., ThermoScientific Pierce Crosslinking Technical Handbook and US Publication No. 20050169933, each of which is hereby incorporated by reference) and include but are not limited to, N-succinimidyl 4-(maleimidomethyl)cyclohexanecarboxylate (SMCC), N-succinimidyl-4-(N-maleimidomethyl)-cyclohexane-1-carboxy-(6-amidocaproate), which is a "long chain" analog of SMCC (LC-SMCC), κ-maleimidoundecanoic acid N-succinimidyl ester (KMUA), β-maleimidopropanoic acid N-succinimidyl ester (BMPS), γ-maleimidobutyric acid N-succinimidyl ester (GMBS), ε-maleimidocaproic acid N-hydroxysuccinimide ester (EMCS), m-maleimidobenzoyl-N-hydroxysuccinimide ester (MBS), N-(α-maleimidoacetoxy)-succinimide ester (AMAS), succinimidyl-6-(β-maleimidopropionamido)hexanoate (SMPH), N-succinimidyl 4-(p-maleimidophenyl)-butyrate (SMPB), and N-(p-maleimidophenyl)isocyanate (PMPI), N-succinimidyl-4-(iodoacetyl)-aminobenzoate (SIAB), N-succinimidyl iodoacetate (SIA), N-succinimidyl bromoacetate (SBA), and N-succinimidyl 3-(bromoacetamido)propionate (SBAP). Preferably, the antibody is modified with crosslinking reagents such as succinimidyl 4-(N-maleimidomethyl)-cyclohexane-1-carboxylate (SMCC), sulfo-SMCC, maleimidobenzoyl-N-hydroxysuccinimide ester (MBS), sulfo-MBS or succinimidyl-iodoacetate, as described in the literature, to introduce 1-10 reactive groups (Yoshitake et al, Eur. J. Biochem., 101:395-399 (1979); Hashida et al, J. Applied Biochem., 56-63 (1984); and Liu et al, Biochem., 18:690-697 (1979)). The modified antibody is then reacted with the thiol-containing maytansinoid derivative to produce a conjugate. The conjugate can be purified by gel filtration through a Sephadex G25 column or by dialysis or tangential flow filtration. The modified antibodies are treated with the thiol-containing maytansinoid (1 to 2 molar equivalent/maleimido group) and antibody-maytansinoid conjugates are purified by gel filtration through a Sephadex G-25 column, chromatography on a ceramic hydroxyapatite column, dialysis or tangential flow filtration or a combination of methods thereof. Typically, an average of 1-10 maytansinoids per antibody are linked. A preferred method is to modify antibodies with succinimidyl 4-(N-maleimidomethyl)-cyclohexane-1-carboxylate (SMCC) to introduce maleimido groups followed by reaction of the modified antibody with a thiol-containing maytansinoid to give a thioether-linked conjugate. Again conjugates with 1 to 10 drug molecules per antibody molecule result. Maytansinoid conjugates of antibodies, antibody fragments, protein hormones, protein growth factors and other proteins are made in the same way.

In another aspect of the invention, the CD20 antibody is linked to the drug via a non-cleavable bond through the intermediacy of a PEG spacer. Suitable crosslinking reagents comprising hydrophilic PEG chains that form linkers between a drug and the anti-CD20 antibody or fragment are also well known in the art, or are commercially available (for example from Quanta Biodesign, Powell, Ohio). Suitable PEG-containing crosslinkers can also be synthesized from commercially available PEGs themselves using standard synthetic chemistry techniques known to one skilled in the art. The drugs can be reacted with bifunctional PEG-containing cross linkers to give compounds of the following formula, $Z-X_l-(-CH_2-CH_2-O-)_n-Y_p-D$, by methods described in detail in US Patent Publication 20090274713 and in WO2009/0134976, which can then react with the cell binding agent to provide a conjugate. Alternatively, the cell binding can be modified with the bifunctional PEG crosslinker to introduce a thiol-reactive group (such as a maleimide or haloacetamide) which can then be treated with a thiol-containing maytansinoid to provide a conjugate. In another method, the cell binding can be modified with the bifunctional PEG crosslinker to introduce a thiol moiety which can then be treated with a thiol-reactive maytansinoid (such as a maytansinoid bearing a maleimide or haloacetamide), to provide a conjugate.

Accordingly, another aspect of the present invention is an anti-CD20 antibody drug conjugate of formula (II) or of formula (II'):

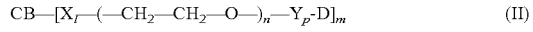   (II)

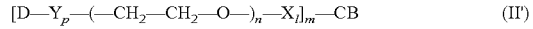   (II')

wherein,
CB represents an anti-CD20 antibody or fragment;
D represents a drug;

X represents an aliphatic, an aromatic or a heterocyclic unit bonded to the cell-binding agent via a thioether bond, an amide bond, a carbamate bond, or an ether bond;
Y represents an aliphatic, an aromatic, or a heterocyclic unit bonded to the drug via a covalent bond selected from the group consisting of a thioether bond, an amide bond, a carbamate bond, an ether bond, an amine bond, a carbon-carbon bond and a hydrazone bond;
l is 0 or 1;
p is 0 or 1;
m is an integer from 2 to 15; and
n is an integer from 1 to 2000.
Preferably, m is an integer from 2 to 8; and
Preferably n is an integer from 1 to 24.
More preferably, m is an integer from 2 to 6.
Also, even more preferably, m is an integer from 3 to 5.
Also, more preferably, n is an integer from 2 to 8. Examples of suitable PEG-containing linkers include linkers having an N-succinimidyl ester or N-sulfosuccinimidyl ester moiety for reaction with the anti-CD20 antibody or fragment thereof, as well as a maleimido- or haloacetyl-based moiety for reaction with the compound. A PEG spacer can be incorporated into any crosslinker known in the art by the methods described herein. Crosslinking reagents comprising a maleimido-based moiety that can be incorporated with a PEG spacer include, but are not limited to, N-succinimidyl 4-(maleimidomethyl) cyclohexanecarboxylate (SMCC), N-succinimidyl-4-(N-maleimidomethyl)-cyclohexane-1-carboxy-(6-amidocaproate), which is a "long chain" analog of SMCC (LC-SMCC), κ-maleimidoundecanoic acid N-succinimidyl ester (KMUA), γ-maleimidobutyric acid N-succinimidyl ester (GMBS), ε-maleimidocaproic acid N-hydroxysuccinimide ester (EMCS), m-maleimidobenzoyl-N-hydroxysuccinimide ester (MBS), N-(α-maleimidoacetoxy)-succinimide ester (AMAS), succinimidyl-6-(β-maleimidopropionamido)hexanoate (SMPH), N-succinimidyl 4-(p-maleimidophenyl)-butyrate (SMPB), and N-(p-maleimidophenyl)isocyanate (PMPI). Cross-linking reagents comprising a haloacetyl-based moiety include N-succinimidyl-4-(iodoacetyl)-aminobenzoate (SIAB), N-succinimidyl iodoacetate (SIA), N-succinimidyl bromoacetate (SBA), and N-succinimidyl 3-(bromoacetamido)propionate (SBAP).

Other crosslinking reagents lacking a sulfur atom can also be used. Such linkers can be derived from dicarboxylic acid based moieties. Suitable dicarboxylic acid based moieties include, but are not limited to, α,ω-dicarboxylic acids of the general formula shown below:

wherein A' is an optional linear or branched alkyl, alkenyl, or alkynyl group having 2 to 20 carbon atoms, E' is an optional cycloalkyl or cycloalkenyl group having 3 to 10 carbon atoms, G' is an optional substituted or unsubstituted aromatic group having 6 to 10 carbon atoms, or a substituted or unsubstituted heterocyclic group wherein the hetero atom is selected from N, O or S, and wherein p, q and r are each 0 or 1, provided that p, q, and r are all not zero at the same time, n is an integer from 1 to 2000.

Many of the linkers disclosed herein are described in detail in U.S. Patent Publication Nos. 20050169933 and 20090274713, and in WO2009/0134976; the contents of which are entirely incorporated herein by reference.

The present invention also provides charged linkers, wherein the charges are retained both after modification of the anti-CD20 antibody or fragment thereof and in the resulting drug conjugate. More specifically, the present invention relates to the use of charged linkers to link drugs to an anti- CD20 antibody. In one aspect of the invention, the charged linkers are used to modify cell-binding agents and link them to drugs. In another aspect of the invention, the charged linkers are used to modify drugs and link them to the anti-CD20 antibody or fragment. In yet another aspect of the invention, the charged linkers are used to simultaneously link drugs and the cell-binding agents. In all instances, the preferred end result is a drug-charged linker-cell-binding agent conjugate, which can be represented by the formula, CB—(-$L^c$-D)$_q$, wherein CB is a cell-binding agent that is an anti-CD20 antibody or fragment thereof, $L^c$ is a charged linker, D is a drug molecule, and q is an integer from 1 to 20. The presence of a charged group(s) in the linker in the cell-binding agent-drug conjugate provides several advantages, such as i) greater water solubility of the final product, ii) ability to operate at a higher concentration in aqueous solutions, iii) ability to link a greater number of drug molecules per molecule of cell-binding agent, resulting in higher potency, iv) potential for the charged conjugate species to be retained inside the target cell, resulting in higher potency, and v) improved sensitivity of multidrug resistant cells, which would be unable to export the charged drug species from the cell. The invention also describes linkers, which can be coupled to a drug and a cell binding agent to give a conjugate which can be metabolized in a cell to produce a drug metabolite containing one or more charged moieties. These linkers will be referred to as pro-charged linkers. Moieties of the linker which will become charged after cell processing will be referred to as pro-charged moieties.

In one aspect of the present invention, the charged or pro-charged cross linker is represented by formula (III) wherein Y' can react with a cell-binding agent and Q can react with a cytotoxic drug:

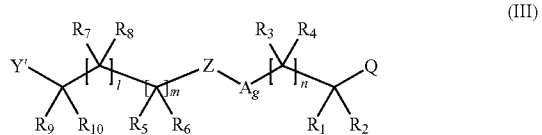

(III)

wherein:

Y' represents a functional group that enables reaction with an anti-CD20 antibody or fragment thereof;

Q represents a functional group that enables linkage of a cytotoxic drug via a disulfide, thioether, thioester, peptide, hydrazone, ether, ester, carbamate or amide bond;

$R_1$, $R_2$, $R_3$, $R_4$, $R_5$, $R_6$, $R_7$, $R_8$, $R_9$, and $R_{10}$ are the same or different and are H, linear alkyl having from 1-6 carbon atoms, branched or cyclic alkyl having from 3 to 6 carbon atoms, linear, branched or cyclic alkenyl or alkynyl having from 2 to 6 carbon atoms, anions, such as but not limited to, $SO_3^-$, X—$SO_3^-$, $OPO_3^{2-}$, X—$OPO_3^{2-}$, $PO_3^{2-}$, X—$PO_3^{2-}$, $CO_2^-$, and cations, such as but not limited to, a nitrogen containing heterocycle, $N^+R_{11}R_{12}R_{13}$ or X—$N^+R_{11}R_{12}R_{13}$, or a phenyl, wherein:

$R_{11}$, $R_{12}$ and $R_{13}$ are the same or different and are H, linear alkyl having from 1 to 6 carbon atoms, or branched or cyclic alkyl having from 3 to 6 carbon atoms and X represents phenyl or a linear alkyl having from 1 to 6 carbon atoms, or a branched or cyclic alkyl having from 3 to 6 carbon atoms;

l, m and n are 0 or an integer from 1 to 4; and

A is a phenyl or a substituted phenyl, wherein the substituent is a linear alkyl having from 1 to 6 carbon atoms, or a branched or cyclic alkyl having from 3 to 6 carbon atoms, or a charged substituent selected from anions, such as but not limited to, $SO_3^-$, X—$SO_3^-$, $OPO_3^{2-}$, X—$OPO_3^{2-}$, $PO_3^{2-}$, X—$PO_3^{2-}$, $CO_2^-$, and cations, such as but not limited to, a nitrogen containing heterocycle, $N^+R_{11}R_{12}R_{13}$ or X—$N^+R_{11}R_{12}R_{13}$, wherein X has the same definition as above, and wherein g is 0 or 1;

Z is an optional polyethyleneoxy unit of formula $(OCH_2CH_2)_p$, wherein p is 0 or an integer from 2 to about 1000, or F1-E1-P-E2-F2 unit in which E1 and E2 are the same or different and are C=O, O, or $NR_{14}$, wherein $R_{14}$ is H, a linear alkyl having from 1-6 carbon atoms, a branched or cyclic alkyl having from 3 to 6 carbon atoms, a linear, branched or cyclic alkenyl or alkynyl having from 2 to 6 carbon atoms; P is a peptide unit between 2 and 20 amino acids in length, wherein E1 or E2 can be linked to the peptide through the terminal nitrogen, terminal carbon or through a side chain of one of the amino acids of the peptide; and F1 and F2 are the same or different and are an optional polyethyleneoxy unit of formula $(OCH_2CH_2)_p$, wherein p is 0 or an integer from 2 to about 1000, provided that when Z is not F1-E1-P-E2-F2, at least one of $R_1$, $R_2$, $R_3$, $R_4$, $R_5$, $R_6$, $R_7$, $R_8$, $R_9$, and $R_{10}$ is a charged substituent or when g is 1, at least one of A, $R_1$, $R_2$, $R_3$, $R_4$, $R_5$, $R_6$, $R_7$, $R_8$, $R_9$, and $R_{10}$ is a charged substituent. This is one exemplary embodiment of a conjugate having a charged linker. Other examples are described in U.S. patent application Ser. No. 12/433,604, published as 2009-0274713 (Ravi, et al.), the contents of which is entirely incorporated herein by reference. Suitable charged linkers are well known in the art and include those described in, for example, 20090274713, the contents of which is incorporated herein entirely by reference.

The present invention includes aspects wherein about 2 to about 8 drug molecules ("drug load"), for example, maytansinoid, are linked to an anti-CD20 antibody or fragment thereof, the anti-tumor effect of the conjugate is much more efficacious as compared to a drug load of a lesser or higher number of drugs linked to the same cell binding agent. "Drug load", as used herein, refers to the number of drug molecules (e.g., a maytansinoid) that can be attached to a cell binding agent (e.g., an anti-CD20 antibody or fragment thereof). In one aspect the number of drug molecules that can be attached to a cell binding agent may average from about 2 to about 8 (e.g., 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1). In a preferred aspect, the number of drug molecules that can be attached to a cell binding agent may average from about 2 to about 7 (e.g., 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1). In an even more preferred aspect the number of drug molecules that can be attached to a cell binding agent may average from about 2 to about 6 (e.g., 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1). In the most preferred embodiment, the number of drug molecules that can be attached to a cell binding agent may average from about 2 to about 5 (e.g., 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5, 5.1). The term "average", as used herein, is determined by spectrophotometric measurement of the absorbance of an anti-CD20 antibody or fragment thereof and the drug linked to it. In another aspect, the drug anti-CD20 antibody or fragment thereof conjugate is represented by the formula (D)$_{about\ 2-about\ 8}$-L-Anti-CD20Ab, wherein D is a drug (e.g., a maytansinoid, a taxane or a CC1065 analog), L is a linker, wherein the linker is selected from a cleavable linker (e.g., linkers cleavable through disulfide exchange) or a linker substantially resistant to cleavage (e.g., linkers having an N-succinimidyl ester or N-sulfosuccinimidyl ester moiety for reaction with the cell-binding agent, as well as a maleimido- or haloacetyl-based moiety) and Anti-CD20Ab is an antibody or fragment thereof that binds CD20 as described herein. In a preferred element, the drug cell binding agent conjugate (e.g., an immunoconjugate) represented by formula (May)$_{about\ 2-about\ 8}$-L-Anti-CD20Ab, wherein May is a maytansinoid, L is a linker, wherein said linker is a cleavable linker or a linker substantially resistant to cleavage; and Anti-CD20Ab is an antibody or fragment thereof that binds CD20 as described herein. The drugs suitable for use in this invention are cytotoxic drugs capable of being linked to a cell-binding agent as described herein. One aspect of the invention is a suitable analogue of maytansinol having a modified aromatic ring, including: (1) C-19-dechloro (U.S. Pat. No. 4,256, 746) (prepared by LAH reduction of ansamitocin P2); (2) C-20-hydroxy (or C-20-demethyl) +/−C-19-dechloro (U.S. Pat. Nos. 4,361,650 and 4,307,016) (prepared by demethylation using *Streptomyces* or *Actinomyces* or dechlorination using LAH); and (3) C-20-demethoxy, C-20-acyloxy (—OCOR), +/−dechloro (U.S. Pat. No. 4,294,757) (prepared by acylation using acyl chlorides). Specific examples of suitable analogues of maytansinol having modifications of other positions include: (1) C-9-SH (U.S. Pat. No. 4,424,219) (prepared by the reaction of maytansinol with $H_2S$ or $P_2S_5$); (2) C-14-alkoxymethyl (demethoxy/$CH_2OR$) (U.S. Pat. No. 4,331,598); (3) C-14-hydroxymethyl or acyloxymethyl ($CH_2OH$ or $CH_2OAc$) (U.S. Pat. No. 4,450,254) (prepared from *Nocardia*); (4) C-15-hydroxy/acyloxy (U.S. Pat. No. 4,364,866) (prepared by the conversion of maytansinol by *Streptomyces*); (5) C-15-methoxy (U.S. Pat. Nos. 4,313,946 and 4,315,929) (isolated from *Trewia nudiflora*); (6) C-18-N-demethyl (U.S. Pat. Nos. 4,362,663 and 4,322,348) (prepared by the demethylation of maytansinol by *Streptomyces*); and (7) 4,5-deoxy (U.S. Pat. No. 4,371,533) (prepared by the titanium trichloride/LAH reduction of maytansinol). The synthesis of thiol-containing maytansinoids useful in the present invention is fully disclosed in U.S. Pat. Nos. 5,208, 020, 5,416,064, and 7,276,497. Maytansinoids with a thiol moiety at the C-3 position, the C-14 position, the C-15 position or the C-20 position are all useful. The C-3 position is preferred and the C-3 position of maytansinol is especially preferred. Also preferred are an N-methyl-alanine-containing C-3 thiol moiety maytansinoid, and an N-methyl-cysteine-containing C-3 thiol moiety maytansinoid, and analogues of each. Preferred maytansinoids are those described in U.S. Pat. Nos. 5,208,020; 5,416,064; 6,333.410; 6,441,163; 6,716, 821; RE39,151 and 7,276,497. Of these, $N^{2'}$-deacetyl-$N^{2'}$-(3-mercapto-1-oxopropyl)-maytansine (DM1) and $N^{2'}$-deacetyl-$N^{2'}$-(4-mercapto-4-methyl-1-oxopentyl) maytansine (DM4) are preferred. Other drugs can be used in the present aspect of the invention, for example, such as those described herein. Other examples are described in U.S. Provisional Application No. 61/049,296 and U.S. patent application Ser. No. 12/574,430; the entire contents of which are incorporated herein by reference.

The anti-CD20 antibody or fragment thereof can be modified by reacting a bifunctional crosslinking reagent with the anti-CD20 antibody or fragment thereof, thereby resulting in the covalent attachment of a linker molecule to the anti-CD20 antibody or fragment thereof. As used herein, a "bifunctional crosslinking reagent" is any chemical moiety that covalently links a cell-binding agent to a drug, such as the drugs described herein. In another method, a portion of the linking moiety is provided by the drug. In this respect, the drug comprises a linking moiety that is part of a larger linker molecule that is used to join the cell-binding agent to the drug. For example, to form the maytansinoid DM1, the side chain at the C-3 hydroxyl group of maytansine is modified to have a free sulfhydryl group (SH). This thiolated form of maytansine can react with a modified cell-binding agent to form a conjugate. Therefore, the final linker is assembled from two components, one of which is provided by the crosslinking reagent, while the other is provided by the side chain from DM1.

The drug molecules can also be linked to the antibody molecules through an intermediary carrier molecule such as serum albumin.

As used herein, the expression "linked to a cell-binding agent" or "linked to an anti-CD20 antibody or fragment" refers to the conjugate molecule comprising at least one drug derivative bound to a cell-binding agent anti-CD20 antibody or fragment via a suitable linking group, or a precursor thereof. A preferred linking group is SMCC.

Especially preferred cytotoxic agents useful in the present invention are maytansinoids and maytansinoid analogs. Examples of suitable maytansinoids include esters of maytansinol and maytansinol analogs. Included are any drugs that inhibit microtubule formation and that are highly toxic to mammalian cells, as are maytansinol and maytansinol analogs.

Examples of suitable maytansinol esters include those having a modified aromatic ring and those having modifications at other positions. Such suitable maytansinoids are disclosed in U.S. Pat. Nos. 4,424,219; 4,256,746; 4,294,757; 4,307, 016; 4,313,946; 4,315,929; 4,331,598; 4,361,650; 4,362,663; 4,364,866; 4,450,254; 4,322,348; 4,371,533; 5,208,020; 5,416,064; 5,475,092; 5,585,499; 5,846,545; 6,333,410; 7,276,497 and 7,473,796.

Specific examples of suitable analogues of maytansinol having a modified aromatic ring include:

(1) C-19-dechloro (U.S. Pat. No. 4,256,746) (prepared by LAH reduction of ansamytocin P2);

(2) C-20-hydroxy (or C-20-demethyl) +/−C-19-dechloro (U.S. Pat. Nos. 4,361,650 and 4,307,016) (prepared by demethylation using *Streptomyces* or *Actinomyces* or dechlorination using LAH); and (3) C-20-demethoxy, C-20-acyloxy (—OCOR), +/−dechloro (U.S. Pat. No. 4,294,757) (prepared by acylation using acyl chlorides).

Specific examples of suitable analogues of maytansinol having modifications of other positions include:

(1) C-9-SH (U.S. Pat. No. 4,424,219) (prepared by the reaction of maytansinol with H2S or P2S5);

(2) C-14-alkoxymethyl (demethoxy/CH2OR) (U.S. Pat. No. 4,331,598);

(3) C-14-hydroxymethyl or acyloxymethyl (CH2OH or CH2OAc) (U.S. Pat. No. 4,450,254) (prepared from *Nocardia*);

(4) C-15-hydroxy/acyloxy (U.S. Pat. No. 4,364,866) (prepared by the conversion of maytansinol by *Streptomyces*);

(5) C-15-methoxy (U.S. Pat. Nos. 4,313,946 and 4,315, 929) (isolated from *Trewia nudiflora*);

(6) C-18-N-demethyl (U.S. Pat. Nos. 4,362,663 and 4,322, 348) (prepared by the demethylation of maytansinol by *Streptomyces*); and (7) 4,5-deoxy (U.S. Pat. No. 4,371,533) (prepared by the titanium trichloride/LAH reduction of maytansinol).

In a preferred aspect, the conjugates of the present invention utilize the thiol-containing maytansinoid (DM1), formally termed N²'-deacetyl-N²'-(3-mercapto-1-oxopropyl)-maytansine, as the cytotoxic agent. DM1 is represented by the following structural formula (IV):

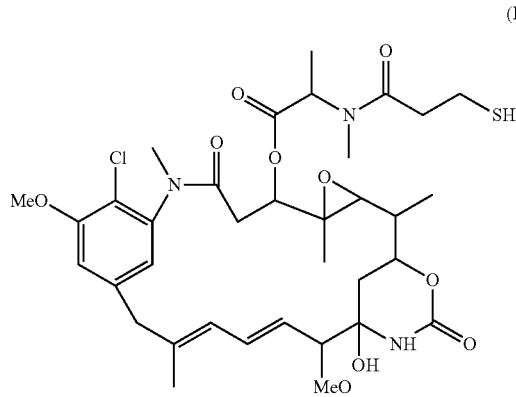

(IV)

In a preferred aspect, the conjugates of the present invention utilize the thiol-containing maytansinoid N²'-deacetyl-N²'(4-methyl-4-mercapto-1-oxopentyl)-maytansine (e.g., DM4) as the cytotoxic agent. DM4 is represented by the following structural formula (V):

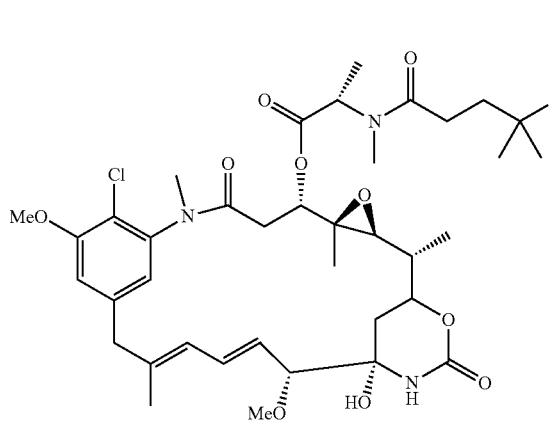

(V)

Other preferred maytansinoids comprising a side chain that contains a sterically hindered thiol bond is N²'-deacetyl-N-²'(4-mercapto-1-oxopentyl)-maytansine (termed DM3), represented by the following structural formula (VI):

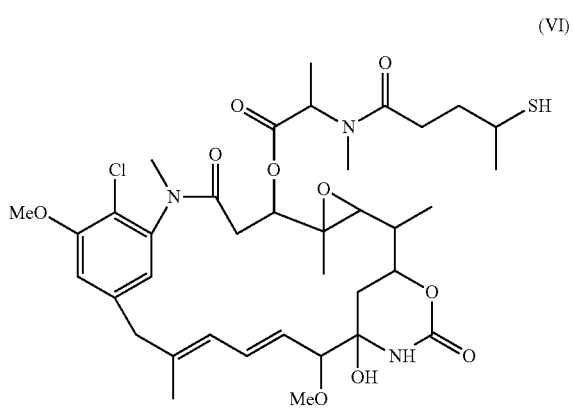 [SMILES: COc1cc2cc(c1Cl)N(C)C(=O)CC(OC(=O)C(C)N(C)C(=O)CCC(C)S)C1(C)OC1C(C)C1CC(O)(NC(=O)O1)C(OC)/C=C/C=C(\C)C2]

(VI)

Additional maytansinoids include compounds represented by formula (VII-L), (VII-D), or (VII-D,L):

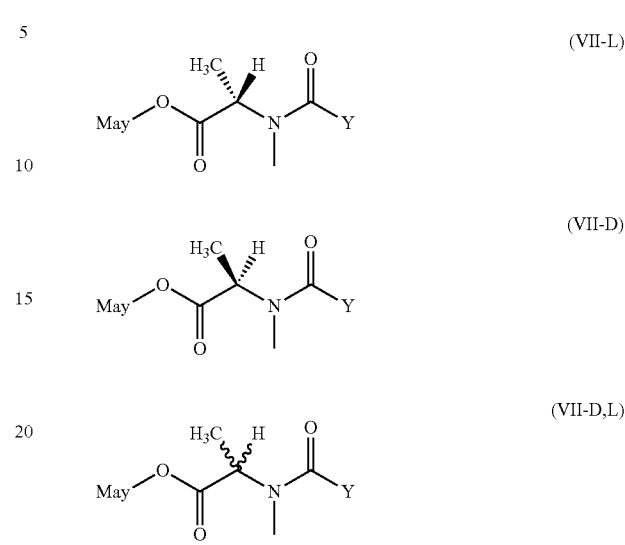

wherein:

Y represents $(CR_7R_8)_l(CR_5R_5)_m(CR_3R_4)_nCR_1R_2SZ$, wherein:

$R_1$ and $R_2$ are each independently, linear alkyl or alkenyl having from 1 to 10 carbon atoms, branched or cyclic alkyl or alkenyl having from 3 to 10 carbon atoms, phenyl, substituted phenyl, or heterocyclic group and in addition one of $R_1$ and $R_2$ can be H;

$R_3$, $R_4$, $R_5$, $R_6$, $R_7$ and $R_8$ are each independently H, linear alkyl or alkenyl having from 1 to 10 carbon atoms, branched or cyclic alkyl or alkenyl having from 3 to 10 carbon atoms, phenyl, substituted phenyl, or heterocyclic aromatic or heterocycloalkyl radical;

l, m and n are each independently an integer of from 1 to 5, and in addition n can be 0;

Z is H, SR or —COR wherein R is linear or branched alkyl or alkenyl having from 1 to 10 carbon atoms, cyclic alkyl or alkenyl having from 3 to 10 carbon atoms, or unsubstituted or substituted aryl or heterocyclic group; and May represents a maytansinoid which bears the side chain at C-3, C-14 hydroxymethyl, C-15 hydroxy or C-20 desmethyl.

Preferred aspects of formulas (VII-L), (VII-D) and (VII-D,L) include compounds of formulas (VII-L), (VII-D) and (VII-D,L) wherein:

$R_1$ is H, $R_2$ is methyl, $R_5$, $R_6$, $R_7$, and $R_8$ are each H, l and m are each 1, n is 0, and Z is H.

$R_1$ and $R_2$ are methyl, $R_5$, $R_6$, $R_7$, $R_8$ are each H, l and m are 1, n is 0, and Z is H.

$R_1$ is H, $R_2$ is methyl, $R_5$, $R_6$, $R_7$, $R_8$ are each H, l and m are each 1, n is 0, and Z is —SCH$_3$.

$R_1$ and $R_2$ are methyl, $R_5$, $R_6$, $R_7$, $R_8$ are each H, l and m are 1, n is 0, and Z is —SCH$_3$.

Additional maytansinoids also include compounds represented by formula (VIII):

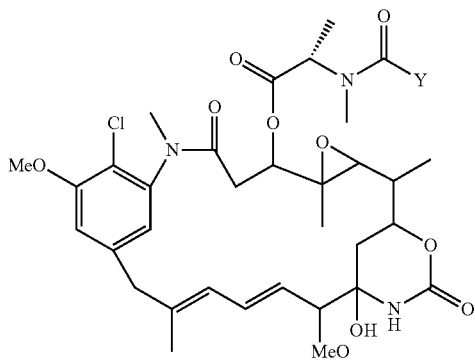

(VIII)

wherein Y is as defined for formula (VII).

Preferred aspects of formula (VIII) include compounds of formula (VIII) wherein:

$R_1$ is H, $R_2$ is methyl, $R_5$, $R_6$, $R_7$, and $R_8$ are each H; l and m are each 1; n is 0; and Z is H.

$R_1$ and $R_2$ are methyl, $R_5$, $R_6$, $R_7$, and $R_8$ are each H, l and m are 1; n is 0; and Z is H.

$R_1$ is H, $R_2$ is methyl, $R_5$, $R_6$, $R_7$, and $R_8$ are each H, l and m are each 1, n is 0, and Z is —$SCH_3$.

$R_1$ and $R_2$ are methyl, $R_5$, $R_6$, $R_7$, and $R_8$ are each H, l and m are 1, n is 0, and Z is —$SCH_3$.

Additional maytansines further include compounds represented by formula (IX-L), (IX-D), or (IX-D,L):

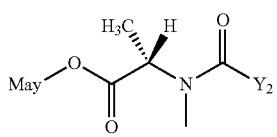

(IX-L)

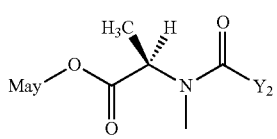

(IX-D)

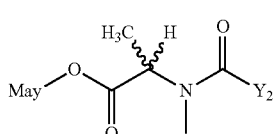

(IX-D,L)

wherein: $Y_2$ represents

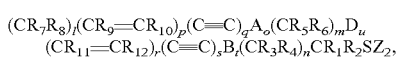

wherein:

$R_1$ and $R_2$ are each independently linear alkyl or alkenyl having from 1 to 10 carbon atoms, branched or cyclic alkyl or alkenyl having from 3 to 10 carbon atoms, phenyl, substituted phenyl or heterocyclic group, and in addition one of $R_1$ and $R_2$ can be H;

A, B, and D each independently is cycloalkyl or cycloalkenyl having 3 to 10 carbon atoms, simple or substituted aryl, or heterocyclic aromatic or heterocycloalkyl radical;

$R_3$, $R_4$, $R_5$, $R_6$, $R_7$, $R_8$, $R_9$, $R_{10}$, $R_{11}$ and $R_{12}$ are each independently H, linear alkyl or alkenyl having from 1 to 10 carbon atoms, branched or cyclic alkyl or alkenyl having from 3 to 10 carbon atoms, phenyl, substituted phenyl or heterocyclic group;

l, m, n, o, p, q, r, s, and t are each independently 0 or an integer of from 1 to 5, provided that at least two of l, m, n, o, p, q, r, s and t are not zero at any one time; and Z, is SR or —COR, wherein R is linear alkyl or alkenyl having from 1 to 10 carbon atoms, branched or cyclic alkyl or alkenyl having from 3-10 carbon atoms, or simple or substituted aryl or heterocyclic aromatic or heterocycloalkyl radical and May is a maytansinoid.

Preferred aspects of compounds of formula (IX) include compounds wherein $R_1$ is H and $R_2$ is methyl, and $R_1$ is methyl and $R_2$ is methyl.

Further maytansinoids include compounds represented by formula (X):

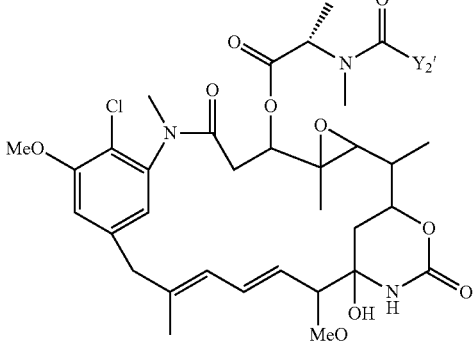

(X)

wherein $Y_2'$ is as defined the same as $Y_2$ for formula (IX).

Each of the maytansinoids taught in U.S. Pat. Nos. 5,208,020 and 7,276,497, may also be used in the conjugate of the present invention. In this regard, the entire disclosure of 5,208,020 and 7,276,697 is incorporated herein by reference.

Many positions on maytansinoids can serve as the position to chemically link the linking moiety. For example, the C-3 position having a hydroxyl group, the C-14 position modified with hydroxymethyl, the C-15 position modified with hydroxy and the C-20 position having a hydroxy group are all expected to be useful. However the C-3 position is preferred and the C-3 position of maytansinol is especially preferred.

Structural representations of preferred conjugates are shown below:

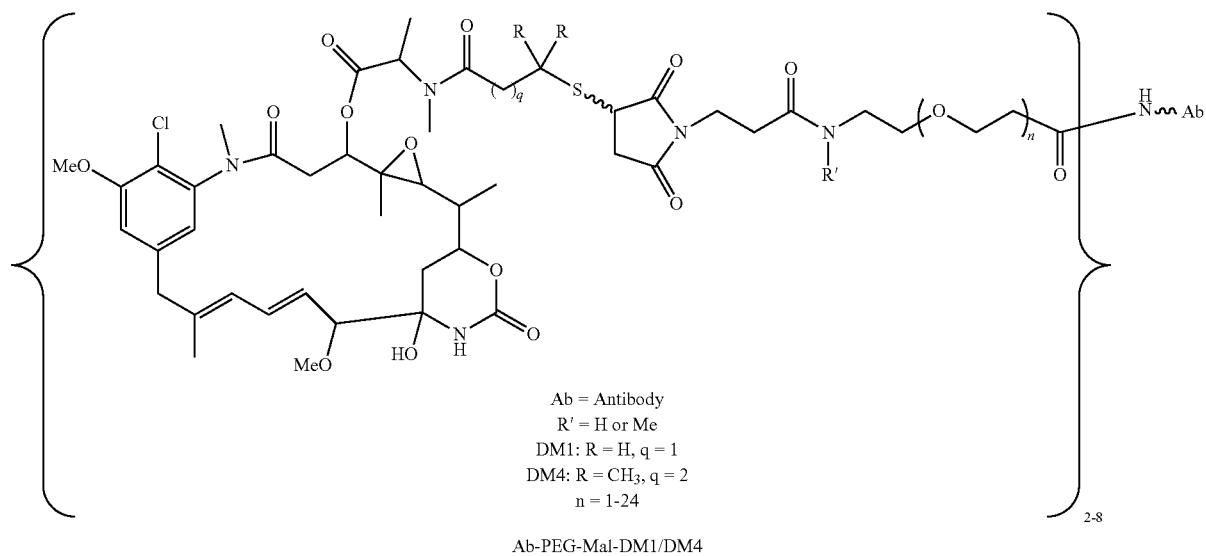
Ab = Antibody
R' = H or Me
DM1: R = H, q = 1
DM4: R = CH$_3$, q = 2
n = 1-24
Ab-PEG-Mal-DM1/DM4
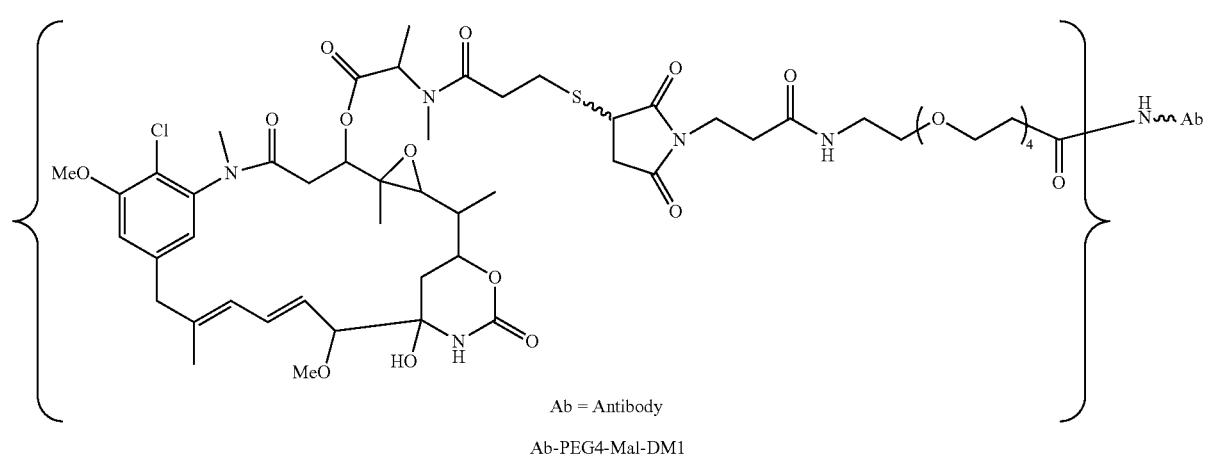
Ab = Antibody
Ab-PEG4-Mal-DM1
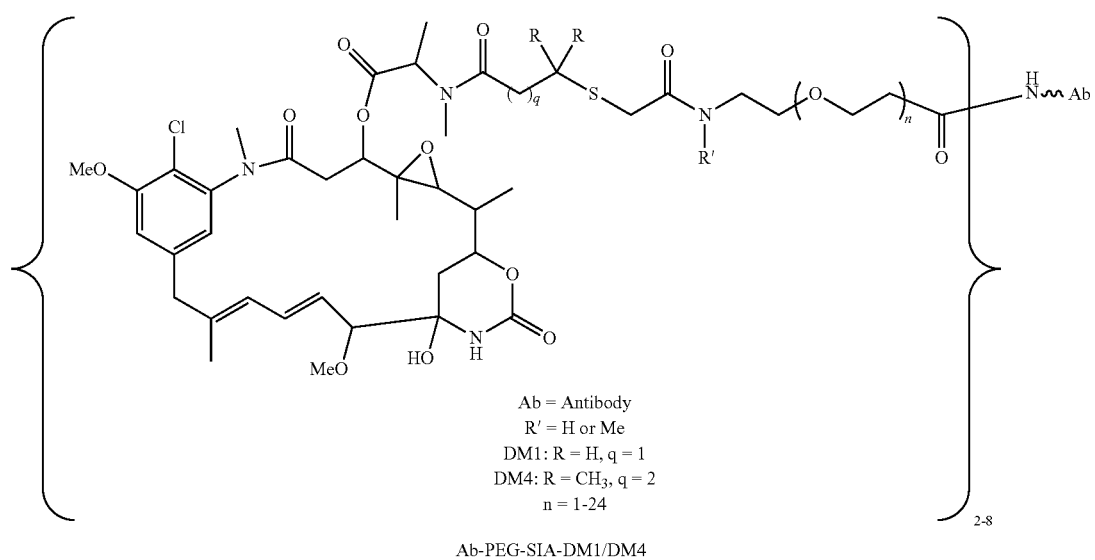
Ab = Antibody
R' = H or Me
DM1: R = H, q = 1
DM4: R = CH$_3$, q = 2
n = 1-24
Ab-PEG-SIA-DM1/DM4

(XIV)
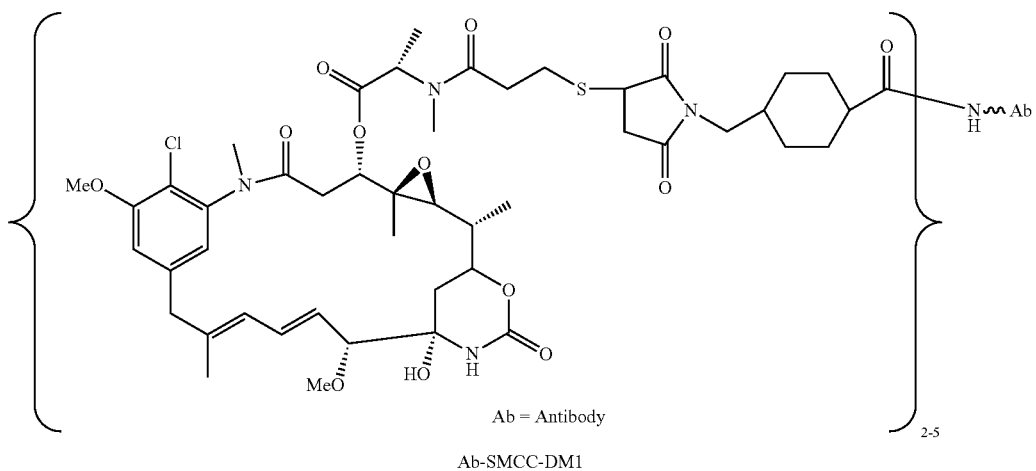
Ab = Antibody
Ab-SMCC-DM1
(XV)
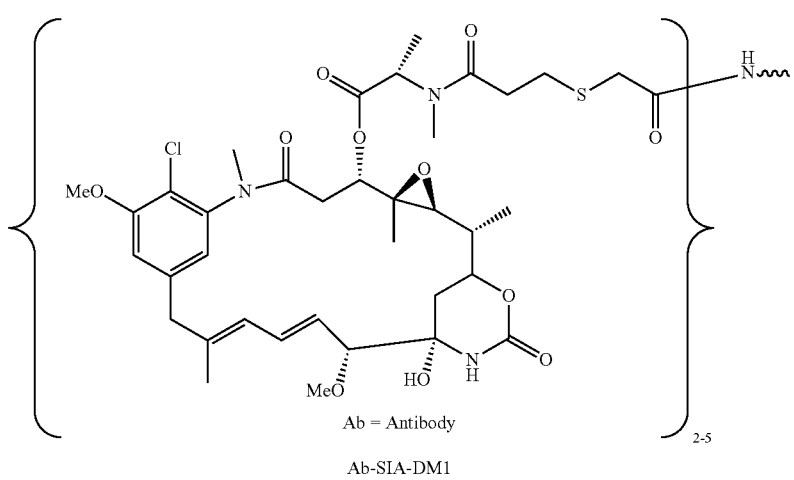
Ab = Antibody
Ab-SIA-DM1
(XVI)
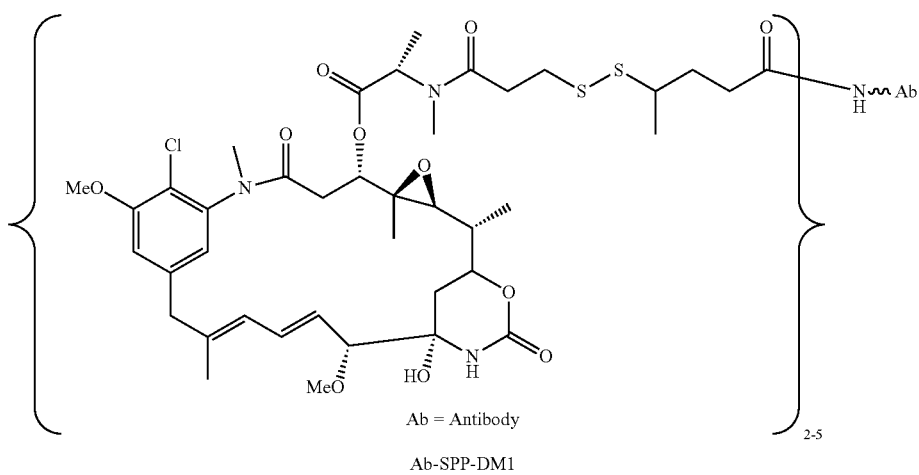
Ab = Antibody
Ab-SPP-DM1

(XVII)

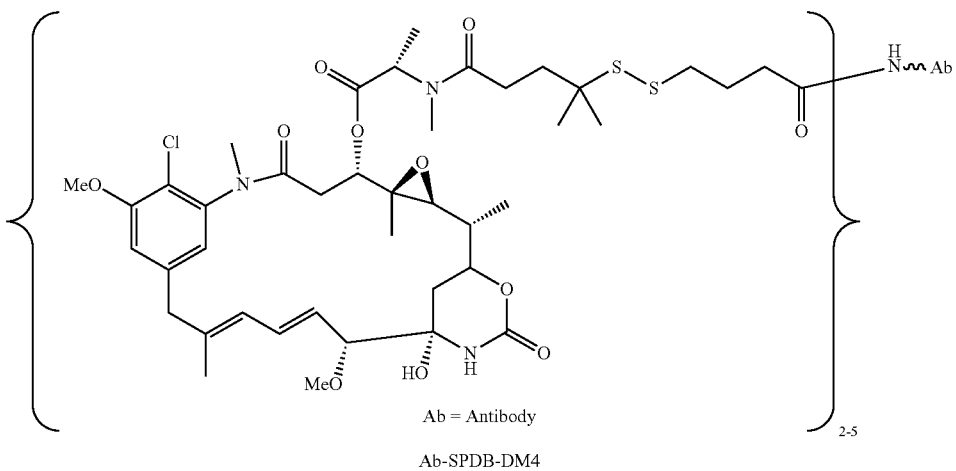

Ab-SPDB-DM4

(XVIII)

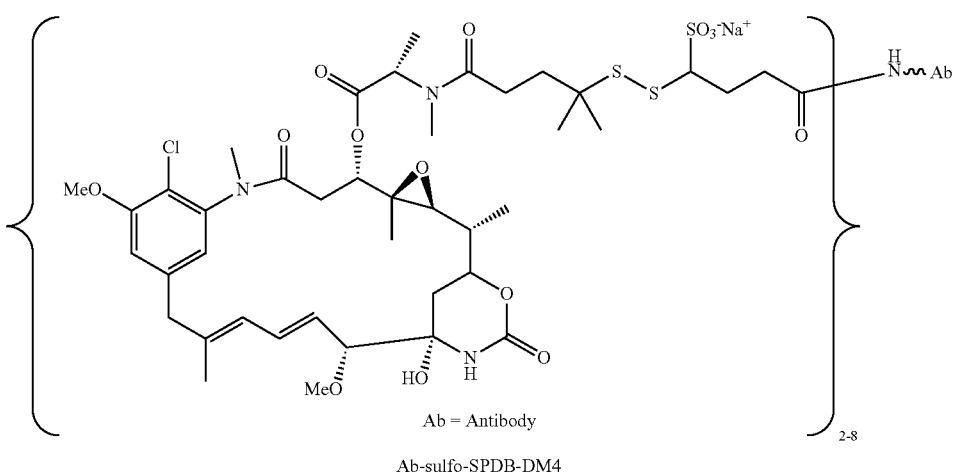

Ab-sulfo-SPDB-DM4

Several descriptions for producing such antibody-maytansinoid conjugates are provided in U.S. Pat. No. 6,333,410, and U.S. application Ser. Nos. 09/867,598, 10/161,651 and 10/024,290, each of which is incorporated herein in its entirety.

In general, a solution of an antibody in aqueous buffer may be incubated with a molar excess of maytansinoids having a disulfide moiety that bears a reactive group. The reaction mixture can be quenched by addition of excess amine (such as ethanolamine, taurine, etc.). The maytansinoid-antibody conjugate may then be purified by gel filtration.

The number of maytansinoid molecules bound per antibody molecule can be determined by measuring spectrophotometrically the ratio of the absorbance at 252 nm and 280 nm. An average of 1-10 maytansinoid molecules/antibody molecule is preferred and an average of 2-5 is still more preferred.

Conjugates of antibodies with maytansinoid drugs can be evaluated for their ability to suppress proliferation of various unwanted cell lines in vitro. For example, cell lines such as the human lymphoma cell line Daudi and the human lymphoma cell line Ramos, can easily be used for the assessment of cytotoxicity of these compounds. Cells to be evaluated can be exposed to the compounds for 4 to 5 days and the surviving fractions of cells measured in direct assays by known methods. $IC_{50}$ values can then be calculated from the results of the assays.

Benzodiazepine compounds described in U.S. Provisional Appl No. 61/150,201 (e.g., indolinobenzodiazepines or oxazolidinobenzodiazepines), derivatives thereof, intermediates thereof, may also be used to prepare anti-CD20 antibody fragment or conjugates.

Useful benzodiazepines include compounds of formula (XIX), (XX) and (XXI), in which the dimer compounds optionally bear a linking group that allows for linkage to cell binding agents.

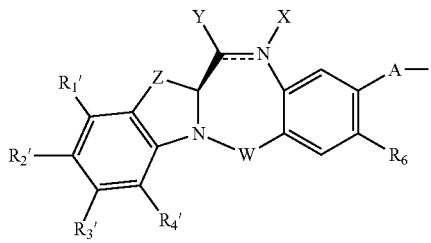 (XIX)

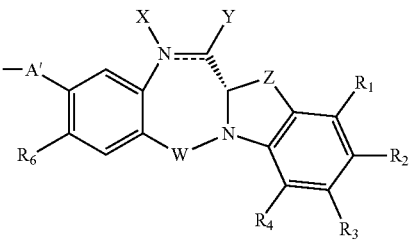

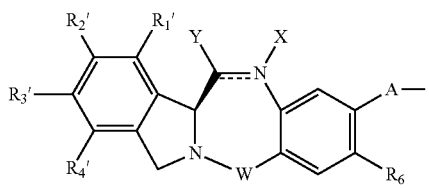 (XX)

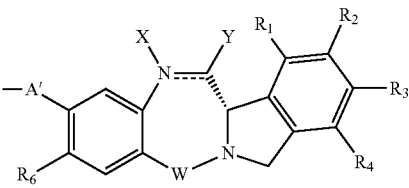

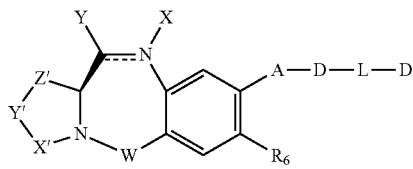 (XXI)

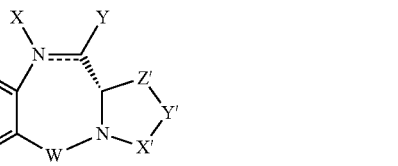

wherein the double line $=$ between N and C represents a single bond or a double bond, provided that when it is a double bond X is absent and Y is H, and when it is a single bond, X is H or an amine protecting moiety that converts the compound into a prodrug;

Y is selected from —OR, an ester represented by —OCOR', a carbonate represented by —OCOOR', a carbamate represented by —OCONR'R", an amine or a hydroxyl amine represented by NR'R", amide represented by —NRCOR', a peptide represented by NRCOP, wherein P is an amino acid or a polypeptide containing between 2 to 20 amino acid units, a thioether represented by SR', a sulfoxide represented by SOR', a sulfone represented by —SO$_2$R', a sulfite —SO$_3$, a bisulfite —OSO$_3$, a halogen, cyano, an azido, or a thiol, wherein R, R' and R" are same or different and are selected from H, substituted or unsubstituted linear, branched or cyclic alkyl, alkenyl or alkynyl having from 1 to 10 carbon atoms, a polyethylene glycol unit (—OCH$_2$CH$_2$)n, wherein n is an integer from 1 to 2000, aryl having from 6 to 10 carbon atoms, heterocyclic ring having from 3 to 10 carbon atoms wherein the substituent is selected from halogen, OR$_7$, NR$_8$R$_9$, NO$_2$, NRCOR', SR$_{10}$, a sulfoxide represented by SOR', a sulfone represented by —SO$_2$R', a sulfite —SO$_3$, a bisulfite —OSO$_3$, a sulfonamide represented by SO$_2$NRR', cyano, an azido, —COR$_{11}$, OCOR$_{11}$ or OCONR$_{11}$R$_{12}$, wherein the definitions of R$_7$, R$_8$, R$_9$, R$_{10}$, R$_{11}$ and R$_{12}$ are as given above, optionally R" is OH;

W is C=O, C=S, CH$_2$, BH, SO or SO$_2$;

R$_1$, R$_2$, R$_3$, R$_4$, R$_1$', R$_2$', R$_3$' and R$_4$' are each independently selected from H, substituted or unsubstituted linear, branched or cyclic alkyl, alkenyl or alkynyl having from 1 to 10 carbon atoms, a polyethylene glycol unit (—OCH$_2$CH$_2$)n, wherein n is an integer from 1 to 2000, or a substituent selected from a halogen, guanidinium [—NH(C=NH)NH$_2$], OR$_7$, NR$_8$R$_9$, NO$_2$, NRCOR', SR$_{10}$, a sulfoxide represented by SOR', a sulfone represented by —SO$_2$R', a sulfite —SO$_3$, a bisulfite —OSO$_3$, a sulfonamide represented by SO$_2$NRR', cyano, an azido, —COR$_{11}$, OCOR$_{11}$ or OCONR$_{11}$R$_{12}$ wherein R$_7$, R$_8$, R$_9$, R$_{10}$, R$_{11}$ and R$_{12}$ are each independently selected from H, linear, branched or cyclic alkyl, alkenyl or alkynyl having from 1 to 10 carbon atoms, a polyethylene glycol unit (—OCH$_2$CH$_2$)$_n$, wherein n is an integer from 1 to 2000, aryl having from 6 to 10 carbon atoms, heterocyclic ring having from 3 to 10 carbon atoms, optionally R$_{10}$ is SR$_{13}$ or COR$_{13}$, wherein R$_{13}$ is selected from linear, branched or cyclic alkyl, alkenyl or alkynyl having from 1 to 10 carbon atoms, a polyethylene glycol unit (—OCH$_2$CH$_2$)$_n$, wherein n is an integer from 1 to 2000, aryl having from 6 to 10 carbon atoms, heterocyclic ring having from 3 to 10 carbon atoms, optionally R$_{11}$ is OR$_{14}$, wherein R$_{14}$ has the same definition as R, optionally, any one of R$_1$, R$_2$, R$_3$, R$_4$, R$_1$', R$_2$', R$_3$', or R$_4$' is a linking group that enables linkage to a cell binding agent via a covalent bond or is selected from a polypyrrolo, polyindolyl, poly-imidazolyl, polypyrrolo-imidazolyl, poly-pyrrolo-indolyl or polyimidazolo-indolyl unit optionally bearing a linking group that enables linkage to a cell binding agent;

Z is selected from (CH$_2$)$_n$, wherein n is 1, 2 or 3, CR$_{15}$R$_{16}$, NR$_{17}$, O or S, wherein R$_{15}$, R$_{16}$ and R$_{17}$ are each independently selected from H, linear, branched or cyclic alkyl having from 1 to 10 carbon atoms, a polyethylene glycol unit (—OCH$_2$CH$_2$)$_n$, wherein n is an integer from 1 to 2000;

R$_6$ is OR, SR or NRR', wherein R and R' have the same definition as given above;

X' is selected from CH$_2$, NR, CO, BH, SO or SO$_2$ wherein R has the same definition as given above;

Y' is O, CH$_2$, NR or S, wherein R has the same definition as given above;

Z' is CH$_2$ or (CH$_2$)$_n$, wherein n is 2, 3 or 4, provided that X', Y' and Z' are not all CH$_2$ at the same time;

A and A' are the same or different and are selected from O, —CRR'O, S, —CRR'S, —NR$_{15}$ or CRR'NHR$_{15}$, wherein R and R' have the same definition as given above and wherein R$_{15}$ has the same definition as given above for R;

D and D' are same or different and independently selected from linear, branched or cyclic alkyl, alkenyl or alkynyl having 1 to 10 carbon atoms, optionally substituted with any one of halogen, OR$_7$, NR$_8$R$_9$, NO$_2$, NRCOR', SR$_{10}$, a sulfoxide represented by SOR', a sulfone represented by —SO$_2$R', a sulfite —SO$_3$, a bisulfite —OSO$_3$, a sulfonamide represented by SO$_2$NRR', cyano, an azido, —COR$_{11}$, OCOR$_{11}$ or OCONR$_{11}$R$_{12}$, wherein the definitions of R$_7$, R$_8$, R$_9$, R$_{10}$, R$_{11}$ and R$_{12}$ are as given above, a polyethylene glycol unit (—OCH$_2$CH$_2$)$_n$, wherein n is an integer from 1 to 2000;

L is an optional phenyl group or a heterocycle ring having from 3 to 10 carbon atoms that is optionally substituted, wherein the substituent is a linking group that enables linkage to a cell binding agent via a covalent bond, or is selected from linear, branched or cyclic alkyl, alkenyl or alkynyl having from 1 to 10 carbon atoms, optionally substituted with any one of halogen, OR$_7$, NR$_8$R$_9$, NO$_2$, NRCOR', SR$_{10}$, a sulfoxide represented by SOR', a sulfone represented by —SO$_2$R', a sulfite —SO$_3$, a bisulfite —OSO$_3$, a sulfonamide represented by SO$_2$NRR', cyano, an azido, —COR$_{11}$, OCOR$_{11}$ or OCONR$_{11}$R$_{12}$, wherein the definitions of R$_7$, R$_8$, R$_9$, R$_{10}$, R$_{11}$ and R$_{12}$ are as given above, a polyethylene glycol unit (—OCH$_2$CH$_2$)$_n$, wherein n is an integer from 1 to 2000; optionally, L itself is a linking group that enables linkage to a cell binding agent via a covalent bond; or their pharmaceutically acceptable solvates, salts, hydrates or hydrated salts, their optical isomers, racemates, diastereomers, enantiomers A and A' are each O;

D and D' are same or different and independently selected from linear, branched or cyclic alkyl, alkenyl or alkynyl having from 1 to 10 carbon atoms;

L is an optional phenyl group or a heterocycle ring having from 3 to 10 carbon atoms that is optionally substituted, wherein the substituent is a linking group that enables linkage to a cell binding agent via a covalent bond, or is selected from linear, branched or cyclic alkyl, alkenyl or alkynyl having from 1 to 10 carbon atoms, optionally substituted with any one of halogen, OR$_7$, NR$_8$R$_9$, NO$_2$, NRCOR', SR$_{10}$, a sulfoxide represented by SOR', a sulfone represented by —SO$_2$R', a sulfite —SO$_3$, a bisulfite —OSO$_3$, a sulfonamide represented by SO$_2$NRR', cyano, an azido, —COR$_{11}$, OCOR$_{11}$ or OCONR$_{11}$R$_{12}$, a polyethylene glycol unit (—OCH$_2$CH$_2$)n, wherein n is an integer from 1 to 2000; optionally, L itself is a linking group that enables linkage to a cell binding agent via a covalent bond; or their pharmaceutically acceptable solvates, salts, hydrates or hydrated salts, their optical isomers, racemates, diastereomers, enantiomers or the polymorphic crystalline structures of these compounds.

In another preferred aspect the compound is represented by formula (XXII):

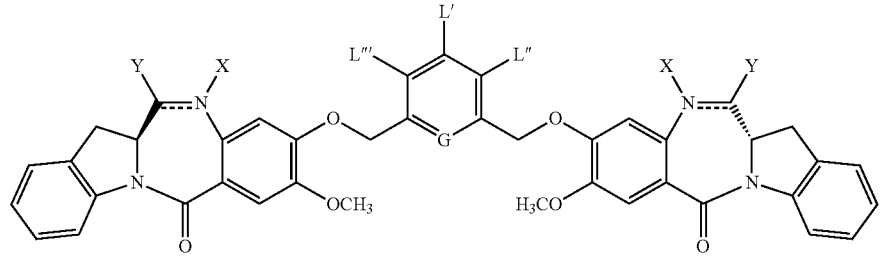

(XXII)

or the polymorphic crystalline structures of these compounds; provided that the compound has no more than one linking group that enables linkage to a cell binding agent via a covalent bond.

In one preferred aspect, the double line == between N and C represents a single bond or a double bond, provided that when it is a double bond X is absent and Y is H, and when it is a single bond, X is H or an amine protecting group that converts the compound into a prodrug;

Y is selected from —OR, NR'R", a sulfite —SO$_3$, or a bisulfite —OSO$_3$, wherein R is selected from H, linear, branched or cyclic alkyl, alkenyl or alkynyl having from 1 to 10 carbon atoms, a polyethylene glycol unit (—OCH$_2$CH$_2$)$_n$, wherein n is an integer from 1 to 2000, aryl having from 6 to 10 carbon atoms, heterocyclic ring having from 3 to 10 carbon atoms;

W is C=O, CH$_2$ or SO$_2$;

R$_1$, R$_2$, R$_3$, R$_4$, R$_1$', R$_2$', R$_3$' and R$_4$' are each independently selected from H, NO$_2$ or a linking group that enables linkage to a cell binding agent via a covalent bond;

R$_6$ is OR$_{18}$, wherein R$_{18}$ has the same definition as R;

Z is selected from (CH$_2$)$_n$, wherein n is 1, 2 or 3, CR$_{15}$R$_{16}$, NR$_{17}$, O or S, wherein R$_{15}$, R$_{16}$ and R$_{17}$ are each independently selected from H, linear, branched or cyclic alkyl having from 1 to 10 carbon atoms, a polyethylene glycol unit (—OCH$_2$CH$_2$)$_n$, wherein n is an integer from 1 to 2000;

X' is selected from CH$_2$, or C=O;

Y' is O, NR, or S, wherein R is defined as above;

Z' is CH$_2$ or (CH$_2$)$_2$;

wherein the double line == between N and C represents a single bond or a double bond, provided that when it is a double bond X is absent and Y is H, and when it is a single bond, X is H or an amine protecting group that converts the compound into a prodrug, and Y is selected from OH, an ether represented by —OR, a sulfite —SO$_3$, or a bisulfite —OSO$_3$, wherein R is selected from linear, branched or cyclic alkyl, alkenyl or alkynyl bearing from 1 to 10 carbon atoms one of R2, R3 is a linking group that enables linkage to a cell binding agent via a covalent bond and the other is H, one of L', L" or L'" is a linking group that enables linkage to a cell binding agent, while the others are H; preferably L' is the linking group and G is CH or N. Other examples are described in U.S. Patent Application No. 61/150,201, the entire content of which is incorporated herein by reference.

The cytotoxic agent used in the cytotoxic conjugates according to the present invention may also be a taxane or derivative thereof. Taxanes are a family of compounds that includes paclitaxel (Taxol), a cytotoxic natural product, and docetaxel (Taxotere), a semi-synthetic derivative, two compounds that are widely used in the treatment of cancer. Taxanes are mitotic spindle poisons that inhibit the depolymerization of tubulin, resulting in cell death. While docetaxel and paclitaxel are useful agents in the treatment of cancer, their antitumor activity is limited because of their non-specific toxicity towards normal cells. Further, compounds like paclitaxel and docetaxel themselves are not sufficiently potent to be used in conjugates of cell binding agents such as the anti-CD20 antibodies and fragments thereof of the present invention. Taxanes suitable for use in the present invention are disclosed in U.S. Pat. Nos. 6,372,738 and 6,340,701. Conjugates of the taxanes of the invention and a cell binding agent can be formed using any techniques presently known or later developed. Numerous methods of conjugation are taught in U.S. Pat. No. 5,416,064 and U.S. Pat. No. 5,475,092. Taxanes are also taught in U.S. Pat. No. 7,598,290, 20090099336, 20070031402, 20060233814, 20060233811, 20050123549, 20050085513, and 20040039176, all of which are incorporated herein by reference in their entireties.

CC-1065 and its analogs are also preferred cytotoxic drugs for use in the present invention. CC-1065 and its analogs are disclosed in U.S. Pat. Nos. 6,372,738; 6,340,701; 5,846,545; and 5,585,499. CC-1065 is a potent anti-tumor antibiotic isolated from the culture broth of Streptomyces zelensis. CC-1065 is about 1000-fold more potent in vitro than commonly used anti-cancer drugs, such as doxorubicin, methotrexate and vincristine (B. K. Bhuyan et al., Cancer Res., 42, 3532-3537 (1982)).

Duocarmycins are cytotoxic drugs well suited for use in the present invention and are disclosed herein and in the art, for example, in U.S. Pat. Nos. 6,281,354; 6,066,742; 5,703,080; 4,994,578; 4,923,990. Each reference is herein incorporated by reference in its entirety.

Enediynes, such as calicheamicins, are cytotoxic drugs well suited for use in the present invention and are disclosed herein and in the art, for example, in U.S. Pat. Nos. 5,436,361; 5,053,394; and 20090105461. Each reference is herein incorporated by reference in its entirety.

Dolastins and dolastin analogs, including auristatins, are cytotoxic drugs suited for use in the present invention and are disclosed herein and in the art, for example, in U.S. Pat. Nos. 7,084,110; 6,737,409; 6,686,445; 6,632,795; 6,458,765; 6,323,315; 6,248,865; 6,239,104; 6,143,721; 6,103,698; 6,034,065; 5,985,837; 5,965,537; 5,886,147; 5,554,725; 5,138,036; 5,076,973; 4,986,988; 4,978,744; and 4,879,278. Each reference is herein incorporated by reference in its entirety.

Tomaymycin derivatives are cytotoxic drugs suited for use in the present invention and are disclosed herein and in the art, for example, in U.S. Pat. No. 4,427,588, Arima et al., "J. Antibiotics", vol. 25, No. 8, pp. 437-444, (1972); Kariyone et al., "Chem. Pharm. Bull.", vol. 19, No. 11, pp. 2289-2293, (1971); and Leimgruber et al., "J. Am. Chem. Soc.", vol. 90, pp. 5641-5643, (1968). Each reference is herein incorporated by reference in its entirety.

Leptomycin derivatives are cytotoxic drugs suited for use in the present invention and are disclosed herein and in the art, for example, in U.S. Pat. No. 7,446,196; Kudo et al. Experimental Cell Research, 1998, 242(2), 54-546; Kuhnt et al., Applied Environmental Microbiology, 1998, 64(2), 714-720; U.S. application Ser. No. 10/856,703; Carl et al., J. Med. Chem. 1981, 24 (3), 479-480, "A Novel Connector Linkage Applicable in Prodrug Design"; Chemical Abstracts No. 105: 102629 (abstract of JP 61-109717 A2 (1986)); Doherty et al., J. Nat. Cancer Inst. 2003, 95(24), 1859-1868, "Cell Cycle Checkpoint Function in Bladder Cancer"; Fukuda et al., Nature 1997, 390, 308-311, "CRM1 is responsible for intracellular transport mediated by the nuclear export signal"; Hamamoto et al., J. Antibiotics 1983, 36 (6), 639-645, "Leptomycins A and B, New Antifungal Antibiotics I. Taxonomy of the Producing Strain and Their Fermentation, Purification and Characterization"; Hayakawa et al., J. Antibiotics 1987, 40 (9), 1349-1352, "New Antitumor Antibiotics, Anguinomycins A and B"; Inoue et al., J. Biol. Chem. 2002, 277 (17), 15053-15060, "Nuclear Import and Export Signals in Control of the p53-related Protein p73"; Kobayashi et al., Ensho, Saisei 2004, 24(5), 578-583, "Role of matrix metalloproteinase-9 expression on cutaneous inflammation: possible treatment by leptomycin B application" (abstract); Komiyama et al., J. Antibiotics 1985, 38 (2), 220-223, "Structural Study of a New Antitumor Antibiotic, Kazusamycin"; Komiyama et al., J. Antibiotics 1985, 38 (2), 224-229, "Antitumor Activity of a New Antibiotic, Kazusamycin"; Komiyama et al., J. Antibiotics 1985, 38 (3), 427-429, "Antitumor activity of leptomycin B"; Kudo et al., Exp. Cell Res. 1998, 242, 540-547, "Lepto-mycin B Inhibition of Signal Mediated Nuclear Export by Direct Binding to CRM1"; Kudo et al., Proc. Nat'l Acad. Sci. (USA) 1999, 96 (3), 9112-9117, "Leptomycin B inactivates CRM1/exportin 1 by covalent modification at a cysteine residue in the central conserved region"; Kuhnt et al., Applied Environ. Microbiol. 1998, 64 (2), 714-720, "Microbial Conversion Products of Leptomycin B"; Lane et al., Proc. Nat'l Acad. Sci. (USA) 2000, 97, 8501-8506, "Activation of p53 in cervical carcinoma cells by small molecules"; Marabese et al., Nucleic Acids Res. 2003 31 (22), 6624-6632, "DNA damage induces transcriptional activation of p73 by removing C-EBPa repression on E2F1"; Meissner et al., FEBS Letters 2004, 576(1-2), 27-30, "Ratjadone and leptomycin B block CRM1-dependent nuclear export by identical mechanisms" (abstract); Nishi et al., J. Biol. Chem. 1994, 269 (9), 6320-6324, "Leptomycin B Targets a Regulatory Cascade of crml, a Fission Yeast Nuclear Protein, Involved in Control of Higher Order Chromosome Structure and Gene Expression"; Peehl et al., Prostate 2003, 54, 258-267, "Leptomycin B Stabilizes and Activates p53 in Primary Prostatic Epithelial Cells and Induces Apoptosis in the LNCaP Cell Line"; and University of Dundee, Dept. Surgery & Molecular Oncology, Lain Group "Non-genotoxic activation of the p53 tumor suppressor function". Each reference is herein incorporated by reference in its entirety.

In another aspect of the invention siRNA molecules can be linked to the antibodies of the present invention instead of a drug. siRNAs can be linked to the antibodies of the present invention by methods commonly used for the modification of oligonucleotides (see, for example, US Patent Publications 20050107325 and 20070213292). Thus the siRNA in its 3' or 5'-phosphoromidite form can be reacted with one end of the crosslinker bearing a hydroxyl functionality to give an ester bond between the siRNA and the crosslinker. Similarly reaction of the siRNA phosphoramidite with a crosslinker bearing a terminal amino group results in linkage of the crosslinker to the siRNA through an amine. Alternatively, the siRNA can be derivatized by standard chemical methods to introduce a thiol group. This thiol-containing siRNA can be reacted with an antibody, that has been modified to introduce an active disulfide or maleimide moiety, to produce a cleavable or non cleavable conjugate. Between 1-20 siRNA molecules can be linked to an antibody by this method.

Diagnostic and Research Applications

In addition to the therapeutic uses of the antibodies discussed herein, the antibodies and/or fragments of the present invention can be employed in many known diagnostic and research applications. Antibodies and or fragments of the present invention may be used, for example, in the purification, detection, and targeting of CD20, included in both in vitro and in vivo diagnostic methods. For example, the antibodies and/or fragments may be used in immunoassays for qualitatively and quantitatively measuring levels of CD20 expressed by cells in biological samples. See, e.g., Harlow et al., Antibodies: A Laboratory Manual (Cold Spring Harbor Laboratory Press, 2nd ed. 1988), incorporated by reference herein in its entirety.

The antibodies of the present invention may be used in, for example, competitive binding assays, direct and indirect sandwich assays, and immunoprecipitation assays (Zola, Monoclonal Antibodies: A Manual of Techniques, pp. 147-158 (CRC Press, Inc., 1987)).

For example, the present invention also provides the above anti-CD20 peptides and antibodies, detectably labeled, as described below, for use in diagnostic methods for detecting CD20 in patients known to be or suspected of having a CD20-mediated condition. Anti-CD20 peptides and/or antibodies of the present invention are useful for immunoassays which detect or quantitate CD20, or anti-CD20 antibodies, in a sample. An immunoassay for CD20 typically comprises incubating a biological sample in the presence of a detectably labeled high affinity anti-CD20 peptide and/or antibody of the present invention capable of selectively binding to CD20, and detecting the labeled peptide or antibody which is bound in a sample. Various clinical assay procedures are well known in the art, e.g., as described in Immunoassays for the 80's, A. Voller et al., eds., University Park, 1981. Thus, an anti-CD20 peptide or antibody or fragment thereof can be added to nitrocellulose, or another solid support which is capable of immobilizing cells, cell particles or soluble proteins. The support can then be washed with suitable buffers followed by treatment with the detectably labeled CD20-specific peptide or antibody or fragment thereof. The solid phase support can then be washed with the buffer a second time to remove unbound peptide or antibody or fragment thereof. The amount of bound label on the solid support can then be detected by known method steps.

By "solid phase support" or "carrier" is intended any support capable of binding peptide, antigen or antibody or fragment thereof. Well-known supports or carriers, include glass, polystyrene, polypropylene, polyethylene, dextran, nylon, amylases, natural and modified celluloses, polyacrylamides, agaroses, and magnetite. The nature of the carrier can be either soluble to some extent or insoluble for the purposes of the present invention. The support material can have virtually any possible structural configuration so long as the coupled molecule is capable of binding to CD20 or an anti-CD20 antibody or fragment thereof. Thus, the support configuration can be spherical, as in a bead, or cylindrical, as in the inside surface of a test tube, or the external surface of a rod. Alternatively, the surface can be flat, such as a sheet, culture dish, test strip, etc. Preferred supports include polystyrene beads. Those skilled in the art will know many other suitable carriers for binding antibody or fragment thereof, peptide or antigen, or can ascertain the same by routine experimentation.

Well known method steps can determine binding activity of a given lot of anti-CD20 peptide and/or antibody or fragment thereof. Those skilled in the art can determine operative and optimal assay conditions by routine experimentation.

Detectably labeling a CD20-specific peptide and/or antibody or fragment thereof can be accomplished by linking to an enzyme for use in an enzyme immunoassay (EIA), or enzyme-linked immunosorbent assay (ELISA). The linked enzyme reacts with the exposed substrate to generate a chemical moiety which can be detected, for example, by spectrophotometric, fluorometric or by visual means. Enzymes which can be used to detectably label the CD20-specific antibodies or fragment thereof of the present invention include, but are not limited to, malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase.

By radioactively labeling the CD20-specific antibodies and/or fragment thereof, it is possible to detect CD20 through the use of a radioimmunoassay (RIA) (see, for example, Work, et al., Laboratory Techniques and Biochemistry in Molecular Biology, North Holland Publishing Company, N.Y. (1978)). The radioactive isotope can be detected by such means as the use of a gamma counter or a scintillation counter or by autoradiography. Isotopes which are particularly useful for the purpose of the present invention are: $^3H$, $^{125}I$, $^{131}I$, $^{35}S$, $^{14}C$, and, preferably, $^{125}I$.

It is also possible to label the CD20-specific antibodies and or fragments thereof with a fluorescent compound. When the fluorescent labeled antibody is exposed to light of the proper wave length, its presence can then be detected due to fluorescence. Among the most commonly used fluorescent labelling compounds are fluorescein isothiocyanate, rhodamine, phycoerythrin, phycocyanin, allophycocyanin, o-phthaldehyde and fluorescamine.

The CD20-specific antibodies or fragments thereof can also be detectably labeled using fluorescence-emitting metals such as $^{125}Eu$, or others of the lanthanide series. These metals can be attached to the CD20-specific antibody or fragment thereof using such metal chelating groups as diethylenetriaminepentaacetic acid (DTPA) or ethylenediamine-tetraacetic acid (EDTA).

The CD20-specific antibodies or fragments thereof also can be detectably labeled by coupling to a chemiluminescent compound, The presence of the chemiluminescently labeled antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester. Likewise, a bioluminescent compound can be used to label the CD20-specific antibody, fragment or derivative thereof of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Detection of the CD20-specific antibody, fragment or derivative thereof can be accomplished by a scintillation counter, for example, if the detectable label is a radioactive gamma emitter, or by a fluorometer, for example, if the label is a fluorescent material. In the case of an enzyme label, the detection can be accomplished by colorometric methods which employ a substrate for the enzyme. Detection can also be accomplished by visual comparison of the extent of enzymatic reaction of a substrate in comparison with similarly prepared standards.

For the purposes of the present invention, the CD20 which is detected by the above assays can be present in a biological sample. Any sample containing CD20 can be used. Preferably, the sample is a biological fluid such as, for example, blood, serum, lymph, urine, inflammatory exudate, cerebrospinal fluid, amniotic fluid, a tissue extract or homogenate, and the like. However, the invention is not limited to assays using only these samples, it being possible for one of ordinary skill in the art to determine suitable conditions which allow the use of other samples.

In situ detection can be accomplished by removing a histological specimen from a patient, and providing the combination of labeled antibodies of the present invention to such a specimen. The antibody or fragment thereof is preferably provided by applying or by overlaying the labeled antibody or fragment thereof to a biological sample. Through the use of such a procedure, it is possible to determine not only the presence of CD20 but also the distribution of CD20 in the examined tissue. Using the present invention, those of ordinary skill will readily perceive that any of a wide variety of histological methods (such as staining procedures) can be modified in order to achieve such in situ detection.

The antibody or fragment thereof of the present invention can be adapted for utilization in an immunometric assay, also known as a "two-site" or "sandwich" assay. In a typical immunometric assay, a quantity of unlabeled antibody or fragment thereof is bound to a solid support that is insoluble in the fluid being tested and a quantity of detectably labeled soluble antibody is added to permit detection and/or quantitation of the ternary complex formed between solid-phase antibody, antigen, and labeled antibody.

Typical, and preferred, immunometric assays include "forward" assays in which the antibody bound to the solid phase is first contacted with the sample being tested to extract the CD20 from the sample by formation of a binary solid phase antibody-CD20 complex. After a suitable incubation period, the solid support is washed to remove the residue of the fluid sample, including unreacted CD20, if any, and then contacted with the solution containing a known quantity of labeled antibody (which functions as a "reporter molecule"). After a second incubation period to permit the labeled antibody to complex with the CD20 bound to the solid support through the unlabeled antibody or fragment thereof, the solid support is washed a second time to remove the unreacted labeled antibody or fragment thereof. This type of forward sandwich assay can be a simple "yes/no" assay to determine whether CD20 is present or can be made quantitative by comparing the measure of labeled antibody or fragment thereof with that obtained for a standard sample containing known quantities of CD20. Such "two-site" or "sandwich" assays are described by Wide (Radioimmune Assay Method, Kirkham, ed., Livingstone, Edinburgh, 1970, pp. 199-206).

Other type of "sandwich" assays, which can also be useful with CD20, are the so-called "simultaneous" and "reverse" assays. A simultaneous assay involves a single incubation step wherein the antibody bound to the solid support and labeled antibody are both added to the sample being tested at the same time. After the incubation is completed, the solid support is washed to remove the residue of fluid sample and uncomplexed labeled antibody. The presence of labeled antibody associated with the solid support is then determined as it would be in a conventional "forward" sandwich assay.

In the "reverse" assay, stepwise addition first of a solution of labeled antibody to the fluid sample followed by the addition of unlabeled antibody bound to a solid support after a suitable incubation period, is utilized. After a second incubation, the solid phase is washed in conventional fashion to free it of the residue of the sample being tested and the solution of unreacted labeled antibody. The determination of labeled antibody associated with a solid support is then determined as in the "simultaneous" and "forward" assays. In one aspect, a combination of antibodies of the present invention specific for separate epitopes can be used to construct a sensitive three-site immunoradiometric assay.

The antibodies or fragments thereof of the invention also are useful for in vivo imaging, wherein an antibody or fragment thereof labeled with a detectable moiety such as a radio-opaque agent or radioisotope is administered to a subject, preferably into the bloodstream, and the presence and location of the labeled antibody in the host is assayed. This imaging technique is useful in the staging and treatment of malignancies. The antibody or fragment thereof may be labeled with any moiety that is detectable in a host, whether by nuclear magnetic resonance, radiology, or other detection means known in the art.

The label can be any detectable moiety that is capable of producing, either directly or indirectly, a detectable signal. For example, the label may be a biotin label, an enzyme label (e.g., luciferase, alkaline phosphatase, beta-galactosidase and horseradish peroxidase), a radio-label (e.g., $^{3}$H, $^{14}$C, $^{32}$P, $^{35}$S, and $^{125}$I), a fluorophore such as fluorescent or chemiluminescent compound (e.g., fluorescein isothiocyanate, rhodamine), an imaging agent (e.g., Tc-m99 and indium ($^{111}$In)) and a metal ion (e.g., gallium and europium).

Any method known in the art for conjugating the antibody or fragment thereof to the label may be employed, including those exemplary methods described by Hunter, et al., 1962, *Nature* 144:945; David et al., 1974, *Biochemistry* 13:1014; Pain et al., 1981, *J. Immunol. Meth.* 40:219; Nygren, J., 1982, *Histochem. and Cytochem.* 30:407.

The antibodies or fragments thereof of the invention also are useful as reagents in biological research, based on their inhibition of the function of CD20 in cells.

The antibodies or fragments thereof of the invention also are useful as affinity purification agents. In this process, the antibodies, for example, are immobilized on a suitable support, such a Sephadex resin or filter paper, using methods well known in the art. Thus, CD20 may be isolated and purified from a biological sample.

The present invention further provides polynucleotides comprising a nucleotide sequence encoding an antibody or fragment thereof of the invention or epitope-binding fragments thereof.

The present invention also encompasses polynucleotides encoding a polypeptide that can bind CD20 and that hybridize under stringent hybridization conditions to polynucleotides that encode an antibody or fragment thereof of the present invention, wherein said stringent hybridization conditions include: pre-hybridization for 2 hours at 60° C. in 6×SSC, 0.5% SDS, 5×Denhardt's solution, and 100 µg/ml heat denatured salmon sperm DNA; hybridization for 18 hours at 60° C.; washing twice in 4×SSC, 0.5% SDS, 0.1% sodium pyrophosphate, for 30 min at 60° C. and twice in 2×SSC, 0.1% SDS for 30 min at 60° C.

The polynucleotides may be obtained, and the nucleotide sequence of the polynucleotides determined, by any method known in the art. For example, using the nucleotide sequence of the antibody or fragment thereof set forth herein, a polynucleotide encoding the antibody may be assembled from chemically synthesized oligonucleotides (e.g., as described in Kutmeier et al., 1994, *BioTechniques* 17:242) which, briefly, involves the synthesis of overlapping oligonucleotides containing portions of the sequence encoding the antibody, annealing and ligation of those oligonucleotides, and then amplification of the ligated oligonucleotides by PCR.

Methods for the construction of recombinant vectors containing anti-CD20 antibody or fragment coding sequences and appropriate transcriptional and translational control signals are well known in the art. These methods include, for example, in vitro recombinant DNA techniques, synthetic techniques, and in vivo genetic recombination. The invention, thus, provides replicable vectors comprising a nucleotide sequence encoding an antibody molecule of the present invention, or a heavy or light chain thereof, or a heavy or light chain variable domain, or an epitope-binding fragment of any of these, operably linked to a promoter.

The recombinant vector is transferred to a host cell by conventional techniques and the transfected cells are then cultured by conventional techniques to produce an antibody of the invention. Thus, the invention includes host cells containing a polynucleotide encoding an antibody of the invention, or an epitope-binding fragment thereof, operably linked to a heterologous promoter. In preferred aspects, vectors encoding both the heavy and light chains may be co-expressed in the host cell for expression of an entire immunoglobulin molecule.

A variety of host-expression vector systems may be utilized to express the anti-CD20 antibody or fragment molecules of the invention. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter).

Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., 1986, Gene 45:101; Cockett et al., 1990, Bio/Technology 8:2).

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.) and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compounds that interact directly or indirectly with the antibody molecule.

Once an antibody molecule of the invention has been recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. In this regard, U.S. Pat. No. 7,538,195 has been referred to in the present disclosure, the teachings of which are hereby incorporated in its entirety by reference.

In another aspect, diverse antibodies and antibody fragments, as well as antibody mimics may be readily produced by mutation, deletion and/or insertion within the variable and constant region sequences that flank a particular set of CDRs using methods as disclosed herein or known in the art. Thus, for example, different classes of Ab are possible for a given set of CDRs by substitution of different heavy chains, whereby, for example, IgG1-4, IgM, IgA1-2, IgD, IgE antibody types and isotypes may be produced. Similarly, artificial antibodies within the scope of the invention may be produced by embedding a given set of CDRs within an entirely synthetic framework. The term "variable" is used herein to describe certain portions of the variable domains that differ in sequence among antibodies and are used in the binding and specificity of each particular antibody for its antigen. However, the variability is not usually evenly distributed through the variable domains of the antibodies. It is typically concentrated in three segments called complementarity determining regions (CDRs) or hypervariable regions both in the light chain and the heavy chain variable domains. The more highly conserved portions of the variable domains are called the framework (FR). The variable domains of heavy and light chains each comprise four framework regions, largely adopting a beta-sheet configuration, connected by three CDRs, which form loops connecting, and in some cases forming part of the beta-sheet structure. The CDRs in each chain are held together in close proximity by the FR regions and, with the CDRs from the other chain, contribute to the formation of the antigen binding site of antibodies (E. A. Kabat et al. *Sequences of Proteins of Immunological Interest*, fifth edition, 1991, NIH). The constant domains are not involved directly in binding an antibody to an antigen, but exhibit various effector functions, such as participation of the antibody in antibody-dependent cellular toxicity.

Humanized antibodies, or antibodies adapted for non-rejection by other mammals, may be produced using several technologies such as resurfacing and CDR grafting. In the resurfacing technology, molecular modeling, statistical analysis and mutagenesis are combined to adjust the non-CDR surfaces of variable regions to resemble the surfaces of known antibodies of the target host. Strategies and methods for the resurfacing of antibodies, and other methods for reducing immunogenicity of antibodies within a different host, are disclosed in U.S. Pat. No. 5,639,641, which is hereby incorporated in its entirety by reference. In the CDR grafting technology, the murine heavy and light chain CDRs are grafted into a fully human framework sequence.

The invention also includes functional equivalents of the antibodies described in this specification. Functional equivalents have binding characteristics that are comparable to those of the antibodies, and include, for example, chimerized, humanized and single chain antibodies as well as fragments thereof. Methods of producing such functional equivalents are disclosed in PCT Application WO 93/21319, European Patent Application No. 239,400; PCT Application WO 89/09622; European Patent Application 338,745; and European Patent Application EP 332,424, which are incorporated in their respective entireties by reference.

Functional equivalents include polypeptides with amino acid sequences substantially the same as the amino acid sequence of the variable or hypervariable regions of the antibodies of the invention. "Substantially the same" as applied to an amino acid sequence is defined herein as a sequence with at least about 90%, and more preferably at least about 95% sequence identity to another amino acid sequence, as determined by the FASTA search method in accordance with Pearson and Lipman, Proc. Natl. Acad. Sci. USA 85, 2444-2448 (1988).

Chimerized antibodies preferably have constant regions derived substantially or exclusively from human antibody constant regions and variable regions derived substantially or exclusively from the sequence of the variable region from a mammal other than a human. Humanized forms of the antibodies are made by substituting the complementarity determining regions of, for example, a mouse antibody, into a human framework domain, e.g., see PCT Pub. No. WO92/22653. Humanized antibodies preferably have constant regions and variable regions other than the complementarity determining regions (CDRs) derived substantially or exclusively from the corresponding human antibody regions and CDRs derived substantially or exclusively from a mammal other than a human.

Functional equivalents also include single-chain antibody fragments, also known as single-chain antibodies (scFvs). These fragments contain at least one fragment of an antibody variable heavy-chain amino acid sequence ($V_H$) tethered to at least one fragment of an antibody variable light-chain sequence ($V_L$) with or without one or more interconnecting linkers. Such a linker may be a short, flexible peptide selected to assure that the proper three-dimensional folding of the ($V_L$) and ($V_H$) domains occurs once they are linked so as to maintain the target molecule binding-specificity of the whole antibody from which the single-chain antibody fragment is derived. Generally, the carboxyl terminus of the ($V_L$) or ($V_H$) sequence may be covalently linked by such a peptide linker to the amino acid terminus of a complementary ($V_L$) and ($V_H$) sequence. Single-chain antibody fragments may be generated by molecular cloning, antibody phage display library or similar techniques. These proteins may be produced either in eukaryotic cells or prokaryotic cells, including bacteria.

Single-chain antibody fragments contain amino acid sequences having at least one of the variable or complementarity determining regions (CDRs) of the whole antibodies described in this specification, but are lacking some or all of the constant domains of those antibodies. These constant domains are not necessary for antigen binding, but constitute a major portion of the structure of whole antibodies. Single-chain antibody fragments may therefore overcome some of the problems associated with the use of antibodies containing a part or all of a constant domain. For example, single-chain antibody fragments tend to be free of undesired interactions between biological molecules and the heavy-chain constant region, or other unwanted biological activity. Additionally, single-chain antibody fragments are considerably smaller than whole antibodies and may therefore have greater capillary permeability than whole antibodies, allowing single-chain antibody fragments to localize and bind to target antigen-binding sites more efficiently. Also, antibody fragments can be produced on a relatively large scale in prokaryotic cells, thus facilitating their production. Furthermore, the relatively small size of single-chain antibody fragments makes them less likely to provoke an immune response in a recipient than whole antibodies.

The knowledge of the amino acid and nucleic acid sequences for the anti-CD20 antibody and its humanized variants, which are described herein, can be used to develop other antibodies which also bind to human CD20. Several studies have surveyed the effects of introducing one or more amino acid changes at various positions in the sequence of an antibody, based on the knowledge of the primary antibody sequence, on its properties such as binding and level of expression (Yang, W. P. et al., 1995, *J. Mol. Biol.*, 254, 392-403; Rader, C. et al., 1998, *Proc. Natl. Acad. Sci. USA*, 95, 8910-8915; Vaughan, T. J. et al., 1998, *Nature Biotechnology*, 16, 535-539).

In these studies, variants of the primary antibody have been generated by changing the sequences of the heavy and light chain genes in the CDR1, CDR2, CDR3, or framework regions, using methods such as oligonucleotide-mediated site-directed mutagenesis, cassette mutagenesis, error-prone PCR, DNA shuffling, or mutator-strains of *E. coli* (Vaughan, T. J. et al., 1998, *Nature Biotechnology*, 16, 535-539; Adey, N. B. et al., 1996, Chapter 16, pp. 277-291, in "*Phage Display of Peptides and Proteins*", Eds. Kay, B. K. et al., Academic Press). These methods of changing the sequence of the primary antibody have resulted in improved affinities of the secondary antibodies (Gram, H. et al., 1992, *Proc. Natl. Acad. Sci. USA*, 89, 3576-3580; Boder, E. T. et al., 2000, *Proc. Natl. Acad. Sci. USA*, 97, 10701-10705; Davies, J. and Riechmann, L., 1996, *Immunotechnolgy*, 2, 169-179; Thompson, J. et al., 1996, *J. Mol. Biol.*, 256, 77-88; Short, M. K. et al., 2002, *J. Biol. Chem.*, 277, 16365-16370; Furukawa, K. et al., 2001, *J. Biol. Chem.*, 276, 27622-27628).

By a similar directed strategy of changing one or more amino acid residues of the antibody, the antibody sequences described in this invention can be used to develop anti-CD20 antibodies with improved functions, such as those methods described in patent application publication 20090246195, the contents of which is incorporated in its entirety herein by reference.

Any method known in the art for conjugating the antibody to the detectable moiety may be employed, including those methods described by Hunter, et al., Nature 144:945 (1962); David, et al., Biochemistry 13:1014 (1974); Pain, et al., J. Immunol. Meth. 40:219 (1981); and Nygren, J. Histochem. and Cytochem. 30:407 (1982).

The antibodies of the present invention can be employed in any known assay method, such as competitive binding assays, direct and indirect sandwich assays, and immunoprecipitation assays (Zola, Monoclonal Antibodies: A Manual of Techniques, pp. 147-158 (CRC Press, Inc., 1987)).

The antibodies of the invention also are useful for in vivo imaging, wherein an antibody labeled with a detectable moiety such as a radio-opaque agent or radioisotope is administered to a subject, preferably into the bloodstream, and the presence and location of the labeled antibody in the host is assayed. This imaging technique is useful in the staging and treatment of malignancies. The antibody may be labeled with any moiety that is detectable in a host, whether by nuclear magnetic resonance, radiology, or other detection means known in the art.

The antibodies of the invention also are useful as affinity purification agents. In this process, the antibodies are immobilized on a suitable support, such a Sephadex resin or filter paper, using methods well known in the art.

Therapeutic Applications

Also included in the present invention are methods for inhibiting the growth of cells expressing CD20. These methods make use of the antibodies or fragments or conjugates of the present invention, as well as the antibodies or fragments or immunoconjugates of the present invention in conjunction with one or more additional therapeutic agents. Suitable therapeutic agents include those that inhibit the growth of a cell expressing CD20 directly or indirectly.

As used herein the terms "inhibit" and "inhibiting" should be understood to include any inhibitory effect on cell growth, including cell death. The inhibitory effects include temporary effects, sustained effects and permanent effects.

The therapeutic applications of the present invention include methods of treating a subject having a disease. The diseases treated with the methods of the present invention are those characterized by the expression of CD20. Such diseases include B cell derived malignancies such non-Hodgkin's lymphoma, B-cell chronic lymphocytic leukemia and B-cell acute lymphoblastic leukemia as well as non-malignant autoimmune or inflammatory disorders, including RA, in which CD20 positive B cells play a role in disease pathophysiology. The skilled artisan will understand that the methods of the present invention may also be used to treat other diseases yet to be described but characterized by the expression of CD20.

The therapeutic applications of the present invention can be also practiced in vitro and ex vivo.

Examples of in vitro uses include the purification of cell populations contaminated with CD20-positive cells such as cells of B-cell lineage. The method comprises culturing the cell populations in the presence of a cytotoxic huCD20-4 conjugate and then removal of dead, CD20-positive cells. The conditions for non-clinical in vitro use are well known (see, e.g., Uckun et al., 1986, *J Exp. Med.* 163, 347-368; Uckun et al., 1985, *J. Immunol.* 134, 3504-3515; Ramakrishnan et al., 1985, *J. Immunol.* 135, 3616-3622).

The antibodies, fragments and regions, fragments, or derivatives of this invention, attached to a solid support, can also be used to remove CD20 from fluids or tissue or cell extracts. In a preferred aspect, they are used to remove CD20 from blood or blood plasma products. In another preferred aspect, the murine and chimeric antibodies, fragments and regions are advantageously used in extracorporeal immunoadsorbent devices, which are known in the art (see, for example, Seminars in Hematology, 26 (2 Suppl. 1) (1989)). Patient blood or other body fluid is exposed to the attached antibody, resulting in partial or complete removal of circulating CD20 (free or in immune complexes), following which the fluid is returned to the body. This immunoadsorption can be implemented in a continuous flow arrangement, with or without interposing a cell centrifugation step. See, for example, Terman, et al., J. Immunol. 11 7:1971-1975 (1976).

The present invention also includes therapeutic applications of the antibodies or conjugates of the present invention wherein the antibodies or conjugates may be administered to a subject, in a pharmaceutically acceptable dosage form. They can be administered intravenously as a bolus or by continuous infusion over a period of time, by intramuscular, subcutaneous, intra-articular, intrasynovial, intrathecal, oral, topical, or inhalation routes. They may also be administered by intratumoral, peritumoral, intralesional, or perilesional routes, to exert local as well as systemic therapeutic effects.

Pharmaceutical Formulations

For therapeutic applications, the antibodies or conjugates of the invention are administered to a subject, in a pharmaceutically acceptable dosage form. They can be administered intravenously as a bolus or by continuous infusion over a period of time, by intramuscular, subcutaneous, intra-articular, intrasynovial, intrathecal, oral, topical, or inhalation routes. The antibodies or conjugates may also be administered by intratumoral, peritumoral, intralesional, or perilesional routes, to exert local as well as systemic therapeutic effects. Suitable pharmaceutically acceptable carriers, diluents, and excipients are well known and can be determined by those of skill in the art as the clinical situation warrants. Examples of suitable carriers, diluents and/or excipients include: (1) Dulbecco's phosphate buffered saline, pH about 7.4, containing about 1 mg/ml to 25 mg/ml human serum albumin, (2) 0.9% saline (0.9% w/v NaCl), (3) 5% (w/v) dextrose and (4) 10 mM histidine sulfate p115.8, 6% sucrose, 0.02% polysorbate 20.

When present in an aqueous dosage form, rather than being lyophilized, the antibody or conjugate typically will be formulated at a concentration of about 0.1 mg/ml to 100 mg/ml, although wide variation outside of these ranges is permitted. For the treatment of disease, the appropriate dosage of antibody or fragment or conjugate will depend on the type of disease to be treated, as defined above, the severity and course of the disease, whether the antibodies or conjugates are administered for preventive or therapeutic purposes, the course of previous therapy, the patient's clinical history and response to the treatment, and the discretion of the attending physician. The antibody or fragment or conjugate is suitably administered to the patient at one time or over a series of treatments.

Depending on the type and severity of the disease, about 0.015 to 25 mg of antibody or conjugate per kg of patient weight is an initial candidate dosage for administration to the patient, whether, for example, by one or more separate administrations, or by continuous infusion. For repeated administrations over several days or longer, depending on the condition, the treatment is repeated until a desired suppression of disease symptoms occurs. However, other dosage regimens may be useful and are not excluded.

For pulmonary administration, preferably at least one anti-CD20 antibody or antibody fragment or conjugate composition is delivered in a particle size effective for reaching the lower airways of the lung or sinuses. According to the invention, at least one anti-CD20 antibody or fragment or conjugate can be delivered by any of a variety of inhalation or nasal devices known in the art for administration of a therapeutic agent by inhalation. These devices capable of depositing aerosolized formulations in the sinus cavity or alveoli of a patient include metered dose inhalers, nebulizers, dry powder generators, sprayers, and the like. Other devices suitable for directing the pulmonary or nasal administration of antibodies are also known in the art. All such devices can use of formulations suitable for the administration for the dispensing of antibody in an aerosol. Such aerosols can be comprised of either solutions (both aqueous and non aqueous) or solid particles. Metered dose inhalers like the Ventolin™ metered dose inhaler, typically use a propellant gas and require actuation during inspiration (See, e.g., WO 94/16970, WO 98/35888). Dry powder inhalers like Turbuhaler™ (Astra), Rotahaler™ (Glaxo), Diskus™ (Glaxo), Spiros™ inhaler (Dura), devices marketed by Inhale Therapeutics, and the Spinhaler™ powder inhaler (Fisons), use breath-actuation of a mixed powder (U.S. Pat. No. 4,668,218 Astra, EP 237507 Astra, WO 97/25086 Glaxo, WO 94/08552 Dura, U.S. Pat. No. 5,458,135 Inhale, WO 94/06498 Fisons, entirely incorporated herein by reference). Nebulizers like AERx™ Aradigin, the Ultravent™ nebulizer (Mallinckrodt), and the Acorn II™ nebulizer (Marquest Medical Products) (U.S. Pat. No. 5,404,871 Aradigm, WO 97/22376), the above references entirely incorporated herein by reference, produce aerosols from solutions, while metered dose inhalers, dry powder inhalers, etc. generate small particle aerosols. These specific examples of commercially available inhalation devices are intended to be a representative of specific devices suitable for the practice of this invention, and are not intended as limiting the scope of the invention. Preferably, a composition comprising at least one anti-CD20 antibody or fragment or conjugate is delivered by a dry powder inhaler or a sprayer. There are a several desirable features of an inhalation device for administering at least one antibody of the present invention. For example, delivery by the inhalation device is advantageously reliable, reproducible, and accurate. The inhalation device can optionally deliver small dry particles, e.g. less than about 10 µm, preferably about 1-5 µm, for good respirability.

For absorption through mucosal surfaces, compositions and methods of administering at least one anti-CD20 antibody or fragment or conjugate include an emulsion comprising a plurality of submicron particles, a muco adhesive macromolecule, a bio active peptide, and an aqueous continuous phase, which promotes absorption through mucosal surfaces by achieving mucoadhesion of the emulsion particles (U.S. Pat. No. 5,514,670). Mucous surfaces suitable for application of the emulsions of the present invention can include corneal, conjunctival, buccal, sublingual, nasal, vaginal, pulmonary, stomachic, intestinal, and rectal routes of administration. Formulations for vaginal or rectal administration, e.g. suppositories, can contain as excipients, for example, polyalkyleneglycols, vaseline, cocoa butter, and the like. Formulations for intranasal administration can be solid and contain as excipients, for example, lactose or can be aqueous or oily solutions of nasal drops. For buccal administration excipients include sugars, calcium stearate, magnesium stearate, pregelinatined starch, and the like (U.S. Pat. No. 5,849,695).

For transdermal administration, the at least one anti-CD20 antibody or conjugate is encapsulated in a delivery device such as a liposome or polymeric nanoparticles, microparticle, microcapsule, or microspheres (referred to collectively as microparticles unless otherwise stated). A number of suitable devices are known, including microparticles made of synthetic polymers such as polyhydroxy acids such as polylactic acid, polyglycolic acid and copolymers thereof, polyorthoesters, polyanhydrides, and polyphosphazenes, and natural polymers such as collagen, polyamino acids, albumin and other proteins, alginate and other polysaccharides, and combinations thereof (U.S. Pat. No. 5,814,599).

All publications or patents cited herein are entirely incorporated herein by reference and are evidence of the state of the art. Publications refer to any scientific or patent publications, or any other information available in any media format, including all recorded, electronic or printed formats. The following references are entirely incorporated herein by reference: Ausubel, et al., ed., Current Protocols in Molecular Biology, John Wiley & Sons, Inc., NY, N.Y. (1987-2001); Sambrook, et al., Molecular Cloning: A Laboratory Manual, 2.sup.nd Edition, Cold Spring Harbor, N.Y. (1989); Harlow and Lane, antibodies, a Laboratory Manual, Cold Spring Harbor, N.Y. (1989); Colligan, et al., eds., Current Protocols in Immunology, John Wiley & Sons, Inc., N.Y. (1994-2001); Colligan et al., Current Protocols in Protein Science, John Wiley & Sons, NY, N.Y., (1997-2001), particularly, to contents pertaining to preparing the anti-CD20 antibodies, fragments, conjugates, agents, compositions, etc. as described herein. It is apparent to one of skill in the art that the various references to antibodies and fragments thereof are meant to also refer to, for example, conjugates, without departing from the spirit and scope thereof. Having now generally described the invention, the same will be further understood by reference to certain specific examples which are included herein for purposes of illustration only and are not intended to be limiting unless otherwise specified.

EXAMPLES

Cell Lines and Growth

| Cell line | Origin | Source |
| --- | --- | --- |
| Ramos | Burkitt lymphoma | DSMZ (ACC 603) |
| Raji | Burkitt lymphoma | DSMZ (ACC 319) |
| Daudi | Burkitt lymphoma | DSMZ (ACC 78) |
| BJAB | B-NHL | A gift from Elliot Kieff (Harvard) |
| WSU-DLCL-2 | B-NHL, diffuse large B-cell lymphoma | DSMZ (ACC 575) |
| RL | B-NHL, diffuse large B-cell lymphoma | DSMZ (ACC 613) |
| SU-DHL-4 | B-NHL, diffuse histiocytic lymphoma | DSMZ (ACC 495) |
| DOHH-2 | refractory immunoblastic B cell lymphoma, follicular lymphoma | DSMZ (ACC 47) |
| SC-1 | B-NHL, follicular lymphoma | DSMZ (ACC 558) |
| Jeko-1 | B-NHL, mantle cell lymphoma | DSMZ (ACC 553) |
| Granta-519 | B-NHL, mantle cell lymphoma | DSMZ (ACC 342) |
| JVM-13 | B-CLL, chronic B-lymphocytic leukemia | DSMZ (ACC 19) |
| Molt-4 | T-ALL, acute T-lymphoblastic leukemia | DSMZ (ACC 362) |

Cell lines were grown in the appropriate media, for example RPMI-1640 media supplemented with 10% fetal bovine serum, 2 mM glutamine and 1% penicillin-streptomycin (all reagents from Invitrogen) at 37° C. in a humidified 5% $CO_2$ incubator unless otherwise indicated. Cells were passaged by diluting into fresh media twice per week and maintained between 0.2 to $1 \times 10^6$ cells/ml.

Example 1

Production of Murine CD20 Antibodies

An expression plasmid pSRa-CD20 was constructed that contained the entire CD20 coding sequence (CDS) flanked by XbaI and BamHI restriction sites that allowed expression of human CD20 (GI 23110989). 300-19 cells, a pre-B cell line derived from a Balb/c mouse (Reth et al., Nature, 317:353-355 (1985)), was transfected with this expression plasmid to stably express high levels of human CD20 on the cell surface and used for immunization of Balb/c VAF mice. Mice were subcutaneously immunized with approximately $5 \times 10^6$ CD20-expressing 300-19 cells per mouse every 2-3 weeks by standard immunization protocols known to those of skill, for example, such as those used at ImmunoGen, Inc. Immunized mice were boosted with antigen three days before being sacrificed for hybridoma generation. Spleens from mice was collected according to standard animal protocols, such as, for example grinding tissue between two sterile, frosted microscopic slides to obtain a single cell suspension in RPMI-1640 medium. The spleen cells were centrifuged, pelleted, washed, and fused with a murine myeloma, such as, for example P3X63Ag8.653 cells (Kearney et al., J. Immunol., 123:1548-1550 (1979)) using polyethylene glycol-1500 (Roche 783 641). The fused cells were resuspended in RPMI-1640 selection medium containing hypoxanthine-aminopterin-thymidine (HAT) (Sigma H-0262) and selected for growth in 96-well flat-bottomed culture plates (Corning-Costar 3596, 200 µL of cell suspension per well) at 37° C. with 5% $CO_2$. After 5 days of incubation, 100 µL of culture supernatant were removed from each well and replaced with 100 µL of RPMI-1640 medium containing hypoxanthine-thymidine (HT) supplement (Sigma H-0137). Incubation at 37° C. with 5% $CO_2$ was continued until hydridoma clones were ready for antibody screening. Other techniques of immunization and hybridoma production can also be used, including those described in Langone et al. (Eds., "Immunochemical Techniques, Part I", *Methods in Enzymology*, Academic Press, volume 121, Florida) and Harlow et al. ("Antibodies: A Laboratory Manual"; Cold Spring Harbor Laboratory Press, New York (1988)).

Hybridoma Screening and Selection

Culture supernatants from the hybridoma were screened by flow cytometry for secretion of mouse monoclonal antibodies that bind to CD20 expressing cells, such as CD20-expressing 300-19 cells, but not to the non-transfected 300-19 cells. 100 µl of hybridoma supernatants was incubated for 3 h with either CD20-expressing 300-19 cells or the non-transfected 300-19 cells ($1 \times 10^5$ cells per sample) in 100 µL FACS buffer (RPMI-1640 medium supplemented with 2% normal goat serum). Then, the cells were centrifuged, pelleted, washed, and incubated for 1 h with 100 µL of PE-conjugated goat anti-mouse IgG-antibody (such as obtainable from, for example Jackson Laboratory, 6 µg/mL in FACS buffer). The cells were centrifuged, pelleted again, washed with FACS buffer and resuspended in 2004 of PBS containing 1% formaldehyde. Cells were acquired using a FACSCalibur flow cytometer with the HTS multiwell sampler or a FACS array flow cytometer and analyzed using CellQuest Pro (all from BD Biosciences, San Diego, US).

Positive hybridoma clones were subcloned by limiting dilution. One subclone from each hybridoma, which showed the same reactivity against CD20 as the parental cells by flow cytometry, was chosen for subsequent analysis. Stable subclones were cultured and the isotype of each secreted anti-CD20 antibody was identified using commercial isotyping reagents (Roche 1493027).

Antibody Purification

Antibodies were purified from hybridoma subclone supernatants using standard methods, such as, for example Protein A or G chromatography (HiTrap Protein A or G HP, 1 mL, Amersham Biosciences). Briefly, supernatant was prepared for chromatography by the addition of 1/10 volume of 1 M Tris/HCl buffer, pH 8.0. The pH-adjusted supernatant was filtered through a 0.22 µm filter membrane and loaded onto a column equilibrated with binding buffer (PBS, pH 7.3). The column was washed with binding buffer until a stable baseline was obtained with no absorbance at 280 nm. Antibody was eluted with 0.1 M acetic acid buffer containing 0.15 M NaCl, pH 2.8, using a flow rate of 0.5 mL/min. Fractions of approximately 0.25 mL were collected and neutralized by the addition of 1/10 volume of 1M Tris/HCl, pH 8.0. The peak fraction(s) was dialyzed overnight twice against 1×PBS and sterilized by filtering through a 0.2 µm filter membrane. Purified antibody was quantified by absorbance at A280.

Protein A purified fractions were further polished using ion exchange chromatography (IEX) with quaternary ammonium (Q) chromatography for murine antibodies. Briefly, samples from protein A purification were buffer exchanged into binding buffer (10 mM Tris, 10 mM sodium chloride, pH 8.0) and filtered through 0.22 µm filer. The prepared sample was then loaded onto a Q fast flow resin (GE Lifesciences) that was equilibrated with binding buffer at a flow rate of 120 cm/hr. Column size was chosen to have sufficient capacity to bind all the MAb in the sample. The column was then washed with binding buffer until a stable baseline was obtained with no absorbance at 280 nm. Antibody was eluted by initiating a gradient from 10 mM to 500 mM sodium chloride in 20 column volume (CV). Peak fractions were collected based on absorbance measurement at 280 nm (A280). The percentage of monomer was assessed with size exclusion chromatography (SEC) on a TSK gel G3000SWXL, 7.8×300 mm with a SWXL guard column, 6.0×40 mm (Tosoh Bioscience, Montgomeryville, Pa.) using an Agilent HPLC 1100 system (Agilent, Santa Clara, Calif.). Fractions with monomer content above 95% were pooled, buffer exchanged to PBS (pH 7.4) using a TFF system, and sterilized by filtering through a 0.2 µm filter membrane. The IgG concentration of purified antibody was determined by A280 using an extinction coefficient of 1.47. Alternative methods such as ceramic hydroxyapatite (CHT) were also used to polish antibodies with good selectivity. Type II CHT resin with 40 µM particle size (Bio-Rad Laboratories) were used with a similar protocol as described for IEX chromatography. The binding buffer for CHT corresponds to 20 mM sodium phosphate, pH 7.0 and antibody was eluted with a gradient of 20-160 mM sodium phosphate over 20 CV.

Example 2

Binding Characterization by Flow Cytometry

Figure 1:
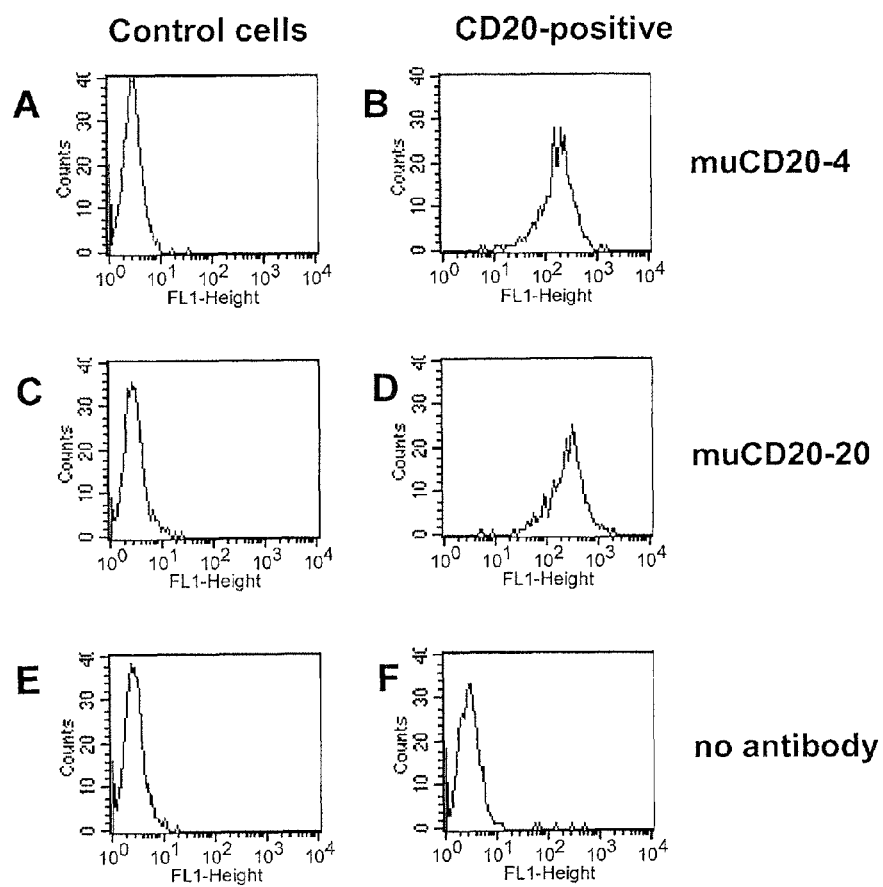
FIG. 1 depicts histograms of antibody binding to non-transfected 300-19 control cells (left panels.

Binding specificity was tested by flow cytometry using purified antibodies. FACS histograms demonstrating the binding of muCD20-4 and muCD20-20 to CD20-expressing 300-19 cells and the absence of binding to the parental 300-19 cells are shown in FIG. 1. Either muCD20-4 or muCD20-20 antibody was incubated for 3 h with either CD20-expressing 300-19 cells or the non-transfected 300-19 cells ($1 \times 10^5$ cells per sample) in 100 µL FACS buffer (RPMI-1640 medium supplemented with 2% normal goat serum). Then, the cells were pelleted, washed, and incubated for 1 h with 100 µL of FITC-conjugated goat anti-mouse IgG-antibody (such as is obtainable from, for example Jackson Laboratory, 6 µg/mL in FACS buffer). The cells were pelleted again, washed with FACS buffer and resuspended in 200 µL of PBS containing 1% formaldehyde. Samples were acquired using a FACSCalibur flow cytometer with the HTS multiwell sampler or a FACS array flow cytometer and analyzed using CellQuest Pro (all from BD Biosciences, San Diego, US).

The FACS histograms of CD20-expressing 300-19 cells incubated with muCD20-4 or muCD20-20 showed a fluorescence shift, while parental 300-19 cells did not (FIG. 1). Also, no significant fluorescence shift was detected when either cell lines was incubated only with FITC-conjugated goat anti-mouse IgG-antibody alone (FIG. 1 bottom).

A fluorescence shift was also observed when BJAB lymphoma cells were incubated with muCD20-4 or muCD20-20 (FIG. 2). BJAB cells were incubated with varying concentrations of muCD20-4 or muCD20-20 antibody and processed as described above for flow cytometry analysis. Data analysis was performed using CellQuest Pro (BD Biosciences, San Diego, US) and for each sample the mean fluorescence intensity for FL1 (MFI) was exported and plotted against the antibody concentration in a semi-log plot. A dose-response curve was generated by non-linear regression and the value for the apparent dissociation constant ($K_d$) of muCD20-4 or muCD20-20 for the binding to BJAB cells was calculated using GraphPad Prism v4 (GraphPad software, San Diego, Calif.) and corresponds to 0.97 nM or 0.59 nM, respectively.

Example 3

Lipid Raft

The reorganization of CD20 into lipid rafts following antibody binding has been correlated with the ability of the antibody to effectively recruit complement factors and elicit CDC activity. As a measure of antibody induced CD20 re-distribution to lipid rafts we employed a flow cytometry based method modified from Cragg et al. (2003), supra). The principle of this assay is based on the TritonX-100 insolubility of lipid raft compartments at low temperatures.

Figure 3:
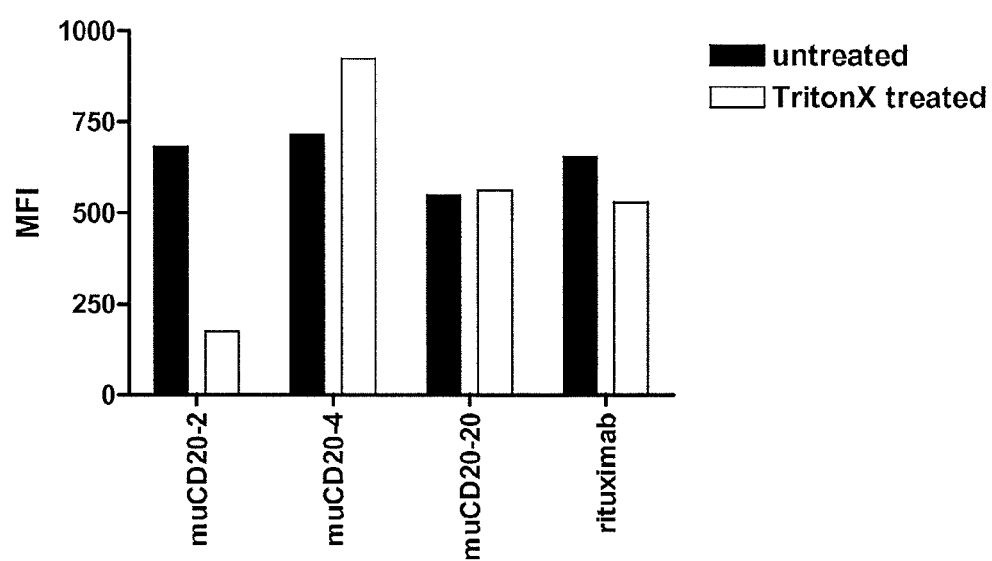
FIG. 3 depicts the results from a lipid raft assay using Ramos cells and muCD20-2, muCD20-4, muCD20-20 and rituximab antibodies at 10 µg/mL. MFI for FL1 from samples in the absence (black bars) and the presence (open bars) of Triton-X 100 is plotted for each antibody treatment. Rituximab refers to the commercially available chimeric anti-CD20 antibody (IDEC).

Cells were harvested by centrifugation, washed and re-suspended in RPMI-1640 with 1% BSA. 0.2 mL of cells at $2.5 \times 10^6$ cells were used for each assay in duplicate. Anti-CD20 antibodies were added at 10 μg/mL and samples were incubated for 15 min at 37° C. Samples were centrifuged, washed twice and re-suspended in 0.2 mL of FACS buffer (1×PBS, 1% BSA, 20 mM Na-azide). Samples were chilled on ice and kept cold from this point on. To detect the fraction of antigen associated with lipid rafts in response to antibody treatment, samples were incubated with 0.5% TritonX-100 for 15 min on ice. To detect the total amount of antibody bound, samples were left on ice for 15 min undisturbed. Samples were washed twice in FACS buffer and stained with FITC-coupled goat anti-mouse-Ab diluted to 1:200 for 1 hr on ice. Samples were centrifuged, washed twice with FACS buffer and resuspended cells in 200 μL PBS, 1% formaldehyde for fixation. Samples were acquired by flow cytometry to determine anti-CD20 antibody binding as mean of FL-1. Mean fluorescence intensity (MFI) was plotted for each sample in the absence (untreated) or presence (Triton treated) of TritonX-100 incubation in FIG. 3.

We used rituximab, an example of a type I antibody that has been previously shown to efficiently translocate CD20 into TritonX-100 insoluble lipid rafts, as a control. As expected, rituximab treated cells show the same level of fluorescence with and without TritonX-100 treatment. In contrast, the MFI of cells stained with muCD20-2 is much lower with TritonX-100 treatment than without. This is consistent with the inability of muCD20-2 to re-distribute CD20 into lipid rafts, a characteristic feature of previously described type II CD20 antibodies. In contrast, muCD20-4 and muCD20-20 both show similar MFI values with and without TritonX-100 treatment. This supports the concept that these antibodies, like rituximab, can efficiently translocate CD20 into the lipid raft compartment of the lymphoma cell membrane.

Example 4

Cloning and Sequencing of the VL and VH Regions of the CD20-4 and CD20-20 Antibodies Total cellular RNA was prepared from $5 \times 10^6$ cells of the CD20-4 and CD20-20 hybridoma using an RNeasy kit (QIAgen) according to the manufacturer's protocol. cDNA was subsequently synthesized from total RNA using the SuperScript II cDNA synthesis kit (Invitrogen).

The procedure for the first round degenerate PCR reaction on the cDNA derived from hybridoma cells was based on methods described in Wang et al. ((2000) J Immunol Methods. January 13; 233(1-2):167-77) and Co et al. ((1992) J Immunol. February 15; 148(4):1149-54). VH sequences were amplified by PCR using the following degenerate primers: EcoMH1 CTTCCGGAATTCSARGTNMAGCTGSAG-SAGTC [SEQ ID NO:39], EcoMH2 CTTCCGGAATTC-SARGTNMAGCTGSAGSAGTCWGG [SEQ ID NO:38] and BamIgG1 GGAGGATCCATAGACAGATGGGGGT-GTCGTTTTGGC [SEQ ID NO:40]. VL sequences were amplified by PCR using the following degenerate primers: SacIMK GGAGCTCGAYATTGTGMTSACMCARWCT-MCA [SEQ ID NO:41] and HindKL TATAGAGCT-CAAGCTTGGATGGTGGGAAGATGGATA-CAGTTGGTGC [SEQ ID NO:42]. (Mixed bases are defined as follows: N=G+A+T+C, S=G+C, Y=C+T, M=A+C, R=A+G, W=A+T).

The PCR reaction mixtures were then run on a 1% low melt agarose gel, the 300 to 400 by bands were excised, purified using Zymo DNA mini columns, and sent to Agencourt Biosciences for sequencing. The respective 5' and 3' PCR primers were used as sequencing primers to generate the variable region cDNAs from both directions. The amino acid sequences of VH and VL regions were deduced from the DNA sequencing results.

The preliminary cDNA sequences were used to search the NCBI IgBlast site for the murine germline sequences from which the antibody sequences are derived. PCR primers were then designed to anneal to the germline linked leader sequence of the murine antibody so that this new PCR reaction would yield a complete variable region cDNA sequence, unaltered by the PCR primers. The PCR reactions, band purifications, and sequencing were performed as described above.

Mass Determination for Sequence Confirmation

The cDNA sequence information for the variable region was combined with the germline constant region sequence to obtain full length antibody cDNA sequences. The molecular weights of the heavy chain and light chain were then calculated and compared with the molecular weights obtained by LC/MS analyses of the murine CD20-4 and CD20-20 antibodies. The molecular weight measurements are consistent with the cDNA sequences for both the CD20-4 and CD20-20 light and heavy chains.

Chimerization

The variable sequence for the light chain variable region is cloned into EcoRI and BsiWI sites in the pchCD20-4LCZ plasmid. The heavy chain variable region is cloned into the HindIII and Apa1 sites in the pchCD20-4HCN plasmid. Equivalent plasmids were constructed for chCD20-20. These plasmids were used to express chimeric antibodies in HEK-293T cells using a standard calcium phosphate procedure (BD Biosciences, CalPhos Mammalian Transfection Kit, Cat #631312). Supernatant was purified using standard Protein A chromatography procedures as described above, but the polishing chromatography steps were performed using either carboxymethyl (CM) fast flow ion exchange (IEX) resin (GE Lifesciences) and 10 mM potassium phosphate, 10 mM sodium chloride binding buffer (pH 7.5) or the alternative CHT methods described above.

Example 5

Antibody Humanization

The CD20-4 antibody was humanized following resurfacing methods previously described, such as, for example in Roguska et al., *Proc. Natl. Acad. Sci., USA,* 91(3):969-973 (1994) and Roguska et al., Protein Eng. 9(10):895-904 (1996), which are incorporated in their entirety herein by reference. Resurfacing generally involves identification of the variable region surface residues in both light and heavy chains and replacing them with human equivalents. Exemplary CDRs are defined as indicated in Table 1.

TABLE 1

Exemplary Resurfacing CD20-4 CDRs

Light Chain

| | | |
|---|---|---|
| CDR1: | KASQNVGTNVA | (SEQ ID NO: 23) |
| CDR2: | SASFRYS | (SEQ ID NO: 24) |
| CDR3: | QQYNNYPLT | (SEQ ID NO: 25) |

Heavy Chain

| | | |
|---|---|---|
| CDR1: | NYWMN | (SEQ ID NO: 26) |
| CDR2: | EIRLKSNNYATH | (SEQ ID NO: 27) |
| CDR3: | WDDYAMDH | (SEQ ID NO: 28) |

Kabat Defined CD20-4 HC CDR2

| | | |
|---|---|---|
| Murine HC CDR2: | EIRLKSNNYATH<u>YVESVKG</u> | (SEQ ID NO: 29) |
| Human HC CDR2: | EIRLKSNNYATH<u>YVDSVKG</u> | (SEQ ID NO: 30) |

The CD20-4 light and heavy chain CDR's as defined for the resurfacing are given by way of example in Table 1. The Kabat definition for heavy chain CDR2 is also given for both the murine and human CD20-4. The underlined sequence marks the portion of the Kabat heavy chain CDR2 not considered a CDR for resurfacing.

Surface residue positions are defined as any position with its relative accessibility of 30% or greater (Pedersen et al., *J. Mol. Biol.*, 235(3):959-973 (1994)). Surface residues are aligned with human germline surface sequences to identify the most homologous human surface sequence. For CD20-4, the human germline sequences used as the replacement surfaces were IGKV1-5*03 and IGHV3-38*02 for $V_L$ and $V_H$, respectively. As can be seen from the lists in FIG. 4, a total of X surface residues in the light chain and X in the heavy chain were replaced with the human counterparts. None of the residue changes raised concerns for impacting the interactions of the CDR's and its target so only a single humanized CD20-4 version was built. FIG. 5 show the alignment of the resurfaced sequences for the CD20-4 variable domain of both light chain and heavy chain with its murine counterparts.

Recombinant Expression of huCD20-4 Antibody

The variable region sequences for huCD20-4 were codon-optimized and synthesized by Blue Heron Biotechnology. The sequences are flanked by restriction enzyme sites for cloning in-frame with the respective constant sequences in single chain mammalian expression plasmids. The light chain variable region is cloned into EcoRI and BsiWI sites in the phCD20-4LCZ plasmid. The heavy chain variable region is cloned into the HindIII and Apa1 sites in the phCD20-4HCN plasmid. These plasmids can be used to express huCD20-4 in either transient or stable transfections in mammalian cells. Transient transfections to express huCD20-4 in HEK-293T cells were performed using a modified PEI procedure (Durocher, Y. et al., Nucleic Acids Res. 30(2):E9 (2002)). Supernatant was purified by Protein A and polishing chromatography steps using standard procedures as described above for chimerized antibodies.

Expression of Reference Antibodies

In order to compare the activity of huCD20-4, previously identified anti-CD20 antibodies were cloned and expressed. The amino acid sequence for the HC and LC variable region of the 2F2 antibody (ofatumumab) was derived from WO 2004/035607 (Teeling et al. (2004), supra) using WO 2004/035607's SEQ ID NO:2 for the HC variable region and WO 2004/035607's SEQ ID NO:4 for the LC variable region. Likewise, the amino acid sequence for the HC and LC variable region of the GA101 antibody (the basis for afutuzumab) was derived from WO 2005/0448959 (Umana, U.S. Pat. No. 5,639,641 (2005)). WO 2005/0448959's SEQ ID NO:40 corresponds to the described B-HH6 construct was used for the HC variable region and WO 2005/0448959's SEQ ID 76 corresponds to the described B-KV1 construct was used for the LC variable region.

The variable region sequences for both antibodies were codon-optimized and synthesized by Blue Heron Biotechnology. The sequences are flanked by restriction enzyme sites for cloning in-frame with the respective constant sequences in single chain mammalian expression plasmids. Cloning, expression and purification was carried out as described for huCD20-4 above. The resulting GA101-F antibody displays the typical fucosylation in the constant region and is thus not the defucosylated version used for afutuzumab.

Example 6

Binding Affinity of huCD20-4

Figure 6:
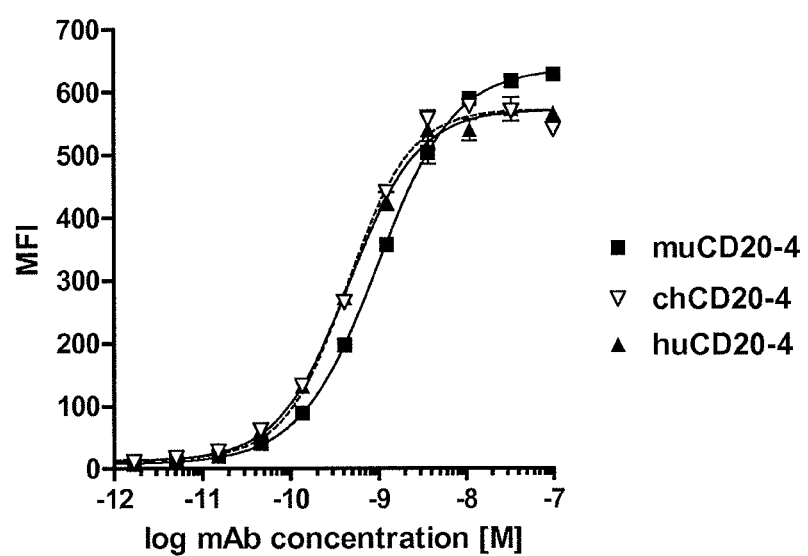
FIG. 6 depicts binding of muCD20-4, chCD20-4 and huCD20-4 to BJAB cells as assayed by flow cytometry. The binding curves were used to determine the EC50 of antibody binding, which corresponds to the apparent Kd of each antibody.

Flow cytometry binding assays using BJAB cells and muCD20-4, chCD20-4 or huCD20-4 antibodies were carried out and analyzed as described in Example 2. FIG. 6 depicts the dose-response curves generated by non-linear regression for each antibody. The value for the apparent dissociation constant ($K_d$) of each antibody was calculated using GraphPad Prism v4 (GraphPad software, San Diego, Calif.). Chimerization or humanization did not affect the binding affinity of CD20-4, as the $K_d$ for muCD20-4, chCD20-4 and huCD20-4 corresponds to 0.97 nM, 0.47 nM and 0.46 nM, respectively.

Binding Affinity of chCD20-20

Figure 7:
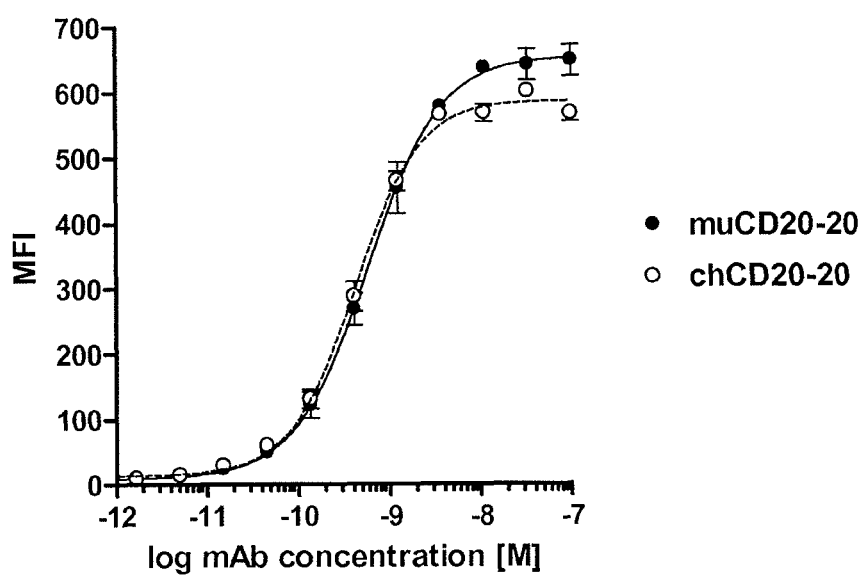
FIG. 7 depicts binding of huCD20-4 and chCD20-20 to BJAB cells as assayed by flow cytometry. The binding curves were used to determine the EC50 of antibody binding, which corresponds to the apparent Kd of each antibody.

Flow cytometry binding assays using BJAB cells and chCD20-20 antibodies were carried out and analyzed as described in Example 2. FIG. 7 depicts the dose-response curves generated by non-linear regression for each antibody. The value for the apparent dissociation constant (Kd) of each antibody was calculated using GraphPad Prism v4 (GraphPad software, San Diego, Calif.). It is apparent that chimerization did not affect the binding affinity of chCD20-20 as the apparent Kd on BJAB cells was 0.42 nM, respectively.

Example 7

Pro-Apoptotic Activity of CD20-4 and CD20-20

The degree of apoptosis was measured by flow cytometry analysis after staining with FITC conjugates of Annexin-V (Invitrogen) and with TO-PRO®-3 (Invitrogen). In healthy, normal cells, phosphatidylserine is on the inside of the membrane bilayer, and the transition of phosphatidylserine from the inner to the outer leaflet of the plasma membrane is one of the earliest detectable signals of apoptosis. Annexin V binds phosphatidylserine on the outside but not on the inside of the cell membrane bilayer of intact cells. The degree of Annexin V binding is therefore an indicator of the induction of apoptosis. TO-PRO®-3 is a monomeric cyanine nucleic acid stain that can only penetrate the plasma membrane when the membrane integrity is breached, as occurs in the later stages of apoptosis. Three populations of cells are distinguishable in two-color flow cytometry: Non-apoptotic cells (Annexin-V negative and TO-PRO®-3 negative), early apoptotic cells (Annexin-V positive and TO-PRO®-3 negative) and necrotic cells or late apoptotic cells (Annexin-V positive and TO-PRO®-3 positive).

Exponentially growing cells were plated at about $2 \times 10^5$ cells/mL in 24-well plates in RMPI-1640 medium supplemented with 10% fetal bovine serum (FBS), 2 mM L glutamine, and 50 µg/mL gentamycin (denoted below as complete RMPI-1640 medium). Cells were generally grown in complete RMPI-1640 medium, unless stated otherwise. Cells were incubated with 10 nM of anti-CD20 antibodies for 20-24 h at 37° C. in a humidified 5% $CO_2$ incubator. The cells were then pelleted, washed twice with 500 μl PBS, resuspended in 100 μL binding buffer (10 mM Hepes-NaOH, pH 7.4, 140 mM NaCl, 2.5 mM $CaCl_2$), and stained with 5 μL of Annexin V-FITC for 15 min on ice. Then, 400 μL of binding buffer and 1 μM of TO-PRO®-3 was added to the mix, and the cell-associated fluorescence of FITC and TO-PRO®-3 was immediately measured by flow cytometry. Five thousand events were collected for each sample. The dot plots for fluorescence of TO-PRO®-3 (FL4-H; y-axis) and fluorescence of Annexin V-FITC (FL1-H; x-axis) were generated using BD CellQuest software.

Figure 8:
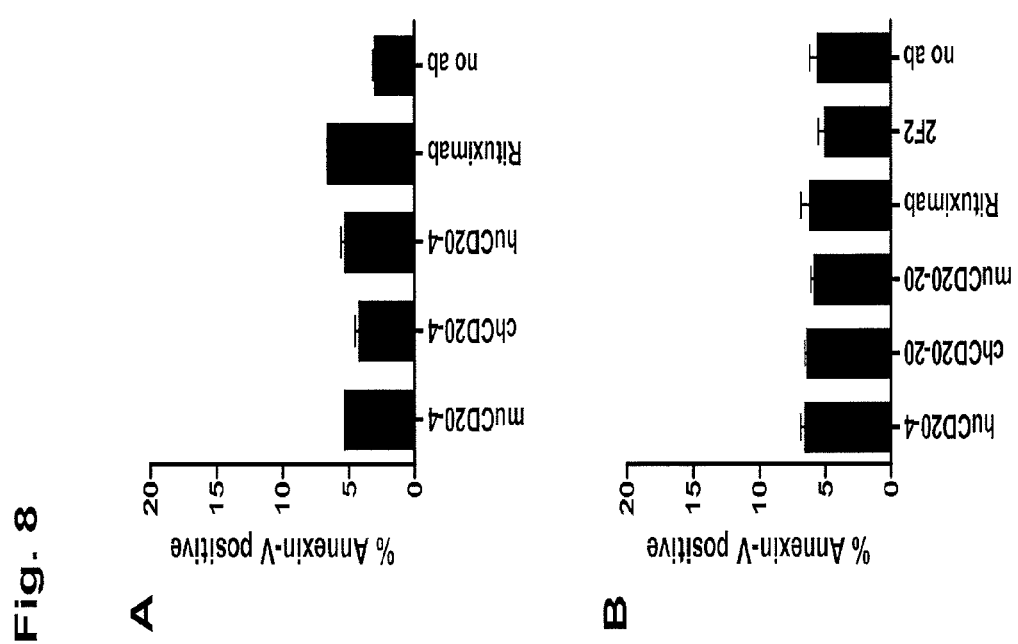
FIG. 8 depicts the results from an Annexin-V assay to measure induction of apoptosis on Ramos lymphoma cells incubated with 10 nM concentration of various antibodies. (A) muCD20-4, chCD20-4, huCD20-4 or rituximab and (B) huCD20-4, muCD20-20, chCD20-20, rituximab or 2F2. Untreated samples in the absence of antibody (no Ab) were used as a control. The term 2F2 corresponds to ofatumumab (Genmab).

The ability of antibodies to induce apoptosis on Ramos cells was compared for muCD20-4, chCD20-4, huCD20-4 and rituximab and measured by using Annexin-V-FITC and TO-PRO-3 staining. Ramos cells were incubated with 10 nM of each antibody for 20 hrs followed by Annexin-V-FITC and TO-PRO-3 staining and flow cytometry analysis. Percent Annexin-V positive cells for each treatment is shown in FIG. 8A in comparison to untreated cells. It is apparent that muCD20-4, chCD20-4 and huCD20-4 show no pro-apoptotic activity as compared to control samples. Approximately 5% of Ramos cells are Annexin-V positive after treatment with 10 nM of muCD20-4, chCD20-4 and huCD20-4. Similarly, 6% of rituximab treated Ramos cells are Annexin-V positive as compared to 3% of isotype control treated cells.

The ability of muCD20-20 and chCD20-20 to induce apoptosis on Ramos cells was compared huCD20-4, rituximab and 2F2. Ramos cells were incubated with 10 nM of each antibody for 20 hrs followed by Annexin-V-FITC and TO-PRO-3 staining and flow cytometry analysis. Percent Annexin-V positive cells for each treatment is shown in FIG. 8B in comparison to untreated cells. It is apparent that muCD20-20 and chCD20-20, like huCD20-4, rituximab, 2F2, show no pro-apoptotic activity as compared to control samples. Approximately 5-7% of Ramos cells are Annexin-V positive after treatment with any of the anti-CD20 antibodies as compared to 5% of isotype control treated cells.

Therefore, CD20-4 or CD20-20 do not induce apoptosis in Ramos cells and this property is the same irrespective of chimerization or humanization.

Pro-Apoptotic Activity of huCD20-4

Figure 9:
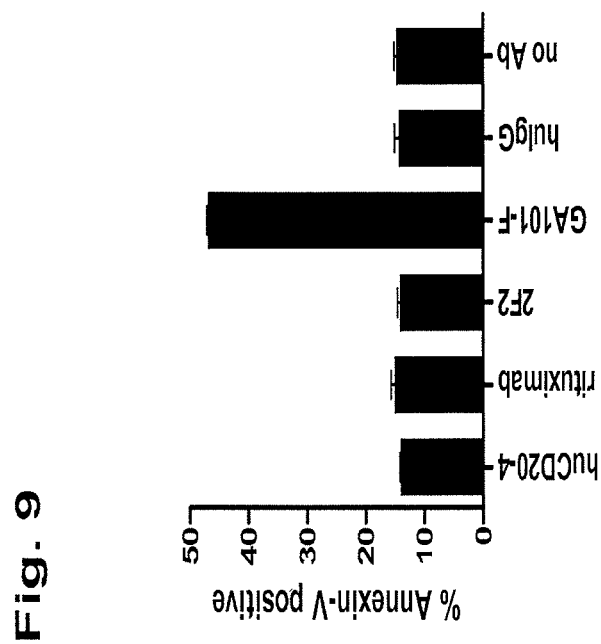
FIG. 9 depicts the results from an Annexin-V assay to measure induction of apoptosis on Granta-519 lymphoma cells incubated with a 10 nM concentration of huCD20-4, rituximab, 2F2, GA101-F or non-binding isotype control Ab. The term "GA101-F" corresponds to the fucosylated version of afutuzumab (Roche).

The huCD20-4 antibody was further tested for pro-apoptotic activity in comparison to a type II antibody GA101. Granta-519 cells were incubated with 10 nM or 1.5 μg/mL of huCD20-4, rituximab, 2F2, GA101-F or a non-binding isotype control antibody for 20 hrs followed by Annexin-V-FITC and TO-PRO-3 staining and flow cytometry analysis. "GA101-F" corresponds to the fucosylated version of afutuzumab or GA101 (Roche); and "2F2" corresponds to ofatumumab (Genmab). The percentage of Annexin-V positive cells was plotted for each antibody in FIG. 9. The percentage of Annexin-V positive Granta-519 cells treated with huCD20-4, rituximab, 2F2 is similar to isotype control antibody or untreated control samples. In contrast, the type II antibody GA101-F induced 45% Annexin-V positive cells.

Example 8

Lipid Raft Assay Using Human Antibodies

Figure 10:
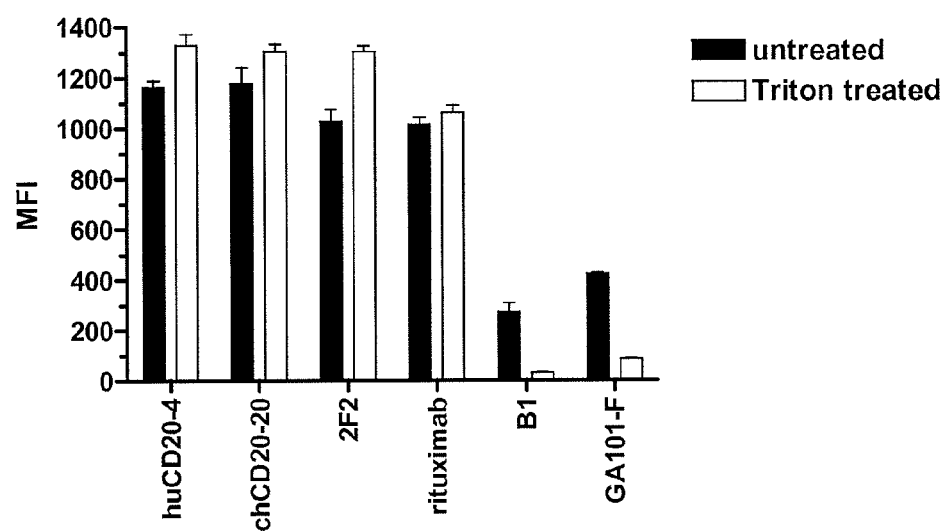
FIG. 10 depicts the results from a lipid raft assay using Ramos cells and huCD20-4, chCD20-20, rituximab, 2F2, B1 and GA101 antibodies at 10 µg/mL. MFI for FL1 from samples in the absence (black bars) and the presence (open bars) of Triton-X 100 is plotted for each antibody treatment. The term "B1" corresponds to the unlabeled form of Bexxar™ (Coulter) or tositumomab.

Lipid raft assays against Ramos cells were carried out for huCD20-4 and chCD20-20 as described above in comparison to other CD20 antibodies. Rituximab and 2F2 are type I antibodies with previously described lipid raft activity, while GA101-F and B1 are type II antibodies that lack lipid raft and consequently CDC activity. "B1" corresponds to the unlabeled form of Bexxar™ (Coulter) or tositumomab. As expected, rituximab and 2F2 treated cells show the same level of fluorescence with and without TritonX-100 treatment (FIG. 10). In contrast, the mean fluorescence of cells stained with B1 or GA101-F is much lower with TritonX-100 treatment than without consistent with their inability to re-distribute CD20 into lipid rafts. Similar to the result with rituximab and 2F2, the mean fluorescence of cells stained with huCD20-4 or chCD20-20 is similar with or without TritonX-100 treatment. This supports the concept that huCD20-4 and chCD20-20, like rituximab and 2F2, can efficiently translocate CD20 into the lipid raft compartment of the B cell membrane.

CDC Activity of Chimeric Abs

To assess complement-dependent cytotoxicity (CDC) activities of anti-CD20 antibodies, cell based assays were performed according to a published method (Gazzano-Santoro H, J Immunol Methods. 1997 Mar. 28; 202(2):163-71). Antibodies were aliquoted in duplicate at 50 μL/well into a flat-bottom 96-well tissue culture plate at various concentrations typically ranging from 5 μg/mL ($=3.3\times10^{-8}$ M) to 2.3 ng/mL ($=1.5\times10^{-11}$ M) in RHBP (RPMI-1640, 20 mM HEPES, 0.1% BSA, 1% penicillin-streptomycin) medium. Target cells were added to the antibodies at $5\times10^4$ cells in 100 μL of RHBP medium per well. Lyophilized human complement (Sigma-Aldrich, St. Louis, US) was reconstituted with 1 mL sterile purified water per vial and diluted 5-fold to a 20% stock with RHBP media immediately before use. 50 μL/well of complement solution was added to each well for a final concentration of 5%. Plate were incubated for 2 h at 37° C. in 5% $CO_2$ humidified incubator to allow for complement mediated lysis. After this incubation time, Alamar Blue reagent (Invitrogen) was added to each well at a final concentration of 10% to measure the viability of the remaining cells. The plate was incubated for 16 to 20 hours at 37° C. before measuring the fluorescence (in relative fluorescence units, RFU) at EX540/EM590 nm. Controls included triplicate wells with media and complement but without cells (media only, 0% viability) and wells with cells and complement but without antibody (cells only, 100% viability). The percentage of specific cell viability for each sample was determined by to the following formula: Percent viability=(sample−media only)/(cells only−media only).

CDC activity of chCD20-4 and chCD20-20 was measured in comparison to rituximab against WSU-DLCL-2 lymphoma cells. Surprisingly, the chCD20-4 and chCD20-20 antibodies had stronger CDC activity than rituximab (FIG. 11). Treatment with chCD20-4 or chCD20-20 reduced WSU-DLCL-2 cell viability completely with an EC50 of 0.027 or 0.084 μg/mL, respectively. Treatment with rituximab reduced WSU-DLCL-2 cell viability to 10% at the highest concentration tested with an EC50 of 0.35 μg/mL.

CDC Activity of huCD20-4

CDC activity of huCD20-4 was measured in comparison to rituximab and 2F2 in additional cell lines. Strikingly, the huCD20-4 antibody had the strongest CDC activity on Daudi and SU-DHL-4 lymphoma cells of all antibodies tested as shown in FIG. 12. Only huCD20-4 treatment reduced Daudi cell viability completely with an EC50 of 0.05 μg/mL. 2F2 treatment reduced Daudi cell viability to 25% with an EC50 of 0.34 μg/mL, while rituximab treatment reduced Daudi cell viability to 30% with an EC50 of 0.30 μg/mL. A similar results was seen SU-DHL-4 lymphoma cells as shown in FIG. 12B, where again huCD20-4 had the most potent CDC activity with the lowest EC50 value. Rituximab, 2F2 or huCD20-4 treatment reduced SU-DHL-4 cell viability completely with an EC50 of 0.31, 0.095 and 0.030 µg/mL, respectively.

In addition, huCD20-4 had more potent CDC activity than rituximab against Raji and Ramos lymphoma cells. Rituximab reduced cell viability of Raji cells to 35% at the highest concentration with an EC50 of 0.11 µg/mL. 2F2 reduced cell viability of Raji cells to 26% at the highest concentration with an EC50 of 0.13 µg/mL. huCD20-4 had the strongest activity and reduced cell viability of Raji cells to 27% at the highest concentration with an EC50 of 0.032 µg/mL (FIG. 13A). Again on Ramos lymphoma cells as shown in FIG. 13B, huCD20-4 had the most potent CDC activity with the lowest EC50 value of all CD20 antibodies tested. Rituximab, 2F2 or huCD20-4 treatment reduced Ramos cell viability completely with an EC50 of 0.06, 0.05 and 0.01 µg/mL, respectively.

Example 9

ADCC Activity of huCD20-4

A lactate dehydrogenase (LDH) release assay was used to measure antibody-dependent cell mediated cytotoxicity (ADCC) of tumor cells lines using freshly isolated human natural killer (NK) cells as effector cells (e.g., Shields, *J. Biol. Chem.*, 276(9):6591-6604 (2001)). NK cells were first isolated from human blood from a normal donor (Research Blood Components, Inc., Brighton, Mass.) using a modified protocol for the NK Isolation Kit II (Miltenyi Biotech, 130-091-152). Blood was diluted 2-fold with 1×PBS. 25 mL of diluted blood was carefully layered over 25 mL of Ficoll Paque in a 50 mL conical tube and centrifuged at 400 g for 45 min at RT. The peripheral blood mononuclear cells (PBMC) were collected from the interface, transferred into a new conical 50 mL tube, and washed once with 1×PBS. The PBMC were resuspended in 2 mL of NK-isolation buffer (1×PBS, 0.5% BSA, 2 mM EDTA), and then 500 µL of Biotin-Antibody Cocktail were added to the cell suspension. The Biotin-Antibody Cocktail contains biotinylated antibodies that bind to the lymphocytes, except for NK cells, resulting in a negative selection of NK cells. The mixture was incubated at 4° C. for 10 min, and then 1.5 mL of NK-isolation buffer and 1 mL of Anti-Biotin Micro Beads were added. The cell-antibody mixture was incubated for another 15 min at 4° C. Next, cells were washed once with 50 mL of NK-isolation buffer and resuspended in 3 mL of NK-isolation buffer. Then, a MACS LS column was mounted on the autoMACS separator (Miltenyi Biotech) and pre-washed with 3 mL of NK-isolation Buffer. The cell suspension was automatically applied onto the column, washed and the effluent fraction with unlabeled NK cells was collected into a new 50-mL conical tube. The resulting NK cells were plated into 30 mL of complete RPMI media (RPMI-1640 supplemented with 5% fetal bovine serum, 1% penicillin-streptomycin, 1 mM HEPES, 1 mM Sodium Pyruvate, 1% 100×MEM non-essential Amino Acid Solution) overnight. The subsequent assay and all dilutions were carried out in RHBP medium (RPMI-1640 medium supplemented with 20 mM HEPES, pH 7.4, 0.1% BSA and 1% penicillin-streptomycin).

Various concentrations of antibodies in RHBP medium were aliquoted in duplicate at 50 µL/well into a round bottom 96-well plate. The target cells were resuspended at $10^6$ cells/mL in RHBP medium and added at 100 µL/well to each well containing antibody dilutions. The plate containing target cells and antibody dilutions was incubated for 30 min at 37° C. NK cells were then added to the wells containing the target cells at 50 µL/well. The typical ratio was about 1 target cell to 3-4 NK cells. At least the following controls were set up for each experiment: NK cells alone, target cells alone (spontaneous LDH release), target cells with NK cells (antibody independent LDH release), target cells with 10% TritonX-100 (maximum LDH release). The mixtures were incubated at 37° C. for 4 h to allow for cell lysis. Plates were centrifuged for 10 min at 1200 rpm, and 100 µL of the supernatant was carefully transferred to a new flat-bottom 96-well plate. LDH reaction mixture (100 µL/well) from the Cytotoxicity Detection Kit (Roche 1 644 793) was added to each well and incubated at room temperature for 5 to 30 min. The optical density of samples was measured at 490 nm (OD490). The percent specific lysis of each sample was determined using the following formula: percent specific lysis=(sample value−spontaneous release)/(maximum release−spontaneous release)*100.

Incubation with huCD20-4 lead to good ADCC activity against Ramos Burkitt's lymphoma and Granta-519 mantle cell lymphoma cells in the presence of human NK effector cells. ADCC activity on Ramos lymphoma cells was compared for huCD20-4, rituximab and 2F2 (FIG. 14A). Treatment with huCD20-4 resulted in approximately 80% Ramos cell lysis similar to what was observed with the other anti-CD20 antibodies. ADCC activity by huCD20-4 had an EC50 of 0.40 ng/mL, rituximab had an EC50 of 3.5 ng/mL, and 2F2 had an EC50 of 1.2 ng/mL. Approximately 22% cell lysis was observed on Granta-519 cells with all anti-CD20 antibodies (FIG. 14B). The EC50 values for huCD20-4, rituximab and 2F2 were 0.28 ng/mL, 1.23 ng/mL and 0.47 ng/mL, respectively.

ADCC activity was compared to rituximab and 2F2 against the DLBC lymphoma cell lines SU-DHL-4 and WSU-DLCL-2. Treatment with anti-CD20 antibodies resulted in approximately 50% cell lysis of SU-DHL-4 cells (FIG. 15A). The EC50 values for huCD20-4, rituximab and 2F2 were 0.20 ng/mL, 0.53 ng/mL and 0.60 ng/mL, respectively. Similarly, treatment with anti-CD20 antibodies resulted in approximately 45% cell lysis of WSU-DLCL-2 cells (F1G. 15B). The EC50 values for huCD20-4, rituximab and 2F2 were 0.40 ng/mL, 1.00 ng/mL and 0.56 ng/mL, respectively.

In addition, huCD20-4 showed strong ADCC activity against JVM-13 chronic lymphocytic leukemia (CLL) cells. Approximately 38% cell lysis was observed on JVM-13 cells with all anti-CD20 antibodies (FIG. 16A). The EC50 values for huCD20-4, rituximab and 2F2 were 0.097 ng/mL, 0.29 ng/mL and 0.17 ng/mL, respectively. Finally, huCD20-4 treatment resulted in strong ADCC activity against DOHH-2 follicular lymphoma cells. Treatment with anti-CD20 antibodies resulted in approximately 50% cell lysis of DOHH-2 cells (FIG. 16B). The EC50 values for huCD20-4, rituximab and 2F2 were 0.57 ng/mL, 1.08 ng/mL and 0.60 ng/mL, respectively.

Figure 17:
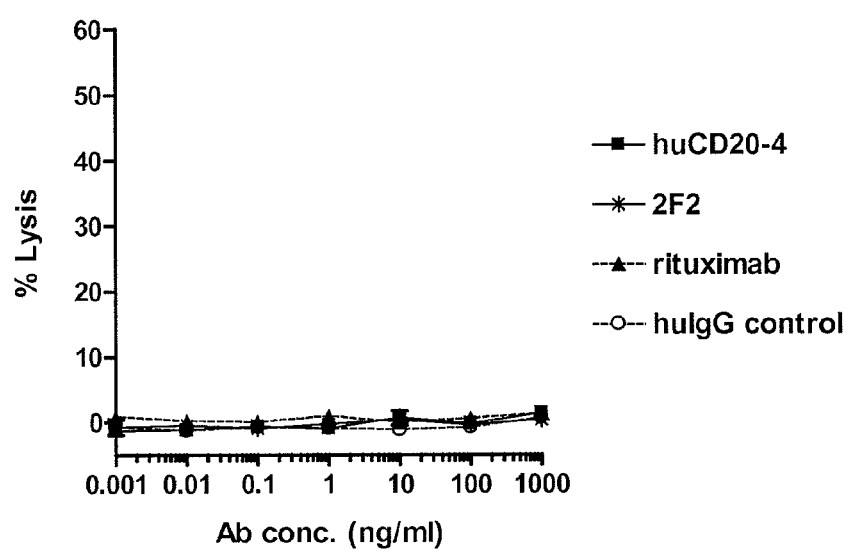
FIG. 17 depicts the results from an ADCC assay on CD20 antigen negative DND-41 T-ALL cells incubated with huCD20-4, rituximab, 2F2 or a huIgG1 isotype control antibody in the presence of purified human NK cells as effector cells.
Figure 18:
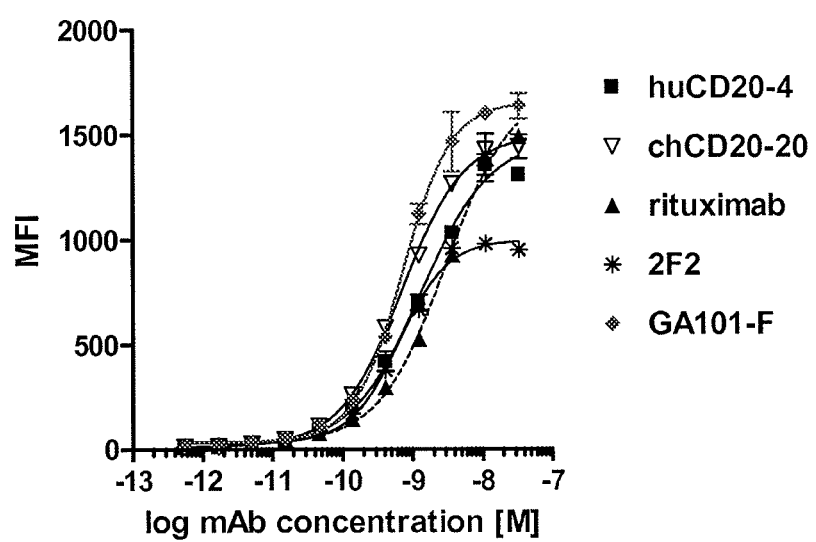
FIG. 18 depicts binding of huCD20-4, chCD20-20, rituximab, 2F2 and GA101-F to cells transfected with human CD20 wildtype antigen as assayed by flow cytometry.
Figure 20:
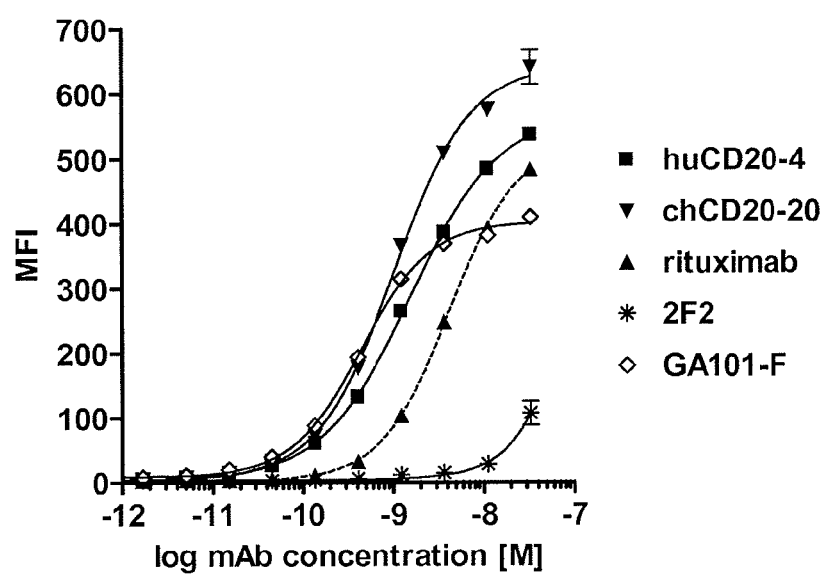
FIG. 20 depicts binding of a panel of CD20 antibodies to cells transfected with human CD20 antigen variants as assayed by flow cytometry. The antibodies huCD20-4, huCD20-19, chCD20-20, rituximab, 2F2 and GA 101-F were tested for binding to cells expressing the CD20-N163D N166D variant.

To verify the specificity of the observed ADCC activity, the CD20 antigen negative T-acute lymphoblastic leukemia (ALL) cell line DND-41 was used as target cells. As can be seen in FIG. 17, none of the anti-CD20 antibodies tested resulted in any measurable cell lysis of these cells.

Example 10

Epitope Mapping

The extracellular domain of CD20 contains two extracellular loops. The larger loop consists of approximately 44 amino acids between the third and fourth transmembrane domain. Most CD20 antibodies described thus require amino acid residues in the larger loop for effective binding. Mutagenesis analysis has identified at least alanine 170 (A170) and proline 172 (P172) as critical residues for antibody binding (Polyak, *Blood,* 99:3256-3262 (2002); and Polyak, *J. Immunol.,* 161:3242-3248 (1.998)). Changing A170 and P172 residues to serines, the amino acid found at this positions in murine CD20, abolished binding of CD20 antibodies, such as B1. Likewise, introduction of the A170 and P172 residues into CD20 containing the murine large extracellular loop allowed binding of most CD20 antibodies including B1 and rituximab. In contrast an unusual set of antibodies, including 2F2, has been described that have been reported to bind to the CD20 A170S P172S variant (Teeling et al. (2006), supra). In addition, changing residue asparagine 163 (N163) or asparagine 166 (N166) to aspartic acid, reduced binding of 2F2, while this did not affect binding of other anti-CD20 antibodies such as B1 or rituximab (Teeling et al. (2006) Blood. 177:363-371) This novel epitope has been suggested to be linked to their biologic activity, which entails potent CDC activity but limited direct pro-apoptotic activity against tumor cells. To further characterize CD20-4 and CD20-20 we analyzed their binding to the CD20 variants.

CD20 Variant Cloning and Expression

The expression plasmid pSRa-CD20 contains the entire human CD20 cDNA sequence, codon optimized and synthesized by Blue Heron Biotechnologies, flanked by XbaI and BamHI restriction sites for cloning into the pSRa vector. The CD20-A170S P172S variant (CD20-AP) was created by PCR mutagenesis, using the 5' primer hCD20sacAP-SS (ATTAGAGCTCACACACCATATATTAACATATA-CAACTGTGAACCATCGAATTCCTCT GAGAAAAACT (SEQ ID NO: 43)) together with a 3' end reverse primer SRaMfe1R (AATGCAATTGTTGTTGTTAACT (SEQ ID NO: 44)) to amplify a SacI to Mfe1 fragment of the pSRa-CD20 plasmid, containing the A170S P172S mutation. This PCR product was cloned into the SacI and Mfe1 sites of the pSRa-CD20 plasmid. Mutagenesis introduced an EcoRI site and the CD20 sequence change in the resulting clones that was verified by restriction enzyme digestion followed by DNA sequencing. The CD20 N163D N166D double (CD20-NNDD) and CD20 N163D (CD20-N163D) single mutants were generated by PCR mutagenesis of the same SacI to Mfe1 fragment, by modifying the specific codons in the 5' end primers. The CD20 N163D N166D mutant fragment was amplified with the hCD20sacNN-DD 5' end primer (ATTAGAGCTCACACACCATATATC-GATATATACGATTGTGAACCA (SEQ ID NO: 45)) and the CD20 N163D fragment was amplified with the hCD20sacN163D 5' end primer (ATTAGAGCTCACACAC-CATATATTGATATCTACAACTGTGA (SEQ ID NO: 46)). The SacI to Mfe1 PCR fragments were cloned into the Sad and Mfe1 sites of pSRa-CD20 and the constructs were screened for the introduced Cla1 or EcoRV sites respectively. Positive clones were further confirmed by DNA sequencing.

Stable cell lines were created by transfection of the CD20 variant expression plasmids into 300-19 cells using known electroporation procedures. Briefly, $5\times10^6$ 300-19 cells were electroporated in cold RPMI-1640 media using a BioRad Gene Pulser set at 260V and 960 µF. Subsequently, cells were diluted and plated into 96-well plates in RPMI-1640 media supplemented with 10% FBS and 50 µM β-mercaptoethanol. After 24 hours G418 (e.g., such as is obtainable from Invitrogen) was added at a final concentration of 2 mg/mL to select for transfected cells. After 2 weeks, single colonies were isolated and expanded.

Antibody Binding to CD20 Variants

Binding of various CD20 antibodies to CD20 AP, expressing human CD20 wildtype and variants was analyzed by flow cytometry. As can be seen in FIG. 18, all antibodies tested bound to cells transfected with wild type CD20. As expected, rituximab and GA101 did not bind the CD20AP variant, while B1 showed minimal binding (FIG. 20A). In contrast, 2F2 can bind the CD20AP variant as previously reported (Teeling J. L. Blood. 2006; 177:363-371). Similar to most anti-CD20 antibodies, huCD20-4 did not bind the CD20AP variant. Also, chCD20-20 was unable to bind the CD20AP variant (FIG. 19B).

As expected, rituximab and GA101 bound the CD20-N163D N166D variant, while 2F2 showed minimal binding (FIG. 20). The individual N163D and N166D mutations have been shown to reduce binding of 2F2, while not affecting binding of other anti-CD20 antibodies such as B1 or rituximab. Like most other anti-CD20 antibodies, huCD20-4 and chCD20-20 were able to bind the CD20-N163D N166D variant.

This result indicates that while huCD20-4 and chCD20-20 show improved CDC activity compared to rituximab as has been demonstrated for 2F2 and related antibodies, both antibodies clearly require a different epitope than 2F2.

Example 11

Preparation of huCD20-4-SPP-DM1

The N-succinimidyl 4-(2-pyridyldithio)pentanoate (SPP) linker was dissolved in ethanol. The huCD20-4 antibody was incubated at 8 mg/mL with a 7 fold molar excess of SPP linker for approximately 100 minutes at room temperature in 50 mM potassium phosphate buffer (pH 6.5) containing 50 mM NaCl, 2 mM EDTA, and 5% ethanol. The reaction mixture was purified using a SEPHADEX™ G25F column equilibrated with the aforementioned potassium phosphate buffer. Antibody containing fractions were pooled and used for subsequent steps.

An exemplary maytansinoid DM1 was dissolved in dimethylacetamide (DMA, final concentration is 3%) and a 1.7 fold molar excess relative to the linker was added drop wise to the SPP modified antibody. After overnight incubation at room temperature, the conjugated antibody was purified by chromatography on SEPHADEX™ G25F equilibrated in phosphate buffered saline (PBS), pH 6.5. The huCD20-4-SPP-DM1 conjugate was then dialyzed into buffer containing 10 mM histidine, 250 mM glycine, 1% sucrose pH 5.5. The number of DM1 molecules linked per antibody molecule was determined using the previously reported extinction coefficients for antibody and DM1 (Liu et al., Proc. Natl. Acad. Sci. USA, 93, 8618-8623 (1996)). The percentage of free maytansinoid present after the conjugation reaction was determined by injecting 20-50 µg conjugate onto a HiSep™ column equilibrated in 25% acetonitrile in 100 mM ammonium acetate buffer, pH 7.0, and eluting in acetonitrile. The peak area of total free maytansinoid species (eluted in the gradient and identified by comparison of elution time with known standards) was measured using an absorbance detector set to a wavelength of 252 nm and compared with the peak area related to bound maytansinoid (eluted in the conjugate peak in the column flow-through fractions) to calculate the percentage of total free maytansinoid species. Conjugates with 3.5-4 DM1 molecules per huCD20-4 antibody were obtained with <1% present as unconjugated maytansinoid.

Preparation of huCD20-4-SMCC-DM1

The (Succinimidyl 4-(N-maleimidomethyl)cyclohexane-1-carboxylate (SMCC, Pierce Biotechnology, Inc) linker was dissolved in DMA. The huCD20-4 antibody was modified with SMCC to introduce maleimides into the antibody by incubating the antibody at 8 mg/mL in 50 mM potassium phosphate, 50 mM NaCl, 2 mM EDTA, pH 6.5 with a 7.5 to 10 molar excess of SMCC. After stirring for 2 to 4 hours under argon at ambient temperature, the reaction mixture was purified using a SEPHADEX™ G25 column equilibrated with the same potassium phosphate buffer. Antibody containing fractions were pooled and used for subsequent steps.

The SMCC-modified antibody was reacted with a 10 mM solution of DM1 at a 1.7 molar excess relative to the maleimide linker. The reaction was stirred at ambient temperature under argon for 4 to about 16 hours. The conjugation reaction mixture was filtered through a SEPHADEX™ G25 gel filtration column equilibrated with 1×PBS at pH 6.5. The huCD20-4-SMCC-DM1 conjugate was then dialyzed into buffer containing 10 mM histidine, 250 mM glycine, 1% sucrose pH 5.5. The number of DM1 molecules linked per antibody molecule and the percentage of total free maytansinoid species were determined as described above. Conjugates with 3.5-4 DM1 molecules per huCD20-4 antibody were obtained with <1% present as unconjugated maytansinoid.

Preparation of huCD20-4-SPDB-DM4

The exemplary N-succinimidyl 4-(2-pyridyldithio)butanoate (SPDB) linker was dissolved in ethanol. The huCD20-4 antibody was incubated at 8 mg/mL with a 5 fold molar excess of SPDB linker for approximately 100 minutes at room temperature in 50 mM potassium phosphate buffer (pH 6.5) containing 50 mM NaCl, 2 mM EDTA, and 3% ethanol. The reaction mixture was purified using a SEPHADEX™ G25F column equilibrated with the aforementioned potassium phosphate buffer. Antibody containing fractions were pooled and used for subsequent steps.

The maytansinoid DM4 was dissolved in dimethylacetamide (DMA, final concentration is 3%) and a 1.7 fold molar excess compared to the linker was added drop wise to the SPDB modified antibody. After overnight incubation at room temperature, the conjugated antibody was purified by chromatography on SEPHADEX™ G25F equilibrated with 1×PBS at pH 6.5. The huCD20-4-SPDB-DM4 conjugate was then dialyzed into buffer containing 10 mM histidine, 250 mM glycine, 1% sucrose pH 5.5. The number of DM4 molecules linked per antibody molecule was determined using the previously reported extinction coefficients for antibody and maytansinoid (Widdison, W C, et al. J Med Chem, 49:4392-4408 (2006)). The percentage of total free maytansinoid species were determined as described above. Conjugates with 3.5-4 DM4 molecules per huCD20-4 antibody were obtained with <1% present as unconjugated maytansinoid.

Example 12

Binding Affinity of Conjugates

Binding affinity of huCD20-4 after conjugation to SMCC-DM1 or SPP-DM1 was assayed by flow cytometry using BJAB lymphoma cells as described in the above example. The value for the apparent dissociation constants (Kd) were calculated from the binding curves shown in FIG. 21 and correspond to 1.0 nM for huCD20-4, 0.9 nM for huCD20-4-SMCC-DM1 and 1.5 nM for huCD20-4-SPP-DM1 conjugates. This result demonstrates that SMCC-DM1 or SPP-DM1 conjugation does not notably alter the affinity of the huCD20-4 antibody.

Pro-Apoptotic Activity of Conjugates

Pro-apoptotic activity of huCD20-4 after conjugation to SMCC-DM1 or SPDB-DM4 was assayed on Ramos cells by Annexin-V assay as described above. Ramos cells were incubated with varying concentrations ranging from $3\times10^{-8}$ M to $1\times10^{-11}$ M of huCD20-4 antibody or conjugates for 20 hrs followed by Annexin-V-FITC and TO-PRO-3 staining and flow cytometry analysis. The percentage of Annexin-V positive cells was plotted against the antibody concentration in a semi-log plot in FIG. 22A. Treatment with huCD20-4 in the absence of cross-linking did not increase the percentage of Annexin-V positive cells, as compared to untreated cells. Treatment with huCD20-4-SMCC-DM1 conjugate resulted in an increase in Annexin-V positive cells to 27%, while treatment with huCD20-4-SPDB-DM4 conjugate resulted in an increase in Annexin-V positive cells to 36%. In contrast, SMCC-DM1 or SPDB-DM4 conjugates of a non-binding isotype control antibody resulted in 4% or 8% Annexin-V positive cells, respectively. This demonstrates that huCD20-4 can have significantly enhanced pro-apoptotic activity Ramos cells after maytansinoid conjugation of the antibody.

The results of similar experiments with huCD20-4-SMCC-DM1 conjugates on WSU-DLCL-2 cells are shown in FIG. 22B. Treatment with huCD20-4 in the absence of cross-linking increased the percentage of Annexin-V positive cells to 23%, as compared to 7% for untreated cells. Treatment with huCD20-4-SMCC-DM1 conjugate resulted in an increase in Annexin-V positive cells to 46%, while treatment with SMCC-DM1 conjugates of a non-binding isotype control antibody resulted in 8% Annexin-V positive cells which is similar to untreated cells. Therefore, pro-apoptotic activity of, for example, huCD20-4 can be enhanced after maytansinoid conjugation of the antibody.

CDC Activity of Conjugates

CDC activity of, for example, huCD20-4 after conjugation was assayed on lymphoma cells in the presence of human complement as described above. As seen in FIG. 23A for Daudi lymphoma cells, exemplary SMCC-DM1 conjugates of huCD20-4 had similar CDC activity as the unconjugated antibody with an EC50 of approximately 0.08 μg/mL and 0.05, respectively. This activity is more potent than that of rituximab, which has CDC activity with an EC50 of 0.30 μg/mL against Daudi cells. On WSU-DLCL-2 diffuse large B-cell lymphoma cells (FIG. 23B), huCD20-4, huCD20-4-MCC-DM1 and huCD20-4-SPDB-DM4 had similar CDC activity with an EC50 of approximately 0.04 μg/mL. Again, this activity is more potent than that of rituximab, which has CDC activity with an EC50 of 0.19 μg/mL WSU-DLCL-2 cells. Therefore, CDC activity of, for example, huCD20-4 is maintained after maytansinoid conjugation.

ADCC Activity of Conjugates

ADCC activity of, for example, huCD20-4 after conjugation to SMCC-DM1 was evaluated on Ramos and Granta-519 cells in the presence of human NK effector cells by LDH release assay as described above. As can be seen in FIG. 24, huCD20-4-MCC-DM1 conjugates have similar ADCC activity as the unconjugated huCD20-4 antibody on SU-DHL-4 cells with 50% maximum cell lysis each and an EC50 of 0.27 ng/mL and 0.20 ng/mL, respectively. Similar results were obtained using Granta-519 MCL cells as target cells. As before, huCD20-4-MCC-DM1 conjugates have comparable ADCC activity to the unconjugated huCD20-4 antibody on Granta-519 cells with approximately 20% maximum cell lysis each and an EC5.0 of 0.28 ng/mL and 0.29 ng/mL, respectively. As seen for CDC, the ADCC activity of huCD20-4 is maintained after maytansinoid conjugation.

Example 13

In Vitro Cytotoxicity Assays

The ability of exemplary huCD20-4 conjugates to inhibit cell growth was measured using in vitro cytotoxicity assays. Generally, target cells were plated at 5,000 cells per well in 100 μL in complete RPMI media (RPMI-1640, 10% fetal bovine serum, 2 mM glutamine, 1% penicillin-streptomycin, all reagents from Invitrogen). Antibodies and conjugates were diluted into complete RPMI media using 3-fold dilution series and 100 μL were added per well. The final concentration typically ranged from $3\times10^{-8}$ M to $4.6\times10^{-12}$ M. Cells were incubated at 37° C. in a humidified 5% $CO_2$ incubator for 4 to 5 days. Viability of remaining cells was determined by colorimetric WST-8 assay (Dojindo Molecular Technologies, Inc., Rockville, Md., US). WST-8 is reduced by dehydrogenases in living cells to an orange formazan product that is soluble in tissue culture medium. The amount of formazan produced is directly proportional to the number of living cells. WST-8 was added to 10% of the final volume and plates were incubated at 37° C. in a humidified 5% $CO_2$ incubator for an additional 2-4 hours. Plates were analyzed by measuring the absorbance at 450 nm ($A_{450}$) in a multiwell plate reader. Background $A_{450}$ absorbance of wells with media and WST-8 only was subtracted from all values. The percent viability was calculated by dividing each treated sample value by the average value of wells with untreated cells. Percent viability=100*($A_{450}$ treated sample–$A_{450}$ background)/ ($A_{450}$ untreated sample–$A_{450}$ background). The percent viability value was plotted against antibody or conjugate concentration in a semi-log plot for each treatment.

In Vitro Cytotoxicity of huCD20-4 and huCD20-4-SMCC-DM1 on Ramos Cells

The in vitro cytotoxicity of huCD20-4 and huCD20-4-SMCC-DM1 against Ramos cells was compared to the activity of rituximab and a non-specific huIgG-SMCC-DM1 conjugate. As seen in FIG. 25A, huCD20-4 incubation resulted in a reduction of viability to 70% at the highest concentration, while rituximab reduced viability more moderately to 80%. Treatment with huCD20-4-SMCC-DM1 completely reduced viability at the highest concentration tested with an EC50 of 0.54 nM, while the non-specific huIgG-SMCC-DM1 conjugate had an EC50 of 20 nM. That corresponds to a 37-fold specificity window for huCD20-4-SMCC-DM1.

In Vitro Cytotoxicity of huCD20-4 and huCD20-4-SMCC-DM1 on Daudi Cells

The in vitro cytotoxicity of huCD20-4 and huCD20-4-SMCC-DM1 against Daudi cells was compared to the activity of rituximab and a non-specific huIgG-SMCC-DM1 conjugate. As seen in FIG. 25B, huCD20-4 or rituximab incubation resulted in a reduction of viability to 80% at the highest concentration. Treatment with huCD20-4-SMCC-DM1 completely reduced viability at the highest concentration tested with an EC50 of 0.29 nM, while the non-specific huIgG-SMCC-DM1 conjugate had an EC50 of 12 nM. That corresponds to a 42-fold specificity window for huCD20-4-SMCC-DM1 against Daudi cells.

In Vitro Cytotoxicity of huCD20-4 and huCD20-4-SMCC-DM1 on Granta-519 Cells

The in vitro cytotoxicity of huCD20-4 and huCD20-4-SMCC-DM1 against Granta-519 MCL cells was compared to the activity of rituximab and a non-specific huIgG-SMCC-DM1 conjugate. As seen in FIG. 26A, huCD20-4 incubation and rituximab resulted in a reduction of viability to 60% at the highest concentration. Treatment with huCD20-4-SMCC-DM1 completely reduced viability at the highest concentration tested with an EC50 of 0.025 nM, while the non-specific huIgG-SMCC-DM1 conjugate had an EC50 of 13 nM. That corresponds to a 520-fold specificity window for huCD20-4-SMCC-DM1 against Granta-519 cells.

In Vitro Cytotoxicity of huCD20-4 and huCD20-4-SMCC-DM1 on SC-1 Cells

The in vitro cytotoxicity of huCD20-4 and huCD20-4-SMCC-DM1 against SC-1 FL cells was compared to the activity of rituximab and a non-specific huIgG-MCC-DM1 conjugate. As seen in FIG. 26B, huCD20-4 or rituximab incubation resulted in a reduction of viability to 85% or 75% respectively at the highest concentration. Treatment with huCD20-4-SMCC-DM1 completely reduced viability at the highest concentration tested with an EC50 of 0.60 nM, while the non-specific huIgG-SMCC-DM1 conjugate had an EC50 of 31 nM. That corresponds to a 52-fold specificity window for huCD20-4-SMCC-DM1 against SC-1 cells.

In Vitro Cytotoxicity of huCD20-4 and huCD20-4-SMCC-DM1 on DOHH-2 Cells

The in vitro cytotoxicity of huCD20-4 and huCD20-4-SMCC-DM1 against DOHH-2 FL cells was compared to the activity of rituximab and a non-specific huIgG-SMCC-DM1 conjugate. As seen in FIG. 27A, huCD20-4 or rituximab incubation resulted in a reduction of viability to 25% at the highest concentration. Treatment with huCD20-4-SMCC-DM1 completely reduced viability at the highest concentration tested with an EC50 of 0.6 nM, while the non-specific huIgG-SMCC-DM1 conjugate had an EC50 of 35 nM. That corresponds to a 318-fold specificity window for huCD20-4-SMCC-DM1 against DOHH-2 cells.

In Vitro Cytotoxicity of huCD20-4-SMCC-DM1 on Antigen Negative Molt-4 Cells

To further verify the specificity of huCD20-4-SMCC-DM1 cytotoxicity, its activity was compared to a non-specific huIgG-SMCC-DM1 conjugate against non-CD20 expressing Molt-4 T-cell acute lymphoblastic leukemia cell line. An increased concentration of both conjugates was used in this experiment to capture the relatively poor non-specific cytotoxicity. As seen in FIG. 27B, huCD20-4-SMCC-DM1 and the non-specific conjugate showed the same cytotoxicity with an $EC_{50}$ of 33 nM.

Summary of In Vitro Cytotoxicity of huCD20-4-SMCC-DM1

Conjugation, for example, SMCC-DM1 conjugation of huCD20-4 adds potent cytotoxic activity to the antibody against Ramos, Daudi, Granta-519, SC-1 and DOHH-2 cells. in all cases the viability of tumor cells was reduced more completely in response to conjugate treatment as compared to antibody treatment alone. When comparing huCD20-4-SMCC-DM1 potency against that of non-targeted huIgG-SMCC-DM1 conjugates a significant specificity window is observed for each CD20-expressing cell line, indicating that cytotoxicity is a result of huCD20-4 antibody binding to target cells. In addition, for example, huCD20-4-SMCC-DM1 and the non-specific conjugate showed the same poor cytotoxicity against antigen-negative Molt-4 cells. Thus, the cytotoxicity observed for huCD20-4-SMCC-DM1 is dependent on CD20 expression.

| $EC_{50}$ for SMCC-DM1 conjugates | | | | | | |
|---|---|---|---|---|---|---|
| | Ramos | Daudi | Granta-519 | SC-1 | DOHH-2 | Molt-4 |
| huCD20-4-SMCC-DM1 | 0.54 nM | 0.29 nM | 0.03 nM | 0.6 nM | 0.11 nM | 33 nM |
| huIgG1-SMCC-DM1 | 20 nM | 12 nM | 13 nM | 31 nM | 35 nM | 33 nM |
| Specificity window | 37 | 42 | 520 | 52 | 318 | 1 |

Example 14 huCD20-4-SMCC-DM1 is More Active than Rituximab-SMCC-DM1 Against Ramos Cells

The in vitro cytotoxicity, for example, of huCD20-4-SMCC-DM1 against Ramos lymphoma cells was compared to the activity of a rituximab-SMCC-DM1 and a non-specific huIgG-SMCC-DM1 conjugate. As seen in FIG. 28A, treatment with huCD20-4-SMCC-DM1 completely reduced viability with an $EC_{50}$ of 0.22 nM, while the non-specific huIgG-SMCC-DM1 conjugate had an $EC_{50}$ of 22 nM. Treatment with rituximab-SMCC-DM1 resulted in cytotoxicity with an $EC_{50}$ of 0.97 nM. Thus, huCD20-4-SMCC-DM1 conjugates have more potent cytotoxic activity in vitro than rituximab-SMCC-DM1.

huCD20-4-SMCC-DM1 is More Active Than Rituximab-SMCC-DM1 Against Daudi Cells

The in vitro cytotoxicity of huCD20-4-SMCC-DM1 against, for example, Daudi lymphoma cells was compared to the activity of a rituximab-SMCC-DM1 and a non-specific huIgG-SMCC-DM1 conjugate. As seen in FIG. 28B, treatment with huCD20-4-SMCC-DM1 abolished viability with an $EC_{50}$ of 0.21 nM, while the non-specific huIgG-SMCC-DM1 conjugate had an $EC_{50}$ of 15 nM. Treatment with rituximab-SMCC-DM1 resulted in cytotoxicity with an $EC_{50}$ of 1.1 nM. Thus, huCD20-4-SMCC-DM1 conjugates have more potent cytotoxic activity than rituximab-SMCC-DM1.

Example 15

In Vitro Cytotoxicity of huCD20-4 Conjugates with Different Linkers

Cytotoxicity of huCD20-4-SMCC-DM1 was compared to that of conjugates prepared with different linkers. As can be seen in FIG. 29A, SPDB-DM4 and SPP-DM1 conjugates of huCD20-4, for example, have similar cytotoxic activity as SMCC-DM1 conjugates against Ramos cells. Either conjugates results in complete reduction of cell viability with an EC50 of 0.35 nM for both huCD20-4-SMCC-DM1 and -SPP-DM1 and an EC50 of 0.39 nM for huCD20-4-SPDB-DM4. As seen in FIG. 29B, SPP-DM1 and SPDB-DM4 conjugates of huCD20-4, for example, also have similar cytotoxic activity as SMCC-DM1 conjugates against Daudi cells. All conjugates result in complete reduction of cell viability with an EC50 of 0.21 nM, 0.4 nM or 0.19 nM for huCD20-4-SMCC-DM1, huCD20-4-SPP-DM1 or huCD20-4-SPDB-DM4, respectively.

Example 16

In Vivo Efficacy of huCD20-4 Antibody in a Raji Xenograft Model

The exemplary huCD20-4 antibody was tested in an established xenograft model using Raji B-cell lymphoma cells implanted subcutaneous into SCID mice. Animals were randomized by tumor volume into treatment groups and treated twice per week for 3 weeks on days 12, 15, 19, 22, 26 and 19 post cell inoculation with 10 mg/kg of huCD20-4, rituximab or 2F2. The median tumor volume of the different treatment groups is plotted in FIG. 30. Median tumor volumes were compared and a T/C value calculated by taking the ratio of median tumor volume of each treated group (T) and the control group (C). Rituximab or 2F2 treatment resulted in a decrease in median tumor volume as compared to the PBS control with a T/C value of 31% or 37% on day 26. In comparison, huCD20-4 treatment resulted in a decrease in median tumor volume as compared to the PBS control with a T/C value of 26% on day 26.

Example 17

In Vivo Efficacy of huCD20-4 Antibody and -SMCC-DM1 Conjugates in a SU-DHL-4 Xenograft Model The huCD20-4 antibody and its SMCC-DM1 conjugate were tested for in vivo efficacy in a palpable xenograft model using SU-DHL-4 diffuse large B-cell lymphoma cells implanted subcutaneous into SCID mice. Animals were randomized by body weight into treatment groups and treated once on day 19 post cell inoculation with either 10 mg/kg of huCD20-4 or 10 mg/kg of huCD20-4-SMCC-DM1. The median tumor volume of the different treatment groups is plotted in FIG. 31. Treatment with huCD20-4 resulted in a decrease in median tumor volume as compared to the PBS control with a T/C value of 30% on day 39. Treatment with huCD20-4-SMCC-DM1 resulted in a more pronounced decrease in median tumor volume as compared to the PBS control with a T/C value of 15% on day 39. At the end of the study on day 112, huCD20-4-SMCC-DM1 treatment resulted in 4 of 10 tumor-free survivors (TFS). In contrast, no TFS were observed in the huCD20-4 treatment of PBS control groups. Therefore, huCD20-4-SMCC-DM1 was much more active in this in vivo model than the unconjugated huCD20-4 antibody.

In Vivo Efficacy of huCD20-4 Antibody and -SPP-DM1 and SMCC-DM1 Conjugates in a DOHH-2 Xenograft Model huCD20-4 antibodies and conjugates thereof were tested for in vivo efficacy in a xenograft model using DOHH-2 lymphoma cells implanted subcutaneous into SCID mice. Animals were randomized by body weight into treatment groups and treated once on day 3 post cell inoculation with either 10 mg/kg of huCD20-4, 10 mg/kg of huCD20-4-MCC-DM1 or 5 mg/kg of huCD20-4-SPP-DM1. The median tumor volume of the different treatment groups is plotted in FIG. 32. huCD20-4 antibody treatment resulted in a decrease in median tumor volume as compared to the PBS control. Enhanced efficacy was seen for huCD20-4 conjugates as compared to the unconjugated antibody. At the end of the study on day 120, huCD20-4 treatment resulted in 3 of 10 tumor-free survivors (TFS), while huCD20-4-MCC-DM1 treatment resulted in 4 of 10 TFS and huCD20-4-SPP-DM1 treatment resulted in 9 of 10 TFS. No TFS were observed in the PBS control group.

In Vivo Efficacy of huCD20-4 Antibody and SMCC-DM1 Conjugates in a JVM-13 Xenograft Model Exemplary huCD20-4 antibodies and conjugates thereof were tested for efficacy against rituximab in a JVM-13 chronic lymphocytic leukemia xenograft model. Animals were randomized by tumor volume into treatment groups and treated twice on days 14 and 21 post cell inoculation with either PBS as a control, or 10 mg/kg of either rituximab, huCD20-4, huCD20-4-SMCC-DM1 or a non-targeted huIgG-SMCC-DM1 conjugate. The median tumor volume of the different treatment groups is plotted in FIG. 33. The non-targeted huIgG-SMCC-DM1 conjugate treatment had no effect on tumor growth as compared to the PBS control group. Rituximab treatment resulted in slight decrease in median tumor volume as compared to the PBS control with a T/C value of 79% on day 25. Similarly, huCD20-4 treatment resulted in a slight decrease in median tumor volume as compared to the PBS control with a T/C value of 71% on day 25. Neither antibody is effective in this model, since compounds are not considered active unless the T/C value is at or below 42%. In contrast, huCD20-4-SMCC-DM1 treatment resulted in a more pronounced decrease in median tumor volume as compared to the PBS control with a T/C value of 35% on day 25. This demonstrates that SMCC-DM1 conjugation can add efficacy to the huCD20-4 antibody even in xenograft model where the antibody itself is considered inactive.

Summary of In Vivo Efficacy of huCD20-4-SMCC-DM1 Conjugates

Conjugates of CD20 antibodies have been described previously. In one case, non-cleavable SMCC-DM1 conjugates of an anti-CD20 antibody showed the same efficacy as the unconjugated antibody, while a cleavable SPP-DM1 conjugate of the same antibody showed improved efficacy in a Granta-519 xenograft model in SCID mice (Polson et al., supra). Similarly, calicheamicin conjugates of rituximab made with an acid-stable amide linker did not show improved in vivo efficacy in a Ramos xenograft model in nude mice. Only calicheamicin conjugates of rituximab made with an acid-labile dimethyl hydrazide Ac-But linker showed improved in vivo efficacy in this study (DiJoseph et al., supra).

Surprisingly, non-cleavable conjugates of huCD20-4, such as for example SMCC-DM1 conjugates, show dramatically improved in vivo efficacy in 3 different xenograft models as compared to the unconjugated antibody. In addition, cleavable conjugates of huCD20-4, such as for example SPP-DM1 conjugates, show equally improved in vivo efficacy as compared to the unconjugated antibody. In light of the previous studies this behavior is quite unexpected and presents a novel activity. This demonstrates that huCD20-4 is an antibody with unique properties that allow it be more efficacious as an SMCC-DM1 conjugate in vivo.

While the invention has been described in detail and with reference to specific aspects thereof, it is apparent to one of skill in the art that various changes and modifications can be made thereto without departing from the spirit and scope thereof.

---

What is claimed is:

1. An isolated antibody or antigen-binding fragment thereof that specifically binds to CD20, wherein said antibody or fragment comprises a light chain variable region and a heavy chain variable region, wherein the CDR-L1, CDR-L2, and CDR-L3 of said light chain variable region comprise the amino acid sequences of SEQ ID NOs: 23-25, respectively, and wherein the CDR-H1, CDR-H2, and CDR-H3 of said heavy chain variable region comprise the amino acid sequences of SEQ ID NOs: 26-28, respectively.

2. The antibody or fragment of claim 1, wherein said antibody or fragment is murine, humanized, chimeric, or resurfaced.

3. The antibody or fragment of claim 1, wherein the antibody or fragment is monoclonal or single-chain.

4. An antibody produced by the hybridoma (ATCC Accession No. PTA-10485) or an antigen-binding fragment thereof.

5. The antibody or fragment thereof of claim 1, obtained from eukaryotic or prokaryotic host cells selected from the group consisting of mammalian, yeast, insect, plant or bacterial cells.

6. The antibody or fragment thereof of claim 5, wherein said mammalian cells are CHO, NSO, SP2/0, PER.C6 or HEK-293 cells.

7. The antibody or fragment thereof of claim 5, wherein said yeast cells are *Pichia pastoris* or *Saccharomyces cerevisiae* cells.

8. The antibody or fragment thereof of claim 5, wherein said insect cells are Sf-9 cells.

9. The antibody or fragment thereof of claim 5, wherein said plant cells are *Lemna* cells.

10. The antibody or fragment thereof of claim 5, wherein said bacterial cells are *E. coli* cells.

11. The antibody or fragment of claim 1, wherein the antibody or fragment specifically binds to at least one amino acid located between the third and fourth transmembrane domains of CD20.

12. A conjugate comprising the antibody or fragment of claim 1 linked to a cytotoxic agent.

13. The conjugate of claim 12, wherein said cytotoxic agent is selected from the group consisting of a maytansinoid, maytansinoid analog, benzodiazepine, taxoid, CC-1065, CC1065 analog, duocarmicin, duocarmicin analog, calicheamicin, dolastatin, dolastatin analog, aristatin, tomaymycin derivative and leptomycin derivative.

14. A pharmaceutical composition comprising the antibody or fragment of claim 1 and a pharmaceutically acceptable carrier.

15. A pharmaceutical composition comprising the conjugate of claim 12 and a pharmaceutically acceptable carrier.

16. The antibody or fragment of claim 1, wherein the antibody or fragment specifically binds to a polypeptide having the amino acid sequence set forth in SEQ ID NO:47.

17. The antibody or fragment of claim 1, wherein said antibody or fragment is a Fab, a Fab', a F(ab')$_2$, a Fd, a single chain Fv or scFv, a disulfide linked Fv, a VNAR domain, a IgNar, an intrabody, an IgG$\Delta$CH2, a minibiody, a F(ab')$_3$, a tetrabody, a triabody, a diabody, a single-domain antibody, DVD-Ig, Fcab, mAb$^2$, a (scFv)$_2$, or a scFv-Fc.

18. The antibody or fragment of claim 1, comprising an immunoglobulin heavy chain constant domain.

19. The antibody or fragment of claim 18, wherein said immunoglobulin heavy chain constant domain is selected from the group consisting of an IgG1 constant domain, an IgG2 constant domain, an IgG3 constant domain and an IgG4 constant domain.

20. The antibody or fragment of claim 1, wherein said heavy chain variable region comprises the amino acid sequence of SEQ ID NO:16.

21. The antibody or fragment of claim 1, wherein said light chain variable region comprises the amino acid sequence of SEQ ID NO:15.

22. The antibody or fragment of claim 1 wherein the heavy chain variable region comprises the amino acid sequence of SEQ ID NO: 16 and the light chain variable region comprises the amino acids of SEQ ID NO: 15.

23. The conjugate of claim 12, wherein said linking of antibody or fragment to said cytotoxic agent is through a linker selected from the group consisting of a disulfide group, a thioether group, an acid labile group, a photolabile group, a peptidase labile group and an esterase labile group.

24. The conjugate of claim 23, wherein the linker is selected from the group consisting of N-succinimidyl 3-(2-pyridyldithio) propionate (SPDP), N-succinimidyl 4-(2-pyridyldithio)butanoate (SPDB), N-succinimidyl 4-(2-pyridyldithio)2-sulfobutanoate (sulfo-SPDB), N-succinimidyl 4-(2-pyridyldithio) pentanoate (SPP), 2-iminothiolane and acetylsuccinic anhydride.

25. The conjugate of claim 23, wherein the linker is selected from the group consisting of N-succinimidyl 4-(maleimidomethyl) cyclohexanecarboxylate (SMCC), N-succinimidyl-4-(N-maleimidomethyl)-cyclohexane-1-carboxy-(6-amidocaproate) (LC-SMCC), κ-maleimidoundecanoic acid N-succinimidyl ester (KMUA), β-maleimidopropanoic acid N-succinimidyl ester (BMPS), γ-maleimidobutyric acid N-succinimidyl ester (GMBS), ε-maleimidocaproic acid N-hydroxysuccinimide ester (EMCS), m-maleimidobenzoyl-N-hydroxysuccinimide ester (MBS), N-(α-maleimidoacetoxy)-succinimide ester (AMAS), succinimidyl-6-(β-maleimidopropionamido)hexanoate (SMPH), N-succinimidyl 4-(p-maleimidophenyl)-butyrate (SMPB), N-(p-maleimidophenyl)isocyanate (PMPI), N-succinimidyl-4-(iodoacetyl)-aminobenzoate (SIAB), N-succinimidyl iodoacetate (SIA), N-succinimidyl bromoacetate (SBA), and N-succinimidyl 3-(bromoacetamido)propionate (SBAP).

26. The conjugate of claim 23, wherein the linker is selected from the group consisting of SPP, SMCC, and SPDB.

27. The antibody or fragment of claim 1, wherein said antibody comprises a heavy chain comprising the amino acid sequence of SEQ ID NO:14 and a light chain comprising the amino acid sequence of SEQ ID NO:13.

28. The conjugate of claim 13, wherein the maytansinoid is DM1 or DM4.

29. The conjugate of claim 28, wherein said maytansinoid is DM1 and where said linking of said antibody or fragment to said DM1 is through the linker SPP.

30. The conjugate of claim 28, wherein said maytansinoid is DM4 and said linking of said antibody or fragment to said DM4 is through the linker SMCC.

31. The conjugate of claim 28, wherein said maytansinoid is DM4 and said linking of said antibody or fragment to said DM4 is through the linker SPDB.

32. A conjugate comprising the antibody or fragment of claim 22 linked to a cytotoxic agent.

33. The conjugate of claim 32, wherein the cytotoxic agent is a maytansinoid.

34. The conjugate of claim 33, wherein the maytansinoid is DM1 or DM4.

35. A conjugate comprising the antibody or fragment of claim 27 linked to a cytotoxic agent.

36. The conjugate of claim 35, wherein the cytotoxic agent is a maytansinoid.

37. The conjugate of claim 36, wherein the maytansinoid is DM1 or DM4.

* * * * *

SEQUENCE LISTING

<160> NUMBER OF SEQ ID NOS: 47

<210> SEQ ID NO 1
<211> LENGTH: 214
<212> TYPE: PRT
<213> ORGANISM: Artificial Sequence
<220> FEATURE:
<223> OTHER INFORMATION: muCD20-4LC

<400> SEQUENCE: 1

```
Asp Ile Val Met Thr Gln Ser Gln Lys Phe Met Ser Thr Ser Val Gly
1               5                   10                  15

Asp Arg Val Ser Val Asn Cys Lys Ala Ser Gln Asn Val Gly Thr Asn
            20                  25                  30

Val Ala Trp Tyr Gln Gln Lys Pro Arg Gln Ser Pro Lys Gly Leu Ile
        35                  40                  45

Tyr Ser Ala Ser Phe Arg Tyr Ser Gly Val Pro Asp Arg Phe Thr Gly
    50                  55                  60

Ser Gly Ser Gly Thr Asp Phe Thr Leu Thr Ile Phe Asn Val Gln Ser
65                  70                  75                  80

Asp Asp Leu Ala Glu Tyr Phe Cys Gln Gln Tyr Asn Asn Tyr Pro Leu
                85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210
```

<210> SEQ ID NO 2
<211> LENGTH: 449
<212> TYPE: PRT
<213> ORGANISM: Artificial Sequence
<220> FEATURE:
<223> OTHER INFORMATION: muCD20-4HC

<400> SEQUENCE: 2

```
Glu Val Lys Val Glu Glu Ser Gly Gly Gly Leu Val Lys Thr Gly Gly
1               5                   10                  15

Ser Met Lys Leu Ser Cys Val Ala Ser Gly Phe Ser Phe Asn Asn Tyr
            20                  25                  30

Trp Met Asn Trp Val Arg Gln Ser Pro Glu Lys Gly Leu Glu Trp Val
        35                  40                  45

Ala Glu Ile Arg Leu Lys Ser Asn Asn Tyr Ala Thr His Tyr Val Glu
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Ala Glu Asp Thr Gly Ile Tyr
                85                  90                  95

Tyr Cys Thr Gly Trp Asp Asp Tyr Ala Met Asp His Trp Gly Gln Gly
            100                 105                 110

Ile Ser Val Thr Val Ser Ser Ala Lys Thr Thr Ala Pro Ser Val Tyr
        115                 120                 125

Pro Leu Ala Pro Val Cys Gly Asp Thr Thr Gly Ser Ser Val Thr Leu
    130                 135                 140

Gly Cys Leu Val Lys Gly Tyr Phe Pro Glu Pro Val Thr Leu Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Thr Ser Ser
            180                 185                 190

Thr Trp Pro Ser Gln Ser Ile Thr Cys Asn Val Ala His Pro Ala Ser
        195                 200                 205

Ser Thr Lys Val Asp Lys Lys Ile Glu Pro Arg Gly Pro Thr Ile Lys
    210                 215                 220

Pro Cys Pro Pro Cys Lys Cys Pro Ala Pro Asn Leu Leu Gly Gly Pro
225                 230                 235                 240

Ser Val Phe Ile Phe Pro Pro Lys Ile Lys Asp Val Leu Met Ile Ser
                245                 250                 255

Leu Ser Pro Ile Val Thr Cys Val Val Val Asp Val Ser Glu Asp Asp
            260                 265                 270

Pro Asp Val Gln Ile Ser Trp Phe Val Asn Asn Val Glu Val His Thr
        275                 280                 285

Ala Gln Thr Gln Thr His Arg Glu Asp Tyr Asn Ser Thr Leu Arg Val
    290                 295                 300

Val Ser Ala Leu Pro Ile Gln His Gln Asp Trp Met Ser Gly Lys Glu
305                 310                 315                 320

Phe Lys Cys Lys Val Asn Asn Lys Asp Leu Pro Ala Pro Ile Glu Arg
                325                 330                 335

Thr Ile Ser Lys Pro Lys Gly Ser Val Arg Ala Pro Gln Val Tyr Val
            340                 345                 350

Leu Pro Pro Pro Glu Glu Glu Met Thr Lys Lys Gln Val Thr Leu Thr
        355                 360                 365
```

```
Cys Met Val Thr Asp Phe Met Pro Glu Asp Ile Tyr Val Glu Trp Thr
    370                 375                 380

Asn Asn Gly Lys Thr Glu Leu Asn Tyr Lys Asn Thr Glu Pro Val Leu
385                 390                 395                 400

Asp Ser Asp Gly Ser Tyr Phe Met Tyr Ser Lys Leu Arg Val Glu Lys
                405                 410                 415

Lys Asn Trp Val Glu Arg Asn Ser Tyr Ser Cys Ser Val Val His Glu
                420                 425                 430

Gly Leu His Asn His His Thr Thr Lys Ser Phe Ser Arg Thr Pro Gly
                435                 440                 445

Lys
```

<210> SEQ ID NO 3
<211> LENGTH: 214
<212> TYPE: PRT
<213> ORGANISM: Artificial Sequence
<220> FEATURE:
<223> OTHER INFORMATION: muCD20-20LC

<400> SEQUENCE: 3

```
Asp Ile Lys Met Thr Gln Ser Pro Ser Ser Met Tyr Thr Ser Leu Gly
1               5                   10                  15

Glu Arg Val Thr Ile Thr Cys Lys Ala Ser Gln Asp Ile Asn Ser Phe
                20                  25                  30

Leu Ser Trp Phe Gln Gln Lys Pro Gly Lys Ser Pro Lys Thr Leu Ile
            35                  40                  45

Tyr Arg Ala Tyr Arg Leu Val Asp Gly Val Pro Ser Arg Phe Ser Gly
        50                  55                  60

Ser Gly Ser Gly Gln Asp Tyr Ser Leu Thr Ile Ser Ser Leu Glu Phe
65                  70                  75                  80

Glu Asp Met Gly Ile Tyr Tyr Cys Leu Gln Ser Gly Ala Phe Pro Leu
                85                  90                  95

Thr Phe Gly Ala Gly Thr Lys Leu Glu Leu Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210
```

<210> SEQ ID NO 4
<211> LENGTH: 446
<212> TYPE: PRT
<213> ORGANISM: Artificial Sequence
<220> FEATURE:
<223> OTHER INFORMATION: muCD20-20HC

<400> SEQUENCE: 4

-continued

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
            35                  40                  45

Gly Ala Ile Tyr Pro Gly Asp Gly Asp Thr Arg Tyr Thr Gln Lys Phe
50                  55                  60

Lys Gly Lys Ala Thr Leu Thr Ala Asp Lys Ser Ser Tyr Thr Ala Tyr
65                  70                  75                  80

Met Gln Leu Ser Ser Leu Ala Ser Glu Asp Ser Ala Val Tyr Tyr Cys
            85                  90                  95

Ala Arg Ser Pro Asp Phe Tyr Gly Ser Gly Tyr Asp Phe Asp Tyr Trp
            100                 105                 110

Gly Gln Gly Thr Thr Leu Thr Val Ser Ser Ala Lys Thr Thr Pro Pro
            115                 120                 125

Ser Val Tyr Pro Leu Ala Pro Gly Ser Ala Ala Gln Thr Asn Ser Met
            130                 135                 140

Val Thr Leu Gly Cys Leu Val Lys Gly Tyr Phe Pro Glu Pro Val Thr
145                 150                 155                 160

Val Thr Trp Asn Ser Gly Ser Leu Ser Ser Gly Val His Thr Phe Pro
            165                 170                 175

Ala Val Leu Glu Ser Asp Leu Tyr Thr Leu Ser Ser Ser Val Thr Val
            180                 185                 190

Pro Ser Ser Met Arg Pro Ser Glu Thr Val Thr Cys Asn Val Ala His
            195                 200                 205

Pro Ala Ser Ser Thr Lys Val Asp Lys Lys Ile Val Pro Arg Asp Cys
210                 215                 220

Gly Cys Lys Pro Cys Ile Cys Thr Val Pro Glu Val Ser Ser Val Phe
225                 230                 235                 240

Ile Phe Pro Pro Lys Pro Lys Asp Val Leu Thr Ile Thr Leu Thr Pro
            245                 250                 255

Lys Val Thr Cys Val Val Val Asp Ile Ser Lys Asp Asp Pro Glu Val
            260                 265                 270

Gln Phe Ser Trp Phe Val Asp Asp Val Glu Val His Thr Ala Gln Thr
            275                 280                 285

Gln Pro Arg Glu Glu Gln Phe Asn Ser Thr Phe Arg Ser Val Ser Glu
290                 295                 300

Leu Pro Ile Met His Gln Asp Trp Leu Asn Gly Lys Glu Phe Lys Cys
305                 310                 315                 320

Arg Val Asn Ser Ala Ala Phe Pro Ala Pro Ile Glu Lys Thr Ile Ser
            325                 330                 335

Lys Thr Lys Gly Arg Pro Lys Ala Pro Gln Val Tyr Thr Ile Pro Pro
            340                 345                 350

Pro Lys Glu Gln Met Ala Lys Asp Lys Val Ser Leu Thr Cys Met Ile
            355                 360                 365

Thr Asp Phe Phe Pro Glu Asp Ile Thr Val Glu Trp Gln Trp Asn Gly
370                 375                 380

Gln Pro Ala Glu Asn Tyr Lys Asn Thr Gln Pro Ile Met Asn Thr Asn
385                 390                 395                 400

Gly Ser Tyr Phe Val Tyr Ser Lys Leu Asn Val Gln Lys Ser Asn Trp
            405                 410                 415

```
Glu Ala Gly Asn Thr Phe Thr Cys Ser Val Leu His Glu Gly Leu His
                420                 425                 430
Asn His His Thr Glu Lys Ser Leu Ser His Ser Pro Gly Lys
        435                 440                 445

<210> SEQ ID NO 5
<211> LENGTH: 108
<212> TYPE: PRT
<213> ORGANISM: Artificial Sequence
<220> FEATURE:
<223> OTHER INFORMATION: muCD20-4VL

<400> SEQUENCE: 5

Asp Ile Val Met Thr Gln Ser Gln Lys Phe Met Ser Thr Ser Val Gly
1               5                   10                  15
Asp Arg Val Ser Val Asn Cys Lys Ala Ser Gln Asn Val Gly Thr Asn
            20                  25                  30
Val Ala Trp Tyr Gln Gln Lys Pro Arg Gln Ser Pro Lys Gly Leu Ile
        35                  40                  45
Tyr Ser Ala Ser Phe Arg Tyr Ser Gly Val Pro Asp Arg Phe Thr Gly
 50                  55                  60
Ser Gly Ser Gly Thr Asp Phe Thr Leu Thr Ile Phe Asn Val Gln Ser
65                  70                  75                  80
Asp Asp Leu Ala Glu Tyr Phe Cys Gln Gln Tyr Asn Asn Tyr Pro Leu
                85                  90                  95
Thr Phe Gly Gly Gly Thr Lys Leu Glu Ile Lys Arg
            100                 105

<210> SEQ ID NO 6
<211> LENGTH: 119
<212> TYPE: PRT
<213> ORGANISM: Artificial Sequence
<220> FEATURE:
<223> OTHER INFORMATION: muCD20-4VH

<400> SEQUENCE: 6

Glu Val Lys Val Glu Glu Ser Gly Gly Gly Leu Val Lys Thr Gly Gly
1               5                   10                  15
Ser Met Lys Leu Ser Cys Val Ala Ser Gly Phe Ser Phe Asn Asn Tyr
            20                  25                  30
Trp Met Asn Trp Val Arg Gln Ser Pro Glu Lys Gly Leu Glu Trp Val
        35                  40                  45
Ala Glu Ile Arg Leu Lys Ser Asn Asn Tyr Ala Thr His Tyr Val Glu
 50                  55                  60
Ser Val Lys Gly Arg Phe Thr Ile Ser Arg Asp Asp Ser Lys Ser Ser
65                  70                  75                  80
Val Tyr Leu Gln Met Asn Asn Leu Arg Ala Glu Asp Thr Gly Ile Tyr
                85                  90                  95
Tyr Cys Thr Gly Trp Asp Asp Tyr Ala Met Asp His Trp Gly Gln Gly
            100                 105                 110
Ile Ser Val Thr Val Ser Ser
        115

<210> SEQ ID NO 7
<211> LENGTH: 108
<212> TYPE: PRT
<213> ORGANISM: Artificial Sequence
<220> FEATURE:
<223> OTHER INFORMATION: muCD20-20VL
```

-continued

```
<400> SEQUENCE: 7

Asp Ile Lys Met Thr Gln Ser Pro Ser Ser Met Tyr Thr Ser Leu Gly
1               5                   10                  15

Glu Arg Val Thr Ile Thr Cys Lys Ala Ser Gln Asp Ile Asn Ser Phe
            20                  25                  30

Leu Ser Trp Phe Gln Gln Lys Pro Gly Lys Ser Pro Lys Thr Leu Ile
        35                  40                  45

Tyr Arg Ala Tyr Arg Leu Val Asp Gly Val Pro Ser Arg Phe Ser Gly
    50                  55                  60

Ser Gly Ser Gly Gln Asp Tyr Ser Leu Thr Ile Ser Ser Leu Glu Phe
65                  70                  75                  80

Glu Asp Met Gly Ile Tyr Tyr Cys Leu Gln Ser Gly Ala Phe Pro Leu
                85                  90                  95

Thr Phe Gly Ala Gly Thr Lys Leu Glu Leu Lys Arg
            100                 105

<210> SEQ ID NO 8
<211> LENGTH: 122
<212> TYPE: PRT
<213> ORGANISM: Artificial Sequence
<220> FEATURE:
<223> OTHER INFORMATION: muCD20-20VH

<400> SEQUENCE: 8

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Ala Ile Tyr Pro Gly Asp Gly Asp Thr Arg Tyr Thr Gln Lys Phe
    50                  55                  60

Lys Gly Lys Ala Thr Leu Thr Ala Asp Lys Ser Ser Tyr Thr Ala Tyr
65                  70                  75                  80

Met Gln Leu Ser Ser Leu Ala Ser Glu Asp Ser Ala Val Tyr Tyr Cys
                85                  90                  95

Ala Arg Ser Pro Asp Phe Tyr Gly Ser Gly Tyr Asp Phe Asp Tyr Trp
            100                 105                 110

Gly Gln Gly Thr Thr Leu Thr Val Ser Ser
        115                 120

<210> SEQ ID NO 9
<211> LENGTH: 324
<212> TYPE: DNA
<213> ORGANISM: Artificial Sequence
<220> FEATURE:
<223> OTHER INFORMATION: muCD20-4VL

<400> SEQUENCE: 9
gacattgtga tgacccagtc tcaaaaattc atgtccacat cagtaggaga cagggtcagc       60
gtcaactgca aggccagtca gaatgtgggc actaatgtag cctggtatca acagaaacca      120
aggcaatctc ctaaaggatt gatttattcg gcatccttcc ggtacagtgg agtccctgat      180
cgcttcacag gcagtggatc tgggacagat tcactctca ccatcttcaa tgtgcagtct       240
gacgacttgg cagagtattt ctgtcagcaa tataataatt atcctctgac gttcggtgga      300
ggcaccaagc tggaaatcaa acgg                                             324
```

<210> SEQ ID NO 10
<211> LENGTH: 358
<212> TYPE: DNA
<213> ORGANISM: Artificial Sequence
<220> FEATURE:
<223> OTHER INFORMATION: muCD20-4VH

<400> SEQUENCE: 10

| | | | | | |
|---|---|---|---|---|---|
| gaagtgaagg | ttgaggagtc | tggaggaggc | ttggtgaaaa | ctggaggatc | catgaaactc | 60 |
| tcctgtgttg | cctctggatt | cagtttcaat | aactattgga | tgaactgggt | ccgccagtct | 120 |
| ccagagaagg | ggcttgagtg | ggttgctgaa | atcagattga | aatctaataa | ttatgcgaca | 180 |
| cattatgtgg | agtctgtgaa | agggaggttc | accatctcaa | gagatgattc | caaaagtagt | 240 |
| gtctacctgc | aaatgaataa | cttaagagct | gaagacactg | gcatttatta | ctgtactggc | 300 |
| tgggacgatt | atgctatgga | ccactggggt | caaggaatct | cagtcaccgt | ctcctcag | 358 |

<210> SEQ ID NO 11
<211> LENGTH: 324
<212> TYPE: DNA
<213> ORGANISM: Artificial Sequence
<220> FEATURE:
<223> OTHER INFORMATION: muCD20-20VL

<400> SEQUENCE: 11

| | | | | | |
|---|---|---|---|---|---|
| gacatcaaga | tgacccagtc | tccatcttcc | atgtatacat | ctctaggaga | gagagtcact | 60 |
| atcacttgca | aggcgagtca | ggacattaat | agcttttta | gctggttcca | acagaaacca | 120 |
| gggaaatctc | ctaagaccct | gatctatcgt | gcatacagat | tggtagatgg | ggtcccatca | 180 |
| aggttcagtg | gcagtggatc | tggacaagat | tattctctca | ccatcagcag | cctggagttt | 240 |
| gaagatatgg | gaatttatta | ttgtctacag | tctggtgcgt | ttccgctcac | gttcggtgct | 300 |
| gggaccaagc | tggaactgaa | acgg | | | | 324 |

<210> SEQ ID NO 12
<211> LENGTH: 366
<212> TYPE: DNA
<213> ORGANISM: Artificial Sequence
<220> FEATURE:
<223> OTHER INFORMATION: muCD20-20VH

<400> SEQUENCE: 12

| | | | | | |
|---|---|---|---|---|---|
| caggttcagc | tccagcagtc | tggggctgag | ctggcaagac | ctggggcttc | agtgaagttg | 60 |
| tcctgcaagg | cttctggcta | cactttact | agctactgga | tgcattgggt | aaaacagagg | 120 |
| cctggacagg | gtctggaatg | gattggggct | atttatcctg | agatggtga | tactaggtac | 180 |
| actcagaagt | ttaagggcaa | ggccacattg | actgcagata | atcctccta | cacagcctac | 240 |
| atgcaactca | gtagcttggc | atctgaagac | tctgcggtct | attactgtgc | aagatcaccc | 300 |
| gatttctacg | gtagtggcta | cgactttgac | tactggggcc | aaggcaccac | tctcacagtc | 360 |
| tcctca | | | | | | 366 |

<210> SEQ ID NO 13
<211> LENGTH: 214
<212> TYPE: PRT
<213> ORGANISM: Artificial Sequence
<220> FEATURE:
<223> OTHER INFORMATION: huCD20-4LC

<400> SEQUENCE: 13

```
Asp Ile Gln Met Thr Gln Ser Pro Ser Thr Met Ser Thr Ser Val Gly
1               5                   10                  15

Asp Arg Val Ser Val Asn Cys Lys Ala Ser Gln Asn Val Gly Thr Asn
            20                  25                  30

Val Ala Trp Tyr Gln Gln Lys Pro Gly Lys Ser Pro Lys Gly Leu Ile
            35                  40                  45

Tyr Ser Ala Ser Phe Arg Tyr Ser Gly Val Pro Ser Arg Phe Thr Gly
50                  55                  60

Ser Gly Ser Gly Thr Asp Phe Thr Leu Thr Ile Phe Asn Val Gln Pro
65                  70                  75                  80

Asp Asp Leu Ala Glu Tyr Phe Cys Gln Gln Tyr Asn Asn Tyr Pro Leu
                85                  90                  95

Thr Phe Gly Gly Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 14
<211> LENGTH: 449
<212> TYPE: PRT
<213> ORGANISM: Artificial Sequence
<220> FEATURE:
<223> OTHER INFORMATION: huCD20-4HC

<400> SEQUENCE: 14

Glu Val Gln Val Glu Glu Ser Gly Gly Gly Leu Val Gln Pro Gly Gly
1               5                   10                  15

Ser Met Arg Leu Ser Cys Val Ala Ser Gly Phe Ser Phe Asn Asn Tyr
            20                  25                  30

Trp Met Asn Trp Val Arg Gln Ser Pro Gly Lys Gly Leu Glu Trp Val
            35                  40                  45

Ala Glu Ile Arg Leu Lys Ser Asn Asn Tyr Ala Thr His Tyr Val Asp
50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Ala Glu Asp Thr Gly Ile Tyr
                85                  90                  95

Tyr Cys Thr Gly Trp Asp Asp Tyr Ala Met Asp His Trp Gly Gln Gly
                100                 105                 110

Ile Ser Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
            130                 135                 140
```

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
        210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
                435                 440                 445

Lys

<210> SEQ ID NO 15
<211> LENGTH: 108
<212> TYPE: PRT
<213> ORGANISM: Artificial Sequence
<220> FEATURE:
<223> OTHER INFORMATION: huCD20-4VL

<400> SEQUENCE: 15

Asp Ile Gln Met Thr Gln Ser Pro Ser Thr Met Ser Thr Ser Val Gly
1               5                   10                  15

Asp Arg Val Ser Val Asn Cys Lys Ala Ser Gln Asn Val Gly Thr Asn
            20                  25                  30

Val Ala Trp Tyr Gln Gln Lys Pro Gly Lys Ser Pro Lys Gly Leu Ile
        35                  40                  45

Tyr Ser Ala Ser Phe Arg Tyr Ser Gly Val Pro Ser Arg Phe Thr Gly
          50                  55                  60

Ser Gly Ser Gly Thr Asp Phe Thr Leu Thr Ile Phe Asn Val Gln Pro
65                  70                  75                  80

Asp Asp Leu Ala Glu Tyr Phe Cys Gln Gln Tyr Asn Asn Tyr Pro Leu
                85                  90                  95

Thr Phe Gly Gly Gly Thr Lys Leu Glu Ile Lys Arg
            100                 105

<210> SEQ ID NO 16
<211> LENGTH: 119
<212> TYPE: PRT
<213> ORGANISM: Artificial Sequence
<220> FEATURE:
<223> OTHER INFORMATION: huCD20-4VH

<400> SEQUENCE: 16

Glu Val Gln Val Glu Glu Ser Gly Gly Leu Val Gln Pro Gly Gly
1               5                   10                  15

Ser Met Arg Leu Ser Cys Val Ala Ser Gly Phe Ser Phe Asn Asn Tyr
                20                  25                  30

Trp Met Asn Trp Val Arg Gln Ser Pro Gly Lys Gly Leu Glu Trp Val
            35                  40                  45

Ala Glu Ile Arg Leu Lys Ser Asn Asn Tyr Ala Thr His Tyr Val Asp
50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Ala Glu Asp Thr Gly Ile Tyr
                85                  90                  95

Tyr Cys Thr Gly Trp Asp Asp Tyr Ala Met Asp His Trp Gly Gln Gly
            100                 105                 110

Ile Ser Val Thr Val Ser Ser
        115

<210> SEQ ID NO 17
<211> LENGTH: 396
<212> TYPE: DNA
<213> ORGANISM: Artificial Sequence
<220> FEATURE:
<223> OTHER INFORMATION: huCD20-4VL

<400> SEQUENCE: 17
gaattcgcca ccatggggtg gtcatgtata atccttttct tggttgctac cgctaccggg      60
gttcactccg acatccagat gacccaatct ccctccacca tgtctacttc cgtcggggac     120
agggtgtcag tgaattgcaa agccagccaa aacgtcggca ccaatgtcgc ttggtaccag     180
cagaagcccg gtaaaagccc taagggactg atctacagcg ctagcttccg ttacagtggt     240
gtcccttctc gcttcacagg gtctggatct ggaaccgact tcactctcac tatttttcaat    300 gttcaaccag atgacctcgc agaatacttt tgccagcagt acaacaatta tccccttacc     360
ttcggtggcg gcaccaagct ggaaatcaag cgtacg                               396

<210> SEQ ID NO 18
<211> LENGTH: 443
<212> TYPE: DNA
<213> ORGANISM: Artificial Sequence
<220> FEATURE:
<223> OTHER INFORMATION: huCD20-4VH

<400> SEQUENCE: 18

```
aagcttgcca ccatgggatg gtcttgcatc atactgttcc tggttgcaac cgctacagga      60
gtgcatagcg aggtgcaggt ggaggagtca ggaggggac tggtacagcc cggcggttct      120
atgagactca gttgcgtcgc cagtggcttc agctttaata actactggat gaattgggtg    180
agacagtcac ccggaaaagg ccttgaatgg gtagctgaga ttcggcttaa gtccaataat    240
tacgctaccc attatgtgga ctctgttaaa ggccgtttta ctatttctag ggacgactct    300
aaatctagcg tctacttgca gatgaacaac cttcgtgccg aggacacagg aatctactat    360
tgtaccggtt gggacgatta cgcaatggac cactggggcc agggtatcag cgtaacagtg    420
tctagcgcat ctacaaaggg ccc                                             443
```

<210> SEQ ID NO 19
<211> LENGTH: 396
<212> TYPE: DNA
<213> ORGANISM: Artificial Sequence
<220> FEATURE:
<223> OTHER INFORMATION: chCD20-4VL

<400> SEQUENCE: 19

```
gaattcgcca ccatgggctg gagttgtatc atcctcttcc tggtagccac agccacagga     60
gttcactcag acattgtcat gacccagtct cagaagttca tgtctacatc cgtcggcgac   120
cgggtgagcg tgaactgtaa ggcaagccaa aatgtgggga ctaacgtcgc ctggtatcaa   180
cagaagccta ggcaatcccc caaagggctc atatattccg caagtttccg ttattccggg   240
gtacctgaca ggtttactgg ttcagggtct ggcaccgatt ttaccctgac catcttcaat   300
gtacagagtg acgatctcgc cgagtacttt tgccaacagt ataacaacta tcctctcact   360
ttcgggggag gtaccaagct ggagattaaa cgtacg                              396
```

<210> SEQ ID NO 20
<211> LENGTH: 443
<212> TYPE: DNA
<213> ORGANISM: Artificial Sequence
<220> FEATURE:
<223> OTHER INFORMATION: chCD20-4VH

<400> SEQUENCE: 20

```
aagcttgcca ccatgggctg gtcctgcatc atcctctttc tggtggccac agctaccggc     60
gttcacagcg aggtgaaggt cgaagaatct ggcggggac tggttaaaac aggcggctct    120
atgaagctct cttgtgtggc ttccggcttc agcttcaaca attattggat gaattgggtg    180
cgccagtctc cagagaaggg gttggaatgg gtcgcagaaa tacgactgaa gagcaataat    240
tatgccaccc attatgtgga aagcgttaaa ggcagattta ccatctcaag ggacgatagt    300
aaatcttccg tgtaccttca gatgaacaat cttagagccg aggataccgg gatctactat    360
tgcactggat gggacgacta tgctatggat cactggggcc agggcattag cgtgaccgtt    420
agctctgcta gtaccaaggg ccc                                             443
```

<210> SEQ ID NO 21
<211> LENGTH: 452
<212> TYPE: DNA
<213> ORGANISM: Artificial Sequence
<220> FEATURE:
<223> OTHER INFORMATION: chCD20-20VH

<400> SEQUENCE: 21

```
aagcttgcca ccatggggtg gagttgtata atcctgtttc ttgtggcaac agccacagga     60
```

```
gtccactccc aggtacagct gcagcagtct ggcgctgagc tggcccgccc cggagcatcc    120
gtgaagttga gctgcaaagc aagtgggtac accttcacca gttattggat gcattgggtg    180
aagcagagac ctggacaggg tctggagtgg attggcgcta tctatcccgg agatggcgat    240
acacggtaca cacagaaatt aagggcaag gccactctta ctgcagataa atccagctac     300
acagcttaca tgcaactctc ttctctggct tccgaagact ctgcagtgta ttattgcgct    360
aggtccccag atttctacgg gagtgggtac gacttcgatt actggggaca aggaactaca    420
cttactgtga gttccgcctc aacaaagggc cc                                  452
```

<210> SEQ ID NO 22
<211> LENGTH: 396
<212> TYPE: DNA
<213> ORGANISM: Artificial Sequence
<220> FEATURE:
<223> OTHER INFORMATION: chCD20-20VL

<400> SEQUENCE: 22

```
gaattcgcca ccatgggctg gtcttgtatt atactgttcc tggtcgctac tgccaccggg    60
gtgcacagcg atattaagat gacccagagt ccatcaagca tgtatacatc ccttggagag    120
agagtgacta aacctgcaa agcatcacaa gacattaaca gcttcctcag ctggttccag    180
cagaagcccg ggaagagtcc aaaacactt atctatagag cataccggct ggtcgacggt    240
gtacctagtc gcttcagcgg ctccggaagt gggcaggatt actcacttac aatctctagt    300
ctggagttcg aggacatggg gatttactac tgtcttcaaa gtggagcatt tccactcaca    360
tttggggcag gcaccaagct ggagctgaag cgtacg                              396
```

<210> SEQ ID NO 23
<211> LENGTH: 11
<212> TYPE: PRT
<213> ORGANISM: Artificial Sequence
<220> FEATURE:
<223> OTHER INFORMATION: CD20-4_LC_CDR1

<400> SEQUENCE: 23

Lys Ala Ser Gln Asn Val Gly Thr Asn Val Ala
1               5                   10

<210> SEQ ID NO 24
<211> LENGTH: 7
<212> TYPE: PRT
<213> ORGANISM: Artificial Sequence
<220> FEATURE:
<223> OTHER INFORMATION: CD20-4_LC_CDR2

<400> SEQUENCE: 24

Ser Ala Ser Phe Arg Tyr Ser
1               5

<210> SEQ ID NO 25
<211> LENGTH: 9
<212> TYPE: PRT
<213> ORGANISM: Artificial Sequence
<220> FEATURE:
<223> OTHER INFORMATION: CD20-4_LC_CDR3

<400> SEQUENCE: 25

Gln Gln Tyr Asn Asn Tyr Pro Leu Thr
1               5

<210> SEQ ID NO 26

```
<211> LENGTH: 5
<212> TYPE: PRT
<213> ORGANISM: Artificial Sequence
<220> FEATURE:
<223> OTHER INFORMATION: CD20-4_HC_CDR

<400> SEQUENCE: 26

Asn Tyr Trp Met Asn
1               5

<210> SEQ ID NO 27
<211> LENGTH: 12
<212> TYPE: PRT
<213> ORGANISM: Artificial Sequence
<220> FEATURE:
<223> OTHER INFORMATION: CD20-4_HC_CDR2-AbM

<400> SEQUENCE: 27

Glu Ile Arg Leu Lys Ser Asn Asn Tyr Ala Thr His
1               5                   10

<210> SEQ ID NO 28
<211> LENGTH: 8
<212> TYPE: PRT
<213> ORGANISM: Artificial Sequence
<220> FEATURE:
<223> OTHER INFORMATION: CD20-4_HC_CDR3

<400> SEQUENCE: 28

Trp Asp Asp Tyr Ala Met Asp His
1               5

<210> SEQ ID NO 29
<211> LENGTH: 19
<212> TYPE: PRT
<213> ORGANISM: Artificial Sequence
<220> FEATURE:
<223> OTHER INFORMATION: murine-HC-CDR2-Kabat

<400> SEQUENCE: 29

Glu Ile Arg Leu Lys Ser Asn Asn Tyr Ala Thr His Tyr Val Glu Ser
1               5                   10                  15

Val Lys Gly

<210> SEQ ID NO 30
<211> LENGTH: 19
<212> TYPE: PRT
<213> ORGANISM: Artificial Sequence
<220> FEATURE:
<223> OTHER INFORMATION: human-HC-CDR2-Kabat

<400> SEQUENCE: 30

Glu Ile Arg Leu Lys Ser Asn Asn Tyr Ala Thr His Tyr Val Asp Ser
1               5                   10                  15

Val Lys Gly

<210> SEQ ID NO 31
<211> LENGTH: 11
<212> TYPE: PRT
<213> ORGANISM: Artificial Sequence
<220> FEATURE:
<223> OTHER INFORMATION: CD20-20_LC_CDR1

<400> SEQUENCE: 31

Lys Ala Ser Gln Asp Ile Asn Ser Phe Leu Ser
1               5                   10
```

<210> SEQ ID NO 32
<211> LENGTH: 7
<212> TYPE: PRT
<213> ORGANISM: Artificial Sequence
<220> FEATURE:
<223> OTHER INFORMATION: CD20-20_LC_CDR2

<400> SEQUENCE: 32

Arg Ala Tyr Arg Leu Val Asp
1               5

<210> SEQ ID NO 33
<211> LENGTH: 9
<212> TYPE: PRT
<213> ORGANISM: Artificial Sequence
<220> FEATURE:
<223> OTHER INFORMATION: CD20-20_LC_CDR3

<400> SEQUENCE: 33

Leu Gln Ser Gly Ala Phe Pro Leu Thr
1               5

<210> SEQ ID NO 34
<211> LENGTH: 5
<212> TYPE: PRT
<213> ORGANISM: Artificial Sequence
<220> FEATURE:
<223> OTHER INFORMATION: CD20-20_HC_CDR1

<400> SEQUENCE: 34

Ser Tyr Trp Met His
1               5

<210> SEQ ID NO 35
<211> LENGTH: 10
<212> TYPE: PRT
<213> ORGANISM: Artificial Sequence
<220> FEATURE:
<223> OTHER INFORMATION: CD20-20_HC_CDR2

<400> SEQUENCE: 35

Ala Ile Tyr Pro Gly Asp Gly Asp Thr Arg
1               5                   10

<210> SEQ ID NO 36
<211> LENGTH: 17
<212> TYPE: PRT
<213> ORGANISM: Artificial Sequence
<220> FEATURE:
<223> OTHER INFORMATION: CD20-20_HC_CDR2-Kabat

<400> SEQUENCE: 36

Ala Ile Tyr Pro Gly Asp Gly Asp Thr Arg Tyr Thr Gln Lys Phe Lys
1               5                   10                  15

Gly

<210> SEQ ID NO 37
<211> LENGTH: 13
<212> TYPE: PRT
<213> ORGANISM: Artificial Sequence
<220> FEATURE:
<223> OTHER INFORMATION: CD20-20_HC_CDR3

<400> SEQUENCE: 37

```
Ser Pro Asp Phe Tyr Gly Ser Gly Tyr Asp Phe Asp Tyr
1               5                   10
```

<210> SEQ ID NO 38
<211> LENGTH: 35
<212> TYPE: DNA
<213> ORGANISM: Artificial Sequence
<220> FEATURE:
<223> OTHER INFORMATION: EcoMH2
<220> FEATURE:
<221> NAME/KEY: misc_feature
<222> LOCATION: (18)..(18)
<223> OTHER INFORMATION: n is a, c, g, or t

<400> SEQUENCE: 38
cttccggaat tcsargtnma gctgsagsag tcwgg         35

<210> SEQ ID NO 39
<211> LENGTH: 32
<212> TYPE: DNA
<213> ORGANISM: Artificial Sequence
<220> FEATURE:
<223> OTHER INFORMATION: EcoMH1
<220> FEATURE:
<221> NAME/KEY: misc_feature
<222> LOCATION: (18)..(18)
<223> OTHER INFORMATION: n is a, c, g, or t

<400> SEQUENCE: 39
cttccggaat tcsargtnma gctgsagsag tc            32

<210> SEQ ID NO 40
<211> LENGTH: 36
<212> TYPE: DNA
<213> ORGANISM: Artificial Sequence
<220> FEATURE:
<223> OTHER INFORMATION: BamIgG1

<400> SEQUENCE: 40
ggaggatcca tagacagatg ggggtgtcgt tttggc        36

<210> SEQ ID NO 41
<211> LENGTH: 31
<212> TYPE: DNA
<213> ORGANISM: Artificial Sequence
<220> FEATURE:
<223> OTHER INFORMATION: SacIMK

<400> SEQUENCE: 41
ggagctcgay attgtgmtsa cmcarwctmc a             31

<210> SEQ ID NO 42
<211> LENGTH: 46
<212> TYPE: DNA
<213> ORGANISM: Artificial Sequence
<220> FEATURE:
<223> OTHER INFORMATION: HindKL

<400> SEQUENCE: 42
tatagagctc aagcttggat ggtgggaaga tggatacagt tggtgc    46

<210> SEQ ID NO 43
<211> LENGTH: 67
<212> TYPE: DNA
<213> ORGANISM: Artificial Sequence
<220> FEATURE:
<223> OTHER INFORMATION: hCD20sacAP-SS

```
<400> SEQUENCE: 43
attagagctc acacaccata tattaacata tacaactgtg aaccatcgaa ttcctctgag    60
aaaaact                                                             67

<210> SEQ ID NO 44
<211> LENGTH: 22
<212> TYPE: DNA
<213> ORGANISM: Artificial Sequence
<220> FEATURE:
<223> OTHER INFORMATION: SRaMfe1R

<400> SEQUENCE: 44
aatgcaattg ttgttgttaa ct                                            22

<210> SEQ ID NO 45
<211> LENGTH: 45
<212> TYPE: DNA
<213> ORGANISM: Artificial Sequence
<220> FEATURE:
<223> OTHER INFORMATION: hCD20sacNN-D

<400> SEQUENCE: 45
attagagctc acacaccata tatcgatata tacgattgtg aacca                   45

<210> SEQ ID NO 46
<211> LENGTH: 41
<212> TYPE: DNA
<213> ORGANISM: Artificial Sequence
<220> FEATURE:
<223> OTHER INFORMATION: hCD20sacN163D

<400> SEQUENCE: 46
attagagctc acacaccata tattgatatc tacaactgtg a                       41

<210> SEQ ID NO 47
<211> LENGTH: 297
<212> TYPE: PRT
<213> ORGANISM: Artificial Sequence
<220> FEATURE:
<223> OTHER INFORMATION: Murine amino acid

<400> SEQUENCE: 47
```

Met Thr Thr Pro Arg Asn Ser Val Asn Gly Thr Phe Pro Ala Glu Pro
1               5                   10                  15

Met Lys Gly Pro Ile Ala Met Gln Ser Gly Pro Lys Pro Leu Phe Arg
            20                  25                  30

Arg Met Ser Ser Leu Val Gly Pro Thr Gln Ser Phe Phe Met Arg Glu
        35                  40                  45

Ser Lys Thr Leu Gly Ala Val Gln Ile Met Asn Gly Leu Phe His Ile
    50                  55                  60

Ala Leu Gly Gly Leu Leu Met Ile Pro Ala Gly Ile Tyr Ala Pro Ile
65                  70                  75                  80

Cys Val Thr Val Trp Tyr Pro Leu Trp Gly Gly Ile Met Tyr Ile Ile
                85                  90                  95

Ser Gly Ser Leu Leu Ala Ala Thr Glu Lys Asn Ser Arg Lys Cys Leu
            100                 105                 110

Val Lys Gly Lys Met Ile Met Asn Ser Leu Ser Leu Phe Ala Ala Ile
        115                 120                 125

Ser Gly Met Ile Leu Ser Ile Met Asp Ile Leu Asn Ile Lys Ile Ser
    130                 135                 140

-continued

```
His Phe Leu Lys Met Glu Ser Leu Asn Phe Ile Arg Ala His Thr Pro
145                 150                 155                 160

Tyr Ile Asn Ile Tyr Asn Cys Glu Pro Ala Asn Pro Ser Glu Lys Asn
                165                 170                 175

Ser Pro Ser Thr Gln Tyr Cys Tyr Ser Ile Gln Ser Leu Phe Leu Gly
            180                 185                 190

Ile Leu Ser Val Met Leu Ile Phe Ala Phe Phe Gln Glu Leu Val Ile
        195                 200                 205

Ala Gly Ile Val Glu Asn Glu Trp Lys Arg Thr Cys Ser Arg Pro Lys
    210                 215                 220

Ser Asn Ile Val Leu Leu Ser Ala Glu Glu Lys Lys Glu Gln Thr Ile
225                 230                 235                 240

Glu Ile Lys Glu Glu Val Val Gly Leu Thr Glu Thr Ser Ser Gln Pro
                245                 250                 255

Lys Asn Glu Glu Asp Ile Glu Ile Ile Pro Ile Gln Glu Glu Glu Glu
            260                 265                 270

Glu Glu Thr Glu Thr Asn Phe Pro Glu Pro Pro Gln Asp Gln Glu Ser
        275                 280                 285

Ser Pro Ile Glu Asn Asp Ser Ser Pro
290                 295
```